(12) United States Patent
Zanetti

(10) Patent No.: US 11,602,568 B2
(45) Date of Patent: Mar. 14, 2023

(54) ENGINEERED B LYMPHOCYTES AND COMPOSITIONS HAVING MICRO-RNA AND METHODS FOR MAKING AND USING THEM

(71) Applicant: The Regents of the University of California, Oakland, CA (US)

(72) Inventor: Maurizio Zanetti, La Jolla, CA (US)

(73) Assignee: The Regents of the University of California, Oakland, CA (US)

( * ) Notice: Subject to any disclaimer, the term of this patent is extended or adjusted under 35 U.S.C. 154(b) by 521 days.

(21) Appl. No.: 16/866,055

(22) Filed: May 4, 2020

(65) Prior Publication Data

US 2021/0015945 A1 Jan. 21, 2021

Related U.S. Application Data

(63) Continuation of application No. 15/841,709, filed on Dec. 14, 2017, now Pat. No. 10,682,425.

(60) Provisional application No. 62/434,347, filed on Dec. 14, 2016.

(51) Int. Cl.
| | | |
|---|---|---|
| A61K 48/00 | (2006.01) | |
| A61K 9/127 | (2006.01) | |
| C12N 15/85 | (2006.01) | |
| A61P 35/00 | (2006.01) | |
| C12N 5/0781 | (2010.01) | |
| A61K 9/51 | (2006.01) | |
| A61K 31/7105 | (2006.01) | |
| A61K 31/713 | (2006.01) | |
| A61K 35/17 | (2015.01) | |
| A61K 9/50 | (2006.01) | |

(52) U.S. Cl.
CPC .......... *A61K 48/0066* (2013.01); *A61K 9/127* (2013.01); *A61K 9/5176* (2013.01); *A61K 31/713* (2013.01); *A61K 31/7105* (2013.01); *A61P 35/00* (2018.01); *C12N 5/0635* (2013.01); *C12N 15/85* (2013.01); *A61K 9/5068* (2013.01); *A61K 35/17* (2013.01); *C12N 2510/00* (2013.01)

(58) Field of Classification Search
CPC .. A61K 48/0066; A61K 9/127; A61K 9/5068; A61K 35/17; A61P 35/00; C12N 5/0635; C12N 15/85; C12N 2510/00
USPC ...... 424/9.1; 435/6.1, 91.1, 91.31, 455, 458; 514/44 A, 44 R; 536/23.1, 24.5
See application file for complete search history.

(56) References Cited

U.S. PATENT DOCUMENTS

| | | |
|---|---|---|
| 2017/0247708 A1 | 8/2017 | Katakowski et al. |
| 2018/0171354 A1 | 6/2018 | Patzel |
| 2018/0339004 A1 | 11/2018 | Greenberg et al. |

OTHER PUBLICATIONS

Almanza et al. "Synthesis and delivery of short, noncoding RNA by B lymphocytes" PNAS, Dec. 10, 2013, v 110, n 50, p. 20182-20187.
Tiwari et al., "Sox4 Is a Master Regulator of Epithelial-Mesenchymal Transition by Controlling Ezh2 Expression and Epigenetic Reprogramming" Cancer Cell, Jun. 10, 2013, v 23, 768-783.
Vervoort et al. "The role of SRY-related HMG box transcription factor 4 (SOX4) in tumorigenesis and metastasis: friend or foe?" Oncogene, 2013, v 32, p. 3397-3409.
Volinia et al., "A microRNA expression signature of human solid tumors defines cancer gene targets" PNAS, Feb. 14, 2006, v 103, n 7, p. 2257-2261.
Wang et al., "MicroRNA-335 represents an independent prognostic marker in cervical cancer" Tumor Biol. 2015, v 36, p. 5825-5830.
Xiong et al., "MicroRNA-335 Acts as a Candidate Tumor Suppressor in Prostate Cancer" Pathol. Oncol, Res., 2013, v 19, p. 529-537.
Almanza et al., "High-efficiency Generation of Multiple Short Noncoding RNA in B-cells and B-cell-derived Extracellular Vesicles" Molecular Therapy—Nucleic Acids. 2015, v 4, p. 1-7.
O'Connell et al., "microRNA Regulation of Inflammatory Responses" Annu. Rev. Immunol., 2012, v 30, p. 295-312.
Pedersen et al., "MicroRNAs in the Immune Response" Cytokine, Sep. 2008. v 43, n 3, p. 391-394.
Png et al., "MicroRNA-335 inhibits tumor reinitiation and is silenced through genetic and epigenetic mechanisms in human breast cancer" Genes and Development, 2011, v 25, p. 226-231.
Restivo et al., "Cardiac Outflow Tract: A Review of Some Embryogenetic Aspects of the Conotruncal Region of the Heart" The Anatomical Record Part A, 2006, v 288A, p. 936-943.

(Continued)

*Primary Examiner* — Jane J Zara
(74) *Attorney, Agent, or Firm* — Greer, Burns & Crain, LTD.; Gregory P. Einhorn

(57) ABSTRACT

Provided are engineered B lymphocytes modified to express one or several different types of microRNAs or anti-miRs where in one embodiments the lymphocytes contain multiple copy numbers of nucleic acids encoding the one or several different types of miRs or anti-miRs. Provided are compositions and methods for treating, ameliorating, or preventing a cancer cell, a breast cancer cell or a triple negative breast cancer, or a breast cancer cell that tests negative for estrogen receptors, progesterone receptors, or HER2, comprising or by administering a composition, formulation or pharmaceutical composition comprising a microRNA or anti-miR. Provided are methods for treating an inflammation, a disease, a condition, infection or cancer capable of being treated by modulation or inhibition or expression of an miRNA or anti-miRs by administering to an individual in need thereof a B lymphocyte that secretes a microRNA or anti-miR, or a B lymphocyte supernatant, extracellular vesicle or exosome having a microRNA or anti-miR.

10 Claims, 34 Drawing Sheets

Specification includes a Sequence Listing.

(56) References Cited

OTHER PUBLICATIONS

Tavazoie et al., "Endogenous human microRNAs that suppress breast cancer metastasis" Nature, Jan. 10, 2008, v 451, n 7175, p. 147-152.

Thomas et al., "Desperately seeking microRNA targets" Nature Structural & Molecular Biology, Oct. 2010, v 17, n 10, p. 1169-1174.

Minn et al., "Genes that mediate breast cancer metastasis to lung" Nature, Jul. 28, 2005, v 436, n 7050, p. 518-524.

Isosaka et al., "A Screen for Epigenetically Silenced microRNA Genes in Gastrointestinal Stromal Tumors" PLOS One, Jul. 27, 2015, p. 1-17.

Foronda et al., "Sox4 Links Tumor Suppression to Accelerated Aging in Mice by Modulating Stem Cell Activation" Cell Reports, Jul. 24, 2014, v 8, p. 487-500.

Friedman et al., "Most mammalian mRNAs are conserved targets of microRNAs" Genome Research, 2009, v 19, p. 92-105.

Garzon et al., "microRNAs in cancer" Annual Review of Medicine, Feb. 2009, v 60, p. 167-179.

Gong et al., "MiR-335 Inhibits Small Cell Lung Cancer Bone Metastases via IGF-IR and RANKL Pathways" Mol. Cancer Re, Jan. 2014, v 12, p. 101-110.

Hong et al., "Sox proteins and neural crest development" Seminars in Cell and Developmental Biology, 2005, v 16, p. 694-703.

Bartel, "MicroRNAs: Genomics, Biogenesis, Mechanism, and Function" Cell, Jan. 23, 2004, v 116, p. 281-297.

Busslinger, "Transcriptional Control of Early B Cell Development" Annu. Rev. Immunol., 2004, v 22, p. 55-79.

Cao et al., "miR-335 Represents an Independent Prognostic Marker in Epithelial Ovarian Cancer" Am. J. Clin. Pathol., 2014, v 141, p. 437-442.

Esquela-Kerscher et al., "Oncomirs—microRNAs with a role in cancer" Nature Reviews, Apr. 2006, v 6, p. 259-269.

Ambros et al., "The functions of animal microRNAs" Nature, Sep. 16, 2004, v 431, p. 350-355.

Arita et al., "B cell activation regulates exosomal HLA production" Eur. J. Immunol., 2008, v 38, p. 1423-1434.

Pegtel et al., "Functional delivery of viral miRNAs via exosomes" PNAS, Apr. 6, 2010, v 107, n 14, p. 6328-6333.

Rapaso et al., "B Lymphocytes Secrete Antigen-presenting Vesicles" J. Exp. Med., Mar. 1996, v 183, p. 1161-1172.

Saunderson et al., "Induction of Exosome Release in Primary B Cells Stimulated via CD40 and the IL-4 Receptor" The Journal Immunology, 2008, v 180, p. 8146-8152.

Wubbolts et al., "Proteomic and Biochemical Analyses of Human B Cell-derived Exosomes" The Journal of Biological Chemistry, 2003, v 278, n 13, p. 10963-10972.

Admyre et al., "B cell-derived exosomes can present allergen peptides and activate allergen-specific T cells to proliferate and produce TH2-like cytokines" J Allergy Clin Immunol., 2007, v 120, n 6, p. 1418-1424.

Oksvold et al., "Expression of B-Cell Surface Antigens in Subpopulations of Exosomes Released From B-Cell Lymphoma Cells" 2014, v 36, n 6, p. 847-862.e1.

Clayton et al., "Antigen-presenting cell exosomes are protected from complement-mediated lysis by expression of CD55 and CD59" Eur. J. Immunol., 2003. v 33, p. 522-531.

Clayton et al., "Adhesion and signaling by B cell-derived exosomes: the role of integrins" The FASEB Journal, Apr. 1, 2004, p. 1-22.

Muntasell et al., "T cell-induced secretion of MHC class II-peptide complexes on B cell exosomes" The EMBO Journal, 2007, v 26, n 19, p. 4263-4272.

Nanbo et al., "Exosomes Derived from Epstein-Barr Virus-Infected Cells Are Internalized via Caveola-Dependent Endocytosis and Promote Phenotypic Modulation in Target Cells" Journal of Virology, Sep. 2013, v 87, n 18, p. 10334-10347.

Chevillet et al., "Quantitative and stoichiometric analysis of the microRNA content of exosomes" PNAS, Oct. 14, 2014, v 111, n 41, p. 14888-14893.

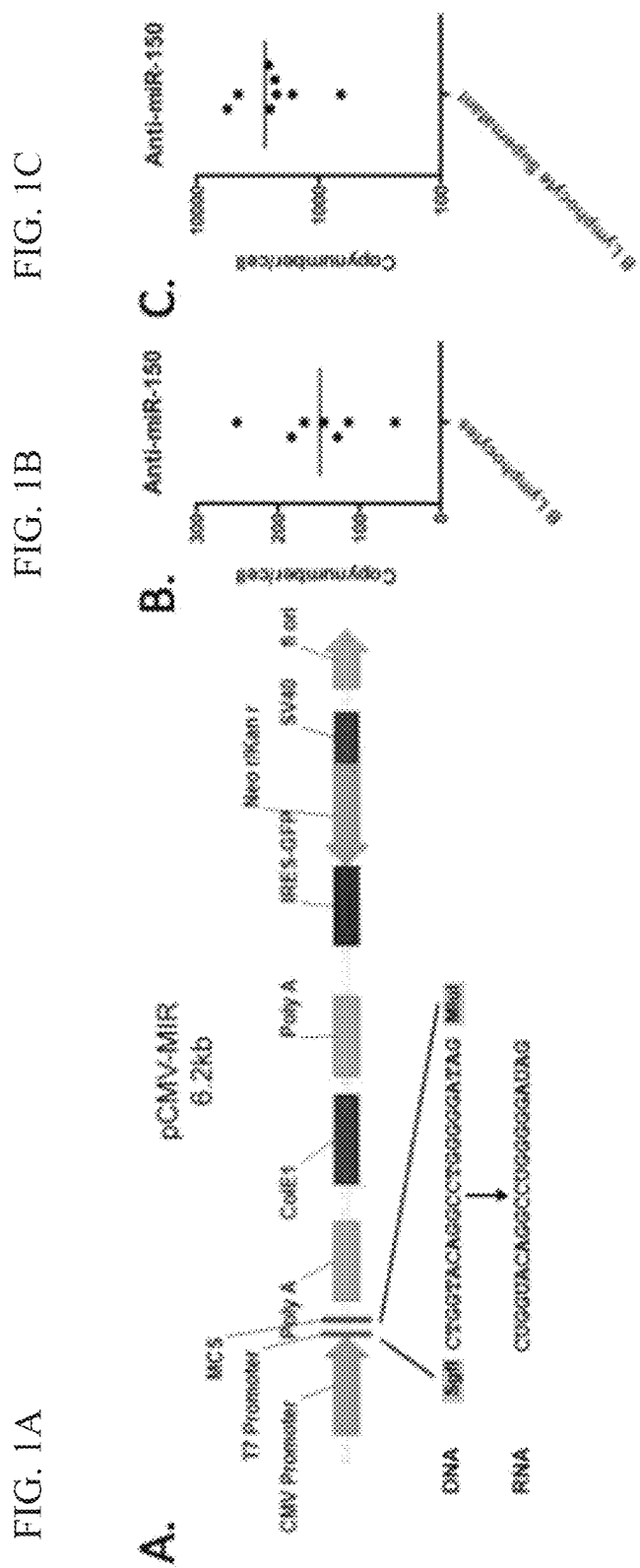

FIG. 7

A. mir150
CCCUGUCUCCCAACCCUUGUACCAGUGCUGUGCCUCAGACCCUGGUACAGGCCUGGGGGAUUAGGG mir155
CUGUUAAUGCUAAUUGUGAUAGGGGUUUUGGCCUCUGACUGACUCCUACCUGUUAGCAUUAACAG anti-mir155
CUGACCCCUAUCACAAUUAGCAUUAAUUUGGCCUCUGACUGACUCCUACCUGUUAGCAUUAACAG

B.

TCTCCCAACCCTTGTACCAGT — mir150
TTAATGCTAATTGTGATAGGGGT — mir155

[random 1]—⟨SgfI⟩—[mir150]—⟨MluI⟩—[random 2]—⟨NotI⟩—[mir155]—⟨NotI⟩—[random 2]

C.

TCTCCCAACCCTTGTACCAGT — mir150
ACCCCTATCACAATTAGCATTAA — α-mir155

[random 1]—⟨SgfI⟩—[mir150]—⟨MluI⟩—[random 2]—⟨NotI⟩—[α-mir155]—⟨NotI⟩—[random 2]

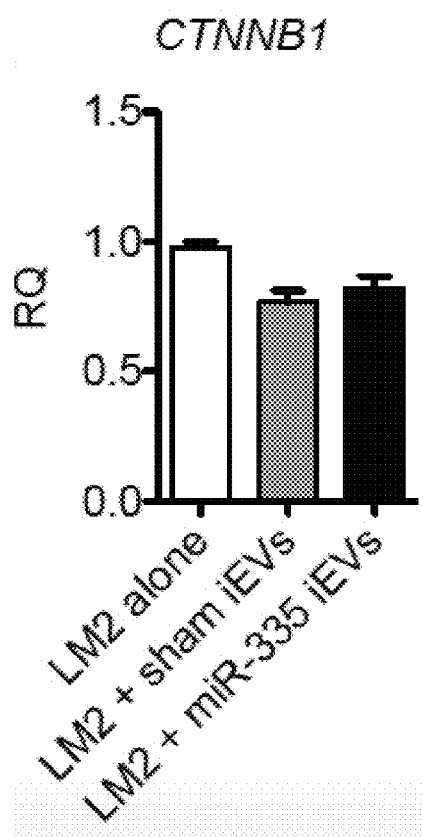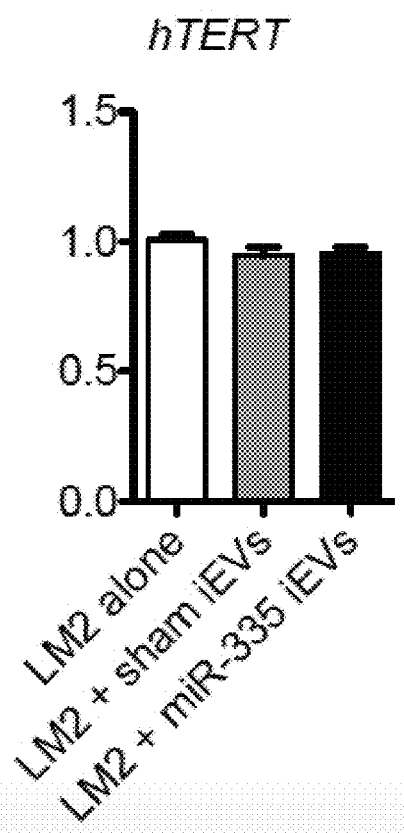

SEQUENCE LISTING

```
<160> NUMBER OF SEQ ID NOS: 10

<210> SEQ ID NO 1
<211> LENGTH: 22
<212> TYPE: DNA
<213> ORGANISM: artificial sequence
<220> FEATURE:
<223> OTHER INFORMATION: synthetic oligonucleotide

<400> SEQUENCE: 1
ctggtacagg cctgggggat ag                                              22

<210> SEQ ID NO 2
<211> LENGTH: 22
<212> TYPE: RNA
<213> ORGANISM: artificial sequence
<220> FEATURE:
<223> OTHER INFORMATION: synthetic oligonucleotide

<400> SEQUENCE: 2
cugguacagg ccuggggau ag                                               22

<210> SEQ ID NO 3
<211> LENGTH: 8
<212> TYPE: PRT
<213> ORGANISM: artificial sequence
<220> FEATURE:
<223> OTHER INFORMATION: synthetic peptide

<400> SEQUENCE: 3

Ser Ile Ile Asn Phe Glu Lys Leu
1               5
```

-continued

```
<210> SEQ ID NO 4
<211> LENGTH: 9
<212> TYPE: PRT
<213> ORGANISM: artificial sequence
<220> FEATURE:
<223> OTHER INFORMATION: synthetic peptide

<400> SEQUENCE: 4

Ala Ser Asn Glu Asn Met Asp Ala Met
1               5

<210> SEQ ID NO 5
<211> LENGTH: 65
<212> TYPE: RNA
<213> ORGANISM: artificial sequence
<220> FEATURE:
<223> OTHER INFORMATION: synthetic oligonucleotide

<400> SEQUENCE: 5
cccugucucc caacccuugu accagugcug ugccucagac ccugguacag gccuggggga      60
uaggg                                                                 65

<210> SEQ ID NO 6
<211> LENGTH: 65
<212> TYPE: RNA
<213> ORGANISM: artificial sequence
<220> FEATURE:
<223> OTHER INFORMATION: synthetic oligonucleotide

<400> SEQUENCE: 6
cuguuaaugc uaauugugau aggguuuug gccucugacu gacuccuacc uguuagcauu       60
aacag                                                                 65

<210> SEQ ID NO 7
<211> LENGTH: 65
<212> TYPE: RNA
<213> ORGANISM: artificial sequence
<220> FEATURE:
<223> OTHER INFORMATION: synthetic oligonucleotide

<400> SEQUENCE: 7
cugaccccua ucacaauuag cauuaauuug gccucugacu gacuccuacc uguuagcauu      60
aacag                                                                 65

<210> SEQ ID NO 8
<211> LENGTH: 21
<212> TYPE: DNA
<213> ORGANISM: artificial sequence
<220> FEATURE:
<223> OTHER INFORMATION: synthetic oligonucleotide

<400> SEQUENCE: 8
tctcccaacc cttgtaccag t                                               21

<210> SEQ ID NO 9
<211> LENGTH: 23
<212> TYPE: DNA
<213> ORGANISM: artificial sequence
<220> FEATURE:
<223> OTHER INFORMATION: synthetic oligonucleotide

<400> SEQUENCE: 9
ttaatgctaa ttgtgatagg ggt                                             23
```

```
<210> SEQ ID NO 10
<211> LENGTH: 23
<212> TYPE: DNA
<213> ORGANISM: artificial sequence
<220> FEATURE:
<223> OTHER INFORMATION: synthetic oligonucleotide

<400> SEQUENCE: 10
acccctatca caattagcat taa                                              23
```

ENGINEERED B LYMPHOCYTES AND COMPOSITIONS HAVING MICRO-RNA AND METHODS FOR MAKING AND USING THEM

RELATED APPLICATIONS

This application is a continuation of U.S. Utility patent application Ser. No. 15/841,709, filed Dec. 14, 2017, which, claims the benefit of priority to U.S. Provisional Patent Application Ser. No. 62/434,347, filed Dec. 14, 2016. The aforementioned applications are expressly incorporated herein by reference in their entirety and for all purposes.

STATEMENT AS TO FEDERALLY SPONSORED RESEARCH

This invention was made with government support under grant nos. R21CA178674 and 2R56A1062894-04A1, awarded by the National Institutes of Health (NIH), DHHS. The government has certain rights in the invention.

TECHNICAL FIELD

This invention generally relates to genetic therapy and molecular and cellular biology. In alternative embodiments, provided are engineered B lymphocytes modified to express one or several different types of microRNAs (miRs), where in alternative embodiments the lymphocytes contain multiple copy numbers of nucleic acids encoding the one or several different types of miRs. In alternative embodiments, provided are compositions and methods for treating, ameliorating, or preventing a cancer cell, a breast cancer cell or a triple negative breast cancer, or a breast cancer cell that tests negative for estrogen receptors (ER-), progesterone receptors (PR-), and/or HER2 (HER2-), comprising or by administering a composition, formulation or pharmaceutical composition comprising a microRNA-335 (miR-335), miR-138 or miR-449.

BACKGROUND

Short noncoding RNAs, evolutionarily conserved 20 to 30 nucleotide long (miRNAs, or miRs), represent a large family of gene expression regulators through their ability to prevent translation of specific mRNA into protein (Bartel, 2004; Thomas et al., 2010). Individual miRNAs may repress up to hundreds of transcripts (Friedman et al., 2009) and can regulate diverse processes including cell growth, metabolism, immunity, inflammation and cancer (Ambros, 2004; O'Connell et al.; Pedersen and David, 2008; Volinia et al., 2006). miRNA mutations or mis-expression exist in human cancers suggesting that miRNAs can function as tumor suppressors or oncogenes (oncomirs) (Esquela-Kerscher and Slack, 2006; Garzon et al., 2009). Thus, suppression of oncomirs or selective miRNA restoration in cancer cells has therapeutic relevance.

miR-335 was identified as being implicated in the growth and metastasis of the triple negative breast cancer (TNBC) cell line MDA-MB-231 derivative 4175 (LM2) (Tavazoie et al., 2008). Clinically, TNBC patients whose primary tumors have low miR-335 expression have a shorter median time to metastatic relapse (Tavazoie et al., 2008). Reportedly, miR-335 inhibits tumor re-initiation and is silenced through genetic and epigenetic mechanisms (Png et al., 2011). One of the targets of miR-335, miR-129, miR-129-2 and miR-93, is SOX4 a transcription factor involved in embryonic development and cell fate determination (Busslinger, 2004; Hong and Saint-Jeannet, 2005; Restivo et al., 2006), and in epithelial to mesenschymal transition (EMT) (Tiwari et al., 2013). SOX4 expression is elevated in various tumors, including lymphoma, colorectal cancer, cervical cancer, lung cancer, pancreatic cancer, and breast cancer. In many cancers, deregulated expression of this developmental factor has been correlated with increased cancer cell proliferation, cell survival, inhibition of apoptosis and the induction of EMT (Vervoort et al., 2013). Experiments in mice with conditional deletion of Sox4 in stratified epithelia showed resistance to chemical carcinogenesis leading to onset delay and tumor size reduction (Foronda et al., 2014).

B cells have been programmed for the enforced biogenesis and synchronous release of sncRNAs (Almanza et al., 2013). sncRNAs have been packaged as a cargo in extracellular vesicles (EVs) produced and released by the programmed B cells, and that thus induced EVs (iEVs) are enriched in predetermined sncRNAs, with an estimate of 3.6 copy number/EV (Almanza and Zanetti, 2015).

SUMMARY

In alternative embodiments, provided are compositions, formulations or pharmaceutical compositions, comprising:
(1) a transfected or transduced B lymphocyte comprising or having contained therein a heterologous micro-RNA (miRNA, or miR), or a heterologous anti-miRNA (antagomir or blockmir),
wherein optionally the heterologous micro-RNA or anti-miRNA is a synthetic RNA,
or an expression system (optionally a plasmid or a vector) capable of expressing the heterologous miRNA or anti-miRNA (or an expression system comprising nucleic acids capable of expressing the miRNA or anti-miRNA); or
(2)
(a) a B lymphocyte supernatant or equivalent thereof,
(b) a B lymphocyte extracellular vesicle (EV) or equivalent thereof,
(c) a B lymphocyte exosome or equivalent thereof,
(d) a B lymphocyte micro-vesicle or equivalent thereof, or
(e) any combination of (a) to (d),
wherein the B lymphocyte supernatant or equivalent thereof, B lymphocyte extracellular vesicle (EV) or equivalent thereof, B lymphocyte exosome or equivalent thereof, or B lymphocyte micro-vesicle or equivalent thereof, comprises or has contained therein: a plurality of the same or different micro-RNA (miRNA, or miR) or anti-miRNA molecules, and optionally the same or different micro-RNA or anti-miRNA molecules are heterologous to the B cells from which they are derived,
wherein optionally the same or different micro-RNA or anti-miRNA is a synthetic RNA,
wherein optionally the B lymphocyte comprises or has contained therein: a plurality of the same or different micro-RNA (miRNA, or miR) or anti-miRNA molecules,
wherein optionally the miRNA or anti-miRNA comprises: miR-335, miR-138, miR-449, miR-129, miR-129-2, miR-93, an miR-141, an miR-150, an miR-155, an miR-15a, an miR-16, an mi-R-21, or an miRNA selected from Table 2, or an miRNA that down-regulates or decreases the activity of SOX4 mRNA, and a combination thereof, wherein the anti-miRNA comprises a sequence complementary to the miRNA, or any combination thereof, and optionally the miR or anti-miRNA can prevent or slow cancer cell proliferation, local and distal metastasis, epithelial to mesenschymal transition (EMT) or the differentiation of cancer initiating/cancer stem cells into more differentiated cancer cells;

wherein one, two, three or more types of miR are contained and expressed in the B lymphocyte, the B lymphocyte supernatant or equivalent thereof, the B lymphocyte extracellular vesicle (EV) or equivalent thereof, the B lymphocyte exosome or equivalent thereof, the B lymphocyte micro-vesicle or equivalent thereof, or any combination thereof, and optionally the miR or anti-miRNA can prevent or slow cancer cell proliferation, local and distal metastasis, epithelial to mesenschymal transition (EMT) or the differentiation of cancer initiating/cancer stem cells into more differentiated cancer cells, and optionally coding sequence for the heterologous miR or anti-miRNA is contained in an expression system, optionally a plasmid or a vector, that expresses the heterologous miR or anti-miRNA in the B lymphocyte.

In alternative embodiments, provided are compositions, formulations or pharmaceutical compositions, made by a method comprising:

(a) providing a B lymphocyte; and providing:
  (i) an expression system capable of expressing a nucleic acid contained therein in the B lymphocyte, and the expression system comprises or has contained therein coding sequence for:
    one or a plurality of the same or different micro-RNA (miRNA) or anti-miRNA molecules, wherein optionally the miRNA or anti-miRNA is heterologous to the B lymphocytes,
    wherein optionally the miRNA or anti-miRNA comprises: miR-335, miR-138, miR-449, miR-129, miR-129-2, miR-93, an miR-141, an miR-150, an miR-155, an miR-15a, an miR-16, an mi-R-21, or an miRNA selected from Table 2, or an miRNA that down-regulates or decreases the activity of SOX4 mRNA, and a combination thereof, wherein the anti-miRNA comprises a sequence complementary to the miRNA, or any combination thereof,
  (ii) a plurality of synthetic micro-RNA or anti-miRNA, and optionally the miR or anti-miRNA can prevent or slow cancer cell proliferation, local and distal metastasis, epithelial to mesenschymal transition (EMT) or the differentiation of cancer initiating/cancer stem cells into more differentiated cancer cells, or treating, ameliorating, or preventing, or the miR or anti-miRNA can control the tumorigenicity of: a cancer, a glioblastoma, a breast cancer or a triple negative breast cancer, or a breast cancer that tests negative for estrogen receptors (ER-), progesterone receptors (PR-), and/or HER2 (HER2-), or
    optionally the miRNA or anti-miRNA has an effect on the cell comprising treating, ameliorating or preventing an infection, a viral or bacterial infection, a condition or a disease, a metabolic disorder (optionally obesity or type 2 diabetes), an immune disorder or autoimmune disease, a cancer, a disease or condition caused by a cell dysplasia, a hypertrophy, a cardiac hypertrophy or a fibrosis;

(b) inserting, placing into or transducing into the B lymphocyte: the miRNA or anti-miRNA; the expression system; or the synthetic miRNA or anti-miRNA;

(c) culturing or manipulating the B lymphocyte such that: the B lymphocyte expresses the one or the plurality of the same or different of the micro-RNA or anti-miRNA molecules, and optionally further comprising culturing or manipulating the B lymphocyte such that:
  a micro-RNA- or anti-miRNA-comprising B lymphocyte supernatant is generated,
  a micro-RNA- or anti-miRNA-comprising B lymphocyte extracellular vesicle (EV) is generated,
  a micro-RNA- or anti-miRNA-comprising B lymphocyte exosome is generated, and/or
  a micro-RNA- or anti-miRNA-comprising B lymphocyte micro-vesicle is generated; and optionally, a step (d), comprising harvesting or isolating the B lymphocyte, the B lymphocyte supernatant, B lymphocyte extracellular vesicle (EV), B lymphocyte exosome or B lymphocyte micro-vesicle, wherein the B lymphocyte, the B lymphocyte supernatant, B lymphocyte extracellular vesicle (EV), B lymphocyte exosome or B lymphocyte micro-vesicle comprises or has contained therein a plurality of the micro-RNA or anti-miRNA molecules.

In alternative embodiments of compositions, formulations or pharmaceutical compositions as provided herein, the B lymphocyte is a mammalian B lymphocyte, or a human B lymphocyte; or the B lymphocyte is a primary lymphocyte or an autologous B lymphocyte.

In alternative embodiments of compositions, formulations or pharmaceutical compositions as provided herein, the expression system for expressing the miR or anti-miRNA or a plurality of different miRs or anti-miRNAs comprises a plasmid or an expression vector; a viral or a non-viral plasmid or expression vector; a DNA plasmid or expression vector; a DNA expression vector; or an integrating, episomal or non-integrating plasmid or expression vector; or the expression system is a genome integrating or genome non-integrating or episomal expression system, wherein optionally the expression system comprises, or has contained therein, two, three, four or five or more copies of the microRNA or anti-miRNA coding sequence, wherein optionally the microRNA or anti-miRNA coding sequences are the same or different, and optionally each microRNA or anti-miRNA coding sequences is operatively linked to a different transcriptional regulator, or promoter, and optionally expression system, optionally a plasmid, is engineered to comprise two (a doublet of) miRs or anti-miRNA, optionally miR-335, miR-138, miR-449, miR-129, miR-129-2, miR-93, an miR-141, an miR-150, an miR-155, an miR-15a, an miR-16, an mi-R-21, precursor stem loops, two pre-miR stem loops in tandem with a nucleotide linker, or two miRs, optionally pre-miR-335, miR-138, miR-449, miR-129, miR-129-2, miR-93, an miR-141, an miR-150, an miR-155, an miR-15a, an miR-16, an mi-R-21, or miR-449, stem loops in tandem with a nucleotide linker, and optionally the expression system, optionally a plasmid, is engineered to comprise multiple copies of miRs, optionally miR-335, miR-138, miR-449, miR-129, miR-129-2, miR-93, an miR-141, an miR-150, an miR-155, an miR-15a, an miR-16, an mi-R-21, as precursor stem loops, or two or more pre-miR stem loops in tandem with a nucleotide linker, or two or more pre-miR stem loops in tandem with a nucleotide linker.

In alternative embodiments of compositions, formulations or pharmaceutical compositions as provided herein, the plurality of microRNA or anti-miRNA coding sequences are designed to or are capable of modulating an RNA or DNA that controls or modulates cell growth, cell maturation or differentiation, cell death, apoptosis, cell metabolism, immunity or inflammation, or that modulation of the RNA or DNA by exposure to or contact with the miRNA therapeutically treats, ameliorates or prevents an infection, a viral or a bacterial infection, a condition or a disease, an immune disorder or autoimmune disease, a cancer, a disease or condition, optionally caused by a cell dysplasia, a hypertrophy, a cardiac hypertrophy or a fibrosis.

In alternative embodiments of compositions, formulations or pharmaceutical compositions as provided herein, the B lymphocyte extracellular vesicle (EV), B lymphocyte exosome or B lymphocyte micro-vesicle comprises or has contained within between about 1 to 10, or 1, 2, 3, 4, 5, 6, 7, 8, 9, or 10 or more copies of the same or different microRNA or anti-miRNA per B lymphocyte extracellular vesicle (EV), B lymphocyte exosome or B lymphocyte micro-vesicle.

In alternative embodiments of compositions, formulations or pharmaceutical compositions as provided herein, the microRNA or anti-miRNA is or comprises an miR-335, an miR-141, an miR-150, an miR-155, an miR-335, an miR-138, an miR-449, an miR-15a, an miR-16, an mi-R-21, or the microRNA (miR) coding sequence has a sequence complementary to an miR-335, an miR-141, an miR-150, an miR-155, an miR-335, an miR-138, an miR-449, an miR-15a, an miR-16, an mi-R-21, or an miR as set forth in Table 2, or an miRNA that down-regulates or decreases the activity of SOX4 mRNA;

and optionally the miR-335, miR-138, miR-449, miR-129, miR-129-2 and/or miR-93, target SOX4 mRNA, and optionally down-regulates or decreases the activity of SOX4 mRNA.

In alternative embodiments, provided are methods for making a composition, formulation or pharmaceutical composition comprising at least one microRNA (miR) or anti-miRNA, wherein optionally the plurality of miRNA or anti-miRNA are synthetic, wherein the method comprises:

(a) providing a B lymphocyte; and providing:
(i) an expression system capable of expressing a nucleic acid contained therein in the B lymphocyte, and the expression system comprises or has contained therein coding sequence for:
one or a plurality of the same or different micro-RNA (miRNA) or anti-miRNA molecules, wherein optionally the miRNA or anti-miRNA is heterologous to the B lymphocytes,
wherein optionally the miRNA or anti-miRNA comprises: an miR-335, an miR-141, an miR-150, an miR-155, an miR-335, an miR-138, an miR-449, an miR-15a, an miR-16, an mi-R-21, or an miRNA selected from Table 2, and a combination thereof, or an miRNA that down-regulates or decreases the activity of SOX4 mRNA, wherein the anti-miRNA comprises a sequence complementary to the miRNA, or any combination thereof,
(ii) a plurality of synthetic micro-RNA or anti-miRNA, and optionally the miR or anti-miRNA can prevent or slow cancer cell proliferation, local and distal metastasis, epithelial to mesenschymal transition (EMT) or the differentiation of cancer initiating/cancer stem cells into more differentiated cancer cells, or treating, ameliorating, or preventing, or the miR or anti-miRNA can control the tumorigenicity of: a cancer, a glioblastoma, a breast cancer or a triple negative breast cancer, or a breast cancer that tests negative for estrogen receptors (ER-), progesterone receptors (PR-), and/or HER2 (HER2-), or optionally the miRNA or anti-miRNA has an effect on the cell comprising treating, ameliorating or preventing an infection, a viral or bacterial infection, a condition or a disease, a metabolic disorder (optionally obesity or type 2 diabetes), an immune disorder or autoimmune disease, a cancer, a disease or condition caused by a cell dysplasia, a hypertrophy, a cardiac hypertrophy or a fibrosis;

(b) inserting, placing into, transfecting or transducing into the B lymphocyte: the miRNA or anti-miRNA; the expression system; or the synthetic miRNA or anti-miRNA;

(c) culturing or manipulating the B lymphocyte such that: the B lymphocyte expresses the one or the plurality of the same or different of the micro-RNA or anti-miRNA molecules, and optionally further comprising culturing or manipulating the B lymphocyte such that:
a micro-RNA- or anti-miRNA-comprising B lymphocyte supernatant is generated,
a micro-RNA- or anti-miRNA-comprising B lymphocyte extracellular vesicle (EV) is generated,
a micro-RNA- or anti-miRNA-comprising B lymphocyte exosome is generated, and/or
a micro-RNA- or anti-miRNA-comprising B lymphocyte micro-vesicle is generated; and optionally, a step (d), comprising harvesting or isolating the B lymphocyte, the B lymphocyte supernatant, B lymphocyte extracellular vesicle (EV), B lymphocyte exosome or B lymphocyte micro-vesicle, wherein the B lymphocyte, the B lymphocyte supernatant, B lymphocyte extracellular vesicle (EV), B lymphocyte exosome or B lymphocyte micro-vesicle comprises or has contained therein a plurality of the micro-RNA or anti-miRNA molecules.

In alternative embodiments, provided are methods for manipulating a cell physiology, a cell function, a cellular genome in a cell, a cellular transcriptome in a cell, or a cellular proteome in a cell, wherein optionally the manipulating is in vitro, ex vivo, or in vivo, comprising:

contacting the cell with, or contacting the cell by administering to an individual in need thereof:

(a) a composition, formulation or pharmaceutical composition or a B lymphocyte as provided herein, or a composition made by the method as provided herein; or, (b) a B lymphocyte, or a primary B lymphocyte, optionally a B lymphocyte autologous to the individual in need thereof, that:
secretes at least one microRNA (miR) or anti-miRNA; or,
secretes a B lymphocyte extracellular vesicle (EV), a B lymphocyte exosome or a B lymphocyte micro-vesicle, comprising: a plurality of miRNA or anti-miRNA, wherein optionally the plurality of miRNA or anti-miRNA are synthetic, and the contacting is for a sufficient period of time and under sufficient conditions such that the plurality of miRNA, or, a B lymphocyte extracellular vesicle (EV), B lymphocyte exosome or B lymphocyte micro-vesicle, is transferred to or taken up into the cell,
wherein optionally the cell is contacted in vitro, ex vivo, or in vivo;
and optionally the cell is a T cell, or an activated T cell, or a T cell activated via its antigen receptor, or a CD8 T cell or a CD4 T cell,
and optionally the cell is a cancer cell, a cancer stem cell or a dysplastic cell, and optionally the cancer cell is a breast cancer cell or a triple negative breast cancer, or a breast cancer cell that tests negative for estrogen receptors (ER-), progesterone receptors (PR-), and/or HER2 (HER2-), a prostate cancer cell, a breast cancer cell, a lymphoma cell, a glioblastoma cell, lung cancer cell, a pancreatic cancer cell, an ovarian cancer cell, a liver cancer cell, a colon cancer cell, a medulloblastoma cell, or a salivary gland cancer cell,
and optionally the cell or T cell is a mammalian or a human cell,
and optionally the miRNA or anti-miRNA has an effect on the cell comprising controlling or modulating cell growth, cell maturation or differentiation, cell death, apoptosis, cell metabolism, immunity or inflammation, tumorigenicity or tumor cell size or viability, or
and optionally the miRNA or anti-miRNA has an effect on the cell comprising treating, ameliorating or preventing an infection, a viral or bacterial infection, a condition or a disease, a metabolic disorder (optionally obesity or type 2 diabetes), an immune disorder or autoimmune disease, a cancer, a disease or condition caused by a cell dysplasia, a hypertrophy, a cardiac hypertrophy or a fibrosis.

In alternative embodiments, provided are methods for treating, ameliorating, or preventing, or controlling the tumorigenicity of: a cancer, a glioblastoma, a breast cancer or a triple negative breast cancer, or a breast cancer that tests negative for estrogen receptors (ER-), progesterone receptors (PR-), and/or HER2 (HER2-), comprising or by administering to an individual in need thereof:
  (a) a composition, formulation or pharmaceutical composition as provided herein,
  (b) a composition made by the method as provided herein; or,
  (c) a composition, formulation or pharmaceutical composition comprising: an miR-335, an miR-141, an miR-150, an miR-155, an miR-15a, an miR-16, an miRNA selected from Table 2, or an miRNA that down-regulates or decreases the activity of SOX4 mRNA, and a combination thereof, or an anti-miRNA having a sequence complementary to the miRNA, or any combination thereof.

In alternative embodiments, provided compositions, formulations or pharmaceutical compositions, comprising:
  a B lymphocyte supernatant, a B lymphocyte extracellular vesicle (EV), a B lymphocyte exosome or a B lymphocyte micro-vesicle, comprising:
  (a) a plurality of anti-sense sequences specifically targeted against at least one microRNA (miR), or an anti-miR (an antagomir or blockmir),
    wherein optionally the anti-miR is an anti-miR-150; and/or
  (b) a plurality of micro-RNA (miRNA) molecules,
    wherein optionally the miRNA comprises an miR-141, an miR-150, an miR-155, an miR-335, an miR-138, an miR-449, an miR-15a or an miR-16, or.

and optionally the B lymphocyte supernatant, B lymphocyte extracellular vesicle (EV), B lymphocyte exosome or B lymphocyte micro-vesicle is made by a method comprising:
(a) providing a B lymphocyte; and providing an expression system capable of expressing a nucleic acid contained therein in a B lymphocyte, and the expression system comprises or has contained therein coding sequence for:
  i) a plurality of anti-sense sequences specifically targeted against at least one microRNA (miR), or an anti-miR; or, a plurality of antagomirs or blockmirs, wherein optionally the anti-miR is an anti-miR-150; and/or
  (ii) a plurality of micro-RNA (miRNA) molecules,
    wherein optionally the miRNA comprises miR-141, an miR-150, an miR-155, an miR-335, an miR-138, an miR-449, an miR-15a or an miR-16;
(b) inserting, placing into or transducing into the B lymphocyte the expression system, and culturing or manipulating the B lymphocyte such that it expresses the plurality of anti-microRNA (miR), or anti-miR, or antagomir or blockmir nucleic acid or sequence, and/or the plurality of micro-RNA (miRNA) molecules; and
(c) harvesting or isolating the B lymphocyte supernatant, B lymphocyte extracellular vesicle (EV), B lymphocyte exosome or B lymphocyte micro-vesicle, wherein the B lymphocyte supernatant, B lymphocyte extracellular vesicle (EV), B lymphocyte exosome or B lymphocyte micro-vesicle comprises or has contained therein the plurality of anti-microRNA (miR), or anti-miR, or antagomir or blockmir nucleic acid or sequence, and/or the plurality of micro-RNA (miRNA) molecules.
and optionally the B lymphocyte is a mammalian B lymphocyte, or a human B lymphocyte; or the B lymphocyte is a primary lymphocyte or an autologous B lymphocyte.
and optionally the expression system for expressing the miR or a plurality of different miRs comprises a plasmid or an expression vector; a viral or a non-viral plasmid or expression vector; a DNA plasmid or expression vector; a DNA expression vector; or an integrating, episomal or non-integrating plasmid or expression vector; or the expression system is a genome integrating or genome non-integrating or episomal expression system,
wherein optionally the expression system comprises, or has contained therein, two, three, four or five or more copies of the microRNA (miR) coding sequence, wherein optionally the microRNA (miR) coding sequences are the same or different, and optionally each microRNA (miR) coding sequences is operatively linked to a different transcriptional regulator, or promoter,
and optionally expression system, optionally a plasmid, is engineered to comprise two (a doublet of) miRs, optionally miR-335, miR-138 or miR-449, precursor stem loops, two pre-miR stem loops in tandem with a nucleotide linker, or two miRs, optionally pre-miR-335, miR-138 or miR-449, stem loops in tandem with a nucleotide linker,
and optionally the expression system, optionally a plasmid, is engineered to comprise multiple copies of miRs, optionally miR-335, miR-138 or miR-449, as precursor stem loops, or two or more pre-miR stem loops in tandem with a nucleotide linker, or two or more pre-miR stem loops in tandem with a nucleotide linker.

In alternative embodiments of compositions, formulations or pharmaceutical compositions, as provided herein:
  (i) the plurality of anti-sense sequences specifically targeted against at least one anti-microRNA (miR) or anti-miR; or, the plurality of antagomirs or blockmirs, or
  (ii) the plurality of microRNA (miR) coding sequences,
are designed to or are capable of modulating an miRNA or anti-miR, or a function of an miRNA or anti-miR, that controls or modulates cell growth, cell maturation or differentiation, cell death, apoptosis, cell metabolism, immunity or inflammation, or
  that by modulation of the miRNA or anti-miR, or the miRNA or anti-miR function, can therapeutically treat, ameliorate or prevent an infection, a viral or bacterial infection, a condition or a disease, a metabolic disorder (optionally obesity or type 2 diabetes), an immune disorder or autoimmune disease, a cancer, a disease or condition, optionally caused by a cell dysplasia, a hypertrophy, a cardiac hypertrophy or a fibrosis.

In alternative embodiments, provided methods for manipulating a cell physiology, a cell function, a cellular genome in a cell, a cellular transcriptome in a cell, or a cellular proteome in a cell, comprising:
  contacting the cell with, or administering to an individual in need thereof:
  (i) a composition, formulation or pharmaceutical composition as provided herein, or a composition, formulation or pharmaceutical composition made by the method as provided herein; or,
  (ii) a B lymphocyte, or a primary B lymphocyte, that:
    secretes at least one microRNA or anti-miR, or, antagomir or blockmir, and/or secretes an miRNA; or,
    secretes a B lymphocyte extracellular vesicle (EV), a B lymphocyte exosome or a B lymphocyte micro-vesicle, comprising: a plurality of anti-sense sequences specifically targeted against at least one microRNA (miR), or anti-miR; or, a plurality of antagomirs or blockmirs, and/or a plurality of miRNA,
    and the contacting is for a sufficient period of time and under sufficient conditions such that the at least one microRNA (miR), or anti-miR, or, antagomir or blockmir, or at least one miRNA, or, a B lymphocyte extracellular vesicle (EV), B lymphocyte exosome or B lymphocyte micro-vesicle, is transferred to or taken up into the cell,
    wherein optionally the cell is contacted in vitro, ex vivo, or in vivo; and optionally the cell is a T cell, or an activated T cell, or a T cell activated via its antigen receptor, or a CD8 T cell or a CD4 T cell,
    and optionally the cell is a cancer cell, a cancer stem cell or a dysplastic cell, and optionally the cancer cell is a prostate cancer cell, a breast cancer cell, a lymphoma cell, a glioblastoma cell, lung cancer cell, a pancreatic cancer cell, an ovarian cancer cell, a liver cancer cell, a colon cancer cell, a medulloblastoma cell, or a salivary gland cancer cell,
    and optionally the cell or T cell is a mammalian or a human cell,
    and optionally the plurality of anti-sense sequences specifically targeted against at least one microRNA (miR), or anti-miR; or, the plurality of antagomirs or blockmirs, and/or miRNA, are designed to or are capable of modulating an miRNA or an miRNA function:
      that controls or modulates cell growth, cell maturation or differentiation, cell death, apoptosis, cell metabolism, immunity or inflammation, or
      that by its modulation can therapeutically treat, ameliorate or prevent an infection, a viral or bacterial infection, a condition or a disease, a metabolic disorder (optionally obesity or type 2 diabetes), an immune disorder or autoimmune disease, a cancer, a disease or condition caused by a cell dysplasia, a hypertrophy, a cardiac hypertrophy or a fibrosis.

In alternative embodiments, provided are methods for:
treating, ameliorating, or preventing an inflammation, a disease, a condition, an infection, a cancer, or as an adjuvant strategy to determine the fate of T cells during an immune reaction or a vaccination, or to restrict the development of FoxP3$^+$ T cells,
for treating, ameliorating, preventing, regulating or modulating any inflammation, disease, condition, infection or cancer capable of being regulated, treated, ameliorated or prevented by modulation or inhibition or expression of an miRNA, or
suppressing an oncomir or restoring an miRNA that suppresses an oncogene or a metastasis,
the method comprising administering to an individual in need thereof:
  (i) a composition, formulation or pharmaceutical composition as provided herein; or,
  (ii) a B lymphocyte, or a primary B lymphocyte, that:
    secretes at least one microRNA (miR), or anti-miR, or, antagomir or blockmir, and/or secretes an miRNA; or,
    secretes a B lymphocyte extracellular vesicle (EV), a B lymphocyte exosome or a B lymphocyte micro-vesicle, comprising: a plurality of anti-sense sequences specifically targeted against at least one microRNA (miR), or anti-miR; or, a plurality of antagomirs or blockmirs, and/or a plurality of miRNA,
    and the contacting is for a sufficient period of time and under sufficient conditions such that the at least one microRNA (miR), or anti-miR, or, antagomir or blockmir, or at least one miRNA, or, a B lymphocyte extracellular vesicle (EV), B lymphocyte exosome or B lymphocyte micro-vesicle, is transferred to or taken up into the cell,
    wherein optionally the cell is contacted in vitro, ex vivo, or in vivo; and optionally the cell is a T cell, or an activated T cell, or a T cell activated via its antigen receptor, or a CD8 T cell or a CD4 T cell,
    and optionally the cell is a cancer cell, a cancer stem cell or a dysplastic cell, and optionally the cancer cell is a prostate cancer cell, a breast cancer cell, a lymphoma cell, a glioblastoma cell, lung cancer cell, a pancreatic cancer cell, an ovarian cancer cell, a liver cancer cell, a colon cancer cell, a medulloblastoma cell, or a salivary gland cancer cell,
    and optionally the cell or T cell is a mammalian or a human cell,
    and optionally the plurality of anti-sense sequences specifically targeted against at least one microRNA (miR), or anti-miR; or, the plurality of antagomirs or blockmirs, and/or miRNA, are designed to or are capable of modulating an miRNA or an miRNA function:

that controls or modulates cell growth, cell maturation or differentiation, cell death, apoptosis, cell metabolism, immunity or inflammation, or that by its modulation can therapeutically treat, ameliorate or prevent an infection, a viral or bacterial infection, a condition or a disease, a metabolic disorder (optionally obesity or type 2 diabetes), an immune disorder or autoimmune disease, a cancer, a disease or condition caused by a cell dysplasia, a hypertrophy, a cardiac hypertrophy or a fibrosis, wherein optionally the miRNA comprises an miR-141, an miR-150, an miR-155, an miR-335, an miR-138, an miR-449, an miR-15a or an miR-16, optionally delivered for the treatment, amelioration or prevention of prostate cancer, breast cancer, a lymphoma, a glioblastoma, lung cancer, a pancreatic cancer, an ovarian cancer, a liver cancer, a colon cancer, a medulloblastoma, or a salivary gland cancer, wherein optionally the miRNA comprises an miR-335, an miR-138, or an miR-449, optionally delivered for the treatment, amelioration or prevention of breast cancer, a metastasis, or a breast cancer metastasis.

In alternative embodiments, provided are kits comprising a composition, formulation or pharmaceutical composition as provided herein, or a composition, formulation or pharmaceutical composition made by the method as provided herein.

In alternative embodiments, provided are methods for making a B lymphocyte supernatant, a B lymphocyte extracellular vesicle (EV), a B lymphocyte exosome or a B lymphocyte micro-vesicle comprising a micro-RNA (miRNA) molecule, the method comprising:

(a) providing a B lymphocyte; and providing an expression system capable of expressing a nucleic acid contained therein in the B lymphocyte, and the expression system comprises or has contained therein coding sequence for:

one or a plurality of the same or different micro-RNA (miR) or anti-miR molecules, wherein optionally the miR or anti-miR is selected from the group consisting of: an miR-335, an miR-138, an miR-449, an miR-141, an miR-150, an miR-155, an miR-15a, an miR-16 or an miR as set forth in Table 2, or an miRNA that down-regulates or decreases the activity of SOX4 mRNA, and a combination thereof, or for the or anti-miR, a sequence complementary to the miR; and (b) inserting, placing into or transducing into the B lymphocyte the expression system, and culturing or manipulating the B lymphocyte such that: the B lymphocyte expresses the one or plurality of same or different micro-RNA or anti-miR molecules, and optionally further comprising culturing or manipulating the B lymphocyte such that: a micro-RNA- or anti-miR-comprising B lymphocyte supernatant is generated, a B lymphocyte extracellular vesicle (EV) is generated, a B lymphocyte exosome is generated, and/or a B lymphocyte micro-vesicle is generated; and optionally (c) harvesting or isolating the B lymphocyte, the B lymphocyte supernatant, B lymphocyte extracellular vesicle (EV), B lymphocyte exosome or B lymphocyte micro-vesicle, wherein the B lymphocyte, the B lymphocyte supernatant, B lymphocyte extracellular vesicle (EV), B lymphocyte exosome or B lymphocyte micro-vesicle comprises or has contained therein a plurality of the micro-RNA (miRNA) molecules.

In alternative embodiments, the compositions, formulations or pharmaceutical compositions, as provided herein are for use in:

manipulating a cell physiology, a cell function, a cellular genome in a cell, a cellular transcriptome in a cell, or a cellular proteome in a cell, wherein optionally the manipulating is in vitro, ex vivo, or in vivo;

modulation of an miRNA or an miRNA function that can therapeutically treat, ameliorate or prevent an infection, a viral or bacterial infection, a condition or a disease, a metabolic disorder (optionally obesity or type 2 diabetes), an immune disorder or an autoimmune disease, a cancer, a disease or condition, optionally caused by a cell dysplasia, a hypertrophy, a cardiac hypertrophy or a fibrosis; or regulating immunity or a metabolism, or for treating, ameliorating, or preventing an inflammation, a disease, a condition, an infection, a cancer, or as an adjuvant strategy to determine the fate of T cells during an immune reaction or a vaccination, or to restrict the development of FoxP3$^+$ T cells, for treating, ameliorating, preventing, regulating or modulating any inflammation, disease, condition, infection or cancer capable of being regulated, treated, ameliorated or prevented by modulation or inhibition or expression of an miRNA, or suppressing an oncomir or restoring an miRNA that suppresses an oncogene or a metastasis.

In alternative embodiments, the compositions, formulations or pharmaceutical compositions, as provided herein are for use in treating, ameliorating, or preventing, or controlling the tumorigenicity of: a cancer, a glioblastoma, a breast cancer or a triple negative breast cancer, or a breast cancer that tests negative for estrogen receptors (ER-), progesterone receptors (PR-), and/or HER2 (HER2-).

The details of one or more embodiments as provided herein are set forth in the accompanying drawings and the description below. Other features, objects, and advantages of the invention will be apparent from the description and drawings, and from the claims.

All publications, patents, patent applications, and GenBank sequences cited herein are hereby expressly incorporated by reference for all purposes.

DESCRIPTION OF DRAWINGS

The drawings set forth herein are illustrative of embodiments as provided herein and are not meant to limit the scope of the invention as encompassed by the claims.

FIG. 1A schematically illustrates an exemplary plasmid DNA encoding anti-miR-150)(pCMV-MIR$^{a15}$), this plasmid codes for the 22 base pairs (bp) corresponding to anti-miR-150 (antisense) under the control of a CMV promoter, where the DNA CTGGTACAGGCCTGGGGGATAG is SEQ ID NO:1, and the RNA CUGGUACAGGCCUGGGGGAUAG is SEQ ID NO:2; as discussed in detail in Example 1, below.

FIG. 1B graphically illustrates that primary B lymphocytes synthesize approximately 140 copies/cell of anti-miR-150 in the first 18 hrs in transfected B lymphocytes (based on intra-cellular synthesis values); as discussed in detail in Example 1, below.

FIG. 1C graphically illustrates that anti-miR-150 molecules were abundantly secreted in the culture medium 18 hrs after transfection, where over an 18 hr period each cell secretes on average 3,000 copies; as discussed in detail in Example 1, below.

FIG. 7A-C illustrate a schematic representation of plasmids used in the study of Example 1: FIG. 7A: the pre-mir nucleotide sequence of miR-150, miR-155 and anti-miR-155; FIG. 7B: schematic view of pCMV miR-150-miR-155; FIG. 7C, schematic view of pCMV mir-150-anti-miR-155:

FIG. 7A shows the primer nucleotide sequence of:

miR-150
(SEQ ID NO: 5)
CCCUG<u>UCUCCCAACCCUUGUACCAGUG</u>CUGUGCCUCAGACCCUGGUACA

GGCCUGGGGGAUAGGG, miR-155
(SEQ ID NO: 6)
CUG<u>UUAAUGCUAAUUGUGAUAGGGG</u>UUUUGGCCUCUGACUGACUCCUA

CCUGUUAGCAUUAACAG,
and anti-miR-155
(SEQ ID NO: 7)
CUG<u>ACCCCUAUCACAAUUAGCAUUAA</u>UUUGGCCUCUGACUGACUCCUAC

CUGUUAGCAUUAACAG;

FIG. 7B is a schematic view of the plasmid containing pCMV miR-150, having the sequence TCTCC-CAACCCTTGTACCAGT (SEQ ID NO:8), and anti-(shown as "α")-miR-155, having the sequence TTAATGCTAAT-TGTGATAGGGGT (SEQ ID NO:9); and, FIG. 7C is a schematic view of the plasmid containing pCMV mir-150 (SEQ ID NO:8) and anti-miR-155, having the sequence ACCCCTATCACAATTAGCATTAA (SEQ ID NO:10).

Figure 8:
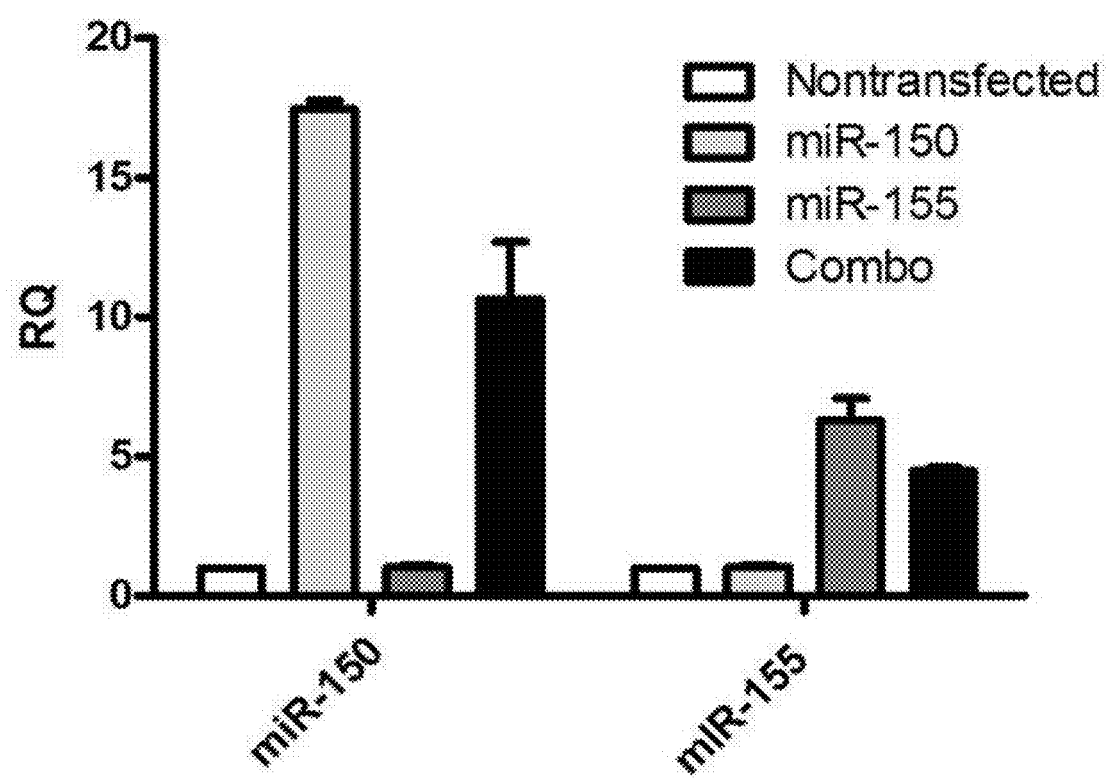

FIG. 8 graphically illustrates data showing expression of two mir-150 in B cells (J558L cells) transfected with a single plasmid DNA, where J558L cells were transfected with plasmid DNA encompassing the coding sequence for miR-150 alone, anti-miR-155 alone, or the combination of both (combo), where the data shows that B cells can be programmed for the expression of two short noncoding RNAs; as discussed in detail in Example 1, below.

Figure 9:
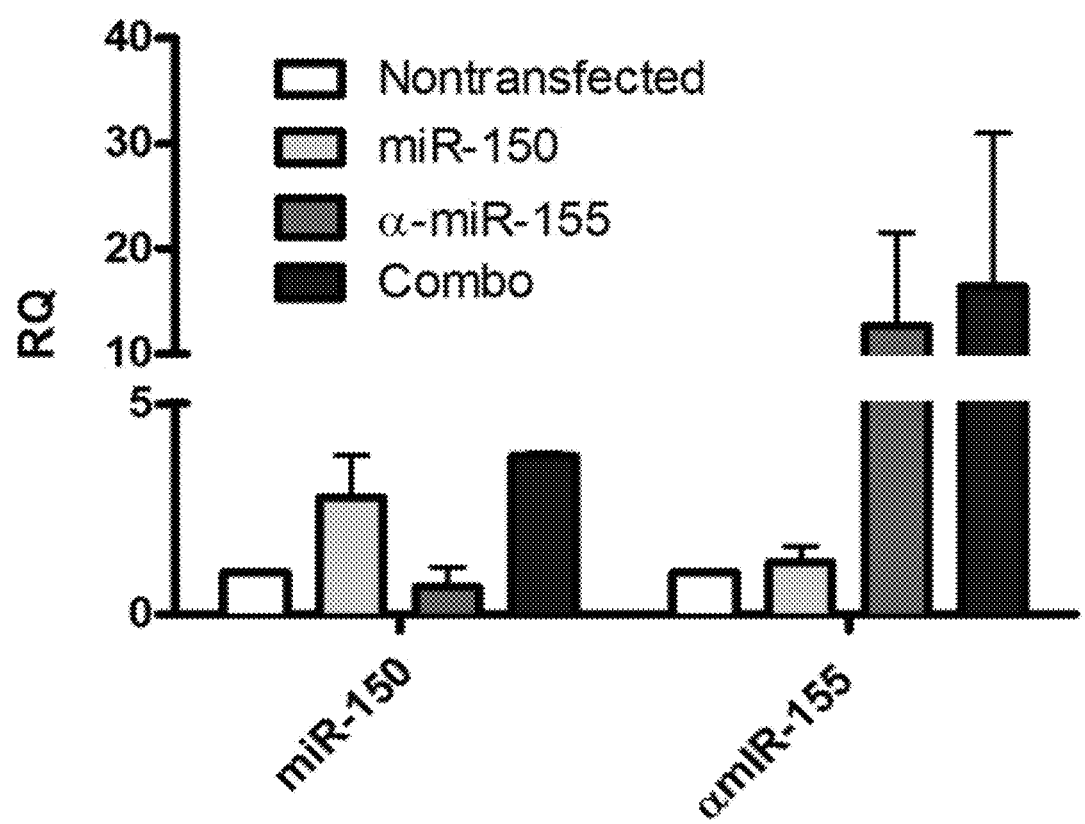

FIG. 9 graphically illustrates data showing expression of miR-150/anti-miR-155 in B cells (J558L cells) transfected with a single plasmid DNA, where J558L cells were transfected with plasmid DNA encompassing the coding sequence for miR-150 alone, anti-miR-155 alone, or the combination of both (combo), where the data shows that B cells can be programmed for the expression of two short noncoding RNAs; as discussed in detail in Example 1, below.

Figure 10:
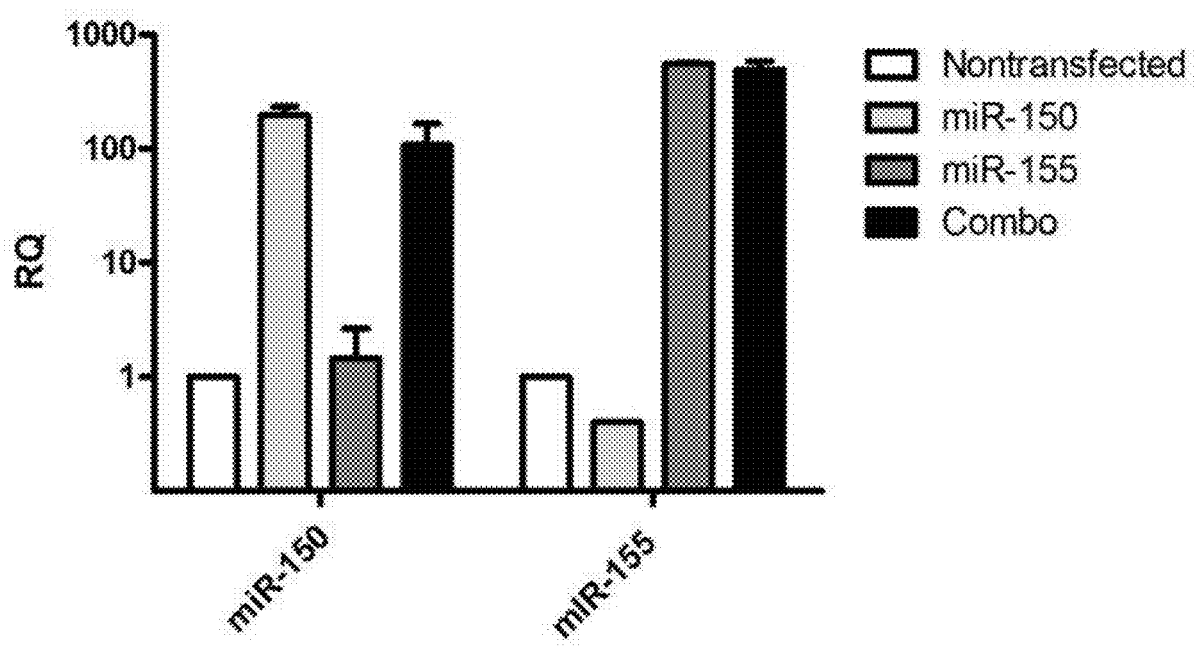

FIG. 10 graphically illustrates data showing detection of mir-150 and anti-miR-155 in the supernatant of B cells (J558L cells) transfected with a single plasmid DNA, where J558L cells were transfected with plasmid DNA encompassing the coding sequence for miR-150 alone, anti-miR-155 alone, or the combination of both (combo), where the data shows that the supernatant of B cells can be programmed for the biogenesis of two short non-coding RNAs; as discussed in detail in Example 1, below.

Figure 11:
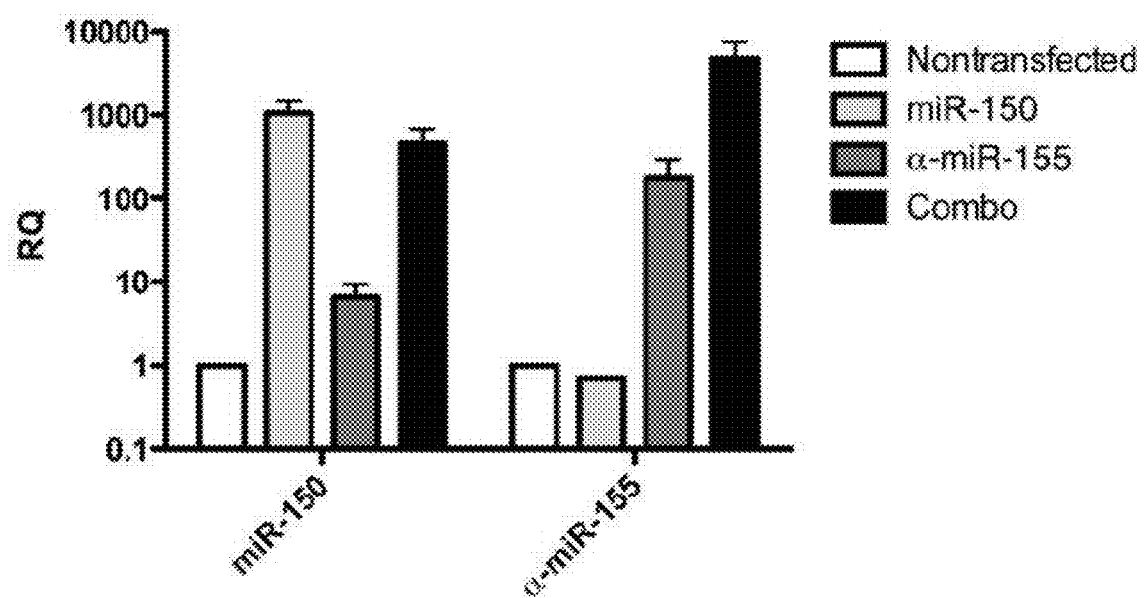

FIG. 11 graphically illustrates data showing detection of mir-150 and anti-miR-155 in the supernatant of B cells (J558L cells) transfected with a single plasmid DNA, where J558L cells were transfected with plasmid DNA encompassing the coding sequence for miR-150 alone, anti-miR-155 alone, or miR-150 and anti-miR-155 alone (combo), where the data shows that the supernatant of B cells can be programmed for the biogenesis of two short non-coding RNAs; as discussed in detail in Example 1, below.

Figure 12:
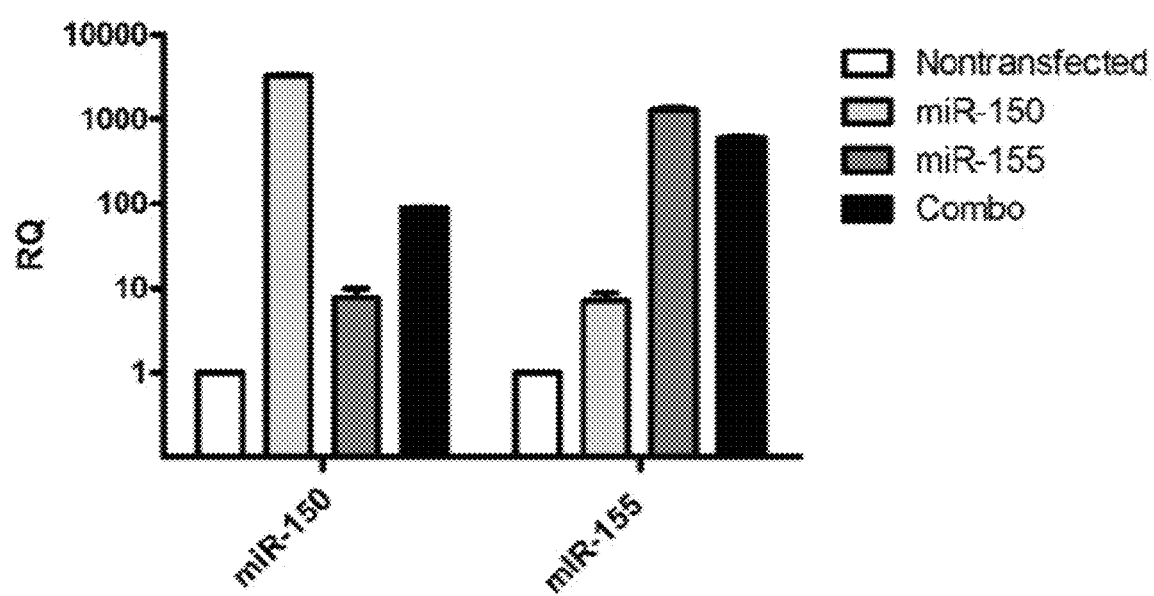

FIG. 12 graphically illustrates data showing that it is possible to transfect B cells with a plasmid coding for two miRNA and yield the release of EVs: the data shows expression of mir-150 and miR-155 in EVs released by B cells (J558L cells) transfected with a single plasmid DNA coding for miR-150 alone, miR-155 alone, or two miR-150 (combo), where the data shows miRNA (mirR) enrichment in EVs released by B cells programmed with two short non-coding RNAs; as discussed in detail in Example 1, below.

Figure 13:
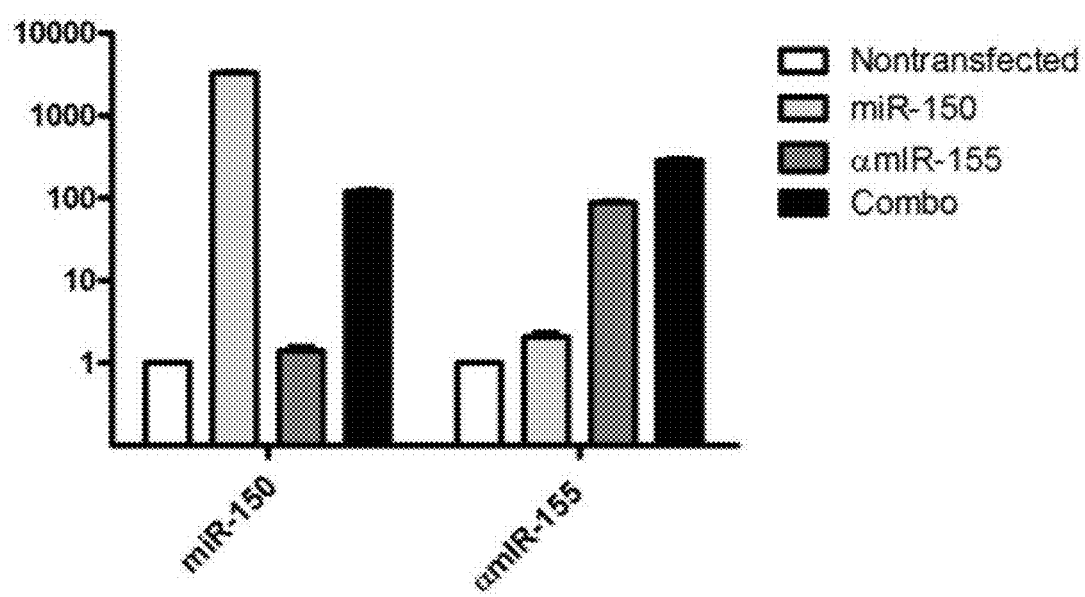

FIG. 13 graphically illustrates data showing that it is possible to transfect B cells with a plasmid coding for two miRNA and yield the release of EVs: the data shows expression of mir-150 and miR-155 in EVs released by B cells (J558L cells) transfected with a single plasmid DNA coding for miR-150 alone, miR-155 alone, or miR-150 and anti-miR-155 alone (combo), where the data shows miRNA (mirR) enrichment in EVs released by B cells programmed with two short non-coding RNAs; as discussed in detail in Example 1, below.

Figure 14A:
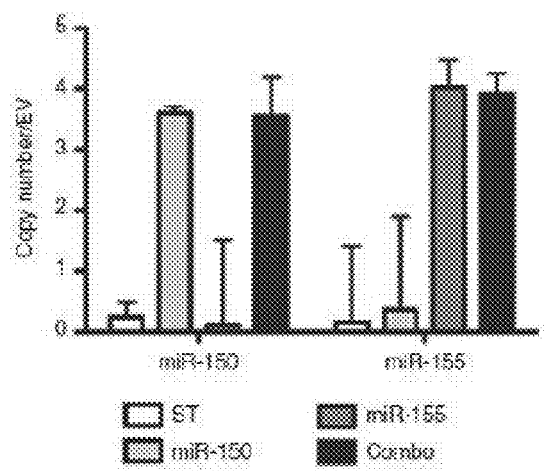
Figure 14B:
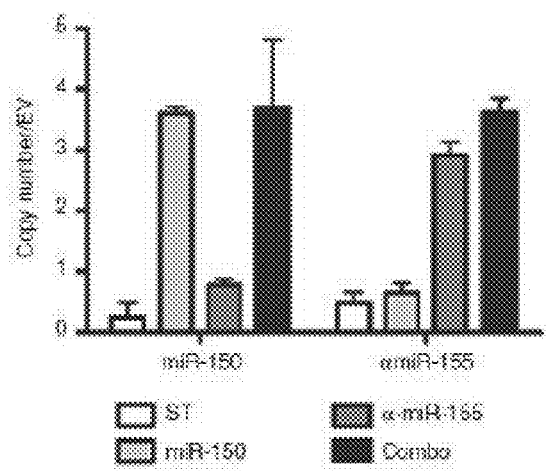

FIG. 14A-B schematically illustrates copy number/EV quantitation of mir-150 and anti-miR-155 in EVs produced by programmed J558L cells. EVs were isolated from the supernatant of J558L cells transfected with a plasmid coding for miR-150 alone, miR-155 alone, or the combination of both (combo) 48 hrs after transfection and culture in complete medium containing exosome-depleted fetal calf serum. Total RNA extraction and cDNA generation were performed as in FIG. 4. Samples were pre-amplified and then subject to RT-qPCR amplification using RT-specific primers. Copy number/EV were calculated as described in material and Methods. ST=Sham transfected. Results refer to the mean±SD of two replicate samples. Representative of two experiments, FIG. 14A and FIG. 14B, with comparable results.

Figure 15:
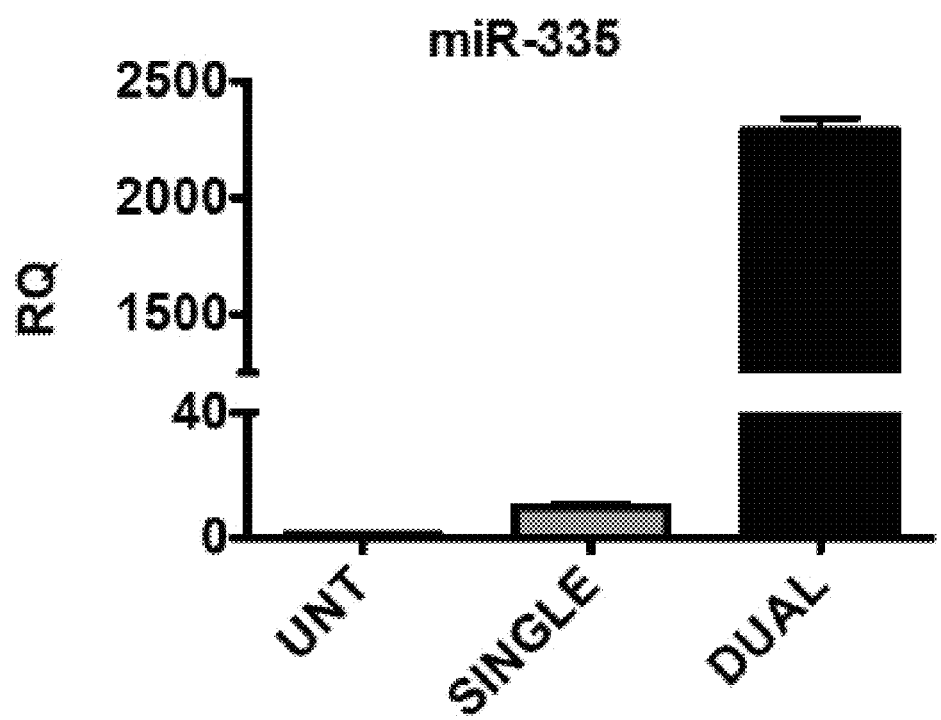

FIG. 15 schematically illustrates the expression levels in the murine myeloma cell line J558L, and comparison of them, after transfection with a pCMVmir coding for one or two pre-miR-335 stem loops; as discussed in detail in Example 3, below.

Figure 16:
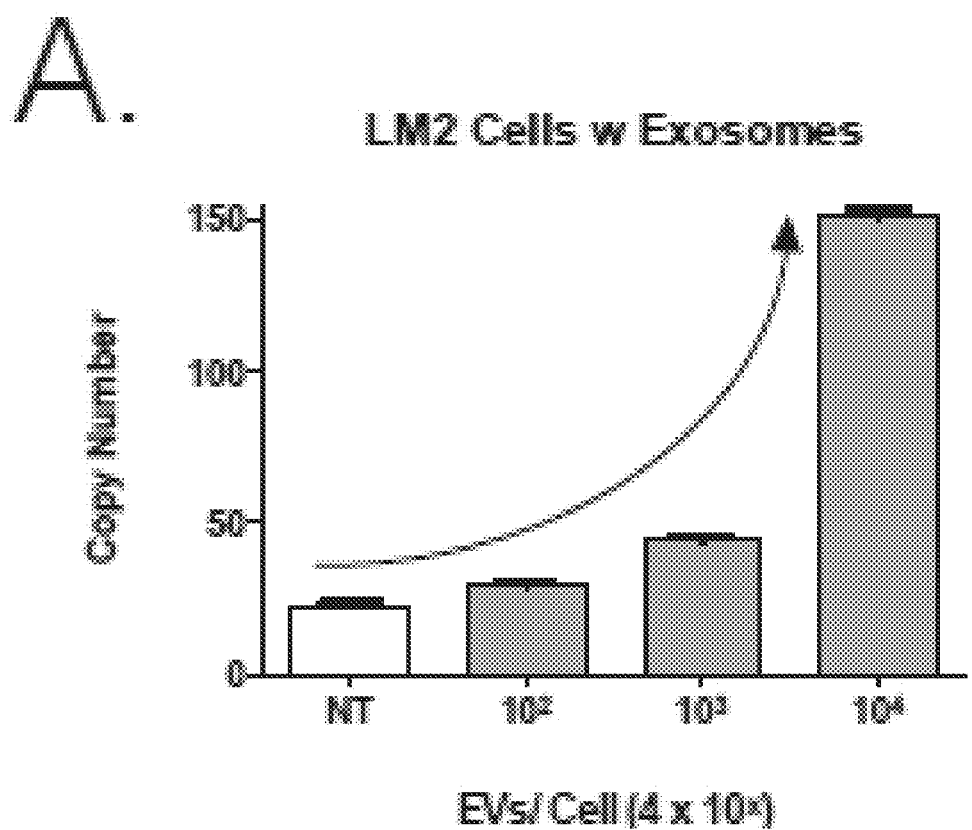

FIG. 16 graphically illustrates data showing the uptake and miR-335 content in LM2 cells incubated in vitro for 48 hrs with iEVs$^{335}$ over a range of iEVs:LM2 cell ratios in order to establish the minimum threshold for effective restoration of miR-335 content in target LM2 cells; an increase in copy number followed a dose response curve, with a greater than 4-fold increase over untreated LM2 cells at the $10^3$ dose; as discussed in detail in Example 3, below.

Figure 17:
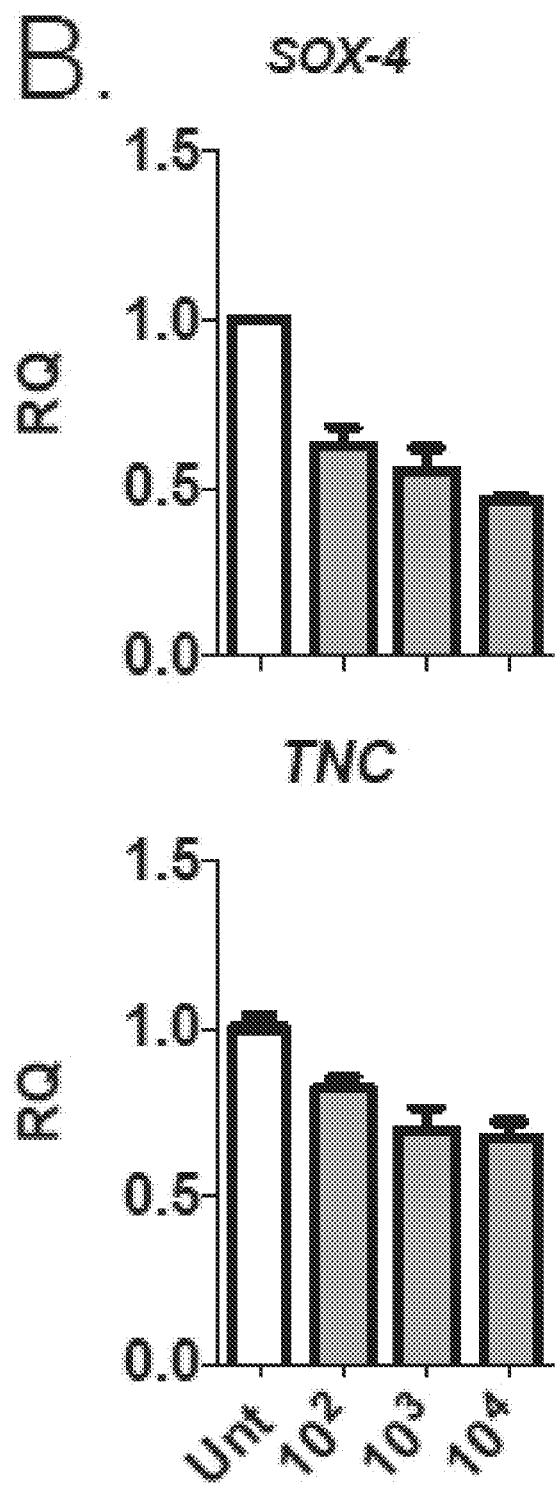

FIG. 17 graphically illustrates data showing that cargo miR-335 downregulates two miR-335 specific targets, SOX4 (upper panel) and tenascin C (TNC) (lower panel); as discussed in detail in Example 3, below.

Figure 18:
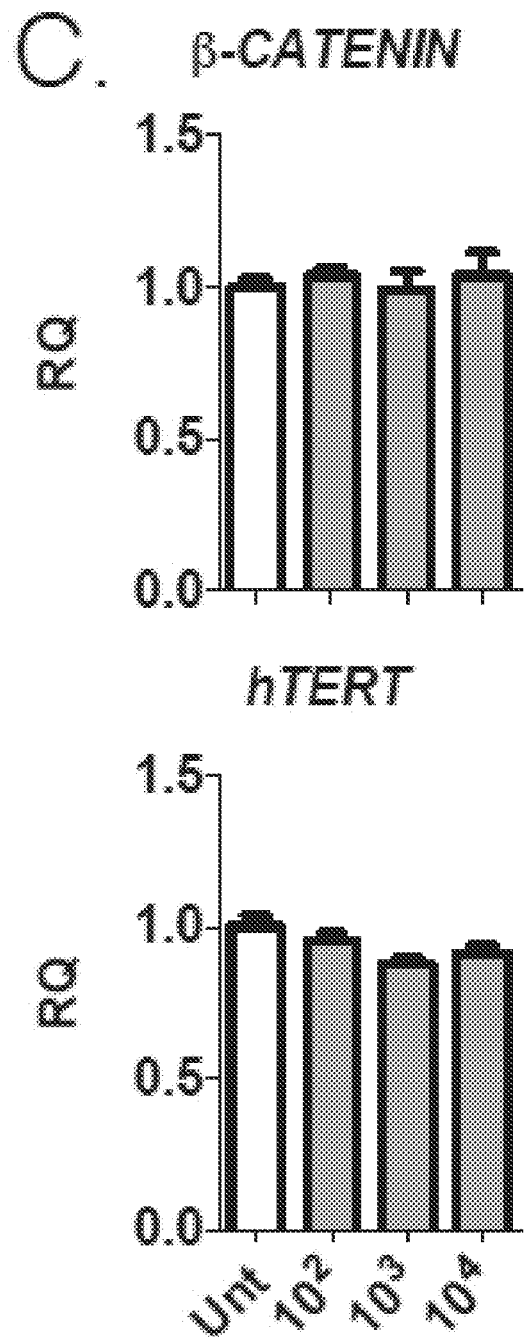
Figure 19:
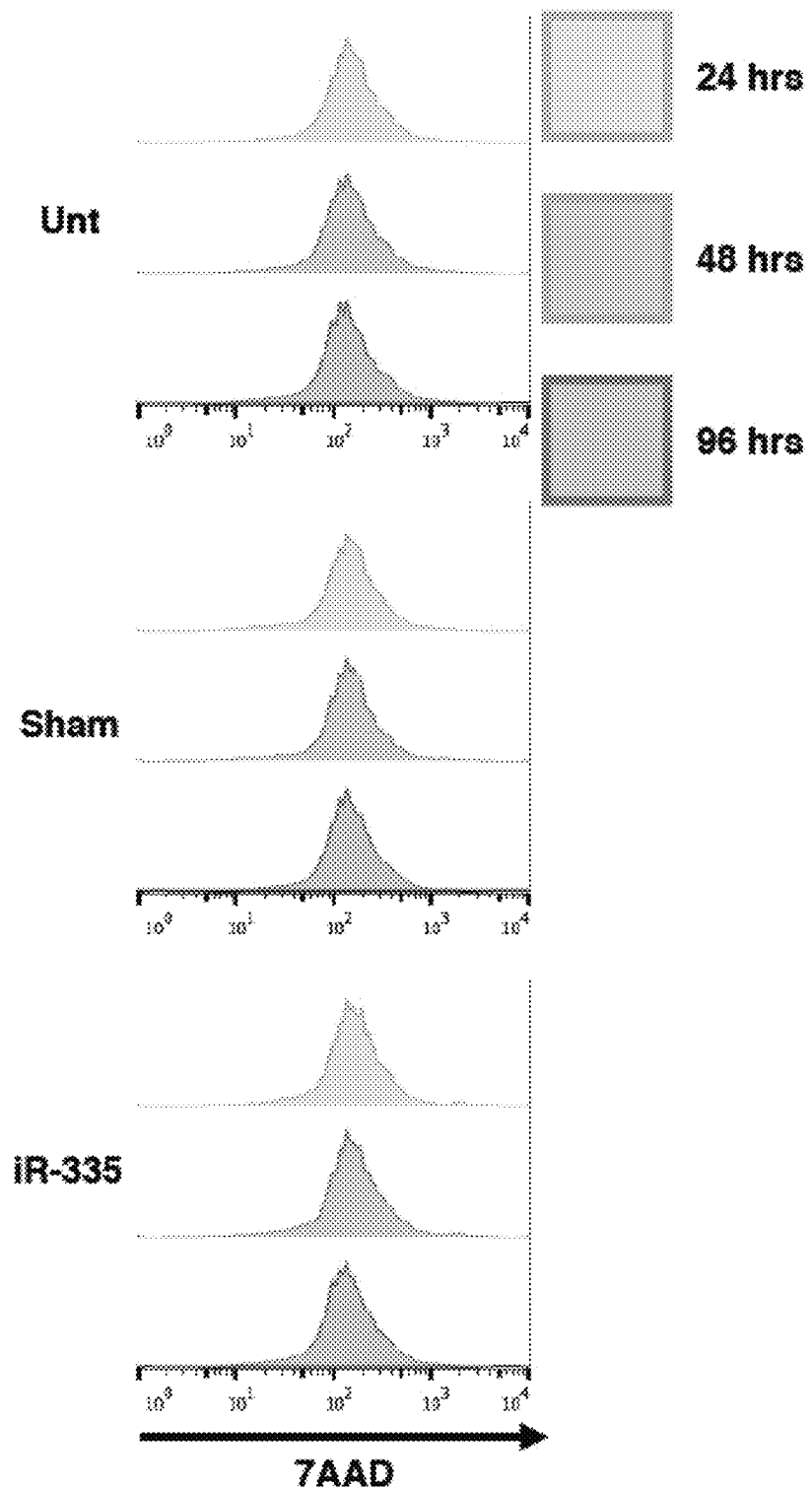

FIG. 18 graphically illustrates data showing that cargo miR-335 has no effects on two endogenous genes β-Catenin (beta-Catenin) (CTNNB1) (upper panel) and human TERT (lower panel); as discussed in detail in Example 3, below;

FIG. 19 illustrates data demonstrating that internalization of iEVs containing an enriched miR-335 cargo does not affect the viability of LM2 cells over a period of 96 hours; Upper panel: Unt; middle panel: Sham; lower panel, MiR-335, where in each panel the upper graph is 24 hours (hrs), and middle graph is 48 hrs, and the lower graph is 96 hrs, after internalization; as discussed in detail in Example 3, below.

Figure 20A:
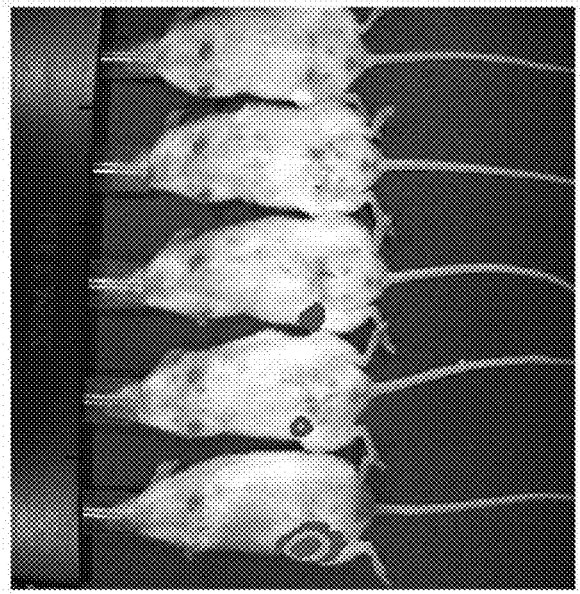
Figure 20B:
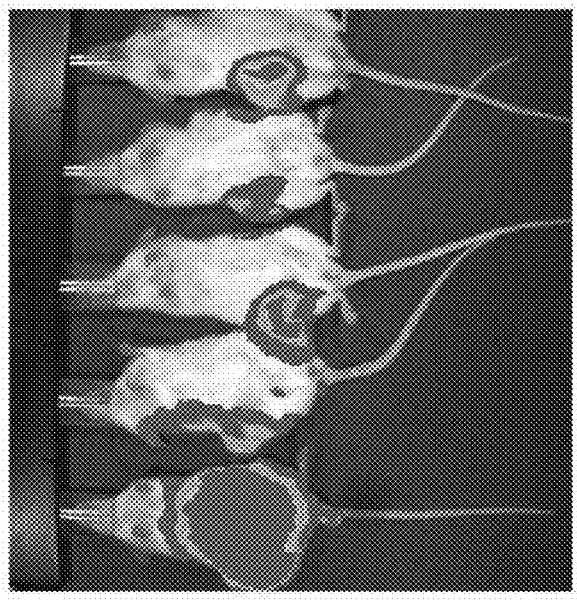

FIG. 20A-D illustrate data showing the ability of iEVs$^{335}$ to control LM2 tumorigenicity, as tested in a model of orthotopic implantation, where LM2 cells were pretreated by incubation with $4×10^4$ fold excess: iEVs$^{335}$, or control iEVs, for 48 hours to allow for their uptake/internalization and release of miR-335, and mice were then injected in the fat pad with $4×10^5$ LM2 cells, as discussed in detail in Example 3, below:

FIG. 20A-B illustrates bioluminescence images representative of orthotopic tumors formed by LM2 cells treated with either sham EVs (left image, FIG. 20A) or iEVs-335 (right image, FIG. 20B). Images were obtained on day 60 after implantation.

Figure 20C:
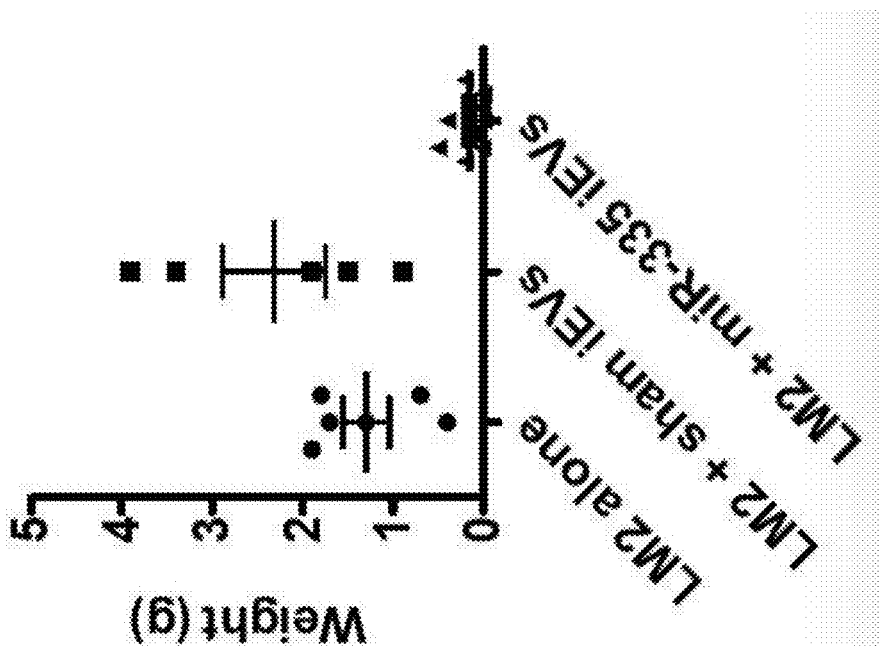

FIG. 20C graphically illustrates average tumor size or volume (mm$^3$) of tumors born out of LM2 cells untreated (N=6), pretreated with sham iEVs (N=5) or iEVs-335 (N=9) implanted in the fat pad of NSG mice, as described in Example 3, below.

Figure 20D:
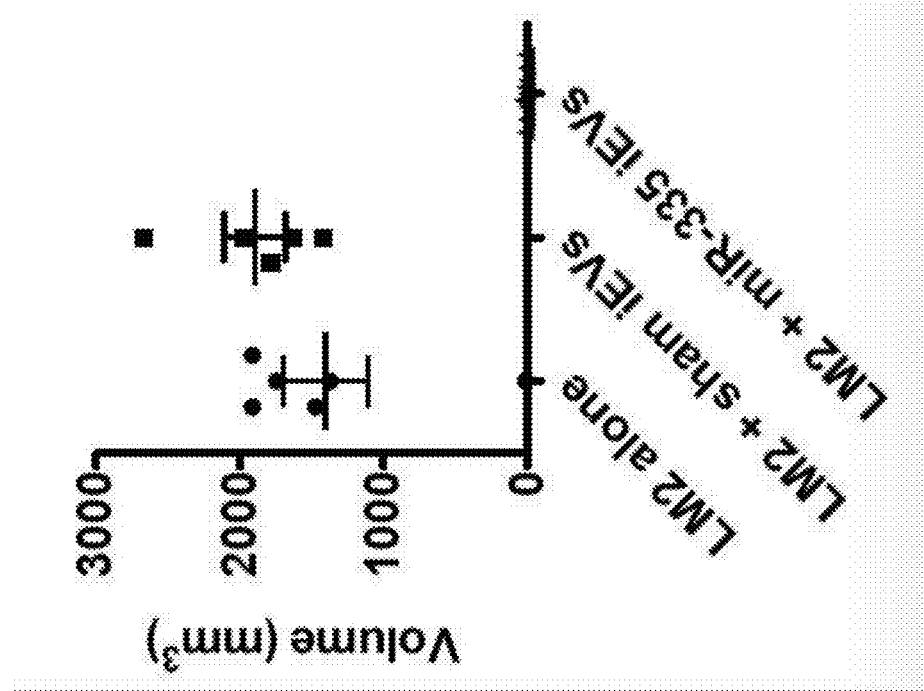

FIG. 20D graphically illustrates tumor weight (gr) of tumors born out of LM2 cells untreated (N=6), pretreated with sham iEVs (N=5) or iEVs-335 (N=4) implanted in the fat pad of NSG mice, as described in Example 3, below.

FIG. 20E-H illustrate data from studies measuring the levels of miR-335 in tumors excised to see if the effect was associated with a higher content of miR-335 in LM2 tumors in which miR-335 content was restored therapeutically, as described in Example 3, below.

Figure 20E:
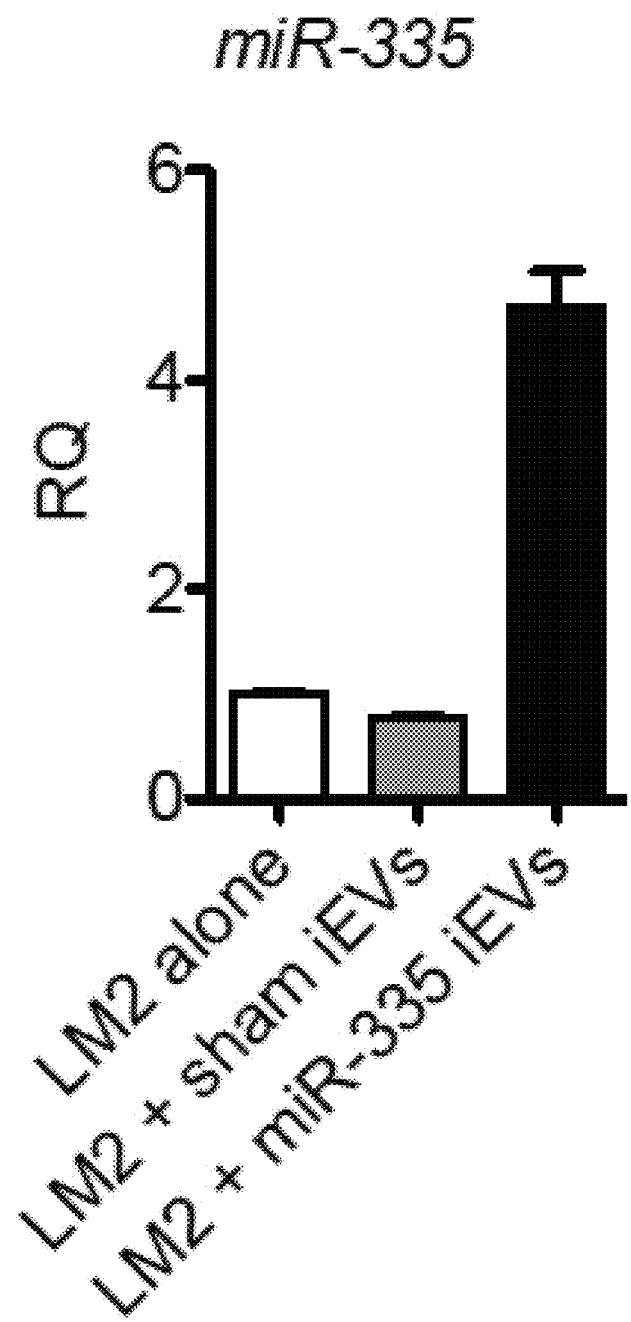

FIG. 20E graphically illustrates that endogenous values for miR-335 were 1.0±0.06 for the 6 control mice and 0.8±0.02 for tumors treated with control iEVs, whereas they were significantly higher (4.7±0.7) in the four tumors borne of LM2 cells pretreated with iEVs$^{335}$ prior to implantation in vivo, as described in Example 3, below.

Figure 20F:
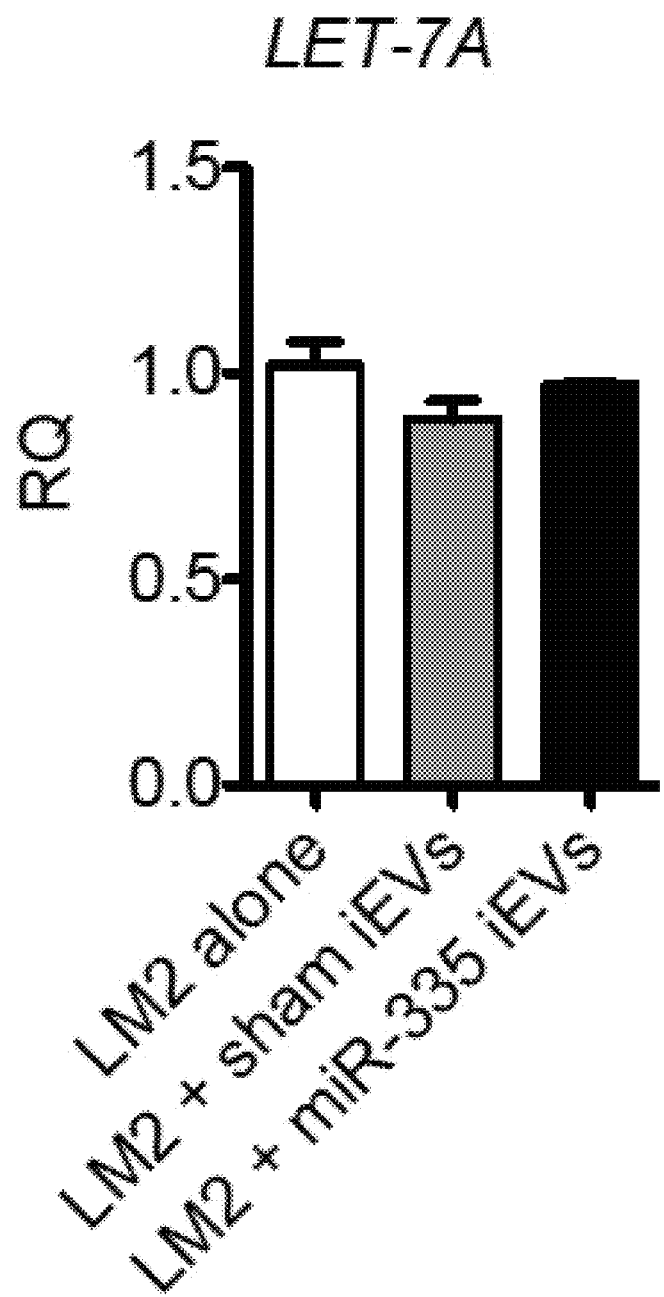

FIG. 20F graphically illustrates that no differences were detected in the endogenous levels of let-7a, a miRNA used as a control in the same tumor groups as in FIG. 20D, as described in Example 3, below.

Figure 20G:
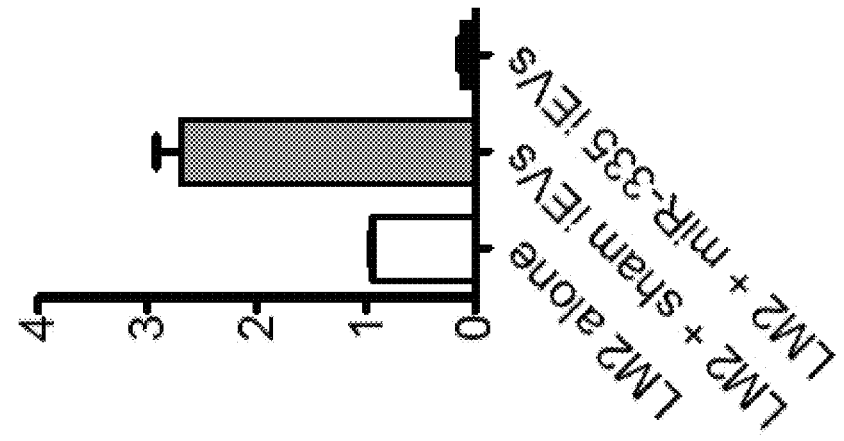
Figure 20H:
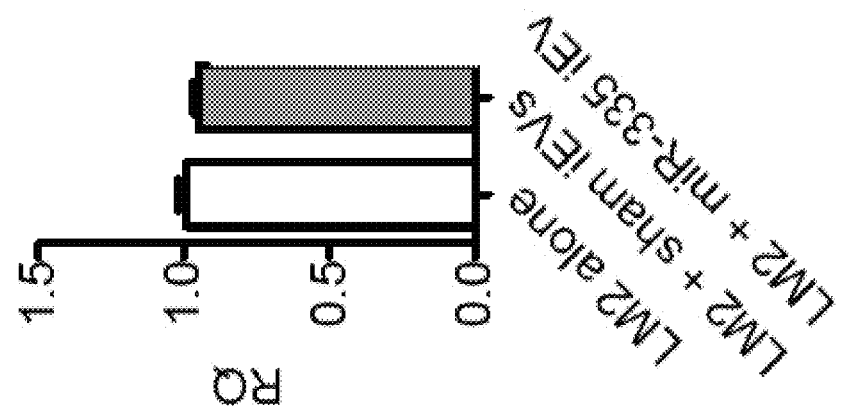

FIG. 20G-H graphically illustrates data showing that restoration of miR-335 in LM2 cells had effects on its target; mRNA levels of endogenous SOX4 (FIG. 20G) and TNC (FIG. 20H) (see FIG. 13F, left and right panels, in the same tumor groups as in FIG. 20E, as described in Example 3, below.

FIG. 20I-J graphically illustrates data no variation was noted in the mRNA levels of two unrelated endogenous genes, CTNNB1 and TERT (see FIG. 13G, left (FIG. 20I) and right (FIG. 20J) panels, respectively) in the same tumor groups as in FIG. 20E, as described in Example 3, below.

Figure 21A:
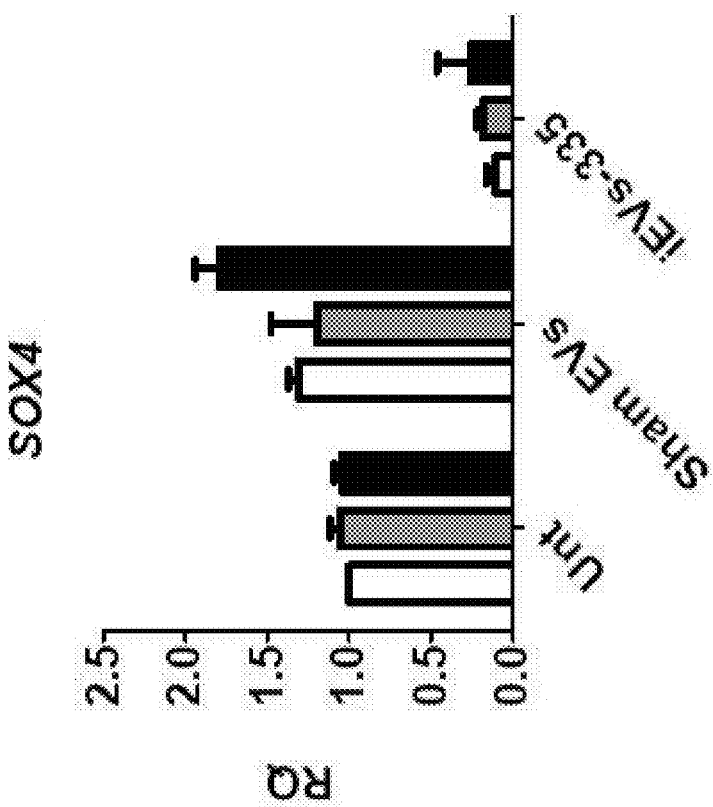
Figure 21B:
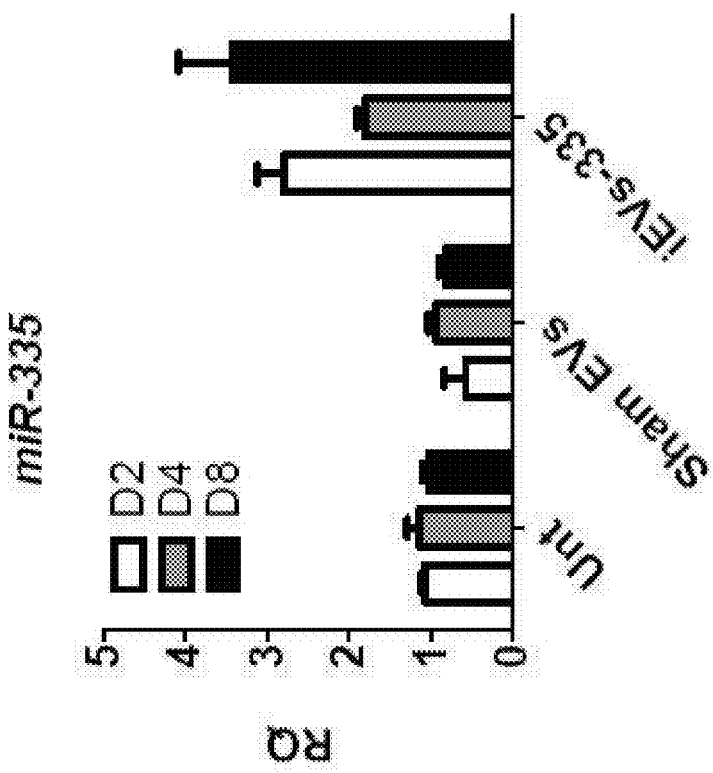

FIG. 21A-B graphically illustrates data showing that restoration of miR-335 (FIG. 21A) and downregulation of SOX4 in LM2 cells (FIG. 21B) lasts up to 8 days after initial treatment with iEVs-335, as described in Example 3, below.

Figure 22:
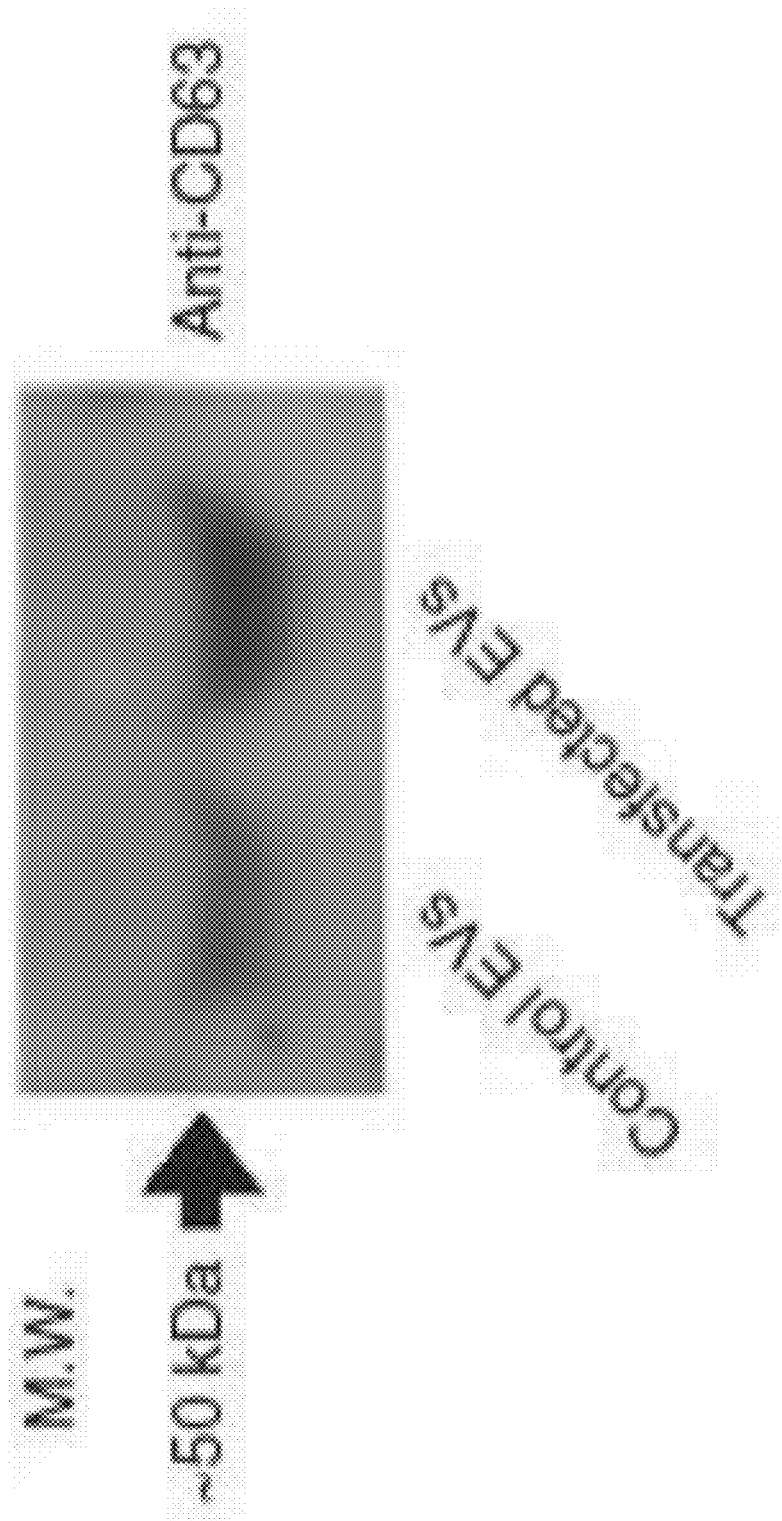

FIG. 22 illustrates an image of a Western blot analysis showing that EVs produced by programmed J558L cells express CD63; as described in Example 2, below.

Like reference symbols in the various drawings indicate like elements.

DETAILED DESCRIPTION

In alternative embodiments, provided are methods and compositions for modulating evolutionarily conserved short (approximately 20 to 30 nucleotides) non-coding RNAs, or microRNAs, which are powerful regulators of gene expression in a variety of physiological and pathological processes. In alternative embodiments, provided are methods and compositions for effectively and efficiently modulating microRNA (miR) function, and therapeutic uses thereof. In alternative embodiments, methods and compositions as provided herein modulate microRNA (miR) function by generating and delivering anti-sense sequences against microRNA (miR), or anti-miR, also called antagomirs or blockmirs, which in alternative embodiments are oligonucleotides that can modulate, inhibit or silence endogenous microRNA (miR) or otherwise intracellular microRNA (miR), e.g., viral microRNA (miR). In alternative embodiments, antagomirs used to practice embodiments provided herein can prevent other molecules from binding to a desired site on a nucleic acid, e.g., a DNA or an RNA, or a gene or an mRNA molecule (a message).

In alternative embodiments, methods and compositions as provided herein can be used to manipulate, e.g., inhibit or accelerate, or decrease or increase the rate of production or expression of, or increase or decrease the stability of, any gene or message by the efficient delivery in vivo (e.g., to an individual in need thereof) of the appropriate miR or antagomir. In alternative embodiments, methods and compositions as provided herein can be used to manipulate any genetic, cellular or biological system controlled or generated at least in part by an miRNA, e.g., including cell growth, maturation and differentiation, cell death (e.g., apoptosis), metabolism, immunity and inflammation, by the efficient delivery in vivo of the appropriate miR or antagomir. In alternative embodiments, methods and compositions as provided herein can be used to therapeutically treat, ameliorate or prevent an infection (a viral or bacterial infection), a condition or a disease, e.g., a disease such as cancer or a disease or condition caused by any cell dysplasia, cardiac hypertrophy and fibrosis, by the efficient delivery in vivo of the appropriate antagomir.

Nucleic acids used to practice embodiments provided herein, whether RNA, cDNA, genomic DNA, vectors, viruses or hybrids thereof, may be isolated from a variety of sources, genetically engineered, amplified, and/or expressed/generated recombinantly (recombinant polypeptides can be modified or immobilized to arrays in accordance with embodiments provided herein). Any recombinant expression system can be used, including bacterial, mammalian, yeast, insect or plant cell expression systems. Nucleic acids used to practice embodiments provided herein can be synthesized in vitro by well-known chemical synthesis techniques, as described in, e.g., Carruthers (1982) Cold Spring Harbor Symp. Quant. Biol. 47:411-418; Adams (1983) J. Am. Chem. Soc. 105:661; Belousov (1997) Nucleic Acids Res. 25:3440-3444; Frenkel (1995) Free Radic. Biol. Med. 19:373-380; Blommers (1994) Biochemistry 33:7886-7896; Narang (1979) Meth. Enzymol. 68:90; Brown (1979) Meth. Enzymol. 68:109; Beaucage (1981) Tetra. Lett. 22:1859; U.S. Pat. No. 4,458,066. Alternatively, nucleic acids can be obtained from commercial sources. Double stranded DNA fragments may then be obtained either by synthesizing the complementary strand and annealing the strands together under appropriate conditions, or by adding the complementary strand using DNA polymerase with a primer sequence. Techniques for the manipulation of nucleic acids, such as, e.g., subcloning, labeling probes (e.g., random-primer labeling using Klenow polymerase, nick translation, amplification), sequencing, hybridization and the like are well described in the scientific and patent literature, see, e.g., Sambrook, ed., MOLECULAR CLONING: A LABORATORY MANUAL (2ND ED.), Vols. 1-3, Cold Spring Harbor Laboratory, (1989); CURRENT PROTOCOLS IN MOLECULAR BIOLOGY, Ausubel, ed. John Wiley & Sons, Inc., New York (1997); LABORATORY TECHNIQUES IN BIOCHEMISTRY AND MOLECULAR BIOLOGY: HYBRIDIZATION WITH NUCLEIC ACID PROBES, Part I. Theory and Nucleic Acid Preparation, Tijssen, ed. Elsevier, N.Y. (1993). The nucleic acids used to practice embodiments provided herein, whether RNA, iRNA, siRNA, antisense nucleic acid, cDNA, genomic DNA, vectors, viruses or hybrids thereof, may be isolated from a variety of sources, genetically engineered, amplified, and/or expressed/generated recombinantly. Recombinant polypeptides generated from these nucleic acids can be individually isolated or cloned and tested for a desired activity. Any recombinant expression system can be used, including bacterial, mammalian, yeast, insect or plant cell expression systems. Techniques for the manipulation of nucleic acids, such as, e.g., subcloning, labeling probes (e.g., random-primer labeling using Klenow polymerase, nick translation, amplification), sequencing, hybridization and the like are well described in the scientific and patent literature, see, e.g., Sambrook, ed., *Molecular Cloning: A Laboratory Manual* (2nd ed.), Vols. 1-3, Cold Spring Harbor Laboratory, (1989); *Current Protocols in Molecular Biology*, Ausubel, ed. John Wiley & Sons, Inc., New York (1997); *Laboratory Techniques in Biochemistry and Molecular Biology: Hybridization with Nucleic Acid Probes*, Part I. Theory and Nucleic Acid Preparation, Tijssen, ed. Elsevier, N.Y. (1993).

Provided are expression systems, e.g., plasmids or vectors, comprising a nucleic acid, e.g., microRNA (miR), or anti-miR, or, antagomir or blockmir, used to practice a composition or method as provided herein. Provided are expression vehicles comprising an expression cassette (e.g., a vector) as provided herein or a nucleic acid e.g., microRNA (miR), or anti-miR, or, antagomir or blockmir, used to practice a composition or method as provided herein. The cloning vehicle can be a vector, a non-viral or a viral vector, a plasmid, a phage, a phagemid, a cosmid, a fosmid, a bacteriophage or an artificial chromosome. The viral vector can comprise an adenovirus vector, a retroviral vector or an adeno-associated viral vector. The cloning vehicle can comprise a bacterial artificial chromosome (BAC), a plasmid, a bacteriophage P1-derived vector (PAC), a yeast artificial chromosome (YAC), or a mammalian artificial chromosome (MAC). Provided are transformed cells comprising a nucleic acid, a microRNA (miR), or anti-miR, or, antagomir or blockmir, used to practice a composition or method as provided herein, or an expression cassette (e.g., a vector) used to practice embodiments provided herein.

Pharmaceutical Compositions and Formulations

In alternative embodiments, provided are pharmaceutical compositions and formulations for practicing methods as provided herein, e.g., methods for preventing or slowing cancer cell proliferation, local and distal metastasis, epithelial to mesenschymal transition (EMT) or the differentiation of cancer initiating/cancer stem cells into more differentiated cancer cells; or, for practicing methods for manipulating a cell physiology, a cell function, a cellular genome in a cell, a cellular transcriptome in a cell, or a cellular proteome in a cell, wherein optionally the manipulating is in vitro, ex vivo, or in vivo. In alternative embodiments, the pharmaceutical compositions and formulations comprise a B lymphocyte supernatant or equivalent thereof, a B lymphocyte extracellular vesicle (EV) or equivalent thereof, a B lymphocyte exosome or equivalent thereof, and/or a B lymphocyte micro-vesicle or equivalent thereof, comprising or having contained therein: a plurality of the same or different micro-RNA (miRNA, or miR) molecules, wherein optionally the miRNA is selected from the group consisting of: an miR-335, an miR-141, an miR-150, an miR-155, an miR-15a, an miR-16 and a combination thereof.

In alternative embodiments, compositions used to practice the methods as provided herein are formulated with a pharmaceutically acceptable carrier. In alternative embodiments, the pharmaceutical compositions used to practice the methods as provided herein can be administered parenterally, topically, orally or by local administration, such as by aerosol, subcutaneous or intradermally. The pharmaceutical compositions and formulations can be formulated in any way and can be administered in a variety of unit dosage forms depending upon the condition or disease and the degree of illness, the general medical condition of each patient, the resulting preferred method of administration and the like. Details on techniques for formulation and administration are well described in the scientific and patent literature, see, e.g., the latest edition of Remington's Pharmaceutical Sciences, Maack Publishing Co, Easton Pa. ("Remington's").

Therapeutic agents used to practice the methods as provided herein can be administered alone or as a component of a pharmaceutical formulation (composition). The compounds may be formulated for administration in any convenient way for use in human or veterinary medicine. Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Formulations of the compositions used to practice the methods as provided herein include those suitable for oral/nasal, topical, parenteral, rectal, and/or intravaginal administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect.

Pharmaceutical formulations used to practice the methods as provided herein can be prepared according to any method known to the art for the manufacture of pharmaceuticals. Such drugs can contain preserving agents. A formulation can be admixtured with nontoxic pharmaceutically acceptable excipients which are suitable for manufacture. Formulations may comprise one or more diluents, emulsifiers, preservatives, buffers, excipients, etc. and may be provided in such forms as liquids, powders, emulsions, lyophilized powders, sprays, creams, lotions, controlled release formulations, tablets, pills, gels, on patches, in implants, etc.

In practicing methods provided herein, the pharmaceutical compounds can be delivered by transdermally, by a topical route, formulated as applicator sticks, solutions, suspensions, emulsions, gels, creams, ointments, pastes, jellies, paints, powders, and aerosols.

In practicing methods provided herein, the pharmaceutical compounds can also be delivered as nanoparticles or microspheres for regulated, e.g., fast or slow release in the body. For example, nanoparticles or microspheres can be administered via intradermal injection of the desired composition, which slowly releases subcutaneously; see Rao (1995) J. Biomater Sci. Polym. Ed. 7:623-645; as biodegradable and injectable gel formulations, see, e.g., Gao (1995) Pharm. Res. 12:857-863 (1995); or, as microspheres for oral administration, see, e.g., Eyles (1997) J. Pharm. Pharmacol. 49:669-674. Nanoparticles can also be given intravenously, for example nanoparticles with linkage to biological molecules as address tags could be targeted to specific tissues or organs.

In practicing methods provided herein, the pharmaceutical compounds can be parenterally administered, such as by intravenous (IV) administration or administration into a body cavity or lumen of an organ. These formulations can comprise a solution of active agent dissolved in a pharmaceutically acceptable carrier. Acceptable vehicles and solvents that can be employed are water and Ringer's solution, an isotonic sodium chloride. In addition, sterile fixed oils can be employed as a solvent or suspending medium. For this purpose, any bland fixed oil can be employed including synthetic mono- or diglycerides. In addition, fatty acids such as oleic acid can likewise be used in the preparation of injectables. These solutions are sterile and generally free of undesirable matter. These formulations may be sterilized by conventional, well known sterilization techniques. The formulations may contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of active agent in these formulations can vary widely, and will be selected primarily based on fluid volumes, viscosities, body weight, and the like, in accordance with the particular mode of administration selected and the patient's needs. For IV administration, the formulation can be a sterile injectable preparation, such as a sterile injectable aqueous or oleaginous suspension. This suspension can be formulated using those suitable dispersing or wetting agents and suspending agents. The sterile injectable preparation can also be a suspension in a nontoxic parenterally-acceptable diluent or solvent, such as a solution of 1,3-butanediol. The administration can be by bolus or continuous infusion (e.g., substantially uninterrupted introduction into a blood vessel for a specified period of time).

The pharmaceutical compounds and formulations used to practice the methods as provided herein can be lyophilized. Provided are a stable lyophilized formulation comprising a composition as provided herein, which can be made by lyophilizing a solution comprising a pharmaceutical as provided herein and a bulking agent, e.g., mannitol, trehalose, raffinose, and sucrose or mixtures thereof. A process for preparing a stable lyophilized formulation can include lyophilizing a solution about 2.5 mg/mL protein, about 15 mg/mL sucrose, about 19 mg/mL NaCl, and a sodium citrate buffer having a pH greater than 5.5 but less than 6.5. See, e.g., U.S. patent app. no. 20040028670.

Extracellular Vesicles (EVs), Exosomes Comprising Synthetic RNA

Provided are B lymphocyte supernatants or equivalents thereof, B lymphocyte extracellular vesicles (EVs) or equivalents thereof, B lymphocyte exosomes or equivalents thereof, and/or B lymphocyte micro-vesicles or equivalents thereof comprising synthetic miRs or synthetic anti-miRs.

In alternative embodiments, these synthetic miRs- or synthetic anti-miRs-comprising B lymphocyte extracellular vesicles (EVs) or equivalents thereof, B lymphocyte exosomes or equivalents thereof, and/or B lymphocyte micro-vesicles or equivalents thereof are produced by first inserting into the B lymphocyte the synthetic miRs or synthetic anti-miRs which can be by any means, e.g., by transfection, e.g., by using LIPOFECTIN™. After culturing, the B lymphocytes then produces extracellular vesicles (EVs) or equivalents thereof, B lymphocyte exosomes or equivalents thereof, and/or B lymphocyte micro-vesicles or equivalents thereof comprising the synthetic miRs or synthetic anti-miRs.

Synthetic miRs or synthetic anti-miRs can be made by any means, e.g., as described in U.S. Pat. Nos. 9,828,603; 9,139,832; 8,969,317.

Products of Manufacture and Kits

Provided are products of manufacture and kits for practicing methods as provided herein, e.g., methods for preventing or slowing cancer cell proliferation, local and distal metastasis, epithelial to mesenschymal transition (EMT) or the differentiation of cancer initiating/cancer stem cells into more differentiated cancer cells; or, for practicing methods for manipulating a cell physiology, a cell function, a cellular genome in a cell, a cellular transcriptome in a cell, or a cellular proteome in a cell. In alternative embodiment, products of manufacture and kits include instructions for practicing methods as provided herein. In alternative embodiment, products of manufacture and kits comprise compositions for practicing methods as provided herein, e.g., a B lymphocyte supernatant, a B lymphocyte extracellular vesicle (EV), a B lymphocyte exosome, and/or a B lymphocyte micro-vesicle, comprising e.g., a plurality of the same or different micro-RNA molecules.

The invention will be further described with reference to the examples described herein; however, it is to be understood that the invention is not limited to such examples.

EXAMPLES

Unless stated otherwise in the Examples, all recombinant DNA techniques are carried out according to standard protocols, for example, as described in Sambrook et al. (1989) Molecular Cloning: A Laboratory Manual, Second Edition, Cold Spring Harbor Laboratory Press, NY and in Volumes 1 and 2 of Ausubel et al. (1994) Current Protocols in Molecular Biology, Current Protocols, USA. Standard materials and methods for plant molecular work are described in Plant Molecular Biology Labfax (1993) by R.D.D. Croy, jointly published by BIOS Scientific Publications Ltd (UK) and Blackwell Scientific Publications, UK. Other references for standard molecular biology techniques include Sambrook and Russell (2001) Molecular Cloning: A Laboratory Manual, Third Edition, Cold Spring Harbor Laboratory Press, NY, Volumes I and II of Brown (1998) Molecular Biology LabFax, Second Edition, Academic Press (UK). Standard materials and methods for polymerase chain reactions can be found in Dieffenbach and Dveksler (1995) PCR Primer: A Laboratory Manual, Cold Spring Harbor Laboratory Press, and in McPherson at al. (2000) PCR—Basics: From Background to Bench, First Edition, Springer Verlag, Germany.

Example 1

In Vivo Delivery of Antagomirs and Therapeutic Uses Thereof

This example demonstrates that methods and compositions as provided herein can be used to manipulate any genetic, cellular or biological system controlled or generated at least in part by an miRNA, e.g., including cell growth, maturation and differentiation, cell death (e.g., apoptosis), metabolism, immunity and inflammation, by the efficient delivery in vivo of the appropriate antagomir. This example demonstrates that methods as provided herein can be used to therapeutically treat, ameliorate or prevent an infection (a viral or bacterial infection), a condition or a disease, e.g., a disease such as cancer or a disease or condition caused by any cell dysplasia, cardiac hypertrophy and fibrosis, by the efficient delivery in vivo of the appropriate antagomir.

Here we demonstrate that primary B lymphocytes can be genetically programmed with plasmid DNA, including non-viral plasmids, for the biogenesis and delivery of antagomirs; in particular, that primary B lymphocytes can be genetically programmed with non-viral plasmid DNA for the biogenesis and delivery of the anti-miR miR-150. As described in detail in the Examples, within 18 hours (hrs) of transfection with an anti-miR-150 construct, primary B lymphocytes secrete approximately 3000 antagomir copies/cell of anti-miR-150 molecules. Anti-miR-150 molecules released by B lymphocytes were internalized by CD8 T lymphocytes during cross-priming in vitro and in vivo, resulting in marked downregulation of endogenous miR-150. However, such internalization was not observed in the absence of cross-priming. These results demonstrated that shuttling anti-miR-150 molecules from B lymphocytes to T cells required the activation of receiver T cells via the antigen receptor. Finally, anti-miR-150 synthesized in B cells were secreted both as free and extracellular vesicle (EV)-associated fractions, but only EV-associated anti-miR-150 were apparently taken up by CD8 T cells. Collectively, these data demonstrate that the methods provided herein, which comprise use of primary B lymphocytes to deliver antagomirs in vivo, provide an efficient platform for the synthesis and delivery of short, non-coding RNA, and also provide a new approach to immunogenomic and other genetic therapies.

Transduced or transfected primary B lymphocytes have been previously proposed as vehicles for the synthesis and delivery of proteins of immunological relevance (13, 14). B lymphocytes are an attractive cell type in which to carry gene manipulations for therapeutic purposes because (i) B lymphocytes are abundant in peripheral blood (about 15% of all leukocytes), (ii) develop a formidable translational capacity once activated through the antigen receptor, and (iii) do not need culture, maturation or differentiation to be used as vehicles of DNA-based regulatory functions (15). For instance, we demonstrated that primary B lymphocytes transfected ex vivo with plasmid DNA and injected intravenously (i.v.) into naïve immune competent mice, synthesize and process transgenic molecules thus initiating a systemic T cell response in vivo (16) while persisting in secondary lymphoid organs for approximately 15 days (15). Because the RNAseIII enzymes (Drosha and Dicer) that are required to process plasmid-borne RNA into small RNA, and ultimately single stranded mature miRNA, are functional in primary B lymphocytes (17, 18), we decided to experimentally verify whether the biogenesis and secretion of short, non-coding anti-microRNA molecules could be activated in primary B lymphocytes transfected with suitable plasmid DNA. To this end, experiments were performed targeting miR-150, a miRNA involved in shaping the characteristics of memory CD8 T cells (19), control of B cell lymphopoiesis (20) and in liquid and solid tumors (21, 22).

Here we report that primary murine B lymphocytes transfected with plasmid DNA (pCMV-MIR) comprising the coding sequence for anti-miR-150 efficiently synthesize and secrete functional anti-miRNA molecules, which are taken up by CD8 T lymphocytes during antigen presentation/T cell activation in vitro and in vivo apparently through small vesicles referred herein as extracellular vesicles (EVs), a collective term inclusive of exosomes and micro-vesicles (23). These findings are discussed with respect to the use of suitably programmed primary B lymphocytes for the new forms of miRNA-based therapies as provided by the methods provided herein.

Results

Synthesis and Secretion of anti-mir150 in B Lymphocytes

To test the possibility that primary B lymphocytes could efficiently sustain the synthesis of anti-miRNAs, primary B lymphocytes purified from the spleen of naive adult mice were transfected with plasmid DNA encoding anti-miR-150 (pCMV-MIR$^{a150}$). This plasmid codes for the 22 bp corresponding to anti-miR-150 (antisense) under the control of the CMV promoter (FIG. 1A). Assuming equal cell distribution, the input during transfection was approximately $3\times10^5$ molecules of plasmid/cell. Copies of anti-miR-150 were produced in every instance as determined by copy number in transfected B lymphocytes. Based on intracellular synthesis values, we estimated that, on average, primary B lymphocytes synthesize approximately 140 copies/cell in the first 18 hrs (FIG. 1B), with a 4-fold variation in synthetic rate from experiment to experiment. The possibility that the qRT-PCR would amplify the input plasmid was ruled out because the anti-miR-150 specific primers did not amplify the plasmid, suggesting that amplification was specific for the short anti-miR-150 after intra-cellular biogenesis.

Secretion of anti-miR-150 was assessed in the culture supernatant harvested 18 hrs after transfection. Anti-miR-150 molecules were abundantly secreted in the culture medium. When the copy number was adjusted for the number of transfected primary B lymphocytes, we found that over the 18 hr period each cell secretes on average 3,000 copies, many more copies than those estimated inside the cell (FIG. 1C). This finding suggests a rapid cellular export of mature anti-miR-150 with accumulation in the extracellular compartment. Collectively, these data show that primary B lymphocytes transfected with pCMV-MIR$^{a150}$ initiate a reproducible, high level synthesis and secretion of specific anti-miRNA molecules.

Uptake of Anti-miR-150 by CD8 T Lymphocytes During Cross Priming In Vitro

Figure 2A:
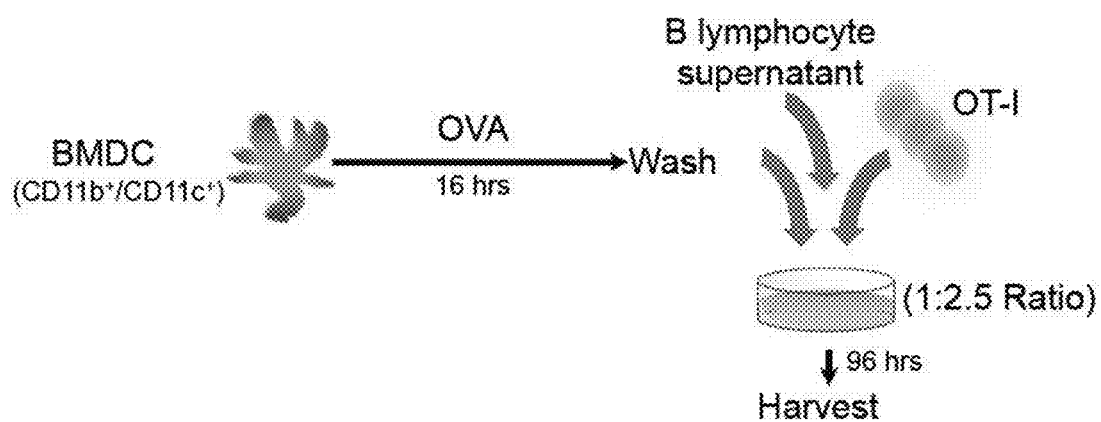
FIG. 2A schematically illustrates an exemplary protocol as provided herein to show that anti-miR-150 secreted by primary B lymphocytes could be internalized by CD8 T cells specifically during antigen activation by dendritic cells (DC); bone marrow-derived CD11b+/CD11c+ DC (BMDC) were cultured in vitro with antigen ovalbumin (OVA) for 16 hrs before adding naïve CD8 T cells from transgenic OT-I mice that express a T cell receptor (TCR) specific for the SIINFEKL (SEQ ID NO:3) OVA peptide presented in WIC Class I molecules, and an anti-miR-150 containing supernatant from 18 hr culture of transfected primary B lymphocytes; as discussed in detail in Example 1, below.
Figure 2B:
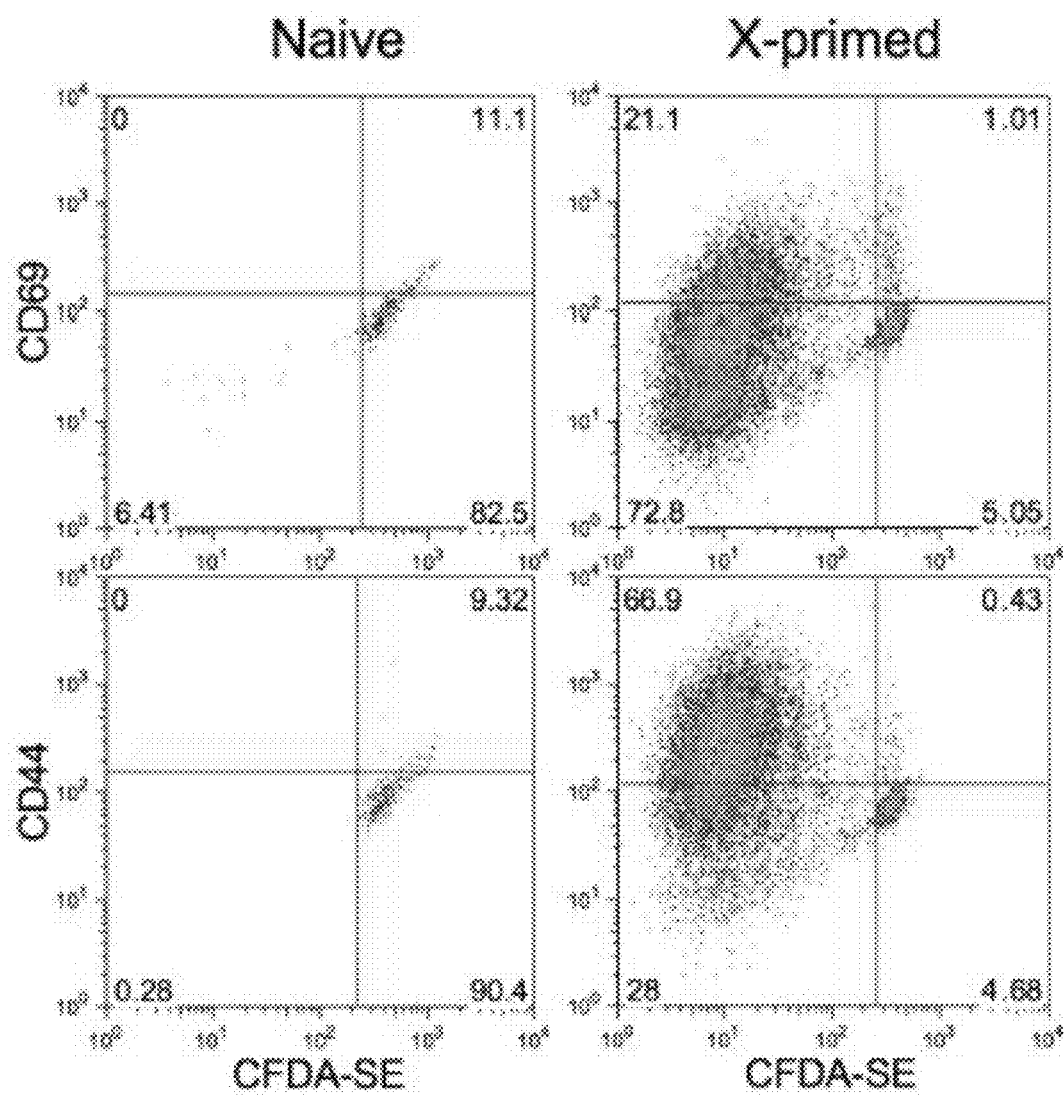
FIG. 2B illustrates images of cell flow cytometry analysis showing cells stained for CD44 and CD69 in co-cultures of naïve and cross-primed T cells using the exemplary protocol of FIG. 2A; as discussed in detail in Example 1, below.
Figure 2C:
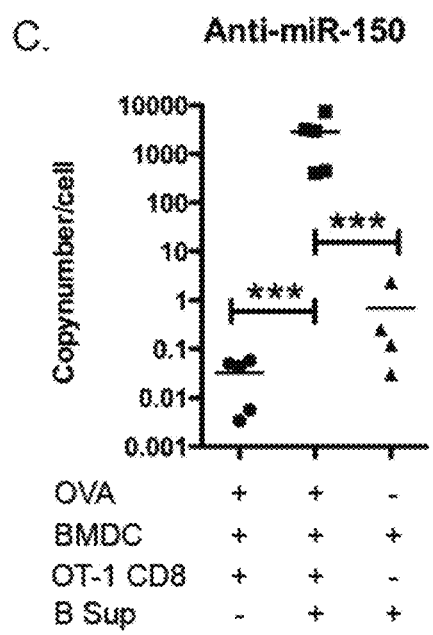
FIG. 2C graphically illustrates data from a copy number analysis of CD8 T cells from the co-cultures of the exemplary protocol of FIG. 2A, which showed that anti-miR-150 was amplified in cross-primed T cells in every instance in which the anti-miR-150 enriched supernatant from transfected primary B lymphocytes was added; as discussed in detail in Example 1, below.

Cross-priming is the property of CD8 T cells to be activated by phagocytic antigen presenting cells after uptake of soluble antigen and processing/presentation in the MHC Class I pathway (24). As such, cross-priming is regarded as the preferential mode of activation of CD8 T cells by host antigen presenting cells after uptake of self-tumor antigens (25). Here, we used in vitro cross-priming to test the possibility that anti-miR-150 secreted by primary B lymphocytes could be internalized by CD8 T cells specifically during antigen activation by dendritic cells (DC). Briefly, bone marrow-derived CD11b+/CD11c+ DC (BMDC) were cultured in vitro with the model antigen ovalbumin (OVA) for 16 hrs before adding (a) naive CD8 T cells from transgenic OT-I mice that express a T cell receptor (TCR) specific for the SIINFEKL (SEQ ID NO:3) OVA peptide presented in MHC Class I molecules (26), and (b) the anti-miR-150 containing supernatant from 18 hr culture of transfected primary B lymphocytes (FIG. 2A). These co-cultures were subsequently incubated for 96 hrs. To ensure that CD8 T cells were activated during cross-priming, cells were stained for CD44 and CD69, two canonical surface markers of activation, and were found to be positive in a large proportion of cross-primed CD8 T cells (FIG. 2B). A copy number analysis of CD8 T cells from these co-cultures revealed that in every instance in which we added the anti-miR-150 enriched supernatant from transfected primary B lymphocytes, anti-miR-150 was markedly amplified in cross-primed T cells (FIG. 2C). In contrast, when the same B lymphocyte supernatant was added to CD8 T cells co-cultured with BMDC without OVA (i.e., no cross-priming) no detectable anti-miR-150 amplification was found. This result suggests that antigen-mediated activation of CD8 T cells via cross-priming is necessary for the internalization of anti-miRNAs.

Figure 3A:
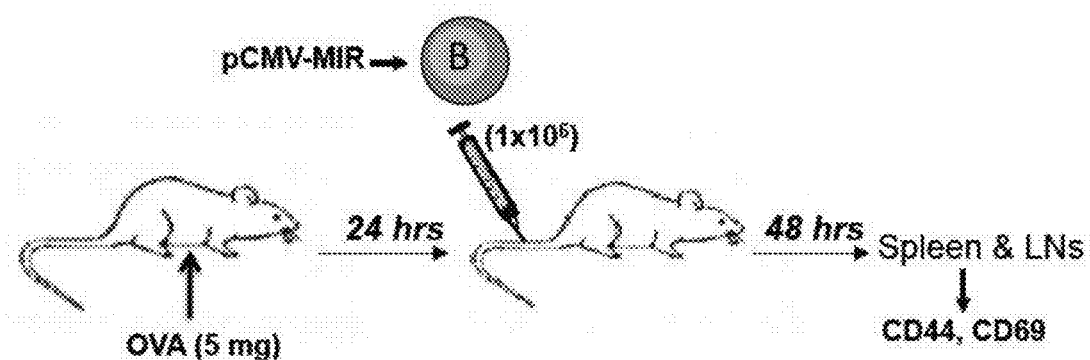
FIG. 3A schematically illustrates an exemplary protocol as provided herein to show that anti-miR-150 secreted by transfected primary B lymphocytes could undergo internalization by CD8 T cells during cross-priming in vivo.
Figure 3B:
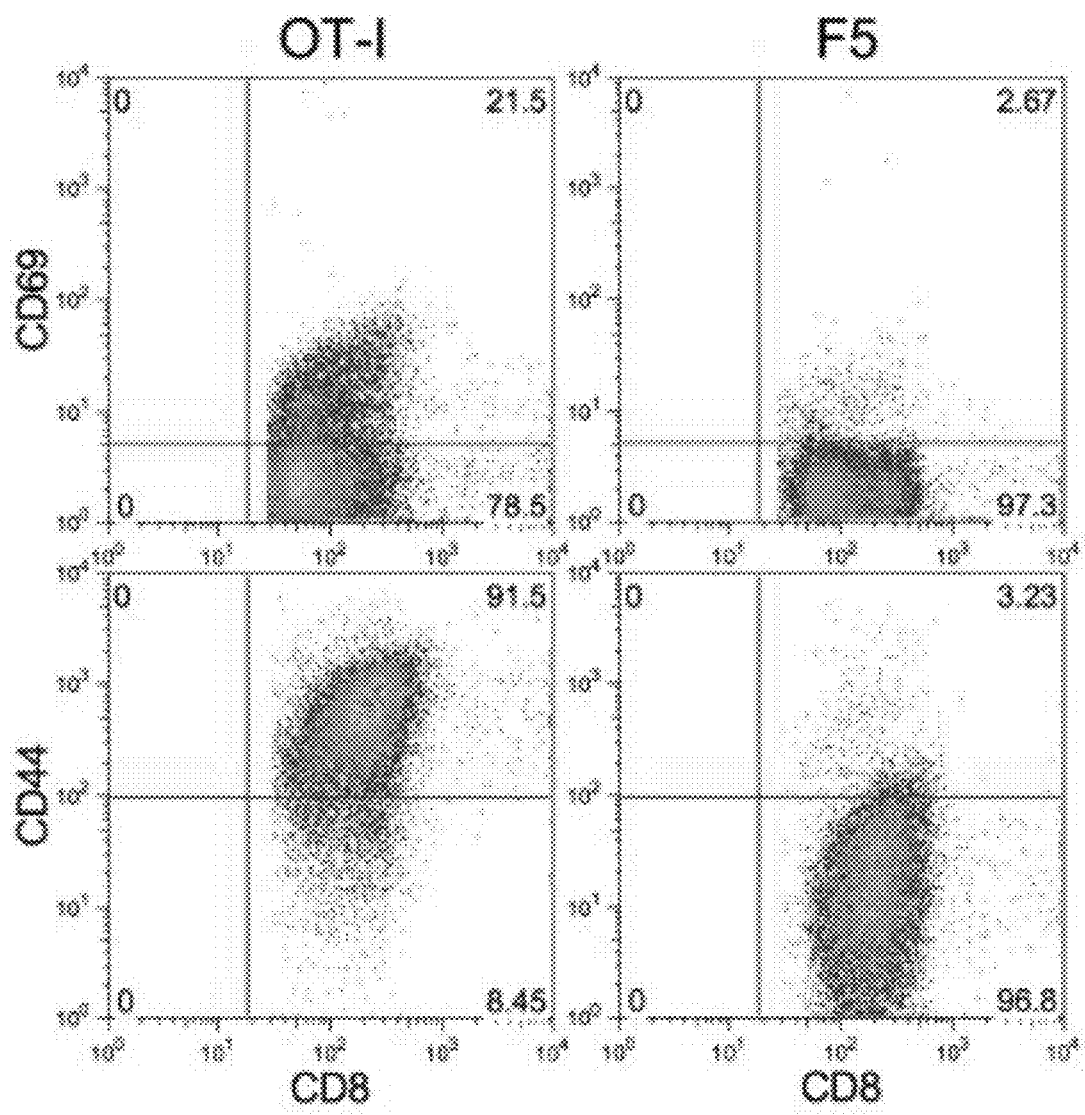
FIG. 3B illustrates images of cell flow cytometry analysis showing spleen and lymph node CD8 T cells stained for CD44 and CD69 surface in two TCR transgenic strains of mice: OT-I mice specific for OVA and F5 mice whose CD8 T cells bear a TCR specific for the ASNENMDAM (SEQ ID NO:4) peptide of the nucleoprotein (NP) antigen of the influenza A virus (27), as a control.
Figure 3C:
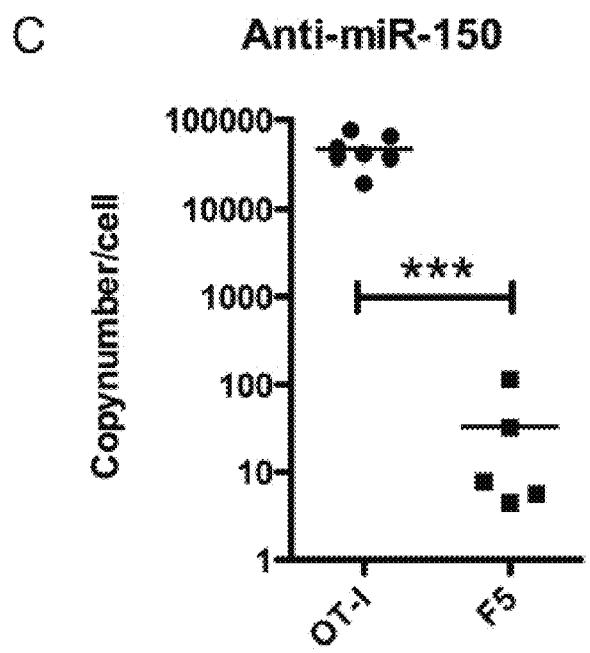
FIG. 3C-D graphically illustrates data from an anti-miR-150 (FIG. 3C) and miR-150 (FIG. 3D) copy number/cell study in OT-I T cells and F5 T cells.

Transfer Anti-miR-150 from Transfected B Lymphocytes to CD8 T Cells During Cross Priming In Vivo Next, we tested the possibility that anti-miR-150 secreted by transfected primary B lymphocytes could undergo internalization by CD8 T cells during cross-priming in vivo. To this end, we used and compared two TCR transgenic strains of mice: OT-I mice specific for OVA and F5 mice whose CD8 T cells bear a TCR specific for the ASNENMDAM (SEQ ID NO:4) peptide of the nucleoprotein (NP) antigen of the influenza A virus (27), as a control. To induce cross-priming, mice were pre-injected i.p. with OVA (5 mg) to cause antigen-specific activation of CD8 T cells in secondary lymphoid organs (28). Twenty-four hrs after OVA administration, mice were injected i.v. with $1\times10^6$ primary B lymphocytes freshly (<1 hr) transfected with pCMV-MIR$^{a150}$ (FIG. 3A). We reasoned that since F5 mice are specific for influenza virus NP antigen, they would not respond to OVA immunization, hence representing an ideal indicator of any effect due the transfected B lymphocytes outside the context of cross-priming (e.g., passive uptake), and also account for any effect due to OVA. As expected, OVA activated CD8 T cells in OT-I but not in F5 mice as determined by CD44 and CD69 surface staining on spleen and lymph node CD8 T cells purified on day 3 (FIG. 3B). In 7 out of 7 instances, we amplified anti-miR-150 in OT-I CD8 T cells, whereas amplification in CD8 T cells from F5 mice was minimal. The average copy number/cell in OT-I T cells was $4\times10^4$ vs. 40 in F5 T cells (FIG. 3C). Thus, anti-miR-150 molecules secreted by transfected primary B lymphocytes are taken-up by CD8 T cells during antigen-specific activation, suggesting local shuttling of anti-miR-150 molecules from B lymphocytes to CD8 T lymphocytes.

In Vitro and In Vivo Down-Modulation of miR-150 in T Cells During Cross-Priming

Figure 2D:
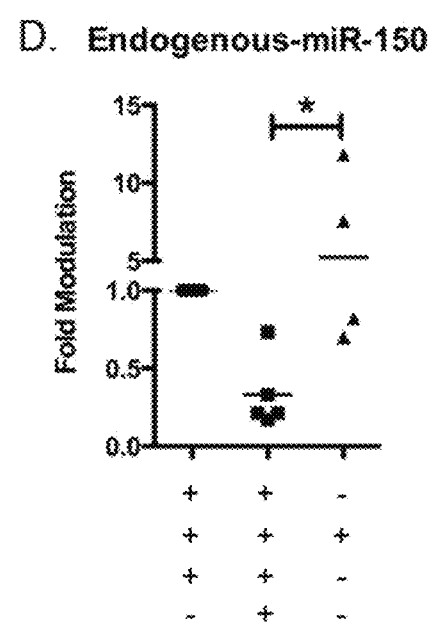
FIG. 2D graphically illustrates fold modulation (RQ) of endogenous miR-150 in CD8 T cells of corresponding cultures of the study of FIG. 2A-C; as discussed in detail in Example 1, below.
Figure 3D:
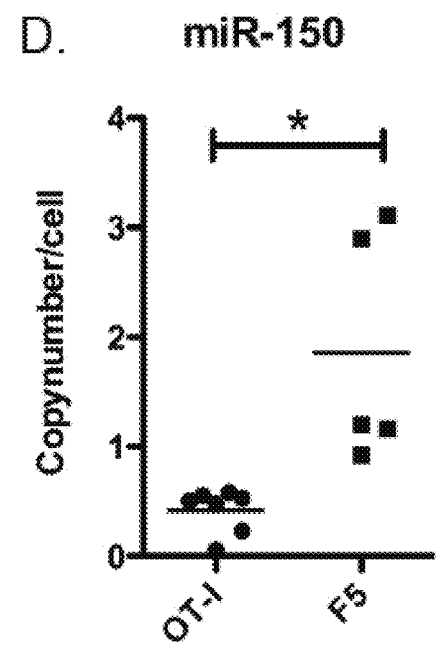

The expression of miR-150 in mature T lymphocytes is not static and is down regulated by TCR engagement (29), making it an ideal target to assess regulation by exogenous anti-miR-150. To determine if anti-miR-150 secreted by B lymphocytes affects miR-150 expression in target T lymphocytes, we measured miR-150 levels in CD8 T cells cross-primed in vitro and in vivo, respectively. We found that the miR-150 expression in CD8 T cells cross-primed in vitro in the presence of B lymphocyte-derived anti-miR-150 supernatant was considerably reduced (approximately 70%) relative to CD8 T cells cross-primed only (FIG. 2D). miR-150 levels in CD8 T cells from co-cultures in which OVA had been omitted were comparable or even increased relative to baseline controls. In these cells the endogenous levels of an unrelated microRNA (let-7a) used as a control were unaffected by anti-miR-150 treatment. Thus, the uptake of anti-miR-150 by CD8 T cells during in vitro antigen cross-priming resulted in marked and specific decrease of endogenous miR-150 expression. Furthermore, we found that the level of miR-150 in CD8 T cells after cross-priming in vivo was also considerably reduced (approximately 60%) relative to levels in naive OT-I T cells (FIG. 3D), but not in control F5 CD8 T cells in which we observed an increase. These findings suggest that anti-miR-150 molecules secreted by transfected primary B lymphocytes, once internalized by CD8 T lymphocytes cross-primed in vivo, specifically and reproducibly down-regulate endogenous miR-150.

Figure 4A:
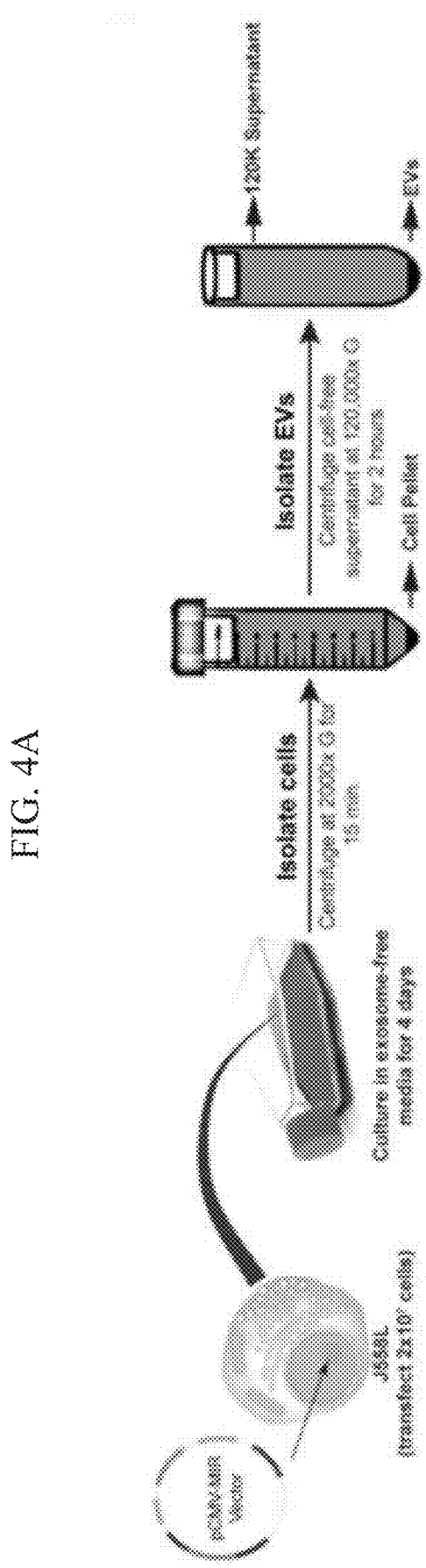
FIG. 4A schematically illustrates an exemplary protocol as provided herein of in vitro production and isolation of EVs from J558L cells transfected with pCMV-MIR$^{a150}$.
Figure 4B:
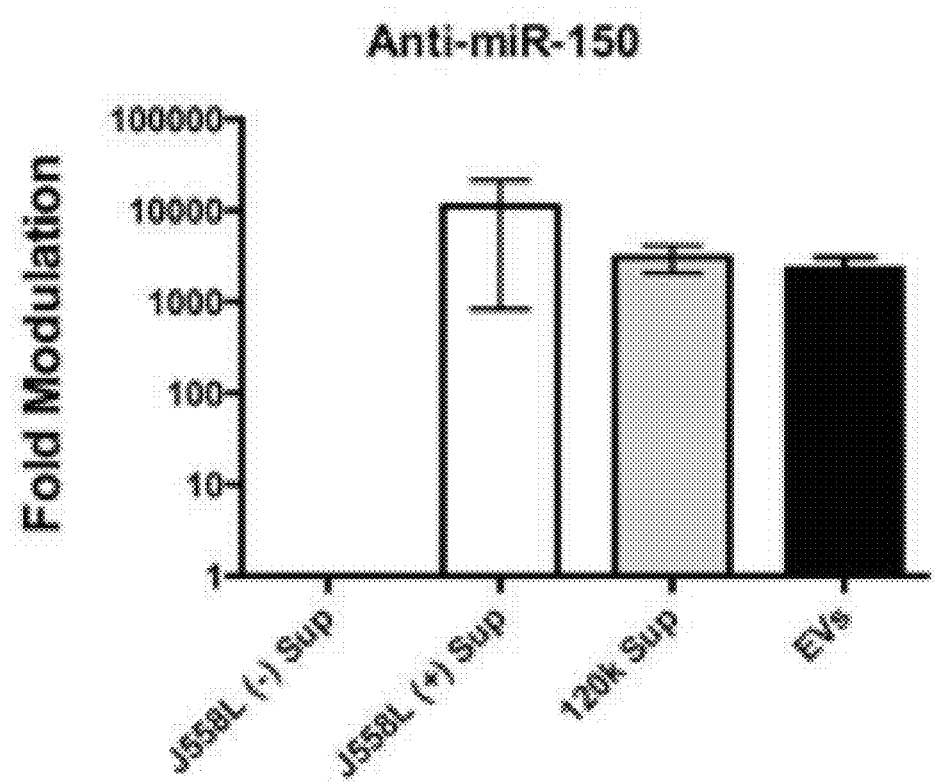
FIG. 4B graphically illustrates data showing the detection of anti-miR-150 in the 120K EV-free supernatant and in the EV-rich pellet of J558L cells after short term transfection with pCMV-MIR$^{a150}$; as discussed in detail in Example 1, below.

Anti-miR-150 is Highly Enriched in B Cell-Derived EVs, which are Internalized by T Cells During Cross Priming In Vitro EVs have been shown to mediate the intercellular transfer of short, non-coding RNA (12). To verify if such a mechanism was operative in our model system, we isolated EVs from murine J558L plasmacytoma cells transfected with pCMV-MIR$^{a150}$. After 96 hr culture in EV-free supernatant 2×10$^7$ transfected cells were subjected to standard centrifugation and the resulting supernatant ultracentrifuged at 120,000×G (120K) to generate two fractions: an EV-free supernatant and an EV-rich pellet, respectively (FIG. 4A). These two fractions were then interrogated by qRT-PCR for anti-miR-150 content. Anti-miR-150 could be amplified from both the 120K EV-free supernatant and the EV-rich pellet (FIG. 4B). Thus, anti-miRs produced in B cells are released both as free and EV-associated RNA molecules. Next, we sought to determine whether both short RNA species were involved in uptake/internalization by CD8 T cells during cross-priming in vitro. By qPCR we determined that anti-miR-150 could be amplified predominantly in CD8 T cells cross-primed in the presence of EVs (FIG. 4C) but not in cells cross-primed without the addition of EVs or in CD8 T cells co-cultured with BMDC without OVA (i.e., no cross-priming), as expected from previous experiments.

Figure 4C:
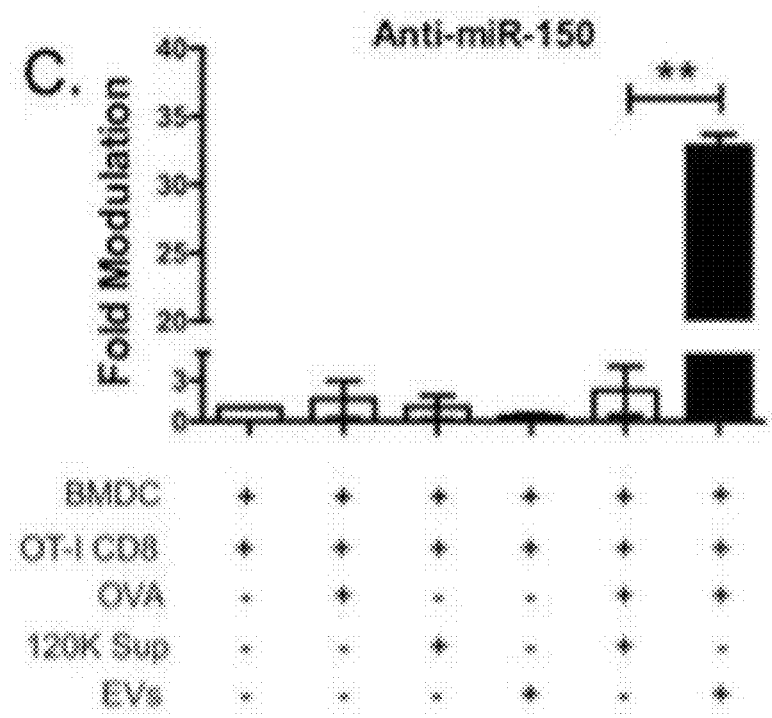
FIG. 4C graphically illustrates data showing the fold modulation of anti-miR-150 inside in vitro cross-primed CD8 T cells, and appropriate controls, with or without addition of the 120K EV-free supernatant or EV-rich ultracentrifugation pellet; as discussed in detail in Example 1, below.
Figure 4D:
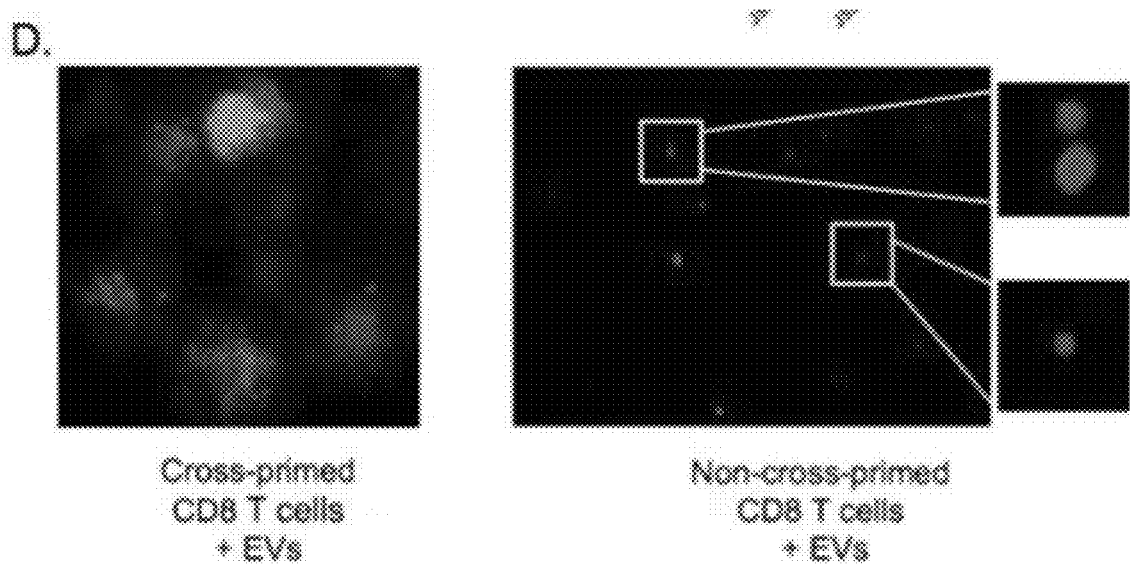
FIG. 4D illustrates images of a fluorescence microscopy analysis of CD8 T cells cross-primed in vitro in the presence of PKH67-labeled EVs (left panel), or co-cultured with dendritic cells without OVA (no cross-priming) but in the presence of PKH67-labeled EVs (right panel); as discussed in detail in Example 1, below.

Surprisingly, amplification in CD8 T cells cross-primed in the presence of the 120K EV-free supernatant was very low (FIG. 4C). To directly visualize the internalization of EV in cross-primed CD8 T cells, EV produced by transfected J558L cells were isolated and labeled with the green fluorescent lipid dye PKH67, and added to OT-I CD8 T cells co-cultured with BMDC with or without OVA as illustrated in FIG. 2A. By fluorescence microscopy PKH67-labeled EVs could be visualized inside CD8 T cells during cross-priming, but not inside CD8 T cells co-cultured with dendritic cells without OVA (i.e., no cross-priming) in the presence of PKH67-labeled EVs (FIG. 4D), indicating that PKH67-labeled EV translocate to CD8 T cells specifically during antigen activation. We estimated that 40% of cross-primed CD8 T cells contain labeled EVs, with approximately 50 EVs per cell (Table 51). Collectively, these experiments demonstrate that upon transfection primary B lymphocytes secrete EVs with an anti-miR-150 cargo that are taken up by activated CD8 T cells.

Discussion

These results demonstrate that primary B lymphocytes transfected with suitably engineered plasmid DNA efficiently synthesize and secrete anti-miR-150 molecules that can be internalized by CD8 T cells during antigen-mediated activation, in vitro and in vivo. Anti-miR-150 molecules produced in primary B lymphocytes also effectively down-regulate endogenous miR-150 levels in cross-primed CD8 T lymphocytes. Finally, we show that EVs serve as the likely vehicle through which anti-miR-150 molecules are shuttled into receiver CD8 T cells. Collectively, these results demonstrate the effectiveness of methods as provided herein for delivering antagomirs in vivo, and that the methods as provided herein provide a new function for B lymphocytes, including the synthesis and secretion of functional short, non-coding RNAs, including (noting the invention is not limited by any particular mechanism of action) their release in the form of EVs.

Provided are methods and compositions to modulate any microRNA, which are powerful regulators of biological processes through translational repression and/or mRNA degradation, mechanisms different from the canonical role of mRNA. Provided are methods for manipulating these mechanisms of action, e.g., including modulating miRNAs that regulate immunity, inflammation and cancer. Provided are methods for manipulating the fate of memory CD8 T cells, which are regulated by a discrete number of selected miRNAs, including miR-150, whose manipulation enables one to direct CD8 T cell fate predictably (19).

The data presented here demonstrate that B lymphocyte-derived anti-miR-150 molecules are internalized in CD8 T cells when these cells are activated by antigen-presenting cells. This implies that the use of B lymphocytes as synthesis and delivery vehicles of short, non-coding RNAs to regulate adaptive T cell immunity is not only possible but also endowed with an intrinsic fail-safe mechanism that limits the effect to antigen-activated CD8 T cells. Our data point to the fact that T cells are permissive to internalization of regulatory RNA only during an antigen-driven immune response, i.e., antigen presentation and activation by antigen presenting cells (dendritic cells). As such, methods provided herein can be used, e.g., as an adjuvant strategy to determine the fate of T cells during, e.g., vaccination (19), to restrict the development of FoxP3$^+$ T cells (30), and/or to modulate inflammation (31). In alternative embodiments, methods as provided herein are used therapeutically to treat, ameliorate or prevent inflammatory conditions and autoimmune diseases (6).

In alternative embodiments, methods as provided herein are used therapeutically to manipulate miRNA "signatures" have been increasingly associated with various types of cancer, different stages of tumorigenesis and cancer prognosis (32-34). In alternative embodiments, methods as provided herein are used therapeutically to modulate miRNAs in cancer stems, e.g., modulate the over-expression of oncogenic miRNAs ("oncomirs") caused by genomic deletion, mutation, epigenetic silencing, and/or miRNA processing alterations, or modulate the loss of suppressor miRNAs (reviewed in (35)).

As an initial proof of principle, we found that murine cancer cells treated in vitro with a primary B lymphocyte supernatant containing anti-miR-150 molecules markedly down-regulate the levels of endogenous miR-150 (FIG. S4). And while the mechanism of miRNA transmission to cancer cells needs to be further investigated, our findings suggest that primary B lymphocytes programmed for the synthesis and secretion of short non-coding RNAs may be used to target cancer cells to either (i) suppress oncomirs (36), or (ii) restore miRNAs that suppress oncogenes or metastases (37, 38). Similarly, the approach may be used to modulate the tumor microenvironment by targeting miRNA that drive mutator activity (39) or promote the metastatic potential of cancer cells (40).

EVs have been implicated in the transfer of miRNAs and mRNAs as a novel mechanism of genetic exchange between cells (41). Many cell types can form and secrete EVs: B lymphocytes in particular have been the object of two reports (42, 43). However, in one case the miRNA content of the EVs was not interrogated, and, in the other, B cells were infected with Epstein Barr virus. At variance, here we show that primary B lymphocytes can be programmed with plasmid DNA to form and secrete EVs containing a cargo of anti-miR-150 molecules, and that these EVs apparently enable and mediate internalization by CD8 T cells (FIGS. 4C and D). Transmission by EVs likely protects the cargo, e.g., miRNA, from RNase degradation, ensuring stability and providing for a mechanism to cross the hydrophilic cell membrane. Whereas the exact mechanism of EV internalization by activated CD8 T cells remains to be clarified, EV-encapsulation of miRNA by B lymphocytes may offer advantages over soluble miRNA molecules that are also released by B lymphocytes.

In conclusion, we demonstrate that the methods and compositions as provided herein are effective for programming primary B lymphocytes for the synthesis and secretion of short, non-coding RNA molecules for miRNA-based therapies. Since autologous B lymphocytes transfected with plasmid DNA have already been used in humans in the context of therapeutic vaccination (44), the new type of "immunogenomic therapy" exemplified here can undergo rapid clinical translation.

Materials and Methods

Mice. C57BL/6 mice were originally purchased from the Jackson Laboratories. TCR transgenic OT-I mice (C57BL/6; Thy1.2$^+$) that are specific for the SIINFEKL OVA peptide (26) were obtained from Dr. Stephen Hedrick (UCSD). TCR transgenic RAG$^{-/-}$ F5 mice are specific for the ASNENMDAM peptide of the nucleoprotein (NP) antigen of the influenza A virus (27) and were obtained from the National Institute of Health (Bethesda, Md.) courtesy of Dr. Jonathan Yewdell. All mice were maintained in the animal facility of the UCSD Moores Cancer Center. All animals were handled in strict accordance with good animal practice as defined by the relevant national and/or local animal welfare bodies, and all animal work was performed based on a protocol approved by the Institutional Animal Subject Committee (UCSD No. S00023).

Plasmid DNA, microRNA, oligonucleotides and antigens. Plasmid DNA expressing anti-miRNA150)(pCMV-MIR$^{a150}$ is a 6.2 kb vector (Origene; Rockville, Md.) into which an 82 bp insert, containing the coding sequence for the 22 bp corresponding to anti-miR-150 (FIG. 1A), was cloned using Sgf I and Mlu I restriction sites. The expression of the anti-miRNA precursor is driven by a CMV promoter (FIG. 1A). Synthetic anti-miR-150 and snoRNA202 was purchased from Integrated DNA Technology (IDT; Indiana). Gene-specific primers for mmu-miR-150, and anti-miR150, let-7a, and snoRNA202 (endogenous control) were purchased from Applied Biosystems (ABI; Sunnyvale, Calif.). Ovalbumin (OVA) was purchased from Sigma (Grade II; Lot No. 20H0763).

Transfection procedures. Primary B lymphocytes were isolated by negative selection (StemCell Tech) from the spleen of C57BL/6 or F5 mice, and were transfected with plasmid pCMV-MIR$^{a150}$ using the Amaxa Cell Line Nucleofector Kit™ (Lonza). Briefly, 5×10$^6$ cells were transfected with 2 µg of plasmid DNA in the buffer solution provided by the manufacturer. After transfection, the cells were re-suspended in 2 mL of complete RPMI medium, plated on a 6-well tissue culture plate, and incubated a 37° C. in a 5% CO2 atmosphere. Untransfected B lymphocytes were plated and used as a negative control. Transfected and negative control cells, and their supernatants, were harvested at the end of 18 hr culture, unless otherwise specified.

qRT-PCR. MicroRNA was extracted from the cells using either the RNAGEM Tissue PLUS™ (Zygem) or the mirVana PARIS Kit™ (Life Technologies). MicroRNA in supernatant samples were isolated using either the mirVANA PARIS Kit™ (Life Technologies) or the miRNeasy Serum/Plasma Kit™ (Qiagen). cDNA was synthesized from the purified microRNA using the High Capacity cDNA Synthesis Kit™ (Life Technologies) with snoRNA202, miR-150, let-7a, or anti-miR150 primers (ABI). qRT-PCR was performed on an ABI StepOne™ system using TaqMan™ reagents for 50 cycles using validated FAM-labeled mouse snoRNA202, miR-150, anti-miR150, and let-7a TaqMan primer/probe sets (Life Technologies) under universal cycling conditions. Target gene expression was normalized to snoRNA202, and analyzed using the –ΔΔCt relative quantification method.

Relative quantification and copy number determination. To determine the copy number of anti-miR-150, samples normalized at 100 ng cDNA/reaction were run concomitantly with a standard curve constructed with known amounts (100-0.01 ng) of anti-miR-150 cDNA. The endogenous control standard curve was constructed using known amounts (100-0.01 ng) of snoRNA202 cDNA. Let-7a total cDNA was similarly extracted, quantified and adjusted to 100 ng/µL. cDNA was generated with Applied Biosystems (ABI) let-7a (002478) and snoRNA202 (001232) specific reverse transcription primers. Samples were run in duplicate with anti-miR150 and snoRNA202 FAM-labeled probe/primer sets. Relative expression was determined by comparing untreated to experimental samples. In all instances, the Ct value of the endogenous control was subtracted from the Ct value of target. Once the amount (ng) of specific target was determined, the copy number present in each reaction was calculated using the following formula: (ng× 6.0223×10$^{23}$)/(number of nucleotides×1.0×10$^{9×650}$) as indicated in http://www.uic.edu/depts/rrc/cgf/realtime/stdcurve.html.

BMDC Generation and CD8 T cell cross-priming in vitro. The preparation of bone marrow derived DC (BMDC) and the isolation of CD8 T cells by negative selection (StemCell Tech) are described in (19). As indicated BMDC were supplemented or not with heat-treated (63° C.×25 min) OVA (1 mg/mL) for 16 hrs prior to adding naïve CD8$^+$ T cells isolated from spleen and lymph nodes cell of OT-I mice. The yield and purity of transgenic OT-I CD8 T cells was determined by Vα2/CD8 positivity by flow cytometry, and was >90%. 2.5×10$^5$ Vα2$^+$/CD8$^+$ T cells were then co-cultured with 10$^5$ BMDC in complete RPMI medium or in complete RPMI medium containing 50% v/v supernatant from pCMV-MIR$^{a150}$ transfected primary B lymphocytes for 96 hrs. T cells were recovered from 96-hr co-cultures using Lympholyte M™ (Cedar Lane), and analyzed by flow cytometry and qPCR.

In vivo studies. Six to 14 week old OT-I or F5 mice were injected i.p. with 5 mg heat-treated (63° C.×25 min) OVA according to (28). Twenty-four hrs later mice were injected i.v. with 10$^6$ primary C57BL/6 B lymphocytes that had been negatively selected from a spleen cell suspension and transfected with plasmid pCMV-MIR$^{a150}$. B lymphocytes were used within 1 hr from transfection. Mice were sacrificed after 48 hrs (i.e., 3 days after OVA injection) and CD8$^+$ T cells were negatively selected from spleen and lymph nodes and analyzed as indicated in the text.

Flow cytometry. Single cell suspensions of CD8+ T cells were stained with fluorophore-conjugated anti-CD8α (eBioscience, clone Ly-2), anti-CD69 (BD Biosciences, clone H12F3), anti-CD44 (BD Biosciences, clone IM7), and anti-Vα2 (BD Biosciences, clone B20.1) antibodies, or appropriate isotype controls. Viability was determined by 7-AAD exclusion. Data were acquired on a FACSCalibur™ flow cytometer (Becton Dickinson) and analyzed using CellQuest Pro™ (BD Biosciences) and FlowJo software (Tree Star).

Extracellular vesicles (EVs) Isolation: For the purpose of isolating EVs, transfection experiments were performed in J558L mouse plasmacytoma cells (45). Briefly, 5×10$^6$ J558L cells were transfected using the Lonza Amaxa Cell Line Nucleofector Kit V™. Cells were transfected with plasmid pCMV-MIR$^{a150}$ (2 μg). After transfection cells were placed in fresh EV-depleted medium prepared by ultracentrifugation of RPMI supplemented with 20% FBS at 120,000×g for 18 hours at 4° C. The medium was then diluted to a final concentration of 10% FBS prior to use. Transfected J558L cells were cultured in EV-free RPMI at 37° C. for 96 hrs after which the EV fraction was isolated by differential centrifugation. Briefly, conditioned media were first centrifuged at 2000×g for 20 minutes to remove cellular debris. The supernatant was collected and further centrifuged at 10,000×g for 30 minutes. The resultant supernatant was then transferred to ultracentrifuge tubes for ultracentrifugation at 120,000×g for 2 hrs. The supernatant was discarded and the EV pellets were re-suspended in PBS for storage at −80° C. prior to RNA isolation. All centrifugation steps were performed at 4° C.

Fluorescence microscopy study. To visualize the uptake of vesicles by cross-primed OT-I CD8 T cells (FIG. 4), EVs were labeled with the fluorescent dye PKH67 (Sigma) according to manufacturer's protocol. Briefly, 4 μl of PKH67 was added to 1 ml of Diluent C and mixed thoroughly before the dye solution was combined with EVs that has been resuspended in 1 ml of Diluent C. After gently mixing for 5 minutes, 2 ml of 1% BSA was added to bind the excess dye. Labeled EVs were pelleted and washed with PBS by ultracentrifugation at 120,000×g for 2 hours at 4° C. Freshly-prepared PKH67-labeled EVs were added to co-cultures of BMDC and OT-I CD8 T cells on day 1 using 50 μl of EVs in 1 mL of standard culture medium. Co-cultures grown in 1 ml of the 120,000×g EV-free spin supernatant served as controls. In both instances, CD8 T cells were harvested on day 4 as detailed above and centrifuged onto a glass slide using a CytoSpin 2 centrifuge (Shandon) and mounted using ProLong Gold antifade reagent with DAPI (Invitrogen). Slides were analyzed on a BZ-9000™ Biorevo fluorescence microscope (Keyence Corporation of America).

Statistical methods to analyzed the data included: Unpaired, two-tailed t test, non-parametric, Mann-Whitney test. Significance is reported as: *P<0.05, P<0.01, *P<0.001.

TABLE 1

Quantification of EV translocation efficiency to cross-primed CD8 T cells.: OT-I CD8 T cells were cross-primed in the presence of PKH67-labeled extracellular vesicles (EVs). The extent of successful EV translocation was quantified by enumerating the percentage of DAPI positive cells containing punctate green fluorescent foci and the number of foci per positive cell.

|  | No cross-priming + EVs | Cross-priming + EVs |
|---|---|---|
| EV Positive Cells (n = 75) | 0% | 47% |
| EVs/cell | 0 | 50 |

FIG. 1. Structure of pCMV-MIR$^{a150}$ and secretion of anti-miR-150 by primary B lymphocytes transfected with pCMV-MIRMIR$^{a150}$. (A) Schematic map of pCMV-MIR$^{a150}$ and anti-miR-150 coding sequence and transcript. (B) Intracellular anti-miR-150 detection (copy number/cell) in primary B lymphocytes transfected with pCMV-MIR$^{a150}$ harvested 18 hrs after transfection. (C) Secreted anti-miR-150 (copy number/cell) based on detection in culture supernatants harvested 18 hrs after transfection. Data points refer to single independent experiments.

FIG. 2. Anti-miR-150 secreted by transfected primary B lymphocytes are internalized by CD8 T cells during cross-priming in vitro. (A) Scheme of experimental design of in vitro T cell cross-priming. (B) Flow cytometry analysis showing that in vitro cross-primed CD8 T cells express CD69 and CD44 activation markers. (C) Detection of anti-miR-150 content (copy number/cell) in purified CD8 T lymphocytes cross-primed in the presence of supernatant from primary B lymphocytes transfected with pCMV-MIR$^{a150}$. CD8 T cells cross-primed without addition of transfected primary B lymphocyte supernatant or CD8 T cells from BMDC-CD8 T cell co-cultures without OVA (BMDC+OT-I CD8+B Sup) to which the supernatant of primary B lymphocytes transfected with pCMV-MIR$^{a150}$ was added, served as controls. Dots refer to single independent experiments. (D) Fold modulation (RQ) of endogenous miR-150 in CD8 T cells of corresponding cultures.

FIG. 4. Isolation of anti-miR-150 activity in EVs and EV visualization inside CD8 T cells after cross-priming in vitro. (A) Schematic of in vitro production and isolation of EVs from J558L cells transfected with pCMV-MIR$^{a150}$. (B) Detection of anti-miR-150 in the 120K EV-free supernatant and in the EV-rich pellet of J558L cells after short term (96 hrs) transfection with pCMV-MIR$^{a150}$. Results are expressed as fold modulation and refer to the results of two independent experiments (mean±SEM). (C) Fold modulation of anti-miR-150 inside in vitro cross-primed CD8 T cells, and appropriate controls, with or without addition of the 120K EV-free supernatant or EV-rich ultracentrifugation pellet. Results refer to two independent experiments (mean±SEM). (D) Fluorescence microscopy analysis of CD8 T cells cross-primed in vitro in the presence of PKH67-labeled EVs (left panel), or co-cultured with dendritic cells without OVA (no cross-priming) but in the presence of PKH67-labeled EVs (right panel). Magnification: 20×, left panel and 10× right panel.

Figure 5:
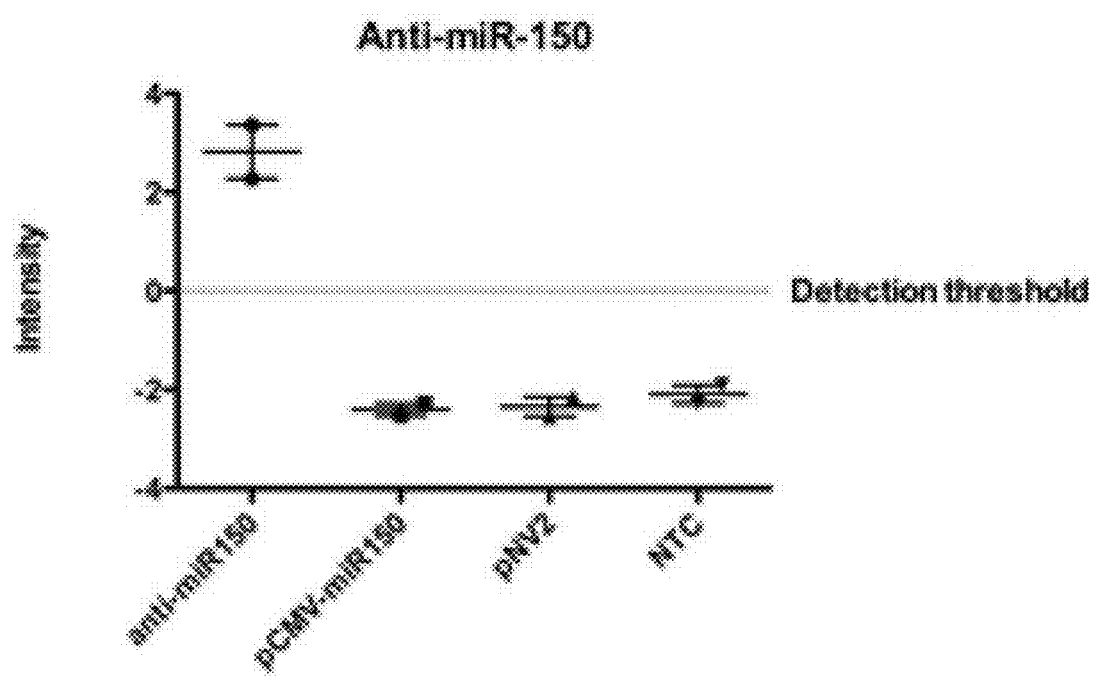
FIG. 5 graphically illustrates data of qRT-PCR using anti-miR-150 primers (ABI), where anti-miR-150 amplification is expressed as the ratio between the fluorescence intensity of the reporter dye (FAM) and that of the passive reference dye (ROX) used for normalization; as discussed in detail in Example 1, below.

FIG. 5 illustrates: Anti-miR-150 is not amplified from plasmid pCMV-MIR$^{a150}$. qRT-PCR was performed as described in Material and Methods using anti-miR-150 primers (ABI). Anti-miR-150 amplification is expressed as the ratio between the fluorescence intensity of the reporter dye (FAM) and that of the passive reference dye (ROX) used for normalization, according to manufacturer's guidelines. Values above the detection threshold indicate amplification of the target sequence, whereas values below the detection threshold imply lack of amplification of the target sequence. The test reflects 30 standard cycles including a denaturing step at 95° C. and an annealing/extension step at 60° C. pNV2=approximately 15 Kb plasmid coding for a full length chimeric immunoglobulin heavy chain gene modified in the CDR2 by insertion of the sequence (NANP-NVDP-NANP). See e.g., Xiong S. et al., Engineering vaccines with heterologous B and T cell epitopes using immunoglobulin genes, Nature Biotech 15:882-886,1997. NTC=Non template control.

Figure 6A:
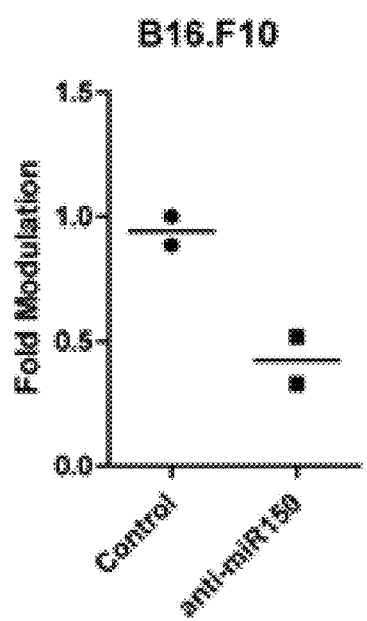
FIG. 6A-C graphically illustrates data showing the down-regulation of endogenous miR-150 in murine tumor cells treated with the supernatant of J558L cells transfected with pCMV-MIR$^{a150}$; Murine melanoma (B10.F10) (FIG. 6A), lung (LLC) (FIG. 6B) and prostate (TC1) (FIG. 6C) tumor cells, were cultured in a 24-well plate for 48 hrs in RPMI medium containing 1 ml supernatant of J558L cells transfected with pCMV-MIR$^{a150}$ or the supernatant of untransfected J558L cells as a control; Results represent two experiments; as discussed in detail in Example 1, below.
Figure 6B:
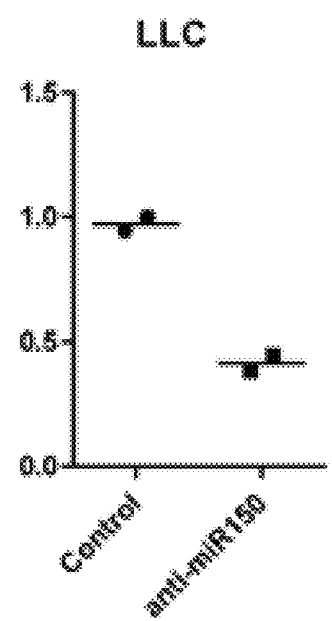
Figure 6C:
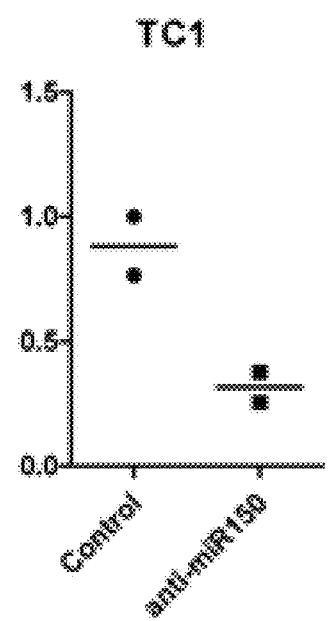

FIG. 6. Downregulation of endogenous miR-150 in murine tumor cells treated with the supernatant of J558L cells transfected with pCMV-MIR$^{a150}$. Murine melanoma (B10.F10), lung (LLC) and prostate (TC1) tumor cells, were cultured in a 24-well plate for 48 hrs in RPMI medium containing 1 ml supernatant of J558L cells transfected with pCMV-MIR$^{a150}$ or the supernatant of untransfected J558L cells as a control. Results represent two experiments.

Example 2

High Efficiency Generation of Multiple Short Noncoding RNA in B Cells and B Cell-Derived Extracellular Vesicles

This example demonstrates and exemplary protocol for the high efficiency generation of multiple short noncoding RNA in B cells and B cell-derived extracellular vesicles. In this example, it is demonstrated that B cells can be programmed for the enforced biogenesis and synchronous release of multiple sncRNAs. Data provided herein shows that this goal is feasible and that multiple sncRNA are released in the extracellular compartment in amounts comparable to those from B cells programmed to express and secrete one scnRNA only.

Furthermore, we found that the cargo of extracellular vesicles (EVs) isolated from programmed B cells is remarkably enriched for multiple sncRNAs. On average, we found that the content of multiple sncRNAs in EVs is 3.6 copy number/EV. Collectively, we demonstrate that by practicing the embodiments provided herein B cells can be easily programmed toward the synthesis and release of multiple sncRNAs, including sncRNA-laden EVs, efficiently and specifically.

Provided herein are systems for the synthesis and delivery of short, non-coding RNAs for therapeutic purposes. In alternative embodiments, these new exemplary approaches comprise use of autologous primary B lymphocytes that can be programmed by transfection with suitably engineered plasmid DNA to the biogenesis and release of sort noncoding (snc)RNA molecules[12]. SncRNAs are secreted in 24 hrs, both as free molecules and cargo in extracellular vesicles (EVs). EVs were further shown to undergo in vitro and in vivo internalization by third party cells, causing marked (approximately 70%) target down-regulation.

Reasoning that in many clinical situations a multi-pronged sncRNA approach would be desirable, here we tested the possibility of programming B cells simultaneously for biogenesis and secretion of multiple sncRNAs, including their release as EV cargo. In recent years only few reports demonstrated the expression of multiple sncRNAs in cells using either a retrovirus or plasmid DNA[13-15] but no attempts were made to assess the release of the sncRNAs in the extracellular compartment or their inclusion in EVs. Results provided here show that B cells transfected with plasmid DNA carrying the nucleotide sequence of multiple sncRNA in tandem undergo the simultaneous biogenesis and secretion of multiple sncRNA, including their release and incorporation in EVs, at high efficiency and specifically.

Results

Engineering Plasmids Comprising Nucleotide Sequences of Multiple sncRNAs

We previously showed that primary murine B lymphocytes and model murine

B cells transfected with plasmid DNA pCMVmir carrying the nucleotide sequence of anti-miR-150, are reproducibly programmed for the synthesis and secretion of anti-miR-150[12]. Here we verified that B cells can be programmed for the synthesis and secretion of multiple sncRNAs simultaneously. To end, we prepared a panel of 5 DNA plasmids each comprising either one or two sncRNA nucleotide sequences for their precursor miR (pre-miR) stem loop. As a model system we used miR-150, miR-155, and anti-miR-155, which are relevant to the regulation of T cell memory[16.]

Specifically, we generated two plasmids, one carrying in tandem miR-150 and miR-155; the other carrying in tandem miR-150 and anti-miR-155. Plasmids carrying miR-150, miR-155, and anti-miR-155 alone served as reference. The precursor stem loop for each pre-miR sncRNA and final individual plasmids bearing precursor sncRNAs as single or tandem elements are illustrated in FIG. 7.

Synchronous Intracellular Expression of Two Short Noncoding RNA

We probed intracellular sncRNA expression in murine J558L myeloma cells transfected by Amaxa electroporation and cultured for 48 hrs after transfection. Total RNA was extracted and tested by RT-qPCR as described in Material and Methods. The expression of miR-150 and miR-155 in J558 cells transfected with pCMVmir carrying the two sncRNAs in tandem (combo) was comparable to that of J558L cells transfected with pCMVmir carrying only one of the corresponding sncRNAs (FIG. 8).

Similarly, the expression of miR-150 and anti-miR-155 in J558L cells transfected with pCMVmir carrying these two sncRNA in tandem was comparable to that of J558L cells transfected with pCMVmir carrying only one of the corresponding sncRNAs (FIG. 9). These results show, therefore, no obvious loss of efficiency in the biogenesis and expression of sncRNA in B cells programmed using a plasmid carrying nucleotide sequences for multiple sncRNAs.

Synchronous Release of Multiple sncRNAs in the Extracellular Compartment

A distinctive feature of our system is that B cells transfected with a single sncRNA-carrying plasmid are very efficient at the release of the sncRNA in the extracellular compartment at levels that, on a per molecule basis, are markedly higher than in the intracellular compartment. Since a 7AAD analysis of J558L cells day 2 or 5 after transfection failed to show any appreciable increase of cell death relative to control cells, the results support an active export mechanism[12]. Here we verified whether this principle would also apply to B cells programmed for tandem sncRNA expression. The levels of miR-150 and miR-155 were markedly and specifically enriched in the culture medium compared to the intracellular compartment in amounts comparable to those from B cells transfected with a single miRNA nucleotide sequence borne on an individual plasmid (FIG. 13A). Likewise, when B cells were transfected with the plasmid carrying the nucleotide sequence of miR-150 and anti-miR-155 in tandem, they secreted each sncRNA in a range comparable to that of B cells transfected with the plasmid carrying the nucleotide sequence of either miR-150 or anti-miR-155, respectively (FIG. 13B). Together these results validate the notion that B cells are very efficient at the extracellular export of newly-expressed sncRNAs leading to their rapid extracellular accumulation.

sncRNAs are Enriched in EVs

A second and important feature of B cells undergoing enforced expression and release of sncRNA molecules is that sncRNAs are packaged in EVs[12]. Here we interrogated the efficiency at which this event occurs by determining whether two sncRNAs synthesized and released synchronously are apportioned equally in EVs, and by estimating the copy number/EV of the sncRNA cargo in different conditions.

EVs isolated from J558L cells cultured for 48 hrs after transfection in medium containing normal fetal calf serum showed a high content of sncRNAs. The RQ values for miR-155 were markedly elevated in EVs released by B cells transfected with a plasmid carrying one scnRNA and only slightly decreased in EVs released by B cells transfected with a plasmid carrying two sncRNAs (FIG. 14). At variance, the RQ values for miR-150 in EVs from B cells transfected with a plasmid carrying two sncRNAs were reduced (90 vs 3298 RQ) compared to reference EVs from B cells transfected with a single sncRNA plasmid.

To obtain a more accurate estimate of the sncRNA content in EVs, experiments were repeated by analyzing the sncRNA content of EVs produced by programmed J558L cells cultured for 48 hrs in commercially-available exosome-depleted medium. EVs were isolated and counted as described in Material and Methods. Their average size ranged between 101 and 111 nm in EVs from J558L transfectants vs. 106 nm in EVs from sham transfected J558L cells with minimal dispersity. Their sncRNA content assayed and quantified by RT-qPCR. From a total of $10^{11}$EVs/sample reconstituted to 200 µl we extracted 0.3 mg/ml and 0.2 mg/ml, respectively, suggesting that there is no substantial bias introduced by the transfection in the generation and protein content of EVs. Interestingly, the tetraspanin CD63, which is expressed in exosomes, is expressed in EVs released by B cells transfected with a plasmid carrying two sncRNAs in relatively higher amounts than in EVs isolated from untransfected B cells (FIG. 15), suggesting a selective enrichment during the enforced sncRNA biogenesis, and EVs formation and release.

Next we determined the copy number of each sncRNA in EVs. FIG. 16 shows that each EV contains, on average, 3.6 copies of predetermined individual sncRNAs. Remarkably, we found comparable sncRNA copy numbers in EVs from B cells programmed with dual or single sncRNA plasmid. When compared to the constitutive content of miR-150 and miR-155 in EVs from sham-transfected J558L cells, the copy number was 15 and 25 fold higher, respectively. A copy number quantitation in EVs produced in exosome-depleted medium yielded on average a 30% to 50% increase, a result accounting for the decrease in B cell-derived EVs by exosomes contained in commercial fetal calf serum (data not shown). Finally, we found that sncRNA generated in tandem are effective at decreasing (approximately 30%) target miRNA or at increasing cellular sncRNA content in transfected J558L cells.

Discussion

We demonstrate that B cells can be efficiently programmed for the synchronous biogenesis and secretion of multiple predetermined scnRNAs. We also found that that the effective extracellular concentration of sncRNAs expressed in tandem in B cells is markedly higher than in the intracellular compartment. Finally, we show that EVs released by B cells programmed for the synchronous biogenesis and secretion of multiple predetermined scnRNAs are markedly enriched in sncRNA content.

Clinical applications of miRNA-based regulation of gene expression and disease may require the combined expression of multiple sncRNAs for therapeutic results. This can involve administering two or more miRNAs or a mixture of miRNAs, and anti-miRNAs. For example, miR-150 and miR-155 exist in B and T lymphocytes in reciprocal balancing regulation[16, 17], necessitating a bimodal regulation. A multipronged approach may apply to other situations. For instance, two miRNAs may be an efficient method to target extracellular metabolic energetics and block cancer progression[18]. Likewise, a multipronged miRNA-based approach may be necessary to simultaneously target complementary functions in cancer cells such as self-renewal and pluripotency[19], and translation initiation[20]. Our data clearly show that that this goal is attainable, in principle, using B cells transfected with plasmid DNA purposely engineered for a multipronged effect. Since B cells transfected with plasmid DNA have already been used in a Phase 1 trial[21] showing no toxicity[22], B cells programmed to secrete and release sncRNAs may be readily exploited for clinical translation. In addition to possessing a formidable and rapidly adjustable synthetic machinery, B cells are capable of miRNA biogenesis[23, 24] and exosomes production[25, 26].

Small (30-100 nm) micro-vesicles, exosomes, have surged to relevance as important inter-cellular messengers[27, 28]. EVs are released by B lymphocytes[26], T lymphocytes[29, 30], dendritic cells[31, 32] and bone marrow derived mesenchymal stem cells[33]. Exosomes also play a relevant role in cancer as intercellular messengers[34, 35] modulating cancer cells growth and metastasis[36-38] promoting therapy resistance[39, 40] and orchestrating immune suppression[41].

Exosomes are also regarded as vehicle for targeted gene therapy[42] and cancer therapies[43]. However, the future of exosomes in therapeutic settings depends a priori on the efficiency with which a predetermined sncRNA cargo can be loaded onto exosomes during biogenesis. This has been found to vary depending on the cell type and the methods to generate the sncRNA cargo[43]. Of particular interest is a recent quantitative analysis to determine the stoichiometric relation between exosomes and their sncRNA content[44]. The study found that, regardless of the cell of origin, natural exosomes contain far less than 1 molecule of a given miRNA per exosome, even for the most abundant exosome preparations. This argues that spontaneously generated exosomes obey to a low occupancy/low miRNA concentration rule[44], possibly the consequence of poor efficiency in either biogenesis or EV packaging. Our results show instead that the enforced and synchronous expression of multiple predetermined sncRNA in B cells yields EVs much enriched for these sncRNAs. We calculated that EVs released by programmed B cells contain, on average, 3.6 copies of specific scnRNA irrespective of whether the originating B cells had been transfected with a dual or a single sncRNA plasmid. Thus, EVs released form programmed B cells are many fold enriched in predetermined sncRNAs over the content of miRNA in natural exosomes[44], a fact mirrored here by the 15-25-fold increase in copy number for miR-150 and miR-155 relative to the constitutive content of EVs from sham transfected J558L cells used as control. Since naturally exosomes carry a highly variable miRNA cargo with low content in specific sncRNA[45,] our method appears to resolve this potential problem in generation and production of EVs for therapeutic application. Importantly, we found that sncRNA generated in tandem are effective at regulating target miRNA or at increasing cellular sncRNA content in target cells as prerequisite for sncRNA therapeutic intervention.

The present demonstration relates to the mechanism of sncRNA cargo generation in vesicles destined to extracellular export. It is known that upon biogenesis sncRNA are packaged in late endosome multivesicular bodies (MVBs)[46]. A recent report showed that the artificial overexpression of a miRNA enriched its content in MVBs, and subsequently in exosomes, and is inversely proportional to the overexpression of miRNA target sequences[47] that can serve as a miRNA negative regulatory element by providing complementary binding sites[48]. Thus, sncRNA sorting to EVs may reflect the ability of the cell to dispose of sncRNA in excess of their RNA cellular target. Accordingly, the production of sncRNA is expected to vary in different cell types. Although the exact mechanism of biogenesis and cargo packaging in our system remains to be elucidated, our study demonstrates that the rate of enforced biogenesis in B cells is sufficient to outperform the ability of the cell to buffer the rate at which artificially expressed sncRNA are enriched in EVs.

In conclusion, we demonstrate that it is possible to program B cells for the enforced biogenesis and release of multiple predetermined sncRNAs. The approach yields a greater sncRNA concentration in the extracellular that in the intracellular compartment suggesting an active transport mechanism. We also show that programmed B cells release EVs with high copy number in predetermined sncRNAs. Collectively, B cells programmed for the synchronous expression and secretion of multiple sncRNAs appear to be a viable candidate for multipronged translational applications to control disease or regulate immunity, and a step forward in the process of optimization and control in the production of EVs for miRNA-based therapies.

Materials and Methods

Plasmid Constructs

Dual miRNA constructs containing miR-150/miR-155 and miR-150/anti-miR-155 were synthesized with unique ends SgfI/XhoI by Integrated DNA Technologies (IDT, Coralville, Iowa). Constructs were cloned into the pCMVmir (Origene, Rockville, Md.) expression vector by digesting with SgfI and XhoI, and subsequent ligation of the insert into the pCMVmir vector. The ligation mixture was transformed into DH5a competent cells. Transformed cells were plated, and clones were selected and grown overnight at 37° C. DNA was extracted with Promega Wizard Plus SV Minipreps DNA Purification System (Promega, Madison Wis.). The resultant plasmids were termed pCMV mir150+mir155 and pCMV mir150+mirα155. The clone inserts were verified via sequencing and stored at −20° C. until transfection. Single miRNA constructs containing miR-150 or miR-155 were generated through excision from the dual miRNA constructs by digestion and ligation using unique restriction sites (SgfI-MluI or NotI-XhoI) within the minigene to yield pCMV miR-150, pCMV miR-155, and pCMV anti-miR-155, respectively. The correctness of each plasmid construct was verified by sequencing.

Cell Culture and Transfection

J558L mouse B cell myeloma cells were grown in suspension in cRPMI with 10% fetal bovine serum (FBS). Cells were grown to 80% confluence. 2×10$^6$ cells were transfected with 1 μg of pCMVmiR plasmid utilizing the Lonza VACA-1003 transfection kit V and Nuclefector 2b device (Lonza, Walkersville, Md.). Cells were allowed to recover in a T25 flask upright at 37° C. with 5% CO$_2$ for 48 hrs. In experiments in which sncRNA copy number was determined transfected B cells were cultured in EXO-FBS-50A-1 exosome-depleted FBS (Exo-FBS, Systems Biosciences, Mountain View, Calif.).

EV Isolation 48 hrs post-transfection 200 μL of culture supernatant were collected and incubated with 200 μL of Total Exosome Isolation solution (Life Technologies, Carlsbad, Calif.) at room temperature for 1 hour. The EV containing mixture was spun at 16,000 RPM at 4° C. for 1 hr. The resultant EV pellet was resuspended in 50 μL of PBS at room temperature and stored in 1.5 mL Eppendorf tubes at −20° C. until use. EVs isolated from untransfected or sham transfected (electroporated only) J558L cells served as a control.

Nanoparticle Tracking Analysis

The number of vesicles recovered was determined by Nanoparticle Tracking Analysis (NTA) on a NanoSight LM-10HS equipped with a 405 nm laser (NanoSight, Wiltshire, UK) that was calibrated with polystyrene latex microbeads at 100 nm and 200 nm prior to analysis. Resuspended vesicles were diluted 1:50 with PBS to achieve between 20-100 objects per frame. EVs were manually injected into the sample chamber at ambient temperature. Each sample was measured in triplicate at camera setting 14 with acquisition time of 30 s and detection threshold setting of 7. At least 200 completed tracks were analyzed per video. The NTA analytical software version 2.3 was used for capturing and analyzing the data.

Western Blot

EVs were lysed in RIPA (1% NP40, 0.5% de-oxycholate, 0.1% SDS in TBS). Protein concentration was determined by NanoDrop spectrophotometer. 15 μg of proteins of each sample were separated in 4-20% acrylamide/bisacrylamide gel and transferred to a polyvinylidene difluoride membrane using Bio-Rad Trans Blot Turbo system 3 min. mini-TGX protocol. After washing in TBST, the membrane was incubated with an anti-CD63 monoclonal antibody (5 μgml$^{-1}$) (abcam) (the kind gift of Dr. Johnny Akers) overnight at 4C on a rocker. After washing in TBST the bound antibody was revealed using goat antibodies to mouse Ig conjugated to horseradish peroxidase (HRP) (5 μgml$^{-1}$) (Bio-Rad). The blot was developed with ECL chemiluminescent substrate and exposed to X-ray film for 3 minutes.

RNA Extraction

5×10$^5$ transfected or untransfected J558L cells, and 1 mL of culture supernatant, were collected for RNA extraction using ZYGEM RNAtissue Plus System™ (Zygem, Hamilton, NZ) according to the manufacturer's protocol. RNA from cell supernatant (200 μL) was extracted with the Qiagen miRNeasy Serum/Plasma kit following the manufacturer's protocol. EVs extraction was performed using the ZYGEM RNAtissue Plus System.

Small RNA Taqman™ cDNA was generated from intracellular, extracellular and exosome miRNA with Taqman small RNA assays. Input RNA was normalized to 100 ng/ sample for intracellular and exosome RNA, and to 25 ng/sample for extracellular miRNA. Taqman MicroRNA Reverse Transcription Kit was utilized for all samples per manufacturer's instructions. Cycling conditions for qPCR were: 40 cycles, 96° C. denature 30 secs, 60° C. anneal/extension 30 secs. Results are expressed as RQ (Relative quantity of sample) that was calculated using the formula: Relative Quantity$_{target}$=E$_{target}$ (Cq (control)−Cq (treatment)). Abbreviations: E=Efficiency of primer set; C$_q$ (control)=Average C$_q$ for the control or untreated sample; C$_q$ (treatment)=Average C$_q$ for treated sample; Target=The gene of interest or reference gene.

Copy Number Determination

To determine the copy number of miR-150, miR-155 and anti-miR-150, samples normalized at 100 ng cDNA/reaction were run concomitantly with a standard curve constructed with known amounts (100-0.01 ng) of each short noncoding RNA cDNA. The endogenous control standard curve was constructed using known amounts (100-0.01 ng) of snoRNA202 cDNA of all the targets (Applied Biosystems snoRNA202—assay No. 001232—specific reverse transcription primers). Samples were run in duplicate. Relative expression was determined by the Ct value of test samples vs. the endogenous control. Once the amount (ng) of specific target was determined, the copy number present in each reaction was calculated using the following formula: (ng× 6.0223×10$^{23}$)/(number of nucleotides×1.0×10$^{9\times650}$).

Figure Legends

FIG. 7C illustrate a schematic representation of plasmids used in the study of Example 1: FIG. 7A: the pre-mir nucleotide sequence of miR-150, miR-155 and anti-miR-155; FIG. 7B: schematic view of pCMV miR-150-miR-155; FIG. 7C, schematic view of pCMV mir-150-anti-miR-155:

FIG. 7A shows the primer nucleotide sequence of:

```
miR-150
                                              (SEQ ID NO: 5)
CCCUGUCUCCCAACCCUUGUACCAGUGCUGUGCCUCAGACCCUGGUACA

GGCCUGGGGGAUAGGG, miR-155
                                              (SEQ ID NO: 6)
CUGUUAAUGCUAAUUGUGAUAGGGGUUUUGGCCUCUGACUGACUCCUA

CCUGUUAGCAUUAACAG,
and anti-miR-155
                                              (SEQ ID NO: 7)
CUGACCCCUAUCACAAUUAGCAUUAAUUUGGCCUCUGACUGACU

CCUACCUGUUAGCAUUAACAG;
```

FIG. 7B is a schematic view of the plasmid containing pCMV miR-150, having the sequence TCTCCCAACCCTTGTACCAGT (SEQ ID NO:8), and anti-(shown as "a")-miR-155, having the sequence TTAATGCTAATTGTGATAGGGGT (SEQ ID NO:9); and, FIG. 7C is a schematic view of the plasmid containing pCMV mir-150 (SEQ ID NO:8) and anti-miR-155, having the sequence ACCCCTATCACAATTAGCATTAA (SEQ ID NO:10).

FIGS. 8 and 9 graphically illustrates data showing that is possible to transfect B cells with a plasmid coding for a miRNA and an anti-miRNA and get biogenesis (FIG. 8) and expression (FIG. 9):

FIG. 8 Detection of mir-150 and anti-miR-155 in B cells (J558L cells) transfected with a single plasmid DNA, where J558L cells were transfected with plasmid DNA encompassing the coding sequence for miR-150 alone, anti-miR-155 alone, or the combination of both (combo), where the data shows that B cells can be programmed for the expression of two short noncoding RNAs. Cells were harvested 36 hrs after transfection and total RNA was extracted by the Zygem kit. cDNA was generated using RT-specific primers using LIFETECH™ microRNA assay kit. Samples were pre-amplified and then subject to RT-qPCR amplification using RT-specific primers. Results refer to the mean±SD of two independent transfection experiments.

FIG. 9 Detection of mir-150 and anti-miR-155 in B cells (J558L cells) transfected with a single plasmid DNA, where J558L cells were transfected with plasmid DNA encompassing the coding sequence for miR-150 alone, anti-miR-155 alone, or the combination of both (combo), where the data shows that B cells can be programmed for the expression of two short noncoding RNAs. The supernatants were harvested 36 hrs after transfection and total RNA was extracted by the MIRNEASY™ (miRNeasy) kit. cDNA was generated using RT-specific primers using LIFETECH™ microRNA assay kit. Samples were pre-amplified and then subject to RT-qPCR amplification using RT-specific primers. Results refer to the mean±SD of two independent transfection experiments.

FIG. 10 Detection of mir-150 and anti-miR-155 in the supernatant of programmed J558L cells transfected with a single plasmid DNA, where J558L were transfected with a single plasmid DNA, where J558L cells were transfected with plasmid DNA encompassing the coding sequence for miR-150 alone, anti-miR-155 alone, or the combination of both (combo), where the data shows that the supernatant of B cells can be programmed for the biogenesis of two short non-coding RNAs. The supernatant was harvested 36 hrs after transfection and total RNA extracted by the Zygem kit. cDNA was generated using RT-specific primers using Lifetech microRNA assay kit. Samples were pre-amplified and then subject to RT-qPCR amplification using RT-specific primers. Results refer to the mean±SD of two independent transfection experiments.

FIG. 11 Detection of mir-150 and anti-miR-155 in the supernatant of programmed J558L cells transfected with a single plasmid DNA, where J558L cells were transfected with plasmid DNA encompassing the coding sequence for miR-150 alone, anti-miR-155 alone, or miR-150 and anti-miR-155 alone (combo), where the data shows that the supernatant of B cells can be programmed for the biogenesis of two short non-coding RNAs. The supernatant was harvested 36 hrs after transfection and total RNA extracted by the Zygem kit. cDNA was generated using RT-specific primers using Lifetech microRNA assay kit. Samples were pre-amplified and then subject to RT-qPCR amplification using RT-specific primers. Results refer to the mean±SD of two independent transfection experiments.

FIG. 12 Detection of mir-150 and anti-miR-155 in EVs released by B cells (J558L cells) transfected with a single plasmid DNA coding for miR-150 alone, miR-155 alone, or two miR-150 (combo), where the data shows miRNA (mirR) enrichment in EVs released by B cells programmed with two short non-coding RNAs.

48 hrs after transfection and culture in complete medium containing non exosome-depleted fetal calf serum. Total RNA was extracted by the Zygem kit. cDNA was generated using RT-specific primers using Lifetech microRNA assay kit. Samples were pre-amplified and then subject to RT-qPCR amplification using RT-specific primers. Results refer to the mean±SD of two independent transfection experiments.

FIG. 13 Detection of mir-150 and anti-miR-155 in EVs released by B cells (J558L cells) transfected with a single plasmid DNA coding for miR-150 alone, miR-155 alone, or miR-150 and anti-miR-155 alone (combo), where the data shows miRNA (mirR) enrichment in EVs released by B cells programmed with two short non-coding RNAs. 48 hrs after transfection and culture in complete medium containing non-exosome-depleted fetal calf serum. Total RNA was extracted by the Zygem kit. cDNA was generated using RT-specific primers using Lifetech microRNA assay kit. Samples were pre-amplified and then subject to RT-qPCR amplification using RT-specific primers. Results refer to the mean±SD of two independent transfection experiments.

FIG. 14. Copy number/EV quantitation of mir-150 and anti-miR-155 in EVs produced by programmed J558L cells. EVs were isolated from the supernatant of J558L cells transfected with a plasmid coding for miR-150 alone, miR-155 alone, or the combination of both (combo) 48 hrs after transfection and culture in complete medium containing exosome-depleted fetal calf serum. After total RNA extraction and cDNA generation samples were pre-amplified and then subject to RT-qPCR amplification using RT-specific primers. Copy number/EV were calculated as described in material and Methods. ST=Sham transfected. Results refer to the mean±SD of two replicate samples. Representative of two experiments with comparable results.

FIG. 22. EVs produced by programmed J558L cells express CD63. EVs from J558L transfected with mir-150 and anti-miR-155 or untransfectd (control) were processed for Western blot analysis as described in Material and Methods and probed with an antibody to CD63. The approximate m.w. was determined using a m.w. ladder (not shown).

Example 3

Extracellular Vesicles Induced in B Cells to Contain miR-335 Control Triple Negative Human Breast Cancer Cells in Immunodeficient Mice This example demonstrates that methods and compositions as provided herein can be used to treat or ameliorate triple negative human breast cancer. We demonstrated that iEVs programmed to contain miR-335 can deliver their cargo to LM2 cells, modulate target mRNA expression in vitro and in vivo, and greatly reduce the growth of LM2 cells as orthotopic tumors in immune deficient NSG mice.

Results

A Plasmid Expressing miR-335 Doublets in B Cells

We reasoned that restoring miR-335 content in LM2 cells would be best achieved by transfecting B cells with a plasmid engineered with two miR-335 precursor stem loops (Almanza and Zanetti, 2015). To this end, we engineered pCMVmir carrying two pre-miR-335 stem loops in tandem with a nucleotide linker. Previous studies from this laboratory showed that the cargo of iEVs can be enriched to contain at least two distinct scnRNAs of predetermined specificity.

We then quantified miR-335 expression levels in the murine myeloma cell line J558L after transfection, and compared them with those in J558L cells transfected with a pCMVmir coding for one pre-miR-335 stem loop only. As shown on FIG. 15, miR-335 content (copy number/EV) in iEVs was considerably greater (approximately 5 folds) when J558L cells had been transfected with the plasmid carrying the miR-335 doublet compared to iEVs from J558L cells transfected with a single pre-miR-335 stem loop plasmid. Therefore, all subsequent experiments were performed using a pCMVmir carrying two miR-335 stem loops.

Effects of iEVs Containing miR-335 on LM2 Cells In Vitro

We determined uptake and miR-335 content in LM2 cells incubated in vitro for 48 hrs with iEVs$^{335}$ over a range of iEVs:LM2 cell ratios ($4 \times 10^{2}$-$10^{4}$: LM2 cell) in order to establish the minimum threshold for effective restoration of miR-335 content in target LM2 cells. An increase in copy number followed a dose response curve, with a >4 folds increase over untreated LM2 cells at the $10^3$ dose, see FIG. 16. To see if internalization was also followed by intracellular release of cargo miR-335, we sought the effect on two miR-335 targets, SOX4 and tenascin C (TNC), as previously reported by Tavazoie et al. (Tavazoie et al., 2008). As shown in FIG. 17, restoration of miR-335 in LM2 cells was associated with a dose dependent reduction in SOX4 messenger RNA expression. The reduction of TNC expression was less pronounced. Two control mRNAs, β-Catenin (CTNNB1) and TERT, which are constitutively expressed in cancer cells, were unaffected, suggesting that the effect on SOX4 was specific FIG. 18. Collectively, iEVs spontaneously internalized into LM2 cells release their cargo miR-335, which effectively modulates its targets, SOX4 in particular.

Incubation of LM2 cells with iEVs$^{335}$ did not cause a loss in cell viability since this was constant throughout the observation period albeit reduced relative to untreated or sham iEVs treated LM2 cultures, see FIG. 19.

Orthotopic Tumor Suppression In Vivo

The ability of iEVs$^{335}$ to control LM2 tumorigenicity was tested in a model of orthotopic implantation. Briefly, LM2 cells were pretreated by incubation with $4 \times 10^4$ fold excess: iEVs$^{335}$, or control iEVs, for 48 hours to allow for their uptake/internalization and release of miR-335. Mice were then injected in the fat pad with $4 \times 10^5$ LM2 cells. They were imaged on day 45 and 60, at which point they were sacrificed. On day 45 (4 out of 6 control mice (no pretreatment) and 5 out of 5 mice injected with LM2 cells pretreated with control iEVs had detectable tumors (not shown). In contrast only 4 out of 9 mice implanted with LM2 cells pretreated with iEVs-335 had developed tumors. On day 60, all control mice including those implanted with untreated LM2 cells alone as well as those implanted with LM2 cells pretreated with control iEVs, had detectable tumors. Among the test group 6 out of 9 mice were confirmed to have a tumor detected by in vivo imaging but all the tumors were smaller than tumors of mice implanted with LM2 cells treated with sham transfected iEVs FIG. 20A. At sacrificed (day 60) tumors were excised, measured by caliper and weighed. As illustrated in FIGS. 20B-C, the average tumor size (mm) was 1,682±250 in the 6 mice given LM2 cells alone and 1,896±479 in control iEV-treated LM2 cells. In contrast, as illustrated in FIG. 13B, the average size for the four tumors treated with iEVs$^{335}$ was 7.2±9.8. Likewise, the average weight (gr), as illustrated in FIG. 13C, was 1.3±0.6 in the 6 mice given LM2 cells alone and 2.3±1.2 for tumors from control iEV-treated LM2 cells. The average size of the tumors treated with iEVs$^{335}$ was 0.16±0.18. Thus, pretreatment of LM2 cells with iEVs-dramatically reduced tumor growth in vivo.

Next, we measured the levels of miR-335 in tumors excised at sacrifice to see if the effect was associated with a higher levels of miR-335 in tumors in which miR-335 content was restored therapeutically. Remarkably, the endogenous values for miR-335 were 1.0±0.06 for the 6 control mice and 0.8±0.02 for tumors treated with control iEVs, whereas they were significantly higher (4.7±0.7) in the four tumors borne of LM2 cells pretreated with iEVs$^{335}$ prior to implantation in vivo (FIG. 20E). No differences were detected in the endogenous levels of let-7a, a miRNA used as a control (FIG. 20F). To confirm that restoration of miR-335 in LM2 cells had effects on its target we quantified the mRNA levels of endogenous SOX4 and TNC (see FIG. 20G, left and right panels, respectively), and found them to be considerably reduced compared to the levels in all control tumors, as illustrated in FIG. 20G-H. No variation was noted in the mRNA levels of two β-Catenin (CTNNB1) (FIG. 20I) and TERT (FIG. 20J) used as control. Thus, restoration of miR-335 through iEVs$^{335}$ was long-lasting and produced marked regulation of target mRNAs. Oddly, sham iEVs treated tumors had an increased TNC expression relative to the untreated condition.

Tumor growth suppression was accompanied by a high content of miR-335 and a concomitant reduction of its target mRNAs. Because the average miRNA half-life has been estimated to be approximately 5 days (Gantier et al., 2011) it became important to interrogate the longevity of miR-335 shuttled in LM2 cells as iEV payload. To this end, cultured LM2 cells were treated for 48 hrs with either EVs: iEVs$^{335}$, or sham EVs, respectively. At the end of the two-day treatment, cells were thoroughly washed and cultured in complete medium for an additional 4 or 8 days. Treatment with iEVs$^{335}$ resulted in a marked upregulation of miR-335 content that was maximal on day 4 (FIG. 21A, left panel). This did not occur in LM2 cells treated with sham EVs. Likewise, mRNA levels of SOX4 remained depressed through day 8 (FIG. 21B, left panel). This suggest, that the uptake of EVs laden with a miR-335 payload leads to a restoration of the endogenous miR-335 pool that exceeds the 5 days half-life mark for miRNA maintaining as well the ability to regulate the SOX4 target mRNA. Western on SOX4.

Discussion

We demonstrate that miR-335 contained in iEVs as cargo generated in B lymphocytes during induced vesicles biogenesis is effective at restoring endogenous miR-335 content in triple negative human breast cancer cells. An increase in endogenous miR335 content in target LM2 cells resulted in a negative regulation of mRNA targets, and tumor growth control in vivo. Our finding on miR-335 ability to regulate the tumorigenic properties of LM2 cells is consistent with a previous report showing that miR-335 silencing through genetic or epigenetic means results in increased tumorigenicity (Png et al., 2011). Moreover, this is in line with reports showing that the inactivation of miR-335 in human cancers is associated with reduced recurrence-free survival and represents an independent indicator of poor overall survival (Cao et al., 2014; Png et al., 2011).

We show that iEVs enriched in miR-335 can be used therapeutically to restore its endogenous content in cancer cells in which its production is silenced, enabling regulation of target mRNAs, e.g., SOX4. SOX4 is the main target of miR-335 and is also a master regulator of epithelial-to-mesenchymal transition (EMT) through direct positive regulation of Ezh2 (Tiwari et al., 2013). We show that the internalization iEVs in LM2 cells was effective at down-regulating SOX4 mRNA in vitro and in vivo. Surprisingly, tumors borne of LM2 cells treated ex vivo with iEVs$^{335}$ showed profound SOX4 decrease sixty days after orthotopic implantation, suggesting that SOX4 negative regulation by miR-335 in TNBC cells is both effective and durable. The mechanism for the sustained effect is unknown and could be related to the persistence of miR-335 inside host cells, or to a permanent negative effect on SOX4 transcription. It is possible that iEVS internalized into LM2 cells degrade slowly, releasing their payload over time. Full elucidation of this effect will require further experimentation.

Therapeutically, a one-time internalization of iEVs proved sufficient to markedly inhibit, and in half cases prevent, orthotopic tumor growth, confirming the tumor-inhibiting properties of miR-335. Since miR-335 is reduced in various cancer types in humans beside TNBC (Cao et al., 2014; Gong et al., 2014; Isosaka et al., 2015; Wang and Jiang, 2015; Xiong et al., 2013) it follows that that the direction of work presented here has a future in the treatment of certain types of human cancers for which methods to precisely target iEVs to cancer cells in vivo should be developed for increased efficacy and diminished risk of off-target effects.

Materials and Methods

Mice 8-10 week old NOD scid gamma (NSG) mice were purchased from The Jackson Laboratories.

Cell Lines

MDA MB 231-4175 (LM2) cells are human TNBC cells derivative of MDA-MB 231 cells stably transduced with a lentivirus expressing a triple-fusion reporter (abbreviated "TGL") encoding herpes simplex virus thymidine kinase 1, green florescence protein and firefly luciferase (Minn et al., 2005). LM2 cells were kindly obtained from the Memorial Sloan-Kettering Cancer Center (New York, NY). MDA-MB 231 cells were purchased from the American Type Cell Collection (ATCC® HTB-26TM).

Plasmid Constructs

A dual miRNA construct containing miR-335-miR-335 was synthesized with unique SgfI/XhoI ends by Integrated DNA Technologies (IDT, Coralville, Iowa). Constructs were cloned into the pCMVmir (Origene, Rockville, Md.) expression vector by digesting with SgfI and XhoI, and subsequent ligation of the insert into the pCMVmir vector. The ligation mixture was transformed into TOP10 competent cells (Life Technologies, Carlsbad Calif.). Transformed cells were plated, and clones were selected and grown overnight at 37° C. DNA was extracted with Promega Wizard Plus SV Minipreps DNA Purification System™ (Promega, Madison Wis.). The resultant plasmids were termed pCMV dual mir335. The clone insert was verified via sequencing and stored at –20° C. until transfection. Single miRNA construct containing miR-335 was generated through excision from the dual miRNA construct by digestion and ligation using unique restriction sites (SgfI-MluI or NotI-XhoI) within the minigene to yield pCMV miR-335. The correctness of each plasmid construct was verified by sequencing.

Cell Culture and Transfection

J558L mouse B cell myeloma cells were grown in suspension in cRPMI with 10% fetal bovine serum (FBS). Cells were grown to 80% confluence. $2 \times 10^6$ cells were transfected with 1 µg of pCMVmiR plasmid utilizing the Lonza VACA-1003™ transfection kit V and Nuclefector 2b device (Lonza, Walkersville, Md.). Cells were allowed to recover in a T25 flask upright at 37° C. with 5% $CO_2$ for 48 hrs. In experiments in which sncRNA copy number was determined transfected J558L cells were cultured in EXO-FBS-50A-1™ exosome-depleted FBS (Exo-FBS, Systems Biosciences, Mountain View, Calif.).

EV Isolation and Enumeration

Forty-eight hours post-transfection 1 mL of culture supernatant was collected and incubated with 0.5 mL of Total Exosome Isolation™ solution (Life Technologies, Carlsbad, Calif.) for 1 hr at room temperature. The EV-containing mixture was spun at 16,000 RPM at 4° C. for 1 hr. The EV pellet was resuspended in 100 µL of PBS at room temperature and stored in 1.5 mL Eppendorf tubes at –20° C. until use. EVs isolated from untransfected or sham transfected (electroporated only) J558L cells served as a control.

The number of vesicles recovered was determined by Nanoparticle Tracking Analysis (NTA) on a NanoSight LM-10HS™ equipped with a 405 nm laser (NanoSight, Wiltshire, UK) that was calibrated with polystyrene latex microbeads at 100 nm and 200 nm prior to analysis. Resuspended vesicles were diluted 1:100-1:300 with PBS to achieve between 20-100 objects per frame. iEVs were manually injected into the sample chamber at room temperature. Each sample was measured in triplicate at camera setting 14 with acquisition time of 30 s and detection threshold setting of 7. At least 200 completed tracks were analyzed per video. The NTA analytical software version 2.3 was used for capturing and analyzing the data.

RNA Extraction and Copy Number Determination $1 \times 10^6$ transfected or untransfected J558L cells, and 1 mL of culture supernatant, were collected for RNA extraction using ZYGEM RNAtissue Plus System™ (Zygem, Hamilton, NZ) according to the manufacturer's protocol. RNA from cell supernatant (200 µL) was extracted with the Qiagen miRNeasy Serum/Plasma Kit™ following the manufacturer's protocol. IEVs extraction was performed using the ZYGEM RNAtissue Plus System.

cDNA was generated from intracellular and iEV miRNA with Taqman small RNA assays. Input RNA was normalized to 100 ng/sample for intracellular and exosome RNA, and to 25 ng/sample for extracellular miRNA. Taqman MicroRNA Reverse Transcription Kit™ was utilized for all samples per manufacturer's instructions. Cycling conditions for qPCR were: 40 cycles, 96° C. denature 30 secs, 60° C. anneal/extension 30 secs. Results are expressed as RQ (Relative quantity of sample) that was calculated using the formula: Relative Quantity$_{target}$=E$_{target}$ (Cq (control)−Cq (treatment)). Abbreviations: E=Efficiency of primer set; C$_q$ (control)=Average C$_q$ for the control or untreated sample; C$_q$ (treatment)=Average C$_q$ for treated sample; Target=The gene of interest or reference gene.

Copy number was determined in samples normalized at 100 ng cDNA/reaction run concomitantly with a standard curve constructed with known amounts (100-0.01 ng) of miR-335 cDNA and an endogenous control standard curve constructed using known amounts (100-0.01 ng) of snoRNA202 cDNA (Applied Biosystems snoRNA202—assay No. 001232™—specific reverse transcription primers). Samples were run in duplicate. Relative expression was determined by the Ct value of test samples vs. the endogenous control. Once the amount (ng) of specific target was determined, the copy number present in each reaction was calculated using the following formula:

$$(ng \times 6.0223 \times 10^{23})/(\text{number of nucleotides} \times 1.0 \times 10^{9 \times 650})$$

as indicated in http://www.uic.edu/depts/rrc/cgf/realtime/stdcurve.html.

Copy number/EV determination was calculated as follows: (Total copy number/No. EVs sample).

Treatment of LM2 Cells with iEVs and In Vivo Studies

LM2 cells were plated at $1 \times 10^6$ and treated with iEVs at $4 \times 10^4$ iEVs: LM2 cell ratio for 48 hours. After treatment cells were washed 3 times, and resuspended in PBS until implanted ($4 \times 10^5$) into the right mammary fat pad in 50 μl. Mice were monitored for tumor take by palpation. When tumors became palpable, tumor size was determined through two-dimensional caliper measurements every three days. On day 30 and prior to sacrifice on day 60 mice received 6 mg of D-luciferin in PBS i.p., rest for 6 minutes, and imaged in a Xenogen IVIS™ system. At sacrifice tumors were resected, weighed and measured by caliper. Tumor volume was calculated using the ellipsoid formula: $V=1/2 (H \times W^2)$. All animal work was approved by the UCSD Institutional Animal Use and Care Committee.

TABLE 1

Exemplary *Homo sapiens* miRNAs incorporated into compositions as provided herein, and in compositions made by methods as provided herein

| ID | Accession | RPM | Chromosome | Start | End | Strand | Confidence Fetch |
|---|---|---|---|---|---|---|---|
| hsa-let-7a-1 | MI0000060 | 4.85e+04 | chr9 | 94175957 | 94176036 | + | ✓ |
| hsa-let-7a-2 | MI0000061 | 3.92e+04 | chr11 | 122146522 | 122146593 | − | ✓ |
| hsa-let-7a-3 | MI0000062 | 3.89e+04 | chr22 | 46112749 | 46112822 | + | ✓ |
| hsa-let-7b | MI0000063 | 2.65e+04 | chr22 | 46113686 | 46113768 | + | ✓ |
| hsa-let-7c | MI0000064 | 3.3e+04 | chr21 | 16539828 | 16539911 | + | — |
| hsa-let-7d | MI0000065 | 8.98e+03 | chr9 | 94178834 | 94178920 | + | ✓ |
| hsa-let-7e | MI0000066 | 1.2e+04 | chr19 | 51692786 | 51692864 | + | ✓ |
| hsa-let-7f-1 | MI0000067 | 4.01e+04 | chr9 | 94176347 | 94176433 | + | ✓ |
| hsa-let-7f-2 | MI0000068 | 4.13e+04 | chrX | 53557192 | 53557274 | + | ✓ |
| hsa-let-7g | MI0000433 | 9e+03 | chr3 | 52268278 | 52268361 | − | ✓ |
| hsa-let-7i | MI0000434 | 9.01e+03 | chr12 | 62603686 | 62603769 | + | — |
| hsa-mir-1-1 | MI0000651 | 6.42e+03 | chr20 | 62554306 | 62554376 | + | ✓ |
| hsa-mir-1-2 | MI0000437 | 1.57e+04 | chr18 | 21829004 | 21829088 | − | — |
| hsa-mir-7-1 | MI0000263 | 2.6e+03 | chr9 | 83969748 | 83969857 | − | ✓ |
| hsa-mir-7-2 | MI0000264 | 2.3e+03 | chr15 | 88611825 | 88611934 | + | — |
| hsa-mir-7-3 | MI0000265 | 2.29e+03 | chr19 | 4770670 | 4770779 | + | — |
| hsa-mir-9-1 | MI0000466 | 2.14e+03 | chr1 | 156420341 | 156420429 | − | ✓ |
| hsa-mir-9-2 | MI0000467 | 2.15e+03 | chr5 | 88666853 | 88666939 | − | ✓ |
| hsa-mir-9-3 | MI0000468 | 2.7e+03 | chr15 | 89368017 | 89368106 | + | ✓ |
| hsa-mir-10a | MI0000266 | 4.94e+03 | chr17 | 48579838 | 48579947 | − | ✓ |
| hsa-mir-10b | MI0000267 | 7.2e+03 | chr2 | 176150303 | 176150412 | + | ✓ |
| hsa-mir-15a | MI0000069 | 2.93e+03 | chr13 | 50049119 | 50049201 | − | ✓ |
| hsa-mir-15b | MI0000438 | 7.14e+03 | chr3 | 160404588 | 160404685 | + | ✓ |
| hsa-mir-16-1 | MI0000070 | 3.93e+03 | chr13 | 50048973 | 50049061 | − | ✓ |
| hsa-mir-16-2 | MI0000115 | 4.32e+03 | chr3 | 160404745 | 160404825 | + | ✓ |
| hsa-mir-17 | MI0000071 | 7.38e+03 | chr13 | 91350605 | 91350688 | + | ✓ |
| hsa-mir-18a | MI0000072 | 1.28e+03 | chr13 | 91350751 | 91350821 | + | ✓ |
| hsa-mir-18b | MI0001518 | 1.03e+03 | chrX | 134170041 | 134170111 | − | — |
| hsa-mir-19a | MI0000073 | 3.33e+03 | chr13 | 91350891 | 91350972 | + | ✓ |
| hsa-mir-19b-1 | MI0000074 | 4.85e+03 | chr13 | 91351192 | 91351278 | + | ✓ |
| hsa-mir-19b-2 | MI0000075 | 4.86e+03 | chrX | 134169671 | 134169766 | − | ✓ |
| hsa-mir-20a | MI0000076 | 4.21e+03 | chr13 | 91351065 | 91351135 | + | ✓ |
| hsa-mir-20b | MI0001519 | 1.3e+03 | chrX | 134169809 | 134169877 | − | ✓ |
| hsa-mir-21 | MI0000077 | 2.56e+04 | chr17 | 59841266 | 59841337 | + | — |
| hsa-mir-22 | MI0000078 | 3.85e+03 | chr17 | 1713903 | 1713987 | − | ✓ |
| hsa-mir-23a | MI0000079 | 1.69e+04 | chr19 | 13836587 | 13836659 | − | ✓ |
| hsa-mir-23b | MI0000439 | 1.67e+04 | chr9 | 95085208 | 95085304 | + | — |
| hsa-mir-23c | MI0016010 | 3.53e+03 | chrX | 20017088 | 20017187 | − | — |
| hsa-mir-24-1 | MI0000080 | 5.34e+03 | chr9 | 95086021 | 95086088 | + | — |
| hsa-mir-24-2 | MI0000081 | 6.35e+03 | chr19 | 13836287 | 13836359 | − | — |
| hsa-mir-25 | MI0000082 | 1.02e+04 | chr7 | 100093560 | 100093643 | − | ✓ |
| hsa-mir-26a-1 | MI0000083 | 1.03e+04 | chr3 | 37969404 | 37969480 | + | ✓ |
| hsa-mir-26a-2 | MI0000750 | 9.82e+03 | chr12 | 57824609 | 57824692 | − | ✓ |
| hsa-mir-26b | MI0000084 | 5.2e+03 | chr2 | 218402646 | 218402722 | + | — |
| hsa-mir-27a | MI0000085 | 7.56e+03 | chr19 | 13836440 | 13836517 | − | ✓ |
| hsa-mir-27b | MI0000440 | 1.02e+04 | chr9 | 95085445 | 95085541 | + | ✓ |
| hsa-mir-28 | MI0000086 | 4.94e+03 | chr3 | 188688781 | 188688866 | + | ✓ |
| hsa-mir-29a | MI0000087 | 1.09e+04 | chr7 | 130876747 | 130876810 | − | ✓ |

TABLE 1-continued

Exemplary *Homo sapiens* miRNAs incorporated into compositions as provided herein, and in compositions made by methods as provided herein

| ID | Accession | RPM | Chromosome | Start | End | Strand | Confidence Fetch |
|---|---|---|---|---|---|---|---|
| hsa-mir-29b-1 | MI0000105 | 6.19e+03 | chr7 | 130877459 | 130877539 | − | ✓ |
| hsa-mir-29b-2 | MI0000107 | 6.13e+03 | chr1 | 207802443 | 207802523 | − | — |
| hsa-mir-29c | MI0000735 | 8.57e+03 | chr1 | 207801852 | 207801939 | − | — |
| hsa-mir-30a | MI0000088 | 1.07e+04 | chr6 | 71403551 | 71403621 | − | ✓ |
| hsa-mir-30b | MI0000441 | 2.22e+03 | chr8 | 134800520 | 134800607 | − | ✓ |
| hsa-mir-30c-1 | MI0000736 | 2.95e+03 | chr1 | 40757284 | 40757372 | + | ✓ |
| hsa-mir-30c-2 | MI0000254 | 2.83e+03 | chr6 | 71376960 | 71377031 | − | ✓ |
| hsa-mir-30d | MI0000255 | 6.9e+03 | chr8 | 134804876 | 134804945 | − | ✓ |
| hsa-mir-30e | MI0000749 | 8.1e+03 | chr1 | 40754355 | 40754446 | + | ✓ |
| hsa-mir-31 | MI0000089 | 3.89e+03 | chr9 | 21512115 | 21512185 | − | ✓ |
| hsa-mir-32 | MI0000090 | 729 | chr9 | 109046229 | 109046298 | − | ✓ |
| hsa-mir-33a | MI0000091 | 1.12e+03 | chr22 | 41900944 | 41901012 | + | ✓ |
| hsa-mir-33b | MI0003646 | 269 | chr17 | 17813836 | 17813931 | − | ✓ |
| hsa-mir-34a | MI0000268 | 1.13e+03 | chr1 | 9151668 | 9151777 | − | ✓ |
| hsa-mir-34b | MI0000742 | 792 | chr11 | 111512938 | 111513021 | + | ✓ |
| hsa-mir-34c | MI0000743 | 1.36e+03 | chr11 | 111513439 | 111513535 | + | ✓ |
| hsa-mir-92a-1 | MI0000093 | 7.52e+03 | chr13 | 91351314 | 91351391 | + | ✓ |
| hsa-mir-92a-2 | MI0000094 | 6.11e+03 | chrX | 134169538 | 134169612 | − | ✓ |
| hsa-mir-92b | MI0003560 | 3.33e+03 | chr1 | 155195177 | 155195272 | + | ✓ |
| hsa-mir-93 | MI0000095 | 1.95e+03 | chr7 | 100093768 | 100093847 | − | ✓ |
| hsa-mir-95 | MI0000097 | 1.06e+03 | chr4 | 8005301 | 8005381 | − | — |
| hsa-mir-96 | MI0000098 | 685 | chr7 | 129774692 | 129774769 | − | ✓ |
| hsa-mir-98 | MI0000100 | 4.35e+03 | chrX | 53556223 | 53556341 | − | ✓ |
| hsa-mir-99a | MI0000101 | 3.4e+03 | chr21 | 16539089 | 16539169 | + | ✓ |
| hsa-mir-99b | MI0000746 | 1.66e+03 | chr19 | 51692612 | 51692681 | + | ✓ |
| hsa-mir-100 | MI0000102 | 2.8e+03 | chr11 | 122152229 | 122152308 | − | ✓ |
| hsa-mir-101-1 | MI0000103 | 4.43e+03 | chr1 | 65058434 | 65058508 | − | ✓ |
| hsa-mir-101-2 | MI0000739 | 4.64e+03 | chr9 | 4850297 | 4850375 | + | — |
| hsa-mir-103a-1 | MI0000109 | 3.7e+04 | chr5 | 168560896 | 168560973 | − | — |
| hsa-mir-103a-2 | MI0000108 | 3.7e+04 | chr20 | 3917494 | 3917571 | + | ✓ |
| hsa-mir-103b-1 | MI0007261 | 22.4 | chr5 | 168560904 | 168560965 | + | — |
| hsa-mir-103b-2 | MI0007262 | — | chr20 | 3917502 | 3917563 | − | — |
| hsa-mir-105-1 | MI0000111 | 152 | chrX | 152392219 | 152392299 | − | ✓ |
| hsa-mir-105-2 | MI0000112 | 152 | chrX | 152394412 | 152394492 | − | ✓ |
| hsa-mir-106a | MI0000113 | 4.41e+03 | chrX | 134170198 | 134170278 | − | ✓ |
| hsa-mir-106b | MI0000734 | 2.46e+03 | chr7 | 100093993 | 100094074 | − | ✓ |
| hsa-mir-107 | MI0000114 | 3.55e+04 | chr10 | 89592747 | 89592827 | − | — |
| hsa-mir-122 | MI0000442 | 292 | chr18 | 58451074 | 58451158 | + | — |
| hsa-mir-124-1 | MI0000443 | 801 | chr8 | 9903388 | 9903472 | − | — |
| hsa-mir-124-2 | MI0000444 | 818 | chr8 | 64379149 | 64379257 | + | — |
| hsa-mir-124-3 | MI0000445 | 760 | chr20 | 63178500 | 63178586 | + | — |
| hsa-mir-125a | MI0000469 | 4.02e+03 | chr19 | 51693254 | 51693339 | + | ✓ |
| hsa-mir-125b-1 | MI0000446 | 7.47e+03 | chr11 | 122099757 | 122099844 | − | ✓ |
| hsa-mir-125b-2 | MI0000470 | 7.32e+03 | chr21 | 16590237 | 16590325 | + | ✓ |
| hsa-mir-126 | MI0000471 | 1.1e+04 | chr9 | 136670602 | 136670686 | + | ✓ |
| hsa-mir-127 | MI0000472 | 2.09e+03 | chr14 | 100882979 | 100883075 | + | — |
| hsa-mir-128-1 | MI0000447 | 4.19e+03 | chr2 | 135665397 | 135665478 | + | ✓ |
| hsa-mir-128-2 | MI0000727 | 3.98e+03 | chr3 | 35744476 | 35744559 | + | ✓ |
| hsa-mir-129-1 | MI0000252 | 1.18e+03 | chr7 | 128207872 | 128207943 | + | ✓ |
| hsa-mir-129-2 | MI0000473 | 1.17e+03 | chr11 | 43581394 | 43581483 | + | ✓ |
| hsa-mir-130a | MI0000448 | 5.44e+03 | chr11 | 57641198 | 57641286 | + | — |
| hsa-mir-130b | MI0000748 | 1.49e+03 | chr22 | 21653304 | 21653385 | + | ✓ |
| hsa-mir-132 | MI0000449 | 616 | chr17 | 2049908 | 2050008 | − | ✓ |
| hsa-mir-133a-1 | MI0000450 | 2.05e+03 | chr18 | 21825698 | 21825785 | − | ✓ |
| hsa-mir-133a-2 | MI0000451 | 2.05e+03 | chr20 | 62564912 | 62565013 | + | ✓ |
| hsa-mir-133b | MI0000822 | 1.42e+03 | chr6 | 52148923 | 52149041 | + | — |
| hsa-mir-134 | MI0000474 | 568 | chr14 | 101054687 | 101054759 | + | ✓ |
| hsa-mir-135a-1 | MI0000452 | 719 | chr3 | 52294219 | 52294308 | − | ✓ |
| hsa-mir-135a-2 | MI0000453 | 846 | chr12 | 97563812 | 97563911 | + | — |
| hsa-mir-135b | MI0000810 | 699 | chr1 | 205448302 | 205448398 | − | ✓ |
| hsa-mir-136 | MI0000475 | 1.04e+03 | chr14 | 100884702 | 100884783 | + | ✓ |
| hsa-mir-137 | MI0000454 | 120 | chr1 | 98046070 | 98046171 | − | — |
| hsa-mir-138-1 | MI0000476 | 850 | chr3 | 44114212 | 44114310 | + | ✓ |
| hsa-mir-138-2 | MI0000455 | 859 | chr16 | 56858518 | 56858601 | + | — |
| hsa-mir-139 | MI0000261 | 495 | chr11 | 72615063 | 72615130 | − | ✓ |
| hsa-mir-140 | MI0000456 | 9.46e+03 | chr16 | 69933081 | 69933180 | + | ✓ |
| hsa-mir-141 | MI0000457 | 3.72e+03 | chr12 | 6964097 | 6964191 | + | ✓ |
| hsa-mir-142 | MI0000458 | 1.3e+04 | chr17 | 58331232 | 58331318 | − | — |
| hsa-mir-143 | MI0000459 | 2.47e+04 | chr5 | 149428918 | 149429023 | + | ✓ |
| hsa-mir-144 | MI0000460 | 3.44e+03 | chr17 | 28861533 | 28861618 | − | ✓ |
| hsa-mir-145 | MI0000461 | 2.39e+04 | chr5 | 149430646 | 149430733 | + | — |
| hsa-mir-146a | MI0000477 | 6.67e+03 | chr5 | 160485352 | 160485450 | + | ✓ |
| hsa-mir-146b | MI0003129 | 4.26e+03 | chr10 | 102436512 | 102436584 | + | — |
| hsa-mir-147a | MI0000262 | 719 | chr9 | 120244979 | 120245050 | − | — |
| hsa-mir-147b | MI0005544 | 720 | chr15 | 45433050 | 45433129 | + | — |

TABLE 1-continued

Exemplary *Homo sapiens* miRNAs incorporated into compositions as provided herein, and in compositions made by methods as provided herein

| ID | Accession | RPM | Chromosome | Start | End | Strand | Confidence Fetch |
|---|---|---|---|---|---|---|---|
| hsa-mir-148a | MI0000253 | 4.3e+03 | chr7 | 25949919 | 25949986 | − | ✓ |
| hsa-mir-148b | MI0000811 | 1.1e+03 | chr12 | 54337216 | 54337314 | + | ✓ |
| hsa-mir-149 | MI0000478 | 913 | chr2 | 240456001 | 240456089 | + | ✓ |
| hsa-mir-150 | MI0000479 | 2.64e+03 | chr19 | 49500785 | 49500868 | − | ✓ |
| hsa-mir-151a | MI0000809 | 7.65e+03 | chr8 | 140732564 | 140732653 | − | ✓ |
| hsa-mir-151b | MI0003772 | 4.29e+03 | chr14 | 100109419 | 100109514 | − | — |
| hsa-mir-152 | MI0000462 | 1.62e+03 | chr17 | 48037161 | 48037247 | − | ✓ |
| hsa-mir-153-1 | MI0000463 | 153 | chr2 | 219294111 | 219294200 | − | — |
| hsa-mir-153-2 | MI0000464 | 159 | chr7 | 157574336 | 157574422 | − | — |
| hsa-mir-154 | MI0000480 | 202 | chr14 | 101059755 | 101059838 | + | ✓ |
| hsa-mir-155 | MI0000681 | 2.94e+03 | chr21 | 25573980 | 25574044 | + | ✓ |
| hsa-mir-181a-1 | MI0000289 | 7.78e+03 | chr1 | 198859044 | 198859153 | − | ✓ |
| hsa-mir-181a-2 | MI0000269 | 7.01e+03 | chr9 | 124692442 | 124692551 | + | — |
| hsa-mir-181b-1 | MI0000270 | 4.24e+03 | chr1 | 198858873 | 198858982 | − | — |
| hsa-mir-181b-2 | MI0000683 | 4.37e+03 | chr9 | 124693710 | 124693798 | + | ✓ |
| hsa-mir-181c | MI0000271 | 1.22e+03 | chr19 | 13874699 | 13874808 | + | — |
| hsa-mir-181d | MI0003139 | 3.65e+03 | chr19 | 13874875 | 13875011 | + | ✓ |
| hsa-mir-182 | MI0000272 | 1.58e+03 | chr7 | 129770383 | 129770492 | − | ✓ |
| hsa-mir-183 | MI0000273 | 844 | chr7 | 129774905 | 129775014 | − | ✓ |
| hsa-mir-184 | MI0000481 | 595 | chr15 | 79209788 | 79209871 | + | — |
| hsa-mir-185 | MI0000482 | 5.32e+03 | chr22 | 20033139 | 20033220 | + | ✓ |
| hsa-mir-186 | MI0000483 | 2.37e+03 | chr1 | 71067631 | 71067716 | − | ✓ |
| hsa-mir-187 | MI0000274 | 331 | chr18 | 35904818 | 35904926 | − | — |
| hsa-mir-188 | MI0000484 | 642 | chrX | 50003503 | 50003588 | + | ✓ |
| hsa-mir-190a | MI0000486 | 703 | chr15 | 62823957 | 62824041 | + | ✓ |
| hsa-mir-190b | MI0005545 | 199 | chr1 | 154193665 | 154193743 | − | — |
| hsa-mir-191 | MI0000465 | 1.24e+04 | chr3 | 49020618 | 49020709 | − | ✓ |
| hsa-mir-192 | MI0000234 | 4.81e+03 | chr11 | 64891137 | 64891246 | − | ✓ |
| hsa-mir-193a | MI0000487 | 3.28e+03 | chr17 | 31559996 | 31560083 | + | ✓ |
| hsa-mir-193b | MI0003137 | 1.96e+03 | chr16 | 14303967 | 14304049 | + | ✓ |
| hsa-mir-194-1 | MI0000488 | 381 | chr1 | 220118157 | 220118241 | − | — |
| hsa-mir-194-2 | MI0000732 | 535 | chr11 | 64891355 | 64891439 | − | ✓ |
| hsa-mir-195 | MI0000489 | 3.34e+03 | chr17 | 7017615 | 7017701 | − | ✓ |
| hsa-mir-196a-1 | MI0000238 | 1.21e+03 | chr17 | 48632490 | 48632559 | − | — |
| hsa-mir-196a-2 | MI0000279 | 1.37e+03 | chr12 | 53991738 | 53991847 | + | ✓ |
| hsa-mir-196b | MI0001150 | 1.21e+03 | chr7 | 27169480 | 27169563 | − | ✓ |
| hsa-mir-197 | MI0000239 | 1.42e+03 | chr1 | 109598893 | 109598967 | + | ✓ |
| hsa-mir-198 | MI0000240 | 107 | chr3 | 120395668 | 120395729 | − | — |
| hsa-mir-199a-1 | MI0000242 | 7.48e+03 | chr19 | 10817426 | 10817496 | − | ✓ |
| hsa-mir-199a-2 | MI0000281 | 7.63e+03 | chr1 | 172144535 | 172144644 | − | ✓ |
| hsa-mir-199b | MI0000282 | 6.16e+03 | chr9 | 128244721 | 128244800 | − | ✓ |
| hsa-mir-200a | MI0000737 | 2.4e+03 | chr1 | 1167863 | 1167952 | + | ✓ |
| hsa-mir-200b | MI0000342 | 6.62e+03 | chr1 | 1167104 | 1167198 | + | ✓ |
| hsa-mir-200c | MI0000650 | 8.46e+03 | chr12 | 6963699 | 6963766 | + | ✓ |
| hsa-mir-202 | MI0003130 | 1.7e+03 | chr10 | 133247511 | 133247620 | − | ✓ |
| hsa-mir-203a | MI0000283 | 2.75e+03 | chr14 | 104117405 | 104117514 | + | ✓ |
| hsa-mir-203b | MI0017343 | 15.8 | chr14 | 104117418 | 104117503 | − | — |
| hsa-mir-204 | MI0000284 | 1.59e+03 | chr9 | 70809975 | 70810084 | − | — |
| hsa-mir-205 | MI0000285 | 1.01e+04 | chr1 | 209432133 | 209432242 | + | — |
| hsa-mir-206 | MI0000490 | 1.86e+03 | chr6 | 52144349 | 52144434 | + | — |
| hsa-mir-208a | MI0000251 | 205 | chr14 | 23388596 | 23388666 | − | — |
| hsa-mir-208b | MI0005570 | 779 | chr14 | 23417987 | 23418063 | − | ✓ |
| hsa-mir-210 | MI0000286 | 2.05e+03 | chr11 | 568089 | 568198 | − | ✓ |
| hsa-mir-211 | MI0000287 | 9.29e+03 | chr15 | 31065032 | 31065141 | − | ✓ |
| hsa-mir-212 | MI0000288 | 285 | chr17 | 2050271 | 2050380 | − | — |
| hsa-mir-214 | MI0000290 | 2.16e+03 | chr1 | 172138798 | 172138907 | − | — |
| hsa-mir-215 | MI0000291 | 1.95e+03 | chr1 | 220117853 | 220117962 | − | — |
| hsa-mir-216a | MI0000292 | 159 | chr2 | 55988950 | 55989059 | − | — |
| hsa-mir-216b | MI0005569 | 188 | chr2 | 56000714 | 56000795 | − | — |
| hsa-mir-217 | MI0000293 | 315 | chr2 | 55982967 | 55983076 | − | — |
| hsa-mir-218-1 | MI0000294 | 1.46e+03 | chr4 | 20528275 | 20528384 | + | ✓ |
| hsa-mir-218-2 | MI0000295 | 1.38e+03 | chr5 | 168768146 | 168768255 | − | — |
| hsa-mir-219a-1 | MI0000296 | 163 | chr6 | 33207835 | 33207944 | + | ✓ |
| hsa-mir-219a-2 | MI0000740 | 1.04e+03 | chr9 | 128392618 | 128392714 | − | ✓ |
| hsa-mir-219b | MI0017299 | 23.2 | chr9 | 128392621 | 128392708 | + | ✓ |
| hsa-mir-221 | MI0000298 | 8.06e+03 | chrX | 45746157 | 45746266 | − | ✓ |
| hsa-mir-222 | MI0000299 | 5.15e+03 | chrX | 45747015 | 45747124 | − | ✓ |
| hsa-mir-223 | MI0000300 | 5.81e+03 | chrX | 66018870 | 66018979 | + | ✓ |
| hsa-mir-224 | MI0000301 | 620 | chrX | 151958578 | 151958658 | − | — |
| hsa-mir-296 | MI0000747 | 355 | chr20 | 58817615 | 58817694 | − | ✓ |
| hsa-mir-297 | MI0005775 | 52.3 | chr4 | 110860582 | 110860647 | − | — |
| hsa-mir-298 | MI0005523 | 16.3 | chr20 | 58818226 | 58818313 | − | — |
| hsa-mir-299 | MI0000744 | 399 | chr14 | 101023794 | 101023856 | + | ✓ |
| hsa-mir-300 | MI0005525 | 56.7 | chr14 | 101041363 | 101041445 | + | — |
| hsa-mir-301a | MI0000745 | 582 | chr17 | 59151136 | 59151221 | − | ✓ |

TABLE 1-continued

Exemplary *Homo sapiens* miRNAs incorporated into compositions as provided herein, and in compositions made by methods as provided herein

| ID | Accession | RPM | Chromosome | Start | End | Strand | Confidence Fetch |
|---|---|---|---|---|---|---|---|
| hsa-mir-301b | MI0005568 | 124 | chr22 | 21652981 | 21653058 | + | ✓ |
| hsa-mir-302a | MI0000738 | 1.87e+04 | chr4 | 112648183 | 112648251 | − | ✓ |
| hsa-mir-302b | MI0000772 | 4.58e+04 | chr4 | 112648485 | 112648557 | − | — |
| hsa-mir-302c | MI0000773 | 1.35e+05 | chr4 | 112648363 | 112648430 | − | ✓ |
| hsa-mir-302d | MI0000774 | 6.57e+04 | chr4 | 112648004 | 112648071 | − | — |
| hsa-mir-302e | MI0006417 | 8.41e+03 | chr11 | 7234766 | 7234837 | + | — |
| hsa-mir-302f | MI0006418 | 3.42e+03 | chr18 | 30298910 | 30298960 | + | — |
| hsa-mir-320a | MI0000542 | 1.28e+04 | chr8 | 22244962 | 22245043 | − | — |
| hsa-mir-320b-1 | MI0003776 | 9.8e+03 | chr1 | 116671749 | 116671827 | + | — |
| hsa-mir-320b-2 | MI0003839 | 1.05e+04 | chr1 | 224257004 | 224257141 | − | — |
| hsa-mir-320c-1 | MI0003778 | 4.98e+03 | chr18 | 21683510 | 21683597 | + | — |
| hsa-mir-320c-2 | MI0008191 | 3.67e+03 | chr18 | 24321686 | 24321735 | + | — |
| hsa-mir-320d-1 | MI0008190 | 3.13e+03 | chr13 | 40727828 | 40727875 | − | — |
| hsa-mir-320d-2 | MI0008192 | 3.14e+03 | chrX | 140926172 | 140926219 | − | — |
| hsa-mir-320e | MI0014234 | 1.62e+03 | chr19 | 46709293 | 46709345 | + | — |
| hsa-mir-323a | MI0000807 | 196 | chr14 | 101025732 | 101025817 | + | ✓ |
| hsa-mir-323b | MI0014206 | 60.2 | chr14 | 101056219 | 101056300 | + | — |
| hsa-mir-324 | MI0000813 | 1.47e+03 | chr17 | 7223297 | 7223379 | − | — |
| hsa-mir-325 | MI0000824 | 42.5 | chrX | 77005404 | 77005501 | − | — |
| hsa-mir-326 | MI0000808 | 128 | chr11 | 75335092 | 75335186 | − | — |
| hsa-mir-328 | MI0000804 | 424 | chr16 | 67202321 | 67202395 | − | ✓ |
| hsa-mir-329-1 | MI0001725 | 198 | chr14 | 101026785 | 101026864 | + | ✓ |
| hsa-mir-329-2 | MI0001726 | 198 | chr14 | 101027100 | 101027183 | + | ✓ |
| hsa-mir-330 | MI0000803 | 2.01e+03 | chr19 | 45638994 | 45639087 | − | ✓ |
| hsa-mir-331 | MI0000812 | 1.43e+03 | chr12 | 95308420 | 95308513 | + | ✓ |
| hsa-mir-335 | MI0000816 | 1.11e+04 | chr7 | 130496111 | 130496204 | + | ✓ |
| hsa-mir-337 | MI0000806 | 792 | chr14 | 100874493 | 100874585 | + | ✓ |
| hsa-mir-338 | MI0000814 | 677 | chr17 | 81125883 | 81125949 | − | ✓ |
| hsa-mir-339 | MI0000815 | 2.02e+03 | chr7 | 1022933 | 1023026 | − | ✓ |
| hsa-mir-340 | MI0000802 | 774 | chr5 | 180015303 | 180015397 | − | ✓ |
| hsa-mir-342 | MI0000805 | 1.39e+03 | chr14 | 100109655 | 100109753 | + | ✓ |
| hsa-mir-345 | MI0000825 | 2.86e+03 | chr14 | 100307859 | 100307956 | + | ✓ |
| hsa-mir-346 | MI0000826 | 102 | chr10 | 86264694 | 86264788 | − | — |
| hsa-mir-361 | MI0000760 | 2.44e+03 | chrX | 85903636 | 85903707 | − | ✓ |
| hsa-mir-362 | MI0000762 | 673 | chrX | 50008964 | 50009028 | + | ✓ |
| hsa-mir-363 | MI0000764 | 4.72e+03 | chrX | 134169378 | 134169452 | − | ✓ |
| hsa-mir-365a | MI0000767 | 3.85e+03 | chr16 | 14309285 | 14309371 | + | ✓ |
| hsa-mir-365b | MI0000769 | 3.76e+03 | chr17 | 31575411 | 31575521 | + | ✓ |
| hsa-mir-367 | MI0000775 | 140 | chr4 | 112647874 | 112647941 | − | — |
| hsa-mir-369 | MI0000777 | 468 | chr14 | 101065598 | 101065667 | + | ✓ |
| hsa-mir-370 | MI0000778 | 179 | chr14 | 100911139 | 100911213 | + | ✓ |
| hsa-mir-371a | MI0000779 | 56.4 | chr19 | 53787675 | 53787741 | + | — |
| hsa-mir-371b | MI0017393 | 294 | chr19 | 53787677 | 53787742 | − | — |
| hsa-mir-372 | MI0000780 | 108 | chr19 | 53787890 | 53787956 | + | — |
| hsa-mir-373 | MI0000781 | 79 | chr19 | 53788705 | 53788773 | + | — |
| hsa-mir-374a | MI0000782 | 2.01e+03 | chrX | 74287286 | 74287357 | − | ✓ |
| hsa-mir-374b | MI0005566 | 1.29e+03 | chrX | 74218547 | 74218618 | − | ✓ |
| hsa-mir-374c | MI0016684 | 563 | chrX | 74218549 | 74218618 | + | — |
| hsa-mir-375 | MI0000783 | 1.05e+03 | chr2 | 219001645 | 219001708 | − | — |
| hsa-mir-376a-1 | MI0000784 | 1.01e+03 | chr14 | 101040782 | 101040849 | + | ✓ |
| hsa-mir-376a-2 | MI0003529 | 1.05e+03 | chr14 | 101040069 | 101040148 | + | ✓ |
| hsa-mir-376b | MI0002466 | 912 | chr14 | 101040436 | 101040535 | + | — |
| hsa-mir-376c | MI0000776 | 1.35e+03 | chr14 | 101039690 | 101039755 | + | ✓ |
| hsa-mir-377 | MI0000785 | 325 | chr14 | 101062050 | 101062118 | + | ✓ |
| hsa-mir-378a | MI0000786 | 7.03e+03 | chr5 | 149732825 | 149732890 | + | ✓ |
| hsa-mir-378b | MI0014154 | 1.17e+03 | chr3 | 10330229 | 10330285 | + | — |
| hsa-mir-378c | MI0015825 | 3.22e+03 | chr10 | 130962588 | 130962668 | − | — |
| hsa-mir-378d-1 | MI0016749 | 1.76e+03 | chr4 | 5923275 | 5923328 | − | — |
| hsa-mir-378d-2 | MI0003840 | 2.28e+03 | chr8 | 93916022 | 93916119 | − | — |
| hsa-mir-378e | MI0016750 | 726 | chr5 | 170028488 | 170028566 | + | — |
| hsa-mir-378f | MI0016756 | 1.95e+03 | chr1 | 23929070 | 23929147 | + | — |
| hsa-mir-378g | MI0016761 | 1.69e+03 | chr1 | 94745860 | 94745900 | − | — |
| hsa-mir-378h | MI0016808 | 609 | chr5 | 154829458 | 154829540 | + | — |
| hsa-mir-378i | MI0016902 | 1.68e+03 | chr22 | 41923222 | 41923297 | − | — |
| hsa-mir-378j | MI0021273 | 101 | chr17 | 37614931 | 37615039 | − | — |
| hsa-mir-379 | MI0000787 | 324 | chr14 | 101022066 | 101022132 | + | ✓ |
| hsa-mir-380 | MI0000788 | 67 | chr14 | 101025017 | 101025077 | + | — |
| hsa-mir-381 | MI0000789 | 486 | chr14 | 101045920 | 101045994 | + | ✓ |
| hsa-mir-382 | MI0000790 | 523 | chr14 | 101054306 | 101054381 | + | ✓ |
| hsa-mir-383 | MI0000791 | 196 | chr8 | 14853438 | 14853510 | − | — |
| hsa-mir-384 | MI0001145 | — | chrX | 76919273 | 76919360 | − | — |
| hsa-mir-409 | MI0001735 | 443 | chr14 | 101065300 | 101065378 | + | ✓ |
| hsa-mir-410 | MI0002465 | 159 | chr14 | 101065912 | 101065991 | + | — |
| hsa-mir-411 | MI0003675 | 533 | chr14 | 101023325 | 101023420 | + | ✓ |
| hsa-mir-412 | MI0002464 | 87.3 | chr14 | 101065447 | 101065537 | + | — |

TABLE 1-continued

Exemplary Homo sapiens miRNAs incorporated into compositions as provided
herein, and in compositions made by methods as provided herein

| ID | Accession | RPM | Chromosome | Start | End | Strand | Confidence Fetch |
|---|---|---|---|---|---|---|---|
| hsa-mir-421 | MI0003685 | 409 | chrX | 74218377 | 74218461 | − | — |
| hsa-mir-422a | MI0001444 | 140 | chr15 | 63870930 | 63871019 | − | — |
| hsa-mir-423 | MI0001445 | 8.78e+03 | chr17 | 30117079 | 30117172 | + | ✓ |
| hsa-mir-424 | MI0001446 | 1.08e+04 | chrX | 134546614 | 134546711 | − | ✓ |
| hsa-mir-425 | MI0001448 | 2.44e+03 | chr3 | 49020148 | 49020234 | − | ✓ |
| hsa-mir-429 | MI0001641 | 904 | chr1 | 1169005 | 1169087 | + | — |
| hsa-mir-431 | MI0001721 | 52.1 | chr14 | 100881007 | 100881120 | + | ✓ |
| hsa-mir-432 | MI0003133 | 761 | chr14 | 100884483 | 100884576 | + | — |
| hsa-mir-433 | MI0001723 | 522 | chr14 | 100881886 | 100881978 | + | ✓ |
| hsa-mir-448 | MI0001637 | 24.7 | chrX | 114823454 | 114823564 | + | — |
| hsa-mir-449a | MI0001648 | 197 | chr5 | 55170532 | 55170622 | − | — |
| hsa-mir-449b | MI0003673 | 195 | chr5 | 55170646 | 55170742 | − | — |
| hsa-mir-449c | MI0003823 | 102 | chr5 | 55172262 | 55172353 | − | — |
| hsa-mir-450a-1 | MI0001652 | 1.75e+03 | chrX | 134540341 | 134540431 | − | ✓ |
| hsa-mir-450a-2 | MI0003187 | 1.73e+03 | chrX | 134540508 | 134540607 | − | ✓ |
| hsa-mir-450b | MI0005531 | 482 | chrX | 134540185 | 134540262 | − | ✓ |
| hsa-mir-451a | MI0001729 | 6.77e+03 | chr17 | 28861369 | 28861440 | − | — |
| hsa-mir-451b | MI0017360 | 150 | chr17 | 28861371 | 28861438 | + | — |
| hsa-mir-452 | MI0001733 | 729 | chrX | 151959628 | 151959712 | − | — |
| hsa-mir-454 | MI0003820 | 377 | chr17 | 59137758 | 59137872 | − | ✓ |
| hsa-mir-455 | MI0003513 | 3.06e+03 | chr9 | 114209434 | 114209529 | + | — |
| hsa-mir-466 | MI0014157 | 65.9 | chr3 | 31161704 | 31161787 | − | — |
| hsa-mir-483 | MI0002467 | 1.11e+03 | chr11 | 2134134 | 2134209 | − | ✓ |
| hsa-mir-484 | MI0002468 | 1.36e+03 | chr16 | 15643294 | 15643372 | + | — |
| hsa-mir-485 | MI0002469 | 252 | chr14 | 101055419 | 101055491 | + | ✓ |
| hsa-mir-486-1 | MI0002470 | 2.87e+03 | chr8 | 41660441 | 41660508 | − | ✓ |
| hsa-mir-486-2 | MI0023622 | 32.1 | chr8 | 41660444 | 41660507 | + | — |
| hsa-mir-487a | MI0002471 | 71.2 | chr14 | 101052446 | 101052525 | + | — |
| hsa-mir-487b | MI0003530 | 306 | chr14 | 101046455 | 101046538 | + | ✓ |
| hsa-mir-488 | MI0003123 | 317 | chr1 | 177029363 | 177029445 | − | ✓ |
| hsa-mir-489 | MI0003124 | 72.4 | chr7 | 93483936 | 93484019 | − | — |
| hsa-mir-490 | MI0003125 | 119 | chr7 | 136903167 | 136903294 | + | ✓ |
| hsa-mir-491 | MI0003126 | 60.6 | chr9 | 20716105 | 20716188 | + | ✓ |
| hsa-mir-492 | MI0003131 | 324 | chr12 | 94834398 | 94834513 | + | — |
| hsa-mir-493 | MI0003132 | 529 | chr14 | 100869060 | 100869148 | + | ✓ |
| hsa-mir-494 | MI0003134 | 214 | chr14 | 101029634 | 101029714 | + | ✓ |
| hsa-mir-495 | MI0003135 | 496 | chr14 | 101033755 | 101033836 | + | ✓ |
| hsa-mir-496 | MI0003136 | 53.9 | chr14 | 101060573 | 101060674 | + | — |
| hsa-mir-497 | MI0003138 | 1.35e+03 | chr17 | 7017911 | 7018022 | − | ✓ |
| hsa-mir-498 | MI0003142 | 57.2 | chr19 | 53674197 | 53674320 | + | — |
| hsa-mir-499a | MI0003183 | 318 | chr20 | 34990376 | 34990472 | + | — |
| hsa-mir-499b | MI0017396 | 2.07 | chr20 | 34990400 | 34990472 | − | — |
| hsa-mir-500a | MI0003184 | 1.35e+03 | chrX | 50008431 | 50008514 | + | ✓ |
| hsa-mir-500b | MI0015903 | 272 | chrX | 50010672 | 50010750 | + | — |
| hsa-mir-501 | MI0003185 | 1.08e+03 | chrX | 50009722 | 50009805 | + | — |
| hsa-mir-502 | MI0003186 | 1.26e+03 | chrX | 50014598 | 50014683 | + | — |
| hsa-mir-503 | MI0003188 | 1.59e+03 | chrX | 134546328 | 134546398 | − | ✓ |
| hsa-mir-504 | MI0003189 | 80.9 | chrX | 138667711 | 138667793 | − | ✓ |
| hsa-mir-505 | MI0003190 | 916 | chrX | 139924148 | 139924231 | − | ✓ |
| hsa-mir-506 | MI0003193 | 619 | chrX | 147230720 | 147230843 | − | ✓ |
| hsa-mir-507 | MI0003194 | 89.2 | chrX | 147230984 | 147231077 | − | — |
| hsa-mir-508 | MI0003195 | 5.42e+03 | chrX | 147236913 | 147237027 | − | ✓ |
| hsa-mir-509-1 | MI0003196 | 5.29e+03 | chrX | 147260532 | 147260625 | − | ✓ |
| hsa-mir-509-2 | MI0005530 | 5.14e+03 | chrX | 147258760 | 147258850 | − | ✓ |
| hsa-mir-509-3 | MI0005717 | 9e+03 | chrX | 147259652 | 147259726 | − | ✓ |
| hsa-mir-510 | MI0003197 | 159 | chrX | 147272335 | 147272408 | − | ✓ |
| hsa-mir-511 | MI0003127 | 78.7 | chr10 | 17845107 | 17845193 | + | — |
| hsa-mir-512-1 | MI0003140 | 72.6 | chr19 | 53666679 | 53666762 | + | — |
| hsa-mir-512-2 | MI0003141 | 73.1 | chr19 | 53669157 | 53669254 | + | — |
| hsa-mir-513a-1 | MI0003191 | 371 | chrX | 147213463 | 147213591 | − | — |
| hsa-mir-513a-2 | MI0003192 | 381 | chrX | 147225826 | 147225952 | − | — |
| hsa-mir-513b | MI0006648 | 314 | chrX | 147199044 | 147199127 | − | — |
| hsa-mir-513c | MI0006649 | 329 | chrX | 147189704 | 147189787 | − | ✓ |
| hsa-mir-514a-1 | MI0003198 | 3.49e+03 | chrX | 147279247 | 147279344 | − | ✓ |
| hsa-mir-514a-2 | MI0003199 | 3.21e+03 | chrX | 147281943 | 147282030 | − | ✓ |
| hsa-mir-514a-3 | MI0003200 | 3.23e+03 | chrX | 147284641 | 147284728 | − | ✓ |
| hsa-mir-514b | MI0014251 | 404 | chrX | 147250151 | 147250230 | − | ✓ |
| hsa-mir-515-1 | MI0003144 | 118 | chr19 | 53679003 | 53679085 | + | — |
| hsa-mir-515-2 | MI0003147 | 116 | chr19 | 53685009 | 53685091 | + | — |
| hsa-mir-516a-1 | MI0003180 | 518 | chr19 | 53756741 | 53756830 | + | — |
| hsa-mir-516a-2 | MI0003181 | 464 | chr19 | 53761133 | 53761222 | + | — |
| hsa-mir-516b-1 | MI0003172 | 193 | chr19 | 53736845 | 53736934 | + | — |
| hsa-mir-516b-2 | MI0003167 | 1.84e+03 | chr19 | 53725442 | 53725526 | + | — |
| hsa-mir-517a | MI0003161 | 169 | chr19 | 53712268 | 53712354 | + | — |
| hsa-mir-517b | MI0003165 | 193 | chr19 | 53721076 | 53721142 | + | — |

TABLE 1-continued

Exemplary Homo sapiens miRNAs incorporated into compositions as provided herein, and in compositions made by methods as provided herein

| ID | Accession | RPM | Chromosome | Start | End | Strand | Confidence Fetch |
|---|---|---|---|---|---|---|---|
| hsa-mir-517c | MI0003174 | 176 | chr19 | 53741313 | 53741407 | + | — |
| hsa-mir-518a-1 | MI0003170 | 125 | chr19 | 53731006 | 53731090 | + | — |
| hsa-mir-518a-2 | MI0003173 | 118 | chr19 | 53739333 | 53739419 | + | — |
| hsa-mir-518b | MI0003156 | 148 | chr19 | 53702737 | 53702819 | + | — |
| hsa-mir-518c | MI0003159 | 83.3 | chr19 | 53708735 | 53708835 | + | — |
| hsa-mir-518d | MI0003171 | 190 | chr19 | 53734877 | 53734963 | + | — |
| hsa-mir-518e | MI0003169 | 205 | chr19 | 53729838 | 53729925 | + | — |
| hsa-mir-518f | MI0003154 | 193 | chr19 | 53700015 | 53700101 | + | — |
| hsa-mir-519a-1 | MI0003178 | 318 | chr19 | 53752397 | 53752481 | + | ✓ |
| hsa-mir-519a-2 | MI0003182 | 347 | chr19 | 53762344 | 53762430 | + | — |
| hsa-mir-519b | MI0003151 | 359 | chr19 | 53695213 | 53695293 | + | — |
| hsa-mir-519c | MI0003148 | 218 | chr19 | 53686469 | 53686555 | + | — |
| hsa-mir-519d | MI0003162 | 199 | chr19 | 53713347 | 53713434 | + | — |
| hsa-mir-519e | MI0003145 | 1.12e+03 | chr19 | 53679940 | 53680023 | + | — |
| hsa-mir-520a | MI0003149 | 45.1 | chr19 | 53690881 | 53690965 | + | — |
| hsa-mir-520b | MI0003155 | 257 | chr19 | 53701227 | 53701287 | + | — |
| hsa-mir-520c | MI0003158 | 362 | chr19 | 53707453 | 53707539 | + | — |
| hsa-mir-520d | MI0003164 | 141 | chr19 | 53720096 | 53720182 | + | — |
| hsa-mir-520e | MI0003143 | 95.4 | chr19 | 53675711 | 53675797 | + | — |
| hsa-mir-520f | MI0003146 | 276 | chr19 | 53682159 | 53682245 | + | — |
| hsa-mir-520g | MI0003166 | 136 | chr19 | 53722166 | 53722255 | + | — |
| hsa-mir-520h | MI0003175 | 127 | chr19 | 53742512 | 53742599 | + | — |
| hsa-mir-521-1 | MI0003176 | 238 | chr19 | 53748636 | 53748722 | + | — |
| hsa-mir-521-2 | MI0003163 | 284 | chr19 | 53716594 | 53716680 | + | — |
| hsa-mir-522 | MI0003177 | 226 | chr19 | 53751211 | 53751297 | + | — |
| hsa-mir-523 | MI0003153 | 190 | chr19 | 53698385 | 53698471 | + | — |
| hsa-mir-524 | MI0003160 | 133 | chr19 | 53711002 | 53711088 | + | — |
| hsa-mir-525 | MI0003152 | 144 | chr19 | 53697533 | 53697617 | + | — |
| hsa-mir-526a-1 | MI0003157 | 192 | chr19 | 53706252 | 53706336 | + | — |
| hsa-mir-526a-2 | MI0003168 | 170 | chr19 | 53726922 | 53726986 | + | — |
| hsa-mir-526b | MI0003150 | 216 | chr19 | 53694393 | 53694475 | + | — |
| hsa-mir-527 | MI0003179 | 199 | chr19 | 53754018 | 53754102 | + | — |
| hsa-mir-532 | MI0003205 | 2.28e+03 | chrX | 50003148 | 50003238 | + | ✓ |
| hsa-mir-539 | MI0003514 | 452 | chr14 | 101047321 | 101047398 | + | ✓ |
| hsa-mir-541 | MI0005539 | 60.1 | chr14 | 101064495 | 101064578 | + | — |
| hsa-mir-542 | MI0003686 | 1.24e+03 | chrX | 134541341 | 134541437 | − | ✓ |
| hsa-mir-543 | MI0005565 | 355 | chr14 | 101031987 | 101032064 | + | ✓ |
| hsa-mir-544a | MI0003515 | 83 | chr14 | 101048658 | 101048748 | + | — |
| hsa-mir-544b | MI0014159 | 100 | chr3 | 124732439 | 124732516 | + | — |
| hsa-mir-545 | MI0003516 | 157 | chrX | 74287104 | 74287209 | − | ✓ |
| hsa-mir-548a-1 | MI0003593 | 197 | chr6 | 18571784 | 18571880 | + | — |
| hsa-mir-548a-2 | MI0003598 | 202 | chr6 | 135239160 | 135239256 | + | — |
| hsa-mir-548a-3 | MI0003612 | 97 | chr8 | 104484369 | 104484465 | − | ✓ |
| hsa-mir-548aa-1 | MI0016689 | 136 | chr8 | 123348034 | 123348130 | + | — |
| hsa-mir-548aa-2 | MI0016690 | 431 | chr17 | 67471489 | 67471585 | + | — |
| hsa-mir-548ab | MI0016752 | 195 | chr3 | 103524033 | 103524116 | − | — |
| hsa-mir-548ac | MI0016762 | 196 | chr1 | 116560024 | 116560111 | − | — |
| hsa-mir-548ad | MI0016770 | 294 | chr2 | 35471405 | 35471486 | + | — |
| hsa-mir-548ae-1 | MI0016779 | 64.3 | chr2 | 184378975 | 184379044 | + | — |
| hsa-mir-548ae-2 | MI0016780 | 344 | chr5 | 58530043 | 58530109 | − | — |
| hsa-mir-548ag-1 | MI0016793 | 99.7 | chr4 | 60922619 | 60922684 | + | — |
| hsa-mir-548ag-2 | MI0016794 | 109 | chr20 | 60564562 | 60564625 | + | — |
| hsa-mir-548ah | MI0016796 | 67.2 | chr4 | 76575551 | 76575626 | + | — |
| hsa-mir-548ai | MI0016813 | 145 | chr6 | 99124609 | 99124696 | + | — |
| hsa-mir-548aj-1 | MI0016814 | 81.6 | chr6 | 132115192 | 132115263 | − | — |
| hsa-mir-548aj-2 | MI0016815 | 165 | chrX | 38023895 | 38023986 | − | — |
| hsa-mir-548ak | MI0016840 | 146 | chr10 | 12130760 | 12130816 | − | — |
| hsa-mir-548al | MI0016851 | 112 | chr11 | 74399237 | 74399333 | + | — |
| hsa-mir-548am | MI0016904 | 316 | chrX | 16627012 | 16627085 | − | — |
| hsa-mir-548an | MI0016907 | 91.8 | chrX | 106639814 | 106639896 | + | — |
| hsa-mir-548ao | MI0017871 | 106 | chr8 | 41271048 | 41271143 | − | — |
| hsa-mir-548ap | MI0017875 | 155 | chr15 | 85825635 | 85825730 | + | — |
| hsa-mir-548aq | MI0019130 | 100 | chr3 | 185767847 | 185767904 | − | — |
| hsa-mir-548ar | MI0019131 | 109 | chr13 | 114244505 | 114244561 | + | ✓ |
| hsa-mir-548as | MI0019132 | 111 | chr13 | 92490163 | 92490220 | + | — |
| hsa-mir-548at | MI0019137 | 56.3 | chr17 | 42494773 | 42494830 | + | — |
| hsa-mir-548au | MI0019145 | 230 | chr9 | 93594841 | 93594894 | + | — |
| hsa-mir-548av | MI0019152 | 69.2 | chr18 | 72853321 | 72853382 | − | — |
| hsa-mir-548aw | MI0019283 | 58.6 | chr9 | 132945707 | 132945771 | + | — |
| hsa-mir-548ax | MI0019286 | 101 | chrX | 11318614 | 11318686 | − | — |
| hsa-mir-548ay | MI0022210 | 334 | chr3 | 32506283 | 32506389 | − | — |
| hsa-mir-548az | MI0022212 | 214 | chr8 | 119325171 | 119325265 | + | — |
| hsa-mir-548b | MI0003596 | 282 | chr6 | 119069047 | 119069143 | − | — |
| hsa-mir-548ba | MI0025747 | 4.23 | chr2 | 49059603 | 49059658 | + | — |
| hsa-mir-548bb | MI0029321 | 4.32 | chr3 | 60617805 | 60617870 | − | — |

TABLE 1-continued

Exemplary Homo sapiens miRNAs incorporated into compositions as provided herein, and in compositions made by methods as provided herein

| ID | Accession | RPM | Chromosome | Start | End | Strand | Confidence Fetch |
|---|---|---|---|---|---|---|---|
| hsa-mir-548c | MI0003630 | 331 | chr12 | 64622509 | 64622605 | + | — |
| hsa-mir-548d-1 | MI0003668 | 341 | chr8 | 123348034 | 123348130 | − | ✓ |
| hsa-mir-548d-2 | MI0003671 | 335 | chr17 | 67471489 | 67471585 | − | ✓ |
| hsa-mir-548e | MI0006344 | 102 | chr10 | 110988926 | 110989013 | + | ✓ |
| hsa-mir-548f-1 | MI0006374 | 129 | chr10 | 54607874 | 54607957 | − | — |
| hsa-mir-548f-2 | MI0006375 | 61.7 | chr2 | 212426263 | 212426360 | − | — |
| hsa-mir-548f-3 | MI0006376 | 59.6 | chr5 | 110513829 | 110513915 | − | — |
| hsa-mir-548f-4 | MI0006377 | 187 | chr7 | 147378017 | 147378121 | − | — |
| hsa-mir-548f-5 | MI0006378 | 28.2 | chrX | 32641474 | 32641559 | − | — |
| hsa-mir-548g | MI0006395 | 109 | chr4 | 147344629 | 147344717 | − | — |
| hsa-mir-548h-1 | MI0006411 | 113 | chr14 | 64095024 | 64095125 | − | — |
| hsa-mir-548h-2 | MI0006412 | 169 | chr16 | 11306440 | 11306527 | − | — |
| hsa-mir-548h-3 | MI0006413 | 367 | chr17 | 13543529 | 13543646 | − | — |
| hsa-mir-548h-4 | MI0006414 | 251 | chr8 | 27048853 | 27048963 | − | ✓ |
| hsa-mir-548h-5 | MI0016751 | 106 | chr6 | 131792172 | 131792231 | + | — |
| hsa-mir-548i-1 | MI0006421 | 226 | chr3 | 125790404 | 125790552 | − | — |
| hsa-mir-548i-2 | MI0006422 | 227 | chr4 | 9556168 | 9556316 | − | — |
| hsa-mir-548i-3 | MI0006423 | 223 | chr8 | 8088941 | 8089089 | − | — |
| hsa-mir-548i-4 | MI0006424 | 205 | chrX | 84225752 | 84225828 | − | — |
| hsa-mir-548j | MI0006345 | 114 | chr22 | 26555212 | 26555323 | − | ✓ |
| hsa-mir-548k | MI0006354 | 157 | chr11 | 70283955 | 70284070 | + | — |
| hsa-mir-548l | MI0006361 | 86.3 | chr11 | 94466495 | 94466580 | − | — |
| hsa-mir-548m | MI0006400 | 49.4 | chrX | 95063141 | 95063226 | − | — |
| hsa-mir-548n | MI0006399 | 232 | chr7 | 34940760 | 34940914 | − | — |
| hsa-mir-548o | MI0006402 | 33.2 | chr7 | 102405742 | 102405855 | − | — |
| hsa-mir-548o-2 | MI0016746 | 288 | chr20 | 38516563 | 38516632 | + | ✓ |
| hsa-mir-548p | MI0006420 | 60.2 | chr5 | 100816482 | 100816565 | − | — |
| hsa-mir-548q | MI0010637 | 111 | chr10 | 12725254 | 12725353 | − | — |
| hsa-mir-548s | MI0014141 | 52.1 | chr2 | 11767444 | 11767525 | + | — |
| hsa-mir-548t | MI0014164 | 116 | chr4 | 173268160 | 173268233 | + | — |
| hsa-mir-548u | MI0014168 | 45.8 | chr6 | 57390132 | 57390212 | + | — |
| hsa-mir-548v | MI0014174 | 160 | chr8 | 17681578 | 17681657 | − | ✓ |
| hsa-mir-548w | MI0014222 | 157 | chr16 | 26025237 | 26025310 | + | — |
| hsa-mir-548x | MI0014244 | 129 | chr21 | 18686090 | 18686164 | − | — |
| hsa-mir-548x-2 | MI0016833 | 187 | chr13 | 65966330 | 65966429 | − | — |
| hsa-mir-548y | MI0016595 | 81.8 | chr14 | 47760995 | 47761104 | − | — |
| hsa-mir-548z | MI0016688 | 213 | chr12 | 64622509 | 64622605 | − | — |
| hsa-mir-549a | MI0003679 | 80.9 | chr15 | 80841978 | 80842073 | − | — |
| hsa-mir-550a-1 | MI0003600 | 329 | chr7 | 30289794 | 30289890 | + | — |
| hsa-mir-550a-2 | MI0003601 | 329 | chr7 | 32732981 | 32733077 | + | — |
| hsa-mir-550a-3 | MI0003762 | 319 | chr7 | 29680734 | 29680828 | + | — |
| hsa-mir-550b-1 | MI0016686 | 147 | chr7 | 30289794 | 30289890 | − | — |
| hsa-mir-550b-2 | MI0016687 | 153 | chr7 | 32732981 | 32733077 | − | — |
| hsa-mir-551a | MI0003556 | 117 | chr1 | 3560695 | 3560790 | − | — |
| hsa-mir-551b | MI0003575 | 237 | chr3 | 168551854 | 168551949 | + | ✓ |
| hsa-mir-552 | MI0003557 | 72.2 | chr1 | 34669599 | 34669694 | + | — |
| hsa-mir-553 | MI0003558 | 16.4 | chr1 | 100281241 | 100281308 | + | — |
| hsa-mir-554 | MI0003559 | 10.5 | chr1 | 151545796 | 151545891 | + | — |
| hsa-mir-555 | MI0003561 | 30.6 | chr1 | 155346350 | 155346445 | − | — |
| hsa-mir-556 | MI0003562 | 71.7 | chr1 | 162342546 | 162342640 | + | ✓ |
| hsa-mir-557 | MI0003563 | 121 | chr1 | 168375524 | 168375621 | + | — |
| hsa-mir-558 | MI0003564 | 446 | chr2 | 32532153 | 32532246 | + | — |
| hsa-mir-559 | MI0003565 | 341 | chr2 | 47377675 | 47377770 | + | — |
| hsa-mir-561 | MI0003567 | 75.7 | chr2 | 188297492 | 188297588 | + | ✓ |
| hsa-mir-562 | MI0003568 | 190 | chr2 | 232172653 | 232172747 | + | — |
| hsa-mir-563 | MI0003569 | 444 | chr3 | 15873771 | 15873849 | + | — |
| hsa-mir-564 | MI0003570 | 56.9 | chr3 | 44861888 | 44861981 | + | — |
| hsa-mir-566 | MI0003572 | 2.13e+03 | chr3 | 50173326 | 50173419 | + | — |
| hsa-mir-567 | MI0003573 | 1.54e+03 | chr3 | 112112801 | 112112898 | + | — |
| hsa-mir-568 | MI0003574 | 83.7 | chr3 | 114316475 | 114316569 | − | — |
| hsa-mir-569 | MI0003576 | 16.9 | chr3 | 171106664 | 171106759 | − | — |
| hsa-mir-570 | MI0003577 | 61.4 | chr3 | 195699401 | 195699497 | + | ✓ |
| hsa-mir-571 | MI0003578 | 18.1 | chr4 | 350157 | 350252 | + | — |
| hsa-mir-572 | MI0003579 | 289 | chr4 | 11368827 | 11368921 | + | — |
| hsa-mir-573 | MI0003580 | 24.3 | chr4 | 24520192 | 24520290 | − | — |
| hsa-mir-574 | MI0003581 | 3.48e+03 | chr4 | 38868032 | 38868127 | + | ✓ |
| hsa-mir-575 | MI0003582 | 176 | chr4 | 82753337 | 82753430 | − | — |
| hsa-mir-576 | MI0003583 | 356 | chr4 | 109488698 | 109488795 | + | ✓ |
| hsa-mir-577 | MI0003584 | 114 | chr4 | 114656759 | 114656854 | + | ✓ |
| hsa-mir-578 | MI0003585 | 17.8 | chr4 | 165386242 | 165386337 | + | — |
| hsa-mir-579 | MI0003586 | 83 | chr5 | 32394378 | 32394475 | − | ✓ |
| hsa-mir-580 | MI0003587 | 75 | chr5 | 36147892 | 36147988 | − | — |
| hsa-mir-581 | MI0003588 | 12.3 | chr5 | 53951504 | 53951599 | − | — |
| hsa-mir-582 | MI0003589 | 471 | chr5 | 59703606 | 59703703 | − | ✓ |
| hsa-mir-583 | MI0003590 | 30.8 | chr5 | 96079138 | 96079212 | + | — |

TABLE 1-continued

Exemplary Homo sapiens miRNAs incorporated into compositions as provided herein, and in compositions made by methods as provided herein

| ID | Accession | RPM | Chromosome | Start | End | Strand | Confidence Fetch |
|---|---|---|---|---|---|---|---|
| hsa-mir-584 | MI0003591 | 1.49e+03 | chr5 | 149062313 | 149062409 | − | ✓ |
| hsa-mir-585 | MI0003592 | 115 | chr5 | 169263601 | 169263694 | − | — |
| hsa-mir-586 | MI0003594 | — | chr6 | 45197674 | 45197770 | − | — |
| hsa-mir-587 | MI0003595 | 27.2 | chr6 | 106784125 | 106784220 | + | — |
| hsa-mir-588 | MI0003597 | 22 | chr6 | 126484631 | 126484713 | + | — |
| hsa-mir-589 | MI0003599 | 284 | chr7 | 5495819 | 5495917 | − | ✓ |
| hsa-mir-590 | MI0003602 | 523 | chr7 | 74191198 | 74191294 | + | ✓ |
| hsa-mir-591 | MI0003603 | 38.6 | chr7 | 96219662 | 96219756 | − | — |
| hsa-mir-592 | MI0003604 | 65.3 | chr7 | 127058088 | 127058184 | − | — |
| hsa-mir-593 | MI0003605 | 148 | chr7 | 128081861 | 128081960 | + | — |
| hsa-mir-595 | MI0003607 | 89 | chr7 | 158532718 | 158532813 | − | — |
| hsa-mir-596 | MI0003608 | 19.8 | chr8 | 1817231 | 1817307 | + | — |
| hsa-mir-597 | MI0003609 | 22.5 | chr8 | 9741672 | 9741768 | + | — |
| hsa-mir-598 | MI0003610 | 327 | chr8 | 11035206 | 11035302 | − | — |
| hsa-mir-599 | MI0003611 | 99 | chr8 | 99536636 | 99536730 | − | — |
| hsa-mir-600 | MI0003613 | 55.2 | chr9 | 123111546 | 123111643 | − | — |
| hsa-mir-601 | MI0003614 | 85 | chr9 | 123402525 | 123402603 | − | — |
| hsa-mir-602 | MI0003615 | 104 | chr9 | 137838419 | 137838516 | + | — |
| hsa-mir-603 | MI0003616 | 66.1 | chr10 | 24275685 | 24275781 | + | — |
| hsa-mir-604 | MI0003617 | 43.9 | chr10 | 29545004 | 29545097 | − | — |
| hsa-mir-605 | MI0003618 | 172 | chr10 | 51299573 | 51299655 | + | — |
| hsa-mir-606 | MI0003619 | 74 | chr10 | 75552458 | 75552553 | + | — |
| hsa-mir-607 | MI0003620 | 33.1 | chr10 | 96828669 | 96828764 | − | — |
| hsa-mir-608 | MI0003621 | 122 | chr10 | 100974985 | 100975084 | + | — |
| hsa-mir-609 | MI0003622 | 43.2 | chr10 | 104218789 | 104218883 | − | — |
| hsa-mir-610 | MI0003623 | 59.4 | chr11 | 28056815 | 28056910 | + | — |
| hsa-mir-611 | MI0003624 | 51.4 | chr11 | 61792495 | 61792561 | − | — |
| hsa-mir-612 | MI0003625 | 104 | chr11 | 65444458 | 65444557 | + | — |
| hsa-mir-613 | MI0003626 | 175 | chr12 | 12764649 | 12764743 | + | — |
| hsa-mir-614 | MI0003627 | 21.3 | chr12 | 12915829 | 12915918 | + | — |
| hsa-mir-615 | MI0003628 | 656 | chr12 | 54033950 | 54034045 | + | ✓ |
| hsa-mir-616 | MI0003629 | 48.4 | chr12 | 57519163 | 57519259 | − | ✓ |
| hsa-mir-617 | MI0003631 | 44.9 | chr12 | 80832533 | 80832629 | + | — |
| hsa-mir-618 | MI0003632 | 31.1 | chr12 | 80935736 | 80935833 | − | — |
| hsa-mir-619 | MI0003633 | 951 | chr12 | 108836908 | 108837006 | − | — |
| hsa-mir-620 | MI0003634 | 142 | chr12 | 116148560 | 116148654 | − | — |
| hsa-mir-621 | MI0003635 | 233 | chr13 | 40810766 | 40810861 | + | — |
| hsa-mir-622 | MI0003636 | 147 | chr13 | 90231182 | 90231277 | + | — |
| hsa-mir-623 | MI0003637 | 20.2 | chr13 | 99356131 | 99356228 | + | — |
| hsa-mir-624 | MI0003638 | 107 | chr14 | 31014646 | 31014742 | − | ✓ |
| hsa-mir-625 | MI0003639 | 416 | chr14 | 65471102 | 65471186 | + | ✓ |
| hsa-mir-626 | MI0003640 | 65.3 | chr15 | 41691585 | 41691678 | + | — |
| hsa-mir-627 | MI0003641 | 109 | chr15 | 42199570 | 42199666 | − | ✓ |
| hsa-mir-628 | MI0003642 | 153 | chr15 | 55372940 | 55373034 | − | ✓ |
| hsa-mir-629 | MI0003643 | 571 | chr15 | 70079372 | 70079468 | − | ✓ |
| hsa-mir-630 | MI0003644 | 0.222 | chr15 | 72587217 | 72587313 | + | — |
| hsa-mir-631 | MI0003645 | 17.8 | chr15 | 75353611 | 75353685 | − | — |
| hsa-mir-632 | MI0003647 | 293 | chr17 | 32350109 | 32350202 | + | — |
| hsa-mir-633 | MI0003648 | 24.1 | chr17 | 62944215 | 62944312 | + | — |
| hsa-mir-634 | MI0003649 | 255 | chr17 | 66787072 | 66787168 | + | — |
| hsa-mir-635 | MI0003650 | 305 | chr17 | 68424451 | 68424548 | − | — |
| hsa-mir-636 | MI0003651 | 2.37e+03 | chr17 | 76736450 | 76736548 | − | — |
| hsa-mir-637 | MI0003652 | 744 | chr19 | 3961414 | 3961512 | − | — |
| hsa-mir-638 | MI0003653 | 227 | chr19 | 10718404 | 10718503 | + | — |
| hsa-mir-639 | MI0003654 | 677 | chr19 | 14529543 | 14529640 | + | — |
| hsa-mir-640 | MI0003655 | 137 | chr19 | 19435063 | 19435158 | + | — |
| hsa-mir-641 | MI0003656 | 92.4 | chr19 | 40282543 | 40282641 | − | — |
| hsa-mir-642a | MI0003657 | 202 | chr19 | 45674928 | 45675024 | + | ✓ |
| hsa-mir-642b | MI0016685 | 172 | chr19 | 45674932 | 45675008 | − | — |
| hsa-mir-643 | MI0003658 | 17.2 | chr19 | 52281797 | 52281893 | + | — |
| hsa-mir-644a | MI0003659 | 49.9 | chr20 | 34466325 | 34466418 | + | — |
| hsa-mir-645 | MI0003660 | 21 | chr20 | 50585786 | 50585879 | + | — |
| hsa-mir-646 | MI0003661 | 38 | chr20 | 60308474 | 60308567 | + | — |
| hsa-mir-647 | MI0003662 | 338 | chr20 | 63942631 | 63942726 | − | — |
| hsa-mir-648 | MI0003663 | 106 | chr22 | 17980868 | 17980961 | − | — |
| hsa-mir-649 | MI0003664 | 46.1 | chr22 | 21034176 | 21034272 | − | — |
| hsa-mir-650 | MI0003665 | 109 | chr22 | 22822776 | 22822871 | + | — |
| hsa-mir-651 | MI0003666 | 168 | chrX | 8126965 | 8127061 | + | ✓ |
| hsa-mir-652 | MI0003667 | 1.58e+03 | chrX | 110055329 | 110055426 | + | ✓ |
| hsa-mir-653 | MI0003674 | 109 | chr7 | 93482760 | 93482855 | − | — |
| hsa-mir-654 | MI0003676 | 227 | chr14 | 101040219 | 101040299 | + | ✓ |
| hsa-mir-655 | MI0003677 | 222 | chr14 | 101049550 | 101049646 | + | — |
| hsa-mir-656 | MI0003678 | 73.9 | chr14 | 101066724 | 101066801 | + | — |
| hsa-mir-657 | MI0003681 | 130 | chr17 | 81125276 | 81125373 | − | — |
| hsa-mir-658 | MI0003682 | 96.1 | chr22 | 37844272 | 37844371 | − | — |

TABLE 1-continued

Exemplary Homo sapiens miRNAs incorporated into compositions as provided
herein, and in compositions made by methods as provided herein

| ID | Accession | RPM | Chromosome | Start | End | Strand | Confidence Fetch |
|---|---|---|---|---|---|---|---|
| hsa-mir-659 | MI0003683 | 57.9 | chr22 | 37847678 | 37847774 | − | — |
| hsa-mir-660 | MI0003684 | 1.22e+03 | chrX | 50013241 | 50013337 | + | ✓ |
| hsa-mir-661 | MI0003669 | 65.4 | chr8 | 143945191 | 143945279 | − | — |
| hsa-mir-662 | MI0003670 | 65.2 | chr16 | 770183 | 770277 | + | — |
| hsa-mir-663a | MI0003672 | 654 | chr20 | 26208186 | 26208278 | − | — |
| hsa-mir-663b | MI0006336 | 286 | chr2 | 132256966 | 132257080 | − | — |
| hsa-mir-664a | MI0006442 | 979 | chr1 | 220200538 | 220200619 | − | — |
| hsa-mir-664b | MI0019134 | 198 | chrX | 154768596 | 154768656 | + | ✓ |
| hsa-mir-665 | MI0005563 | 225 | chr14 | 100875033 | 100875104 | + | — |
| hsa-mir-668 | MI0003761 | 12.7 | chr14 | 101055258 | 101055323 | + | — |
| hsa-mir-670 | MI0003933 | 26.6 | chr11 | 43559656 | 43559753 | + | — |
| hsa-mir-671 | MI0003760 | 589 | chr7 | 151238421 | 151238538 | + | ✓ |
| hsa-mir-675 | MI0005416 | 1.31e+03 | chr11 | 1996759 | 1996831 | − | ✓ |
| hsa-mir-676 | MI0016436 | 42.4 | chrX | 70022857 | 70022923 | + | — |
| hsa-mir-708 | MI0005543 | 943 | chr11 | 79402022 | 79402109 | − | ✓ |
| hsa-mir-711 | MI0012488 | 68.4 | chr3 | 48578902 | 48578977 | − | — |
| hsa-mir-718 | MI0012489 | 236 | chrX | 154019920 | 154019989 | − | — |
| hsa-mir-744 | MI0005559 | 1.22e+03 | chr17 | 12081899 | 12081996 | + | ✓ |
| hsa-mir-758 | MI0003757 | 212 | chr14 | 101026020 | 101026107 | + | ✓ |
| hsa-mir-759 | MI0004065 | 71.6 | chr13 | 52810050 | 52810140 | + | — |
| hsa-mir-760 | MI0005567 | 753 | chr1 | 93846832 | 93846911 | + | — |
| hsa-mir-761 | MI0003941 | 164 | chr1 | 51836344 | 51836402 | − | — |
| hsa-mir-762 | MI0003892 | 192 | chr16 | 30893903 | 30893985 | + | — |
| hsa-mir-764 | MI0003944 | 47.3 | chrX | 114639435 | 114639519 | + | — |
| hsa-mir-765 | MI0005116 | 188 | chr1 | 156936131 | 156936244 | − | — |
| hsa-mir-766 | MI0003836 | 503 | chrX | 119646738 | 119646848 | − | ✓ |
| hsa-mir-767 | MI0003763 | 283 | chrX | 152393421 | 152393529 | − | ✓ |
| hsa-mir-769 | MI0003834 | 243 | chr19 | 46018932 | 46019049 | + | ✓ |
| hsa-mir-770 | MI0005118 | 46.7 | chr14 | 100852390 | 100852487 | + | — |
| hsa-mir-802 | MI0003906 | 40.1 | chr21 | 35720715 | 35720808 | + | — |
| hsa-mir-873 | MI0005564 | 316 | chr9 | 28888879 | 28888955 | − | ✓ |
| hsa-mir-874 | MI0005532 | 494 | chr5 | 137647572 | 137647649 | − | ✓ |
| hsa-mir-875 | MI0005541 | 60.4 | chr8 | 99536786 | 99536861 | − | — |
| hsa-mir-876 | MI0005542 | 368 | chr9 | 28863626 | 28863706 | − | ✓ |
| hsa-mir-877 | MI0005561 | 888 | chr6 | 30584332 | 30584417 | + | — |
| hsa-mir-885 | MI0005560 | 184 | chr3 | 10394489 | 10394562 | − | ✓ |
| hsa-mir-887 | MI0005562 | 343 | chr5 | 15935182 | 15935260 | + | ✓ |
| hsa-mir-888 | MI0005537 | 7.45 | chrX | 145994784 | 145994860 | − | — |
| hsa-mir-889 | MI0005540 | 178 | chr14 | 101047901 | 101047979 | + | — |
| hsa-mir-890 | MI0005533 | 33.8 | chrX | 145994275 | 145994351 | − | — |
| hsa-mir-891a | MI0005524 | 38.9 | chrX | 146027794 | 146027872 | − | — |
| hsa-mir-891b | MI0005534 | 16.1 | chrX | 146001053 | 146001131 | − | — |
| hsa-mir-892a | MI0005528 | 0.506 | chrX | 145996669 | 145996743 | − | — |
| hsa-mir-892b | MI0005538 | 32.3 | chrX | 145997198 | 145997274 | − | — |
| hsa-mir-892c | MI0022560 | 287 | chrX | 145992750 | 145992826 | − | — |
| hsa-mir-920 | MI0005712 | 37.5 | chr12 | 24212421 | 24212495 | + | — |
| hsa-mir-921 | MI0005713 | 33.8 | chr1 | 166154743 | 166154798 | − | — |
| hsa-mir-922 | MI0005714 | 166 | chr3 | 197674496 | 197674576 | − | — |
| hsa-mir-924 | MI0005716 | 372 | chr18 | 39622123 | 39622199 | − | — |
| hsa-mir-933 | MI0005755 | 31.1 | chr2 | 175167633 | 175167709 | − | — |
| hsa-mir-934 | MI0005756 | 202 | chrX | 136550878 | 136550960 | + | — |
| hsa-mir-935 | MI0005757 | 873 | chr19 | 53982307 | 53982397 | + | — |
| hsa-mir-936 | MI0005758 | 36.2 | chr10 | 104048089 | 104048186 | − | — |
| hsa-mir-937 | MI0005759 | 59.1 | chr8 | 143812957 | 143813042 | − | — |
| hsa-mir-938 | MI0005760 | 30.3 | chr10 | 29602264 | 29602346 | − | — |
| hsa-mir-939 | MI0005761 | 92.7 | chr8 | 144394149 | 144394230 | − | — |
| hsa-mir-940 | MI0005762 | 321 | chr16 | 2271747 | 2271840 | + | — |
| hsa-mir-941-1 | MI0005763 | 601 | chr20 | 63919449 | 63919523 | + | — |
| hsa-mir-941-2 | MI0005764 | 611 | chr20 | 63919505 | 63919576 | + | — |
| hsa-mir-941-3 | MI0005765 | 591 | chr20 | 63919561 | 63919632 | + | — |
| hsa-mir-941-4 | MI0005766 | 590 | chr20 | 63919756 | 63919827 | + | — |
| hsa-mir-941-5 | MI0031520 | 280 | chr20 | 63919868 | 63919939 | + | ✓ |
| hsa-mir-942 | MI0005767 | 208 | chr1 | 117094643 | 117094728 | + | ✓ |
| hsa-mir-943 | MI0005768 | 16.1 | chr4 | 1986384 | 1986477 | − | — |
| hsa-mir-944 | MI0005769 | 864 | chr3 | 189829922 | 189830009 | + | — |
| hsa-mir-1178 | MI0006271 | 117 | chr12 | 119713634 | 119713724 | − | — |
| hsa-mir-1179 | MI0006272 | 133 | chr15 | 88608107 | 88608197 | + | — |
| hsa-mir-1180 | MI0006273 | 631 | chr17 | 19344506 | 19344574 | − | — |
| hsa-mir-1181 | MI0006274 | 258 | chr19 | 10403458 | 10403538 | − | — |
| hsa-mir-1182 | MI0006275 | 164 | chr1 | 231019828 | 231019924 | − | — |
| hsa-mir-1183 | MI0006276 | 78.1 | chr7 | 21471058 | 21471146 | + | — |
| hsa-mir-1184-1 | MI0006277 | 248 | chrX | 154887360 | 154887458 | − | — |
| hsa-mir-1184-2 | MI0015971 | 247 | chrX | 155383100 | 155383198 | − | — |
| hsa-mir-1184-3 | MI0015972 | 247 | chrX | 155457517 | 155457615 | + | — |
| hsa-mir-1185-1 | MI0003844 | 223 | chr14 | 101042977 | 101043062 | + | ✓ |

TABLE 1-continued

Exemplary *Homo sapiens* miRNAs incorporated into compositions as provided herein, and in compositions made by methods as provided herein

| ID | Accession | RPM | Chromosome | Start | End | Strand | Confidence Fetch |
|---|---|---|---|---|---|---|---|
| hsa-mir-1185-2 | MI0003821 | 243 | chr14 | 101044198 | 101044283 | + | ✓ |
| hsa-mir-1193 | MI0014205 | 77.8 | chr14 | 101030052 | 101030129 | + | — |
| hsa-mir-1197 | MI0006656 | 31.6 | chr14 | 101025564 | 101025651 | + | — |
| hsa-mir-1199 | MI0020340 | 0.171 | chr19 | 14073361 | 14073479 | + | — |
| hsa-mir-1200 | MI0006332 | 7.19 | chr7 | 36919357 | 36919432 | − | — |
| hsa-mir-1202 | MI0006334 | 81.2 | chr6 | 155946797 | 155946879 | + | — |
| hsa-mir-1203 | MI0006335 | 329 | chr17 | 48156427 | 48156511 | − | — |
| hsa-mir-1204 | MI0006337 | 22.3 | chr8 | 127795962 | 127796028 | + | — |
| hsa-mir-1205 | MI0006338 | 67.8 | chr8 | 127960633 | 127960695 | + | — |
| hsa-mir-1206 | MI0006339 | — | chr8 | 128008898 | 128008956 | + | — |
| hsa-mir-1207 | MI0006340 | 106 | chr8 | 128049152 | 128049238 | + | — |
| hsa-mir-1208 | MI0006341 | 37 | chr8 | 128150116 | 128150188 | + | — |
| hsa-mir-1224 | MI0003764 | 222 | chr3 | 184241405 | 184241489 | + | — |
| hsa-mir-1225 | MI0006311 | 111 | chr16 | 2090195 | 2090284 | − | — |
| hsa-mir-1226 | MI0006313 | 105 | chr3 | 47849555 | 47849629 | + | — |
| hsa-mir-1227 | MI0006316 | 32.6 | chr19 | 2234062 | 2234149 | − | — |
| hsa-mir-1228 | MI0006318 | 160 | chr12 | 57194504 | 57194576 | + | — |
| hsa-mir-1229 | MI0006319 | 45.2 | chr5 | 179798278 | 179798346 | − | — |
| hsa-mir-1231 | MI0006321 | 549 | chr1 | 201808611 | 201808702 | + | — |
| hsa-mir-1233-1 | MI0006323 | 114 | chr15 | 34382069 | 34382150 | − | — |
| hsa-mir-1233-2 | MI0015973 | 119 | chr15 | 34528290 | 34528371 | − | — |
| hsa-mir-1234 | MI0006324 | 1.38 | chr8 | 144400086 | 144400165 | − | — |
| hsa-mir-1236 | MI0006326 | 49.7 | chr6 | 31956839 | 31956940 | − | — |
| hsa-mir-1237 | MI0006327 | 485 | chr11 | 64368602 | 64368703 | + | — |
| hsa-mir-1238 | MI0006328 | 79.4 | chr19 | 10552122 | 10552204 | + | — |
| hsa-mir-1243 | MI0006373 | 101 | chr4 | 113106863 | 113106955 | + | — |
| hsa-mir-1244-1 | MI0006379 | 84.3 | chr2 | 231713314 | 231713398 | + | — |
| hsa-mir-1244-2 | MI0015974 | 92.3 | chr5 | 118974586 | 118974670 | + | — |
| hsa-mir-1244-3 | MI0015975 | 92.5 | chr12 | 9239467 | 9239551 | − | — |
| hsa-mir-1244-4 | MI0031511 | 9.93 | chr12 | 12111952 | 12112036 | + | — |
| hsa-mir-1245a | MI0006380 | 43.2 | chr2 | 188978092 | 188978161 | + | — |
| hsa-mir-1245b | MI0017431 | 25.7 | chr2 | 188978093 | 188978161 | − | — |
| hsa-mir-1246 | MI0006381 | 9.16e+03 | chr2 | 176600980 | 176601052 | − | — |
| hsa-mir-1247 | MI0006382 | 540 | chr14 | 101560287 | 101560422 | − | — |
| hsa-mir-1248 | MI0006383 | 166 | chr3 | 186786672 | 186786777 | + | — |
| hsa-mir-1249 | MI0006384 | 247 | chr22 | 45200954 | 45201019 | − | ✓ |
| hsa-mir-1250 | MI0006385 | 19.4 | chr17 | 81133196 | 81133308 | − | — |
| hsa-mir-1251 | MI0006386 | 19.8 | chr12 | 97491909 | 97491978 | + | — |
| hsa-mir-1252 | MI0006434 | 41.4 | chr12 | 79419257 | 79419321 | + | — |
| hsa-mir-1253 | MI0006387 | 4.8e+03 | chr17 | 2748078 | 2748182 | − | — |
| hsa-mir-1254-1 | MI0006388 | 397 | chr10 | 68759514 | 68759414 | + | — |
| hsa-mir-1254-2 | MI0016747 | 210 | chr10 | 23393405 | 23393467 | + | — |
| hsa-mir-1255a | MI0006389 | 281 | chr4 | 101330302 | 101330414 | − | — |
| hsa-mir-1255b-1 | MI0006435 | 242 | chr4 | 36426366 | 36426428 | − | — |
| hsa-mir-1255b-2 | MI0006436 | 192 | chr1 | 167998660 | 167998726 | + | — |
| hsa-mir-1256 | MI0006390 | 25.6 | chr1 | 20988314 | 20988432 | − | — |
| hsa-mir-1257 | MI0006391 | 49.2 | chr20 | 61953546 | 61953662 | − | — |
| hsa-mir-1258 | MI0006392 | 22.4 | chr2 | 179860836 | 179860908 | − | — |
| hsa-mir-1260a | MI0006394 | 2.05e+03 | chr14 | 77266250 | 77266306 | + | — |
| hsa-mir-1260b | MI0014197 | 2.02e+03 | chr11 | 96341438 | 96341526 | + | — |
| hsa-mir-1261 | MI0006396 | 1.46e+03 | chr11 | 90869121 | 90869202 | − | — |
| hsa-mir-1262 | MI0006397 | 92.5 | chr1 | 68183518 | 68183610 | − | — |
| hsa-mir-1263 | MI0006398 | 0.772 | chr3 | 164171471 | 164171556 | − | — |
| hsa-mir-1264 | MI0003758 | 212 | chrX | 114652655 | 114652723 | + | — |
| hsa-mir-1265 | MI0006401 | 755 | chr10 | 14436576 | 14436661 | + | — |
| hsa-mir-1266 | MI0006403 | 69.5 | chr15 | 52277117 | 52277200 | − | — |
| hsa-mir-1267 | MI0006404 | 61.7 | chr13 | 107531171 | 107531248 | − | — |
| hsa-mir-1268a | MI0006405 | 1.13e+03 | chr15 | 22225278 | 22225329 | − | — |
| hsa-mir-1268b | MI0016748 | 516 | chr17 | 80098828 | 80098877 | + | — |
| hsa-mir-1269a | MI0006406 | 1.82e+03 | chr4 | 66276824 | 66276928 | + | — |
| hsa-mir-1269b | MI0016888 | 1.77e+03 | chr17 | 12917268 | 12917342 | + | — |
| hsa-mir-1270 | MI0006407 | 127 | chr19 | 20399272 | 20399354 | − | — |
| hsa-mir-1271 | MI0003814 | 336 | chr5 | 176367946 | 176368031 | + | ✓ |
| hsa-mir-1272 | MI0006408 | 75.4 | chr15 | 64762387 | 64762515 | − | — |
| hsa-mir-1273a | MI0006409 | 1.93e+03 | chr8 | 100023982 | 100024084 | − | — |
| hsa-mir-1273c | MI0014171 | 435 | chr6 | 154853360 | 154853436 | + | — |
| hsa-mir-1273d | MI0014254 | 645 | chr1 | 10227718 | 10227803 | + | — |
| hsa-mir-1273e | MI0016059 | 1.22e+03 | chr17 | 64425069 | 64425170 | − | — |
| hsa-mir-1273f | MI0018002 | 1.4e+03 | chr1 | 52928674 | 52928772 | + | — |
| hsa-mir-1273g | MI0018003 | 946 | chr1 | 52940314 | 52940413 | + | — |
| hsa-mir-1273h | MI0025512 | 2.83 | chr16 | 24203116 | 24203231 | + | — |
| hsa-mir-1275 | MI0006415 | 3.32e+03 | chr6 | 33999972 | 34000051 | − | — |
| hsa-mir-1276 | MI0006416 | 58 | chr15 | 85770496 | 85770578 | − | — |
| hsa-mir-1277 | MI0006419 | 133 | chrX | 118386394 | 118386471 | + | — |
| hsa-mir-1278 | MI0006425 | 134 | chr1 | 193136503 | 193136583 | + | ✓ |

TABLE 1-continued

Exemplary Homo sapiens miRNAs incorporated into compositions as provided herein, and in compositions made by methods as provided herein

| ID | Accession | RPM | Chromosome | Start | End | Strand | Confidence Fetch |
|---|---|---|---|---|---|---|---|
| hsa-mir-1279 | MI0006426 | 21.1 | chr12 | 69273157 | 69273218 | − | — |
| hsa-mir-1281 | MI0006428 | 561 | chr22 | 41092513 | 41092566 | + | — |
| hsa-mir-1282 | MI0006429 | 284 | chr15 | 43793659 | 43793759 | − | — |
| hsa-mir-1283-1 | MI0003832 | 395 | chr19 | 53688481 | 53688567 | + | — |
| hsa-mir-1283-2 | MI0006430 | 470 | chr19 | 53758232 | 53758318 | + | — |
| hsa-mir-1284 | MI0006431 | 72.1 | chr3 | 71541970 | 71542089 | − | — |
| hsa-mir-1285-1 | MI0006346 | 686 | chr7 | 92204015 | 92204098 | − | ✓ |
| hsa-mir-1285-2 | MI0006347 | 748 | chr2 | 70252918 | 70253005 | − | — |
| hsa-mir-1286 | MI0006348 | 120 | chr22 | 20249134 | 20249211 | − | — |
| hsa-mir-1287 | MI0006349 | 161 | chr10 | 98395218 | 98395307 | − | ✓ |
| hsa-mir-1288 | MI0006432 | 36.7 | chr17 | 16282014 | 16282088 | + | — |
| hsa-mir-1289-1 | MI0006350 | 756 | chr20 | 35453954 | 35454097 | − | — |
| hsa-mir-1289-2 | MI0006351 | 27.6 | chr5 | 133427596 | 133427706 | − | — |
| hsa-mir-1290 | MI0006352 | 2.55e+03 | chr1 | 18897071 | 18897148 | − | — |
| hsa-mir-1291 | MI0006353 | 102 | chr12 | 48654444 | 48654530 | + | — |
| hsa-mir-1292 | MI0006433 | 36 | chr20 | 2652777 | 2652842 | + | — |
| hsa-mir-1293 | MI0006355 | 176 | chr12 | 50234142 | 50234212 | − | — |
| hsa-mir-1294 | MI0006356 | 146 | chr5 | 154347106 | 154347247 | + | — |
| hsa-mir-1295a | MI0006357 | 89.4 | chr1 | 171101728 | 171101806 | − | — |
| hsa-mir-1295b | MI0019146 | — | chr1 | 171101739 | 171101798 | + | — |
| hsa-mir-1296 | MI0003780 | 449 | chr10 | 63372957 | 63373048 | − | ✓ |
| hsa-mir-1297 | MI0006358 | 224 | chr13 | 54311972 | 54312048 | − | — |
| hsa-mir-1298 | MI0003938 | 22.1 | chrX | 114715233 | 114715344 | + | — |
| hsa-mir-1299 | MI0006359 | 235 | chr9 | 40929010 | 40929092 | − | — |
| hsa-mir-1301 | MI0003815 | 652 | chr2 | 25328640 | 25328721 | − | — |
| hsa-mir-1302-1 | MI0006362 | 30.1 | chr12 | 112695034 | 112695176 | − | — |
| hsa-mir-1302-10 | MI0015979 | 178 | chr15 | 101960459 | 101960596 | − | — |
| hsa-mir-1302-11 | MI0015980 | 193 | chr19 | 71973 | 72110 | + | — |
| hsa-mir-1302-2 | MI0006363 | 193 | chr1 | 30366 | 30503 | + | — |
| hsa-mir-1302-3 | MI0006364 | 178 | chr2 | 113582959 | 113583096 | − | — |
| hsa-mir-1302-4 | MI0006365 | 192 | chr2 | 207269275 | 207269424 | − | — |
| hsa-mir-1302-5 | MI0006366 | 56.8 | chr20 | 50614636 | 50614785 | − | — |
| hsa-mir-1302-6 | MI0006367 | 40.4 | chr7 | 18127220 | 18127309 | − | — |
| hsa-mir-1302-7 | MI0006368 | 34.7 | chr8 | 141786242 | 141786313 | − | — |
| hsa-mir-1302-8 | MI0006369 | 31.9 | chr9 | 97363554 | 97363681 | − | — |
| hsa-mir-1302-9 | MI0015978 | 193 | chr9 | 30144 | 30281 | + | — |
| hsa-mir-1303 | MI0006370 | 997 | chr5 | 154685776 | 154685861 | + | — |
| hsa-mir-1304 | MI0006371 | 189 | chr11 | 93733674 | 93733764 | − | ✓ |
| hsa-mir-1305 | MI0006372 | 54 | chr4 | 182169293 | 182169378 | + | — |
| hsa-mir-1306 | MI0006443 | 213 | chr22 | 20086058 | 20086142 | + | ✓ |
| hsa-mir-1307 | MI0006444 | 2.11e+03 | chr10 | 103394253 | 103394401 | − | ✓ |
| hsa-mir-1321 | MI0006652 | 73.3 | chrX | 85835780 | 85835858 | + | — |
| hsa-mir-1322 | MI0006653 | 45.2 | chr8 | 10825373 | 10825443 | − | — |
| hsa-mir-1323 | MI0003786 | 200 | chr19 | 53671968 | 53672040 | + | — |
| hsa-mir-1324 | MI0006657 | 83.1 | chr3 | 75630763 | 75630858 | + | — |
| hsa-mir-1343 | MI0017320 | 45.3 | chr11 | 34941837 | 34941920 | + | — |
| hsa-mir-1468 | MI0003782 | 78.6 | chrX | 63786002 | 63786087 | − | — |
| hsa-mir-1469 | MI0007074 | 117 | chr15 | 96333261 | 96333307 | + | — |
| hsa-mir-1470 | MI0007075 | 700 | chr19 | 15449548 | 15449606 | + | — |
| hsa-mir-1471 | MI0007076 | 24.4 | chr2 | 231892242 | 231892298 | + | — |
| hsa-mir-1537 | MI0007258 | 41.5 | chr1 | 235853000 | 235853060 | − | — |
| hsa-mir-1538 | MI0007259 | 221 | chr16 | 69565808 | 69565868 | − | — |
| hsa-mir-1539 | MI0007260 | — | chr18 | 49487373 | 49487422 | + | — |
| hsa-mir-1587 | MI0016905 | 46.1 | chrX | 39837561 | 39837613 | + | — |
| hsa-mir-1825 | MI0008193 | 371 | chr20 | 32237795 | 32237847 | + | — |
| hsa-mir-1827 | MI0008195 | 185 | chr12 | 100189884 | 100189949 | + | — |
| hsa-mir-1908 | MI0008329 | 680 | chr11 | 61815161 | 61815240 | − | ✓ |
| hsa-mir-1909 | MI0008330 | 71 | chr19 | 1816159 | 1816238 | − | — |
| hsa-mir-1910 | MI0008331 | 72.6 | chr16 | 85741621 | 85741700 | − | ✓ |
| hsa-mir-1911 | MI0008332 | 40.4 | chrX | 114763184 | 114763263 | + | — |
| hsa-mir-1912 | MI0008333 | 90.3 | chrX | 114651544 | 114651623 | + | — |
| hsa-mir-1913 | MI0008334 | 48.1 | chr6 | 166509354 | 166509433 | − | — |
| hsa-mir-1914 | MI0008335 | 20 | chr20 | 63941465 | 63941544 | − | — |
| hsa-mir-1915 | MI0008336 | 1.45e+03 | chr10 | 21496562 | 21496641 | − | — |
| hsa-mir-1972-1 | MI0009982 | 307 | chr16 | 15010321 | 15010397 | − | — |
| hsa-mir-1972-2 | MI0015977 | 338 | chr16 | 70030346 | 70030422 | + | — |
| hsa-mir-1973 | MI0009983 | 835 | chr4 | 116299725 | 116299768 | + | — |
| hsa-mir-1976 | MI0009986 | 115 | chr1 | 26554542 | 26554593 | + | — |
| hsa-mir-2052 | MI0010486 | — | chr8 | 74705693 | 74705747 | + | — |
| hsa-mir-2053 | MI0010487 | 20 | chr8 | 112643493 | 112643583 | + | — |
| hsa-mir-2054 | MI0010488 | 37 | chr4 | 125507259 | 125507307 | + | — |
| hsa-mir-2110 | MI0010629 | 248 | chr10 | 114174105 | 114174179 | − | — |
| hsa-mir-2113 | MI0003939 | 15.7 | chr6 | 98024531 | 98024621 | + | — |
| hsa-mir-2114 | MI0010633 | 89 | chrX | 150228004 | 150228083 | + | — |
| hsa-mir-2115 | MI0010634 | 51.6 | chr3 | 48316360 | 48316459 | − | — |

TABLE 1-continued

Exemplary Homo sapiens miRNAs incorporated into compositions as provided herein, and in compositions made by methods as provided herein

| ID | Accession | RPM | Chromosome | Start | End | Strand | Confidence Fetch |
|---|---|---|---|---|---|---|---|
| hsa-mir-2116 | MI0010635 | 99.6 | chr15 | 59171183 | 59171262 | − | ✓ |
| hsa-mir-2117 | MI0010636 | 18.5 | chr17 | 43444806 | 43444885 | + | — |
| hsa-mir-2276 | MI0011282 | 45.2 | chr13 | 24162416 | 24162504 | + | — |
| hsa-mir-2277 | MI0011284 | 43.9 | chr5 | 93620696 | 93620788 | − | — |
| hsa-mir-2278 | MI0011285 | 87.9 | chr9 | 94809962 | 94810057 | + | — |
| hsa-mir-2355 | MI0015873 | 198 | chr2 | 207109987 | 207110073 | − | — |
| hsa-mir-2392 | MI0016870 | 85.4 | chr14 | 100814491 | 100814574 | + | — |
| hsa-mir-2467 | MI0017432 | 28.8 | chr2 | 239351724 | 239351804 | − | — |
| hsa-mir-2681 | MI0012062 | 54.4 | chr13 | 101967642 | 101967746 | − | — |
| hsa-mir-2682 | MI0012063 | 121 | chr1 | 98045242 | 98045351 | − | — |
| hsa-mir-2861 | MI0013006 | 195 | chr9 | 127785918 | 127786007 | + | — |
| hsa-mir-2909 | MI0013083 | 86.7 | chr17 | 37033745 | 37033813 | + | — |
| hsa-mir-3064 | MI0017375 | 28.9 | chr17 | 64500774 | 64500839 | − | — |
| hsa-mir-3065 | MI0014228 | 96.2 | chr17 | 81125877 | 81125955 | + | ✓ |
| hsa-mir-3074 | MI0014181 | 52.4 | chr9 | 95086014 | 95086094 | − | ✓ |
| hsa-mir-3115 | MI0014127 | 21.7 | chr1 | 23044305 | 23044372 | + | — |
| hsa-mir-3116-1 | MI0014128 | 13.8 | chr1 | 62078786 | 62078859 | + | — |
| hsa-mir-3116-2 | MI0014129 | 32.7 | chr1 | 62078789 | 62078856 | − | — |
| hsa-mir-3117 | MI0014130 | 63.5 | chr1 | 66628440 | 66628517 | + | — |
| hsa-mir-3118-1 | MI0014131 | 10.4 | chr21 | 13644775 | 13644850 | − | — |
| hsa-mir-3118-2 | MI0014132 | 12 | chr15 | 20832795 | 20832869 | + | — |
| hsa-mir-3118-3 | MI0014133 | 12 | chr15 | 21406385 | 21406459 | + | — |
| hsa-mir-3118-4 | MI0014207 | 13.8 | chr15 | 21843750 | 21843824 | + | — |
| hsa-mir-3119-1 | MI0014134 | 15.7 | chr1 | 170151378 | 170151462 | − | — |
| hsa-mir-3119-2 | MI0014135 | 27.1 | chr1 | 170151378 | 170151462 | + | — |
| hsa-mir-3120 | MI0014136 | 46.8 | chr1 | 172138808 | 172138888 | + | — |
| hsa-mir-3121 | MI0014137 | 17.3 | chr1 | 180438314 | 180438390 | − | — |
| hsa-mir-3122 | MI0014138 | 37.1 | chr1 | 212077613 | 212077685 | − | — |
| hsa-mir-3123 | MI0014139 | 1.12e+03 | chr1 | 241132272 | 241132346 | + | — |
| hsa-mir-3124 | MI0014140 | 34.9 | chr1 | 248826377 | 248826443 | + | — |
| hsa-mir-3125 | MI0014142 | 33.8 | chr2 | 12737367 | 12737444 | + | — |
| hsa-mir-3126 | MI0014143 | 16.3 | chr2 | 69103682 | 69103755 | + | — |
| hsa-mir-3127 | MI0014144 | 78.8 | chr2 | 96798278 | 96798353 | + | — |
| hsa-mir-3128 | MI0014145 | 13.6 | chr2 | 177255945 | 177256010 | − | — |
| hsa-mir-3129 | MI0014146 | 47.8 | chr2 | 189133036 | 189133111 | − | — |
| hsa-mir-3130-1 | MI0014147 | 129 | chr2 | 206783234 | 206783308 | − | ✓ |
| hsa-mir-3130-2 | MI0014148 | 131 | chr2 | 206783234 | 206783308 | + | ✓ |
| hsa-mir-3131 | MI0014151 | 84.7 | chr2 | 219058688 | 219058750 | − | — |
| hsa-mir-3132 | MI0014152 | 71.1 | chr2 | 219549073 | 219549147 | − | — |
| hsa-mir-3133 | MI0014153 | 32.8 | chr2 | 241477905 | 241477982 | + | — |
| hsa-mir-3134 | MI0014155 | 41.5 | chr3 | 15697298 | 15697371 | − | — |
| hsa-mir-3135a | MI0014156 | 118 | chr3 | 20137565 | 20137641 | + | — |
| hsa-mir-3135b | MI0016809 | 316 | chr6 | 32749912 | 32749979 | − | — |
| hsa-mir-3136 | MI0014158 | 59.3 | chr3 | 69048958 | 69049035 | − | — |
| hsa-mir-3137 | MI0014160 | 48.4 | chr3 | 195134506 | 195134580 | − | — |
| hsa-mir-3138 | MI0014161 | 65.9 | chr4 | 10078611 | 10078692 | − | — |
| hsa-mir-3139 | MI0014162 | 20.9 | chr4 | 143343460 | 143343535 | + | — |
| hsa-mir-3140 | MI0014163 | 34.6 | chr4 | 152489327 | 152489416 | − | ✓ |
| hsa-mir-3141 | MI0014165 | 578 | chr5 | 154596012 | 154596072 | − | — |
| hsa-mir-3142 | MI0014166 | 52.8 | chr5 | 160474402 | 160474483 | + | — |
| hsa-mir-3143 | MI0014167 | 33.7 | chr6 | 27147626 | 27147688 | + | — |
| hsa-mir-3144 | MI0014169 | 92.5 | chr6 | 120015179 | 120015257 | + | ✓ |
| hsa-mir-3145 | MI0014170 | 29.9 | chr6 | 138435213 | 138435294 | − | — |
| hsa-mir-3146 | MI0014172 | 6.44 | chr7 | 19705358 | 19705436 | − | — |
| hsa-mir-3147 | MI0014173 | 187 | chr7 | 57405025 | 57405090 | + | — |
| hsa-mir-3148 | MI0014175 | 82.9 | chr8 | 29957272 | 29957348 | − | — |
| hsa-mir-3149 | MI0014176 | 172 | chr8 | 76966768 | 76966850 | − | — |
| hsa-mir-3150a | MI0014177 | 24.5 | chr8 | 95072914 | 95072993 | + | — |
| hsa-mir-3150b | MI0016426 | 348 | chr8 | 95072911 | 95072996 | − | — |
| hsa-mir-3151 | MI0014178 | 49.6 | chr8 | 103154614 | 103154689 | + | — |
| hsa-mir-3152 | MI0014179 | 22.4 | chr9 | 18573306 | 18573379 | + | — |
| hsa-mir-3153 | MI0014180 | 20.2 | chr9 | 89312225 | 89312306 | + | — |
| hsa-mir-3154 | MI0014182 | 105 | chr9 | 128244947 | 128245030 | − | — |
| hsa-mir-3155a | MI0014183 | 31.2 | chr10 | 6152196 | 6152277 | + | — |
| hsa-mir-3155b | MI0016839 | 126 | chr10 | 6152207 | 6152262 | − | — |
| hsa-mir-3156-1 | MI0014184 | 50.8 | chr10 | 45164014 | 45164088 | + | — |
| hsa-mir-3156-2 | MI0014230 | 50.8 | chr18 | 14830166 | 14830242 | + | — |
| hsa-mir-3156-3 | MI0014242 | 55.9 | chr21 | 13406384 | 13406460 | − | — |
| hsa-mir-3157 | MI0014185 | 45.4 | chr10 | 96064315 | 96064399 | − | — |
| hsa-mir-3158-1 | MI0014186 | 59.7 | chr10 | 101601417 | 101601497 | + | ✓ |
| hsa-mir-3158-2 | MI0014187 | 62 | chr10 | 101601417 | 101601497 | − | — |
| hsa-mir-3159 | MI0014188 | 723 | chr11 | 18387787 | 18387860 | + | — |
| hsa-mir-3160-1 | MI0014189 | 119 | chr11 | 46451805 | 46451889 | − | — |
| hsa-mir-3160-2 | MI0014190 | 100 | chr11 | 46451807 | 46451887 | + | — |
| hsa-mir-3161 | MI0014191 | 31.7 | chr11 | 48096782 | 48096858 | + | — |

TABLE 1-continued

Exemplary *Homo sapiens* miRNAs incorporated into compositions as provided herein, and in compositions made by methods as provided herein

| ID | Accession | RPM | Chromosome | Start | End | Strand | Confidence Fetch |
|---|---|---|---|---|---|---|---|
| hsa-mir-3162 | MI0014192 | 209 | chr11 | 59595077 | 59595158 | − | — |
| hsa-mir-3163 | MI0014193 | 62.4 | chr11 | 66934434 | 66934506 | − | — |
| hsa-mir-3164 | MI0014194 | 46.5 | chr11 | 69083176 | 69083258 | + | — |
| hsa-mir-3165 | MI0014195 | 52.8 | chr11 | 72072228 | 72072302 | − | — |
| hsa-mir-3166 | MI0014196 | 21.6 | chr11 | 88176502 | 88176593 | + | — |
| hsa-mir-3167 | MI0014198 | 34.3 | chr11 | 126988458 | 126988542 | − | — |
| hsa-mir-3168 | MI0014199 | 139 | chr13 | 41101019 | 41101100 | − | — |
| hsa-mir-3169 | MI0014200 | 30.7 | chr13 | 61199798 | 61199880 | − | — |
| hsa-mir-3170 | MI0014201 | 101 | chr13 | 98208524 | 98208600 | + | — |
| hsa-mir-3171 | MI0014202 | 36.3 | chr14 | 27633205 | 27633278 | − | — |
| hsa-mir-3173 | MI0014204 | 40.7 | chr14 | 95137919 | 95137986 | − | — |
| hsa-mir-3174 | MI0014208 | 15 | chr15 | 90006755 | 90006841 | + | — |
| hsa-mir-3175 | MI0014209 | 180 | chr15 | 92904399 | 92904475 | + | — |
| hsa-mir-3176 | MI0014210 | 62.1 | chr16 | 543277 | 543366 | + | — |
| hsa-mir-3177 | MI0014211 | 29.8 | chr16 | 1734985 | 1735066 | + | — |
| hsa-mir-3178 | MI0014212 | 1.36e+03 | chr16 | 2531922 | 2532005 | − | — |
| hsa-mir-3179-1 | MI0014213 | 41.6 | chr16 | 14901508 | 14901591 | + | — |
| hsa-mir-3179-2 | MI0014216 | 41.4 | chr16 | 16300159 | 16300242 | + | — |
| hsa-mir-3179-3 | MI0014221 | 41.6 | chr16 | 18411894 | 18411977 | − | — |
| hsa-mir-3179-4 | MI0031510 | 44.5 | chr16 | 18494493 | 18494576 | − | — |
| hsa-mir-3180-1 | MI0014214 | 860 | chr16 | 14911220 | 14911313 | + | — |
| hsa-mir-3180-2 | MI0014215 | 811 | chr16 | 16309879 | 16309966 | + | — |
| hsa-mir-3180-3 | MI0014217 | 770 | chr16 | 18402178 | 18402271 | − | — |
| hsa-mir-3180-4 | MI0016408 | 476 | chr16 | 15154850 | 15155002 | − | — |
| hsa-mir-3180-5 | MI0016409 | 739 | chr16 | 2135977 | 2136129 | − | — |
| hsa-mir-3181 | MI0014223 | 55.2 | chr16 | 50742305 | 50742377 | + | — |
| hsa-mir-3182 | MI0014224 | 53.2 | chr16 | 83508346 | 83508408 | + | — |
| hsa-mir-3183 | MI0014225 | 107 | chr17 | 1022476 | 1022550 | − | — |
| hsa-mir-3184 | MI0014226 | 60.1 | chr17 | 30117086 | 30117160 | − | — |
| hsa-mir-3185 | MI0014227 | 188 | chr17 | 48724408 | 48724475 | − | — |
| hsa-mir-3186 | MI0014229 | 62.8 | chr17 | 81451104 | 81451188 | − | — |
| hsa-mir-3187 | MI0014231 | 35.9 | chr19 | 813584 | 813653 | + | — |
| hsa-mir-3188 | MI0014232 | 30.7 | chr19 | 18282077 | 18282161 | + | — |
| hsa-mir-3189 | MI0014233 | 53.8 | chr19 | 18386562 | 18386634 | + | — |
| hsa-mir-3190 | MI0014235 | 59.4 | chr19 | 47226942 | 47227021 | + | — |
| hsa-mir-3191 | MI0014236 | 13.4 | chr19 | 47226944 | 47227019 | − | — |
| hsa-mir-3192 | MI0014237 | 48.5 | chr20 | 18470615 | 18470691 | + | — |
| hsa-mir-3193 | MI0014238 | 15.6 | chr20 | 31607186 | 31607240 | + | — |
| hsa-mir-3194 | MI0014239 | 83.8 | chr20 | 51452905 | 51452977 | − | — |
| hsa-mir-3195 | MI0014240 | 5.28e+03 | chr20 | 62064802 | 62064885 | + | — |
| hsa-mir-3196 | MI0014241 | 791 | chr20 | 63238779 | 63238842 | + | — |
| hsa-mir-3197 | MI0014245 | 184 | chr21 | 41167557 | 41167629 | + | — |
| hsa-mir-3198-1 | MI0014246 | 45.8 | chr22 | 17764180 | 17764259 | − | — |
| hsa-mir-3198-2 | MI0017335 | 41.8 | chr12 | 54231397 | 54231476 | − | — |
| hsa-mir-3199-1 | MI0014247 | 46.1 | chr22 | 27920525 | 27920612 | − | — |
| hsa-mir-3199-2 | MI0014248 | 44.8 | chr22 | 27920526 | 27920611 | + | — |
| hsa-mir-3200 | MI0014249 | 143 | chr22 | 30731557 | 30731641 | + | — |
| hsa-mir-3201 | MI0014250 | 46.3 | chr22 | 48274364 | 48274415 | + | — |
| hsa-mir-3202-1 | MI0014252 | 308 | chrX | 153981097 | 153981177 | + | — |
| hsa-mir-3202-2 | MI0014253 | 288 | chrX | 153981098 | 153981176 | − | — |
| hsa-mir-3529 | MI0017351 | 27.5 | chr15 | 88611847 | 88611924 | − | — |
| hsa-mir-3591 | MI0017383 | 33.9 | chr18 | 58451080 | 58451152 | − | ✓ |
| hsa-mir-3605 | MI0015995 | 114 | chr1 | 33332393 | 33332492 | − | ✓ |
| hsa-mir-3606 | MI0015996 | 233 | chr2 | 188995630 | 188995692 | + | — |
| hsa-mir-3607 | MI0015997 | 347 | chr5 | 86620497 | 86620575 | + | — |
| hsa-mir-3609 | MI0015999 | 392 | chr7 | 98881650 | 98881729 | + | — |
| hsa-mir-3610 | MI0016000 | 158 | chr8 | 116874728 | 116874800 | − | — |
| hsa-mir-3611 | MI0016001 | 216 | chr10 | 35079598 | 35079680 | − | — |
| hsa-mir-3612 | MI0016002 | 149 | chr12 | 128294092 | 128294178 | + | — |
| hsa-mir-3613 | MI0016003 | 588 | chr13 | 49996415 | 49996501 | − | ✓ |
| hsa-mir-3614 | MI0016004 | 256 | chr17 | 56891270 | 56891355 | − | ✓ |
| hsa-mir-3615 | MI0016005 | 737 | chr17 | 74748613 | 74748699 | + | — |
| hsa-mir-3616 | MI0016006 | 133 | chr20 | 47166967 | 47167058 | + | — |
| hsa-mir-3617 | MI0016007 | 28.5 | chr20 | 45705102 | 45705180 | − | — |
| hsa-mir-3618 | MI0016008 | 72.6 | chr22 | 20085746 | 20085833 | + | — |
| hsa-mir-3619 | MI0016009 | 30.1 | chr22 | 46091044 | 46091126 | + | — |
| hsa-mir-3620 | MI0016011 | 63.7 | chr1 | 228097263 | 228097341 | + | — |
| hsa-mir-3621 | MI0016012 | 189 | chr9 | 137169186 | 137169270 | − | — |
| hsa-mir-3622a | MI0016013 | 167 | chr8 | 27701677 | 27701759 | + | — |
| hsa-mir-3622b | MI0016014 | 40.4 | chr8 | 27701673 | 27701767 | − | — |
| hsa-mir-3646 | MI0016046 | 30.5 | chr20 | 44408120 | 44408203 | + | — |
| hsa-mir-3648-1 | MI0016048 | 1.01e+03 | chr21 | 8208473 | 8208652 | + | — |
| hsa-mir-3648-2 | MI0031512 | 29.2 | chr21 | 8986999 | 8987178 | + | — |
| hsa-mir-3649 | MI0016049 | 37 | chr12 | 1660315 | 1660380 | − | — |
| hsa-mir-3650 | MI0016050 | 120 | chr5 | 38557502 | 38557561 | − | — |

TABLE 1-continued

Exemplary *Homo sapiens* miRNAs incorporated into compositions as provided herein, and in compositions made by methods as provided herein

| ID | Accession | RPM | Chromosome | Start | End | Strand | Confidence Fetch |
|---|---|---|---|---|---|---|---|
| hsa-mir-3651 | MI0016051 | 209 | chr9 | 92292458 | 92292547 | − | — |
| hsa-mir-3652 | MI0016052 | 554 | chr12 | 103930425 | 103930555 | + | — |
| hsa-mir-3653 | MI0016053 | 413 | chr22 | 29333158 | 29333267 | − | — |
| hsa-mir-3654 | MI0016054 | 45.3 | chr7 | 133034860 | 133034915 | − | — |
| hsa-mir-3655 | MI0016055 | 11.7 | chr5 | 140647844 | 140647926 | + | — |
| hsa-mir-3656 | MI0016056 | 2.6e+03 | chr11 | 119018944 | 119019012 | + | — |
| hsa-mir-3657 | MI0016057 | 36.2 | chr12 | 112037599 | 112037715 | − | — |
| hsa-mir-3658 | MI0016058 | 71 | chr1 | 165907921 | 165907976 | + | — |
| hsa-mir-3659 | MI0016060 | 64.7 | chr1 | 38089231 | 38089329 | + | — |
| hsa-mir-3660 | MI0016061 | 60.8 | chr5 | 90016621 | 90016720 | − | — |
| hsa-mir-3661 | MI0016062 | 23 | chr5 | 134225757 | 134225852 | + | — |
| hsa-mir-3662 | MI0016063 | 20.8 | chr6 | 134979338 | 134979432 | − | — |
| hsa-mir-3663 | MI0016064 | 164 | chr10 | 117167678 | 117167774 | − | — |
| hsa-mir-3664 | MI0016065 | 109 | chr11 | 70872270 | 70872368 | − | — |
| hsa-mir-3665 | MI0016066 | 3.77e+03 | chr13 | 77698012 | 77698116 | − | — |
| hsa-mir-3666 | MI0016067 | 177 | chr7 | 114653345 | 114653455 | + | — |
| hsa-mir-3667 | MI0016068 | 143 | chr22 | 49543393 | 49543466 | − | — |
| hsa-mir-3668 | MI0016069 | 15.5 | chr6 | 140205252 | 140205326 | + | — |
| hsa-mir-3670-1 | MI0016071 | 9.62 | chr16 | 14907717 | 14907781 | + | — |
| hsa-mir-3670-2 | MI0019112 | 9.62 | chr16 | 16306370 | 16306434 | + | — |
| hsa-mir-3670-3 | MI0031513 | — | chr16 | 18405698 | 18405762 | − | — |
| hsa-mir-3670-4 | MI0031514 | — | chr16 | 18488301 | 18488365 | − | — |
| hsa-mir-3671 | MI0016072 | — | chr1 | 65057755 | 65057842 | − | — |
| hsa-mir-3672 | MI0016073 | — | chrX | 121370972 | 121371053 | + | — |
| hsa-mir-3674 | MI0016075 | 74.7 | chr8 | 1801125 | 1801192 | + | — |
| hsa-mir-3675 | MI0016076 | 0.197 | chr1 | 16858949 | 16859021 | − | — |
| hsa-mir-3677 | MI0016078 | 32.3 | chr16 | 2270713 | 2270772 | + | — |
| hsa-mir-3678 | MI0016079 | 20.7 | chr17 | 75406069 | 75406162 | + | — |
| hsa-mir-3679 | MI0016080 | 64.1 | chr2 | 134127125 | 134127192 | + | — |
| hsa-mir-3680-1 | MI0016081 | 45.8 | chr16 | 21506049 | 21506135 | − | — |
| hsa-mir-3680-2 | MI0019113 | 56.3 | chr16 | 29599179 | 29599265 | − | — |
| hsa-mir-3681 | MI0016082 | 5.55 | chr2 | 12199130 | 12199201 | + | — |
| hsa-mir-3682 | MI0016083 | 13.9 | chr2 | 53849122 | 53849205 | − | — |
| hsa-mir-3683 | MI0016084 | 51 | chr7 | 7066964 | 7067045 | − | — |
| hsa-mir-3684 | MI0016085 | 1.29 | chr4 | 98997387 | 98997460 | + | — |
| hsa-mir-3685 | MI0016086 | 15.3 | chr12 | 95309923 | 95309984 | + | — |
| hsa-mir-3686 | MI0016087 | 541 | chr8 | 129484057 | 129484142 | − | — |
| hsa-mir-3687-1 | MI0016088 | 465 | chr21 | 8208844 | 8208904 | + | — |
| hsa-mir-3687-2 | MI0031515 | 281 | chr21 | 8987370 | 8987430 | + | — |
| hsa-mir-3688-1 | MI0016089 | 51.9 | chr4 | 159128802 | 159128894 | − | — |
| hsa-mir-3688-2 | MI0017447 | 64 | chr4 | 159128805 | 159128891 | + | — |
| hsa-mir-3689a | MI0016090 | 37 | chr9 | 134849487 | 134849564 | − | — |
| hsa-mir-3689b | MI0016411 | 85.3 | chr9 | 134850125 | 134850272 | − | — |
| hsa-mir-3689c | MI0016832 | 44.5 | chr9 | 134849298 | 134849369 | − | — |
| hsa-mir-3689d-1 | MI0016834 | 55.1 | chr9 | 134849609 | 134849682 | − | — |
| hsa-mir-3689d-2 | MI0016835 | 35.7 | chr9 | 134850277 | 134850356 | − | — |
| hsa-mir-3689e | MI0016836 | 54.3 | chr9 | 134850570 | 134850641 | − | — |
| hsa-mir-3689f | MI0016837 | 35 | chr9 | 134850742 | 134850807 | − | — |
| hsa-mir-3690-1 | MI0016091 | 115 | chrX | 1293918 | 1293992 | + | — |
| hsa-mir-3690-2 | MI0023561 | 51.3 | chrY | 1293918 | 1293992 | + | — |
| hsa-mir-3691 | MI0016092 | 47.4 | chr6 | 5148233 | 5148322 | − | — |
| hsa-mir-3692 | MI0016093 | 4.92 | chr6 | 157529132 | 157529200 | + | — |
| hsa-mir-3713 | MI0016134 | 67.3 | chr15 | 76586647 | 76586691 | + | — |
| hsa-mir-3714 | MI0016135 | 37.7 | chr3 | 16933196 | 16933260 | + | — |
| hsa-mir-3907 | MI0016410 | 203 | chr7 | 151433489 | 151433639 | − | — |
| hsa-mir-3908 | MI0016412 | 378 | chr12 | 123536409 | 123536534 | + | — |
| hsa-mir-3909 | MI0016413 | 387 | chr22 | 35335640 | 35335758 | + | — |
| hsa-mir-3910-1 | MI0016414 | 102 | chr9 | 91636251 | 91636361 | + | — |
| hsa-mir-3910-2 | MI0016431 | 104 | chr9 | 91636264 | 91636345 | − | — |
| hsa-mir-3911 | MI0016415 | 319 | chr9 | 127690687 | 127690795 | − | — |
| hsa-mir-3912 | MI0016416 | 20.4 | chr5 | 171386656 | 171386760 | + | — |
| hsa-mir-3913-1 | MI0016417 | 140 | chr12 | 69584722 | 69584823 | − | — |
| hsa-mir-3913-2 | MI0016418 | 135 | chr12 | 69584723 | 69584822 | + | — |
| hsa-mir-3914-1 | MI0016419 | 211 | chr7 | 71307672 | 71307770 | − | — |
| hsa-mir-3914-2 | MI0016421 | 112 | chr7 | 71307674 | 71307768 | + | — |
| hsa-mir-3915 | MI0016420 | 43.9 | chrX | 32583656 | 32583752 | − | — |
| hsa-mir-3916 | MI0016422 | 733 | chr1 | 247201967 | 247202060 | − | — |
| hsa-mir-3917 | MI0016423 | 68.5 | chr1 | 25906362 | 25906454 | − | — |
| hsa-mir-3918 | MI0016424 | 21.6 | chr6 | 158764661 | 158764753 | − | — |
| hsa-mir-3919 | MI0016425 | 2.55 | chr3 | 159282646 | 159282734 | + | — |
| hsa-mir-3920 | MI0016427 | 30.2 | chr11 | 101519820 | 101519905 | − | — |
| hsa-mir-3921 | MI0016428 | 21.7 | chr3 | 99964314 | 99964398 | − | — |
| hsa-mir-3922 | MI0016429 | 68 | chr12 | 104591633 | 104591716 | + | — |
| hsa-mir-3923 | MI0016430 | 52.8 | chr3 | 79507887 | 79507969 | + | — |
| hsa-mir-3924 | MI0016432 | 42.4 | chr10 | 57304479 | 57304559 | − | — |

TABLE 1-continued

Exemplary Homo sapiens miRNAs incorporated into compositions as provided herein, and in compositions made by methods as provided herein

| ID | Accession | RPM | Chromosome | Start | End | Strand | Confidence Fetch |
|---|---|---|---|---|---|---|---|
| hsa-mir-3925 | MI0016433 | 12.9 | chr6 | 36622436 | 36622512 | − | — |
| hsa-mir-3926-1 | MI0016434 | 96.5 | chr8 | 12727232 | 12727304 | − | — |
| hsa-mir-3926-2 | MI0016437 | 54.9 | chr8 | 12727237 | 12727299 | + | — |
| hsa-mir-3927 | MI0016435 | 134 | chr9 | 109511475 | 109511545 | − | — |
| hsa-mir-3928 | MI0016438 | 130 | chr22 | 31160062 | 31160119 | − | — |
| hsa-mir-3929 | MI0016439 | 1.12e+03 | chr18 | 35934088 | 35934142 | − | — |
| hsa-mir-3934 | MI0016590 | 268 | chr6 | 33698128 | 33698234 | + | — |
| hsa-mir-3935 | MI0016591 | 101 | chr16 | 56245520 | 56245623 | + | — |
| hsa-mir-3936 | MI0016592 | 8.96 | chr5 | 132365490 | 132365599 | − | — |
| hsa-mir-3937 | MI0016593 | 20.6 | chrX | 39661216 | 39661321 | + | — |
| hsa-mir-3938 | MI0016594 | 148 | chr3 | 55852492 | 55852594 | − | — |
| hsa-mir-3939 | MI0016596 | 11.4 | chr6 | 166997807 | 166997912 | − | — |
| hsa-mir-3940 | MI0016597 | 64.5 | chr19 | 6416410 | 6416511 | − | — |
| hsa-mir-3941 | MI0016598 | 28 | chr10 | 122416965 | 122417067 | + | — |
| hsa-mir-3942 | MI0016599 | 71 | chr15 | 35372256 | 35372364 | − | — |
| hsa-mir-3943 | MI0016600 | 33.3 | chr7 | 43150895 | 43150968 | + | — |
| hsa-mir-3944 | MI0016601 | 43.5 | chr10 | 133371556 | 133371663 | − | — |
| hsa-mir-3945 | MI0016602 | 42.9 | chr4 | 184851013 | 184851110 | − | — |
| hsa-mir-3960 | MI0016964 | 4.68e+03 | chr9 | 127785833 | 127785923 | + | — |
| hsa-mir-3972 | MI0016990 | 58 | chr1 | 17277889 | 17277975 | + | — |
| hsa-mir-3973 | MI0016991 | 102 | chr11 | 36010098 | 36010204 | + | — |
| hsa-mir-3974 | MI0016992 | 17.8 | chr12 | 17673299 | 17673394 | + | — |
| hsa-mir-3975 | MI0016993 | 17.7 | chr18 | 35591737 | 35591806 | + | — |
| hsa-mir-3976 | MI0016994 | 30.5 | chr18 | 5840695 | 5840833 | + | — |
| hsa-mir-3977 | MI0016995 | — | chr5 | 82840155 | 82840224 | + | — |
| hsa-mir-3978 | MI0016996 | 17.5 | chrX | 110082118 | 110082218 | + | — |
| hsa-mir-4251 | MI0015861 | 0.171 | chr1 | 3127975 | 3128035 | + | — |
| hsa-mir-4252 | MI0015864 | 275 | chr1 | 6429834 | 6429896 | − | — |
| hsa-mir-4253 | MI0015860 | 11 | chr1 | 22863159 | 22863226 | − | — |
| hsa-mir-4254 | MI0015862 | 358 | chr1 | 31758660 | 31758735 | − | — |
| hsa-mir-4255 | MI0015863 | 169 | chr1 | 37161563 | 37161634 | + | — |
| hsa-mir-4256 | MI0015855 | 68.9 | chr1 | 112461770 | 112461833 | − | — |
| hsa-mir-4257 | MI0015856 | 34.2 | chr1 | 150551929 | 150552014 | + | — |
| hsa-mir-4258 | MI0015857 | 1.23e+03 | chr1 | 154975693 | 154975783 | + | — |
| hsa-mir-4259 | MI0015858 | 125 | chr1 | 159899979 | 159900079 | − | — |
| hsa-mir-4260 | MI0015859 | 0.171 | chr1 | 209623444 | 209623510 | − | — |
| hsa-mir-4261 | MI0015868 | 79.5 | chr2 | 10192614 | 10192671 | − | — |
| hsa-mir-4262 | MI0015872 | 42.4 | chr2 | 11836933 | 11836986 | − | — |
| hsa-mir-4263 | MI0015876 | 62.3 | chr2 | 27996367 | 27996449 | + | — |
| hsa-mir-4264 | MI0015877 | 36.3 | chr2 | 79649294 | 79649359 | − | — |
| hsa-mir-4265 | MI0015869 | 38 | chr2 | 109141490 | 109141588 | − | — |
| hsa-mir-4266 | MI0015870 | 143 | chr2 | 109313571 | 109313625 | − | — |
| hsa-mir-4267 | MI0015871 | 29 | chr2 | 110069961 | 110070042 | − | — |
| hsa-mir-4268 | MI0015874 | 9.62 | chr2 | 219906502 | 219906565 | − | — |
| hsa-mir-4269 | MI0015875 | 88.5 | chr2 | 239305462 | 239305545 | + | — |
| hsa-mir-4270 | MI0015878 | 173 | chr3 | 15496239 | 15496308 | − | — |
| hsa-mir-4271 | MI0015879 | 183 | chr3 | 49274120 | 49274186 | + | — |
| hsa-mir-4272 | MI0015880 | 42.4 | chr3 | 67225464 | 67225527 | + | — |
| hsa-mir-4273 | MI0015881 | 297 | chr3 | 75738280 | 75738363 | + | — |
| hsa-mir-4274 | MI0015884 | 57.2 | chr4 | 7460028 | 7460118 | + | — |
| hsa-mir-4275 | MI0015883 | 18.2 | chr4 | 28819582 | 28819668 | + | — |
| hsa-mir-4276 | MI0015882 | 37 | chr4 | 174423795 | 174423864 | + | — |
| hsa-mir-4277 | MI0015886 | 106 | chr5 | 1708785 | 1708810 | − | — |
| hsa-mir-4278 | MI0015888 | 97.8 | chr5 | 6827853 | 6827921 | − | — |
| hsa-mir-4279 | MI0015887 | 779 | chr5 | 31936102 | 31936159 | − | — |
| hsa-mir-4280 | MI0015889 | 46.2 | chr5 | 87114879 | 87114954 | − | — |
| hsa-mir-4281 | MI0015885 | 332 | chr5 | 176629439 | 176629500 | − | — |
| hsa-mir-4282 | MI0015890 | 21.3 | chr6 | 72967687 | 72967753 | − | — |
| hsa-mir-4283-1 | MI0015892 | 79.4 | chr7 | 56955785 | 56955864 | − | — |
| hsa-mir-4283-2 | MI0015982 | 79.4 | chr7 | 63621090 | 63621169 | + | — |
| hsa-mir-4284 | MI0015893 | 1.49e+03 | chr7 | 73711317 | 73711397 | + | — |
| hsa-mir-4285 | MI0015891 | 1.87 | chr7 | 102293103 | 102293187 | + | — |
| hsa-mir-4286 | MI0015894 | 1.36e+03 | chr8 | 10666978 | 10667070 | + | — |
| hsa-mir-4287 | MI0015895 | 60.7 | chr8 | 27886039 | 27886116 | − | — |
| hsa-mir-4288 | MI0015896 | 178 | chr8 | 28505116 | 28505182 | − | — |
| hsa-mir-4289 | MI0015898 | 620 | chr8 | 88745836 | 88745905 | − | — |
| hsa-mir-4290 | MI0015899 | 53.5 | chr9 | 90023441 | 90023535 | − | — |
| hsa-mir-4291 | MI0015900 | 139 | chr9 | 93819357 | 93819421 | + | — |
| hsa-mir-4292 | MI0015897 | 53.4 | chr9 | 136830957 | 136831023 | + | — |
| hsa-mir-4293 | MI0015826 | 66.5 | chr10 | 14383200 | 14383277 | − | — |
| hsa-mir-4294 | MI0015827 | 138 | chr10 | 48985512 | 48985587 | − | — |
| hsa-mir-4295 | MI0015822 | 13.5 | chr10 | 112634170 | 112634254 | + | — |
| hsa-mir-4296 | MI0015823 | 142 | chr10 | 125032783 | 125032870 | − | — |
| hsa-mir-4297 | MI0015824 | — | chr10 | 129843299 | 129843374 | − | — |
| hsa-mir-4298 | MI0015830 | 168 | chr11 | 1859464 | 1859536 | − | — |

TABLE 1-continued

Exemplary Homo sapiens miRNAs incorporated into compositions as provided
herein, and in compositions made by methods as provided herein

| ID | Accession | RPM | Chromosome | Start | End | Strand | Confidence | Fetch |
|---|---|---|---|---|---|---|---|---|
| hsa-mir-4299 | MI0015829 | 136 | chr11 | 11656651 | 11656722 | − | — | |
| hsa-mir-4300 | MI0015831 | 98.8 | chr11 | 81890741 | 81890836 | − | — | |
| hsa-mir-4301 | MI0015828 | 67.8 | chr11 | 113450023 | 113450088 | − | — | |
| hsa-mir-4302 | MI0015833 | 61.5 | chr12 | 25874020 | 25874079 | − | — | |
| hsa-mir-4303 | MI0015834 | 42.4 | chr12 | 97995383 | 97995448 | − | — | |
| hsa-mir-4304 | MI0015832 | 6.16 | chr12 | 123010667 | 123010728 | − | — | |
| hsa-mir-4305 | MI0015835 | 60.9 | chr13 | 39664034 | 39664135 | − | — | |
| hsa-mir-4306 | MI0015836 | 311 | chr13 | 99643059 | 99643149 | + | — | |
| hsa-mir-4307 | MI0015838 | 234 | chr14 | 26908642 | 26908725 | + | — | |
| hsa-mir-4308 | MI0015839 | 93.4 | chr14 | 54878113 | 54878193 | − | — | |
| hsa-mir-4309 | MI0015837 | 86.7 | chr14 | 102539644 | 102539726 | + | — | |
| hsa-mir-4310 | MI0015840 | 0.322 | chr15 | 41866495 | 41866551 | − | — | |
| hsa-mir-4311 | MI0015841 | 156 | chr15 | 66040233 | 66040332 | + | — | |
| hsa-mir-4312 | MI0015842 | 62.6 | chr15 | 68801850 | 68801925 | − | — | |
| hsa-mir-4313 | MI0015843 | 82 | chr15 | 75762215 | 75762315 | − | — | |
| hsa-mir-4314 | MI0015846 | 46.7 | chr17 | 8088056 | 8088147 | + | — | |
| hsa-mir-4315-1 | MI0015844 | — | chr17 | 45475363 | 45475435 | − | — | |
| hsa-mir-4315-2 | MI0015983 | 0.222 | chr17 | 64822030 | 64822102 | − | — | |
| hsa-mir-4316 | MI0015845 | 16.4 | chr17 | 77396984 | 77397054 | − | — | |
| hsa-mir-4317 | MI0015850 | 781 | chr18 | 6374361 | 6374425 | − | — | |
| hsa-mir-4318 | MI0015847 | — | chr18 | 37657135 | 37657215 | + | — | |
| hsa-mir-4319 | MI0015848 | 120 | chr18 | 44970082 | 44970166 | − | — | |
| hsa-mir-4320 | MI0015849 | 14.3 | chr18 | 50126499 | 50126563 | − | — | |
| hsa-mir-4321 | MI0015852 | 833 | chr19 | 2250639 | 2250718 | + | — | |
| hsa-mir-4322 | MI0015851 | 117 | chr19 | 10230413 | 10230485 | + | — | |
| hsa-mir-4323 | MI0015853 | 81.2 | chr19 | 42133445 | 42133513 | − | — | |
| hsa-mir-4324 | MI0015854 | 1.7e+03 | chr19 | 49308797 | 49308868 | − | — | |
| hsa-mir-4325 | MI0015865 | 41.3 | chr20 | 57321502 | 57321591 | − | — | |
| hsa-mir-4326 | MI0015866 | 46.8 | chr20 | 63286808 | 63286866 | + | — | |
| hsa-mir-4327 | MI0015867 | 62.2 | chr21 | 30375294 | 30375378 | − | — | |
| hsa-mir-4328 | MI0015904 | 799 | chrX | 78901194 | 78901249 | − | — | |
| hsa-mir-4329 | MI0015901 | 60.7 | chrX | 112780718 | 112780788 | − | — | |
| hsa-mir-4330 | MI0015902 | 106 | chrX | 151168222 | 151168326 | + | — | |
| hsa-mir-4417 | MI0016753 | 532 | chr1 | 5564071 | 5564143 | + | — | |
| hsa-mir-4418 | MI0016754 | 42.4 | chr1 | 22266239 | 22266300 | + | — | |
| hsa-mir-4419a | MI0016755 | 2.8e+03 | chr1 | 23057858 | 23057934 | − | — | |
| hsa-mir-4419b | MI0016861 | 209 | chr12 | 128244506 | 128244573 | + | — | |
| hsa-mir-4420 | MI0016757 | 36 | chr1 | 30739156 | 30739232 | − | — | |
| hsa-mir-4421 | MI0016758 | 104 | chr1 | 51059837 | 51059905 | + | — | |
| hsa-mir-4422 | MI0016759 | 37.6 | chr1 | 55225641 | 55225723 | + | — | |
| hsa-mir-4423 | MI0016760 | 245 | chr1 | 85133794 | 85133873 | + | — | |
| hsa-mir-4424 | MI0016763 | 8.49 | chr1 | 178677749 | 178677834 | + | — | |
| hsa-mir-4425 | MI0016764 | 327 | chr1 | 25023503 | 25023586 | + | — | |
| hsa-mir-4426 | MI0016765 | 108 | chr1 | 192716328 | 192716390 | + | — | |
| hsa-mir-4427 | MI0016766 | 74 | chr1 | 233624152 | 233624219 | + | — | |
| hsa-mir-4428 | MI0016767 | 55.8 | chr1 | 237471119 | 237471191 | + | — | |
| hsa-mir-4429 | MI0016768 | 1.19e+03 | chr2 | 11540605 | 11540677 | − | — | |
| hsa-mir-4430 | MI0016769 | 217 | chr2 | 33418516 | 33418564 | + | — | |
| hsa-mir-4431 | MI0016771 | 155 | chr2 | 52702522 | 52702615 | − | — | |
| hsa-mir-4432 | MI0016772 | 78.8 | chr2 | 60387362 | 60387445 | − | — | |
| hsa-mir-4433a | MI0016773 | 22 | chr2 | 64340759 | 64340839 | + | — | |
| hsa-mir-4433b | MI0025511 | 8.23 | chr2 | 64340747 | 64340848 | − | — | |
| hsa-mir-4434 | MI0016774 | 1.9e+03 | chr2 | 64525513 | 64525565 | + | — | |
| hsa-mir-4435-1 | MI0016775 | 69.5 | chr2 | 87629755 | 87629834 | + | — | |
| hsa-mir-4435-2 | MI0016777 | 69.5 | chr2 | 111321013 | 111321086 | − | — | |
| hsa-mir-4436a | MI0016776 | 26 | chr2 | 88812370 | 88812454 | + | — | |
| hsa-mir-4436b-1 | MI0017425 | 81.3 | chr2 | 110086433 | 110086523 | − | — | |
| hsa-mir-4436b-2 | MI0019110 | 75.6 | chr2 | 110284853 | 110284943 | + | — | |
| hsa-mir-4437 | MI0016778 | 38.4 | chr2 | 181305593 | 181305652 | − | — | |
| hsa-mir-4438 | MI0016781 | 13.9 | chr2 | 213758067 | 213758159 | + | — | |
| hsa-mir-4439 | MI0016782 | 15.5 | chr2 | 225010461 | 225010540 | + | — | |
| hsa-mir-4440 | MI0016783 | 35.8 | chr2 | 239068817 | 239068914 | − | — | |
| hsa-mir-4441 | MI0016784 | 12.6 | chr2 | 239085827 | 239085926 | − | — | |
| hsa-mir-4442 | MI0016785 | 179 | chr3 | 25664873 | 25664939 | − | — | |
| hsa-mir-4443 | MI0016786 | 8.43e+03 | chr3 | 48196564 | 48196616 | + | — | |
| hsa-mir-4444-1 | MI0016787 | 116 | chr2 | 177212726 | 177212799 | + | — | |
| hsa-mir-4444-2 | MI0019111 | 119 | chr3 | 75214476 | 75214549 | + | — | |
| hsa-mir-4445 | MI0016788 | 4.01 | chr3 | 109602828 | 109602897 | + | — | |
| hsa-mir-4446 | MI0016789 | 72.5 | chr3 | 113594876 | 113594942 | + | — | |
| hsa-mir-4447 | MI0016790 | 80.3 | chr3 | 116850277 | 116850367 | − | — | |
| hsa-mir-4448 | MI0016791 | 353 | chr3 | 183886800 | 183886885 | + | — | |
| hsa-mir-4449 | MI0016792 | 7.11e+03 | chr4 | 52712682 | 52712747 | + | — | |
| hsa-mir-4450 | MI0016795 | 24.3 | chr4 | 76573568 | 76573632 | + | — | |
| hsa-mir-4451 | MI0016797 | 286 | chr4 | 85722468 | 85722533 | + | — | |
| hsa-mir-4452 | MI0016798 | 134 | chr4 | 86542482 | 86542552 | − | — | |

TABLE 1-continued

Exemplary Homo sapiens miRNAs incorporated into compositions as provided herein, and in compositions made by methods as provided herein

| ID | Accession | RPM | Chromosome | Start | End | Strand | Confidence Fetch |
|---|---|---|---|---|---|---|---|
| hsa-mir-4453 | MI0016799 | 140 | chr4 | 152536428 | 152536516 | + | — |
| hsa-mir-4454 | MI0016800 | 1.57e+03 | chr4 | 163093574 | 163093628 | − | — |
| hsa-mir-4455 | MI0016801 | 132 | chr4 | 184938383 | 184938440 | − | — |
| hsa-mir-4456 | MI0016802 | 22.8 | chr5 | 535840 | 535882 | − | — |
| hsa-mir-4457 | MI0016803 | 6.59 | chr5 | 1309310 | 1309377 | − | — |
| hsa-mir-4458 | MI0016804 | 139 | chr5 | 8460925 | 8460999 | + | — |
| hsa-mir-4459 | MI0016805 | 1.48e+03 | chr5 | 54075518 | 54075583 | − | — |
| hsa-mir-4460 | MI0016806 | 13.3 | chr5 | 129397062 | 129397147 | − | — |
| hsa-mir-4461 | MI0016807 | 82.1 | chr5 | 134928039 | 134928112 | + | — |
| hsa-mir-4462 | MI0016810 | 124 | chr6 | 37555365 | 37555422 | − | — |
| hsa-mir-4463 | MI0016811 | 15.1 | chr6 | 75428407 | 75428473 | + | — |
| hsa-mir-4464 | MI0016812 | 114 | chr6 | 90312742 | 90312833 | + | — |
| hsa-mir-4465 | MI0016816 | — | chr6 | 140683814 | 140683883 | + | — |
| hsa-mir-4466 | MI0016817 | 502 | chr6 | 156779678 | 156779731 | − | — |
| hsa-mir-4467 | MI0016818 | 235 | chr7 | 102471469 | 102471531 | + | — |
| hsa-mir-4468 | MI0016819 | 428 | chr7 | 138123758 | 138123821 | + | — |
| hsa-mir-4469 | MI0016820 | 77.4 | chr8 | 42896197 | 42896275 | − | — |
| hsa-mir-4470 | MI0016821 | 70.6 | chr8 | 61714788 | 61714859 | + | — |
| hsa-mir-4471 | MI0016822 | 2 | chr8 | 100382763 | 100382845 | + | — |
| hsa-mir-4472-1 | MI0016823 | 107 | chr8 | 142176339 | 142176418 | + | — |
| hsa-mir-4472-2 | MI0016824 | 506 | chr12 | 116428252 | 116428318 | − | — |
| hsa-mir-4473 | MI0016825 | 27.1 | chr9 | 20411148 | 20411238 | − | — |
| hsa-mir-4474 | MI0016826 | 1.63 | chr9 | 20502265 | 20502342 | − | — |
| hsa-mir-4475 | MI0016827 | 18 | chr9 | 36823539 | 36823599 | − | — |
| hsa-mir-4476 | MI0016828 | 130 | chr9 | 36893462 | 36893531 | − | — |
| hsa-mir-4477a | MI0016829 | 294 | chr9 | 41233755 | 41233835 | + | — |
| hsa-mir-4477b | MI0016830 | 38.9 | chr9 | 63819574 | 63819654 | + | — |
| hsa-mir-4478 | MI0016831 | 119 | chr9 | 122120082 | 122120167 | − | — |
| hsa-mir-4479 | MI0016838 | 129 | chr9 | 136886733 | 136886803 | + | — |
| hsa-mir-4480 | MI0016841 | 95.2 | chr10 | 12578753 | 12578823 | + | — |
| hsa-mir-4481 | MI0016842 | 47.1 | chr10 | 12653138 | 12653197 | − | — |
| hsa-mir-4482 | MI0016843 | 19.3 | chr10 | 104268336 | 104268405 | − | — |
| hsa-mir-4483 | MI0016844 | 28.2 | chr10 | 113777993 | 113778054 | − | — |
| hsa-mir-4484 | MI0016845 | 972 | chr10 | 125819740 | 125819822 | + | — |
| hsa-mir-4485 | MI0016846 | 1.17e+03 | chr11 | 10508270 | 10508326 | − | — |
| hsa-mir-4486 | MI0016847 | 24.1 | chr11 | 19575310 | 19575372 | + | — |
| hsa-mir-4487 | MI0016848 | 90 | chr11 | 47400970 | 47401042 | + | — |
| hsa-mir-4488 | MI0016849 | 1.59e+03 | chr11 | 61508596 | 61508657 | + | — |
| hsa-mir-4489 | MI0016850 | 18.2 | chr11 | 65649192 | 65649253 | + | — |
| hsa-mir-4490 | MI0016852 | 3.31 | chr11 | 90555774 | 90555857 | − | — |
| hsa-mir-4491 | MI0016853 | 28.2 | chr11 | 111347757 | 111347824 | + | — |
| hsa-mir-4492 | MI0016854 | 715 | chr11 | 118910708 | 118910787 | + | — |
| hsa-mir-4493 | MI0016855 | 47.2 | chr11 | 123381440 | 123381512 | − | — |
| hsa-mir-4494 | MI0016856 | 11 | chr12 | 47364186 | 47364269 | − | — |
| hsa-mir-4495 | MI0016857 | 90.8 | chr12 | 97939056 | 97939121 | − | — |
| hsa-mir-4496 | MI0016858 | 42.5 | chr12 | 108635810 | 108635870 | + | — |
| hsa-mir-4497 | MI0016859 | 3.26e+03 | chr12 | 109833348 | 109833436 | + | — |
| hsa-mir-4498 | MI0016860 | 15 | chr12 | 120155434 | 120155499 | − | — |
| hsa-mir-4499 | MI0016862 | 54.8 | chr13 | 20433778 | 20433846 | − | — |
| hsa-mir-4500 | MI0016863 | 183 | chr13 | 87618665 | 87618740 | − | — |
| hsa-mir-4501 | MI0016864 | 305 | chr13 | 96427229 | 96427292 | + | — |
| hsa-mir-4502 | MI0016865 | 92 | chr13 | 114273828 | 114273908 | + | — |
| hsa-mir-4503 | MI0016866 | — | chr14 | 36952309 | 36952391 | − | — |
| hsa-mir-4504 | MI0016867 | 95 | chr14 | 50299855 | 50299946 | − | — |
| hsa-mir-4505 | MI0016868 | 25.1 | chr14 | 73758747 | 73758819 | + | — |
| hsa-mir-4506 | MI0016869 | 14.2 | chr14 | 93948226 | 93948302 | − | — |
| hsa-mir-4507 | MI0016871 | 46.3 | chr14 | 105858124 | 105858175 | − | — |
| hsa-mir-4508 | MI0016872 | 1.43e+03 | chr15 | 23562062 | 23562131 | − | — |
| hsa-mir-4509-1 | MI0016873 | — | chr15 | 23197827 | 23197920 | + | — |
| hsa-mir-4509-2 | MI0016874 | 0.171 | chr15 | 28426491 | 28426584 | + | — |
| hsa-mir-4509-3 | MI0016875 | 0.748 | chr15 | 28490752 | 28490845 | − | — |
| hsa-mir-4510 | MI0016876 | 2.19e+03 | chr15 | 35926856 | 35926923 | + | — |
| hsa-mir-4511 | MI0016877 | 96.3 | chr15 | 65719246 | 65719332 | − | — |
| hsa-mir-4512 | MI0016878 | 531 | chr15 | 66496958 | 66497034 | − | — |
| hsa-mir-4513 | MI0016879 | 41.8 | chr15 | 74788672 | 74788757 | − | — |
| hsa-mir-4514 | MI0016880 | 0.0977 | chr15 | 80997417 | 80997473 | − | — |
| hsa-mir-4515 | MI0016881 | 41.2 | chr15 | 83067335 | 83067415 | + | — |
| hsa-mir-4516 | MI0016882 | 3.24e+03 | chr16 | 2133119 | 2133204 | + | — |
| hsa-mir-4517 | MI0016883 | 28.1 | chr16 | 28958583 | 28958661 | + | — |
| hsa-mir-4518 | MI0016884 | 211 | chr16 | 30503919 | 30504001 | + | — |
| hsa-mir-4519 | MI0016885 | 23.9 | chr16 | 30875266 | 30875323 | − | — |
| hsa-mir-4520-1 | MI0016886 | 20.7 | chr17 | 6655440 | 6655509 | − | — |
| hsa-mir-4520-2 | MI0017358 | 43 | chr17 | 6655449 | 6655502 | + | — |
| hsa-mir-4521 | MI0016887 | 441 | chr17 | 8186945 | 8187004 | + | — |
| hsa-mir-4522 | MI0016889 | 21.9 | chr17 | 27293910 | 27293996 | − | — |

TABLE 1-continued

Exemplary Homo sapiens miRNAs incorporated into compositions as provided herein, and in compositions made by methods as provided herein

| ID | Accession | RPM | Chromosome | Start | End | Strand | Confidence Fetch |
|---|---|---|---|---|---|---|---|
| hsa-mir-4523 | MI0016890 | 87.2 | chr17 | 29390662 | 29390730 | + | — |
| hsa-mir-4524a | MI0016891 | 45.1 | chr17 | 69099564 | 69099632 | − | ✓ |
| hsa-mir-4524b | MI0019114 | 44.3 | chr17 | 69099542 | 69099656 | + | — |
| hsa-mir-4525 | MI0016892 | 60.7 | chr17 | 82668233 | 82668307 | − | — |
| hsa-mir-4526 | MI0016893 | 74 | chr18 | 13611114 | 13611200 | + | — |
| hsa-mir-4527 | MI0016894 | 47.7 | chr18 | 47380496 | 47380565 | + | — |
| hsa-mir-4528 | MI0016895 | 0.856 | chr18 | 53237101 | 53237190 | + | — |
| hsa-mir-4529 | MI0016896 | 21.7 | chr18 | 55479221 | 55479298 | + | — |
| hsa-mir-4530 | MI0016897 | 116 | chr19 | 39409623 | 39409678 | − | — |
| hsa-mir-4531 | MI0016898 | 758 | chr19 | 44653686 | 44653732 | − | — |
| hsa-mir-4532 | MI0016899 | 6.16e+03 | chr20 | 57895394 | 57895444 | + | — |
| hsa-mir-4533 | MI0016900 | 239 | chr20 | 60478111 | 60478181 | + | — |
| hsa-mir-4534 | MI0016901 | 14.7 | chr22 | 37988794 | 37988853 | + | — |
| hsa-mir-4535 | MI0016903 | — | chr22 | 48780295 | 48780353 | + | — |
| hsa-mir-4536-1 | MI0016906 | 1.06e+03 | chrX | 55451495 | 55451582 | − | ✓ |
| hsa-mir-4536-2 | MI0019149 | 1.11e+03 | chrX | 55451495 | 55451582 | + | — |
| hsa-mir-4537 | MI0016908 | 129 | chr14 | 105859484 | 105859553 | − | — |
| hsa-mir-4538 | MI0016909 | 9.38 | chr14 | 105858165 | 105858242 | − | — |
| hsa-mir-4539 | MI0016910 | 8.93 | chr14 | 105857513 | 105857572 | − | — |
| hsa-mir-4540 | MI0016911 | — | chr9 | 36864254 | 36864308 | − | — |
| hsa-mir-4632 | MI0017259 | 411 | chr1 | 12191713 | 12191773 | + | — |
| hsa-mir-4633 | MI0017260 | 64.8 | chr5 | 129097688 | 129097766 | + | — |
| hsa-mir-4634 | MI0017261 | 343 | chr5 | 174751734 | 174751787 | + | — |
| hsa-mir-4635 | MI0017262 | 59.8 | chr5 | 1062896 | 1062974 | − | — |
| hsa-mir-4636 | MI0017263 | 38.8 | chr5 | 9053816 | 9053895 | − | — |
| hsa-mir-4637 | MI0017264 | 3.6 | chr5 | 14825929 | 14826012 | − | — |
| hsa-mir-4638 | MI0017265 | 18.8 | chr5 | 181222566 | 181222633 | − | — |
| hsa-mir-4639 | MI0017266 | 12.4 | chr6 | 16141556 | 16141624 | + | — |
| hsa-mir-4640 | MI0017267 | 59.8 | chr6 | 30890883 | 30890972 | + | — |
| hsa-mir-4641 | MI0017268 | 57.2 | chr6 | 41598723 | 41598788 | + | — |
| hsa-mir-4642 | MI0017269 | 15.8 | chr6 | 44435641 | 44435722 | + | — |
| hsa-mir-4643 | MI0017270 | 0.222 | chr6 | 91521660 | 91521737 | + | — |
| hsa-mir-4644 | MI0017271 | 85.4 | chr6 | 170330761 | 170330844 | + | — |
| hsa-mir-4645 | MI0017272 | 58.7 | chr6 | 2854031 | 2854107 | − | — |
| hsa-mir-4646 | MI0017273 | 54.1 | chr6 | 31701029 | 31701091 | − | — |
| hsa-mir-4647 | MI0017274 | 60.1 | chr6 | 44254206 | 44254285 | − | — |
| hsa-mir-4648 | MI0017275 | 6.75 | chr7 | 2527074 | 2527145 | + | — |
| hsa-mir-4649 | MI0017276 | 23.8 | chr7 | 44110849 | 44110912 | + | — |
| hsa-mir-4650-1 | MI0017277 | 245 | chr7 | 67114322 | 67114397 | − | — |
| hsa-mir-4650-2 | MI0017278 | 221 | chr7 | 72697903 | 72697978 | + | — |
| hsa-mir-4651 | MI0017279 | 46.3 | chr7 | 75915197 | 75915269 | + | — |
| hsa-mir-4652 | MI0017280 | 4.92 | chr7 | 93716928 | 93717005 | + | — |
| hsa-mir-4653 | MI0017281 | 23.3 | chr7 | 101159473 | 101159555 | + | — |
| hsa-mir-4654 | MI0017282 | 44.1 | chr1 | 162157107 | 162157182 | + | — |
| hsa-mir-4655 | MI0017283 | 291 | chr7 | 1844180 | 1844253 | − | — |
| hsa-mir-4656 | MI0017284 | 112 | chr7 | 4788565 | 4788639 | − | — |
| hsa-mir-4657 | MI0017285 | 21.8 | chr7 | 44881748 | 44881800 | − | — |
| hsa-mir-4658 | MI0017286 | 31.5 | chr7 | 100156605 | 100156669 | − | — |
| hsa-mir-4659a | MI0017287 | 38.3 | chr8 | 6745164 | 6745244 | + | — |
| hsa-mir-4659b | MI0017291 | 21.7 | chr8 | 6745168 | 6745240 | + | — |
| hsa-mir-4660 | MI0017288 | 103 | chr8 | 9048445 | 9048518 | + | — |
| hsa-mir-4661 | MI0017289 | 111 | chr8 | 91205485 | 91205559 | + | — |
| hsa-mir-4662a | MI0017290 | 57.8 | chr8 | 124821985 | 124822051 | + | — |
| hsa-mir-4662b | MI0017293 | 78.7 | chr8 | 124821978 | 124822058 | − | — |
| hsa-mir-4663 | MI0017292 | 116 | chr8 | 123215788 | 123215863 | − | — |
| hsa-mir-4664 | MI0017294 | 105 | chr8 | 143733083 | 143733153 | − | — |
| hsa-mir-4665 | MI0017295 | 30.1 | chr9 | 6007826 | 6007904 | + | — |
| hsa-mir-4666a | MI0017296 | 43.7 | chr1 | 228462074 | 228462152 | + | — |
| hsa-mir-4666b | MI0019299 | 67 | chrX | 29574278 | 29574358 | + | — |
| hsa-mir-4667 | MI0017297 | 87.4 | chr9 | 35608094 | 35608159 | + | — |
| hsa-mir-4668 | MI0017298 | 114 | chr9 | 111932100 | 111932169 | + | — |
| hsa-mir-4669 | MI0017300 | 437 | chr9 | 134379411 | 134379472 | + | — |
| hsa-mir-4670 | MI0017301 | 17.2 | chr9 | 92527984 | 92528058 | − | — |
| hsa-mir-4671 | MI0017302 | — | chr1 | 234306467 | 234306539 | + | — |
| hsa-mir-4672 | MI0017303 | 6.6 | chr9 | 127869415 | 127869495 | − | — |
| hsa-mir-4673 | MI0017304 | 65.7 | chr9 | 136519568 | 136519626 | − | — |
| hsa-mir-4674 | MI0017305 | 40.3 | chr9 | 136546173 | 136546259 | − | — |
| hsa-mir-4675 | MI0017306 | 93.3 | chr10 | 20551970 | 20552046 | + | — |
| hsa-mir-4676 | MI0017307 | 14.2 | chr10 | 72721029 | 72721100 | + | — |
| hsa-mir-4677 | MI0017308 | 25.8 | chr1 | 243346176 | 243346255 | + | — |
| hsa-mir-4678 | MI0017309 | 19.9 | chr10 | 87503881 | 87503954 | + | — |
| hsa-mir-4679-1 | MI0017310 | 33.7 | chr10 | 89063336 | 89063410 | + | — |
| hsa-mir-4679-2 | MI0017311 | 11.7 | chr10 | 89063335 | 89063411 | − | — |
| hsa-mir-4680 | MI0017312 | 10.9 | chr10 | 110898090 | 110898155 | + | — |
| hsa-mir-4681 | MI0017313 | 6.02 | chr10 | 119377972 | 119378043 | + | — |

TABLE 1-continued

Exemplary Homo sapiens miRNAs incorporated into compositions as provided herein, and in compositions made by methods as provided herein

| ID | Accession | RPM | Chromosome | Start | End | Strand | Confidence Fetch |
|---|---|---|---|---|---|---|---|
| hsa-mir-4682 | MI0017314 | 63.1 | chr10 | 119958513 | 119958592 | + | — |
| hsa-mir-4683 | MI0017315 | 155 | chr10 | 35641172 | 35641252 | − | — |
| hsa-mir-4684 | MI0017316 | 16.8 | chr1 | 22719517 | 22719598 | + | — |
| hsa-mir-4685 | MI0017317 | 71.6 | chr10 | 98431292 | 98431360 | − | — |
| hsa-mir-4686 | MI0017318 | 37.2 | chr11 | 2173063 | 2173138 | + | — |
| hsa-mir-4687 | MI0017319 | 147 | chr11 | 3856062 | 3856141 | + | — |
| hsa-mir-4688 | MI0017321 | 25.9 | chr11 | 46376402 | 46376484 | + | — |
| hsa-mir-4689 | MI0017322 | 202 | chr1 | 5862672 | 5862741 | − | — |
| hsa-mir-4690 | MI0017323 | 21.8 | chr11 | 65636310 | 65636369 | + | — |
| hsa-mir-4691 | MI0017324 | 20.2 | chr11 | 68033897 | 68033981 | + | — |
| hsa-mir-4692 | MI0017325 | 2.23 | chr11 | 72783530 | 72783592 | + | — |
| hsa-mir-4693 | MI0017326 | 127 | chr11 | 103849906 | 103849980 | + | — |
| hsa-mir-4694 | MI0017327 | 9.15 | chr11 | 19760004 | 19760083 | − | — |
| hsa-mir-4695 | MI0017328 | 119 | chr1 | 18883202 | 18883275 | − | — |
| hsa-mir-4696 | MI0017329 | 129 | chr11 | 74720268 | 74720337 | − | — |
| hsa-mir-4697 | MI0017330 | 3.01 | chr11 | 133898504 | 133898581 | − | — |
| hsa-mir-4698 | MI0017331 | 125 | chr12 | 47187812 | 47187891 | + | — |
| hsa-mir-4699 | MI0017332 | 18.8 | chr12 | 81158388 | 81158461 | + | — |
| hsa-mir-4700 | MI0017333 | 24.3 | chr12 | 120723193 | 120723266 | + | — |
| hsa-mir-4701 | MI0017334 | 8.02 | chr12 | 48771975 | 48772037 | − | — |
| hsa-mir-4703 | MI0017336 | 287 | chr13 | 51552589 | 51552667 | + | — |
| hsa-mir-4704 | MI0017337 | 79.8 | chr13 | 66218250 | 66218324 | + | — |
| hsa-mir-4705 | MI0017338 | 506 | chr13 | 102045934 | 102046004 | − | — |
| hsa-mir-4706 | MI0017339 | 225 | chr14 | 65044688 | 65044769 | + | — |
| hsa-mir-4707 | MI0017340 | 840 | chr14 | 22956950 | 22957029 | − | ✓ |
| hsa-mir-4708 | MI0017341 | 112 | chr14 | 65335117 | 65335183 | − | — |
| hsa-mir-4709 | MI0017342 | 159 | chr14 | 74480133 | 74480204 | − | — |
| hsa-mir-4710 | MI0017344 | 130 | chr14 | 104677694 | 104677749 | − | — |
| hsa-mir-4711 | MI0017345 | 9.4 | chr1 | 59733227 | 59733296 | − | — |
| hsa-mir-4712 | MI0017346 | 26.5 | chr15 | 50360329 | 50360410 | + | — |
| hsa-mir-4713 | MI0017347 | 38.7 | chr15 | 51242190 | 51242264 | + | — |
| hsa-mir-4714 | MI0017348 | 36.1 | chr15 | 98784426 | 98784502 | + | — |
| hsa-mir-4715 | MI0017349 | 69.1 | chr15 | 25848747 | 25848825 | − | — |
| hsa-mir-4716 | MI0017350 | 170 | chr15 | 49169070 | 49169153 | − | — |
| hsa-mir-4717 | MI0017352 | 3.77 | chr16 | 2274620 | 2274691 | + | — |
| hsa-mir-4718 | MI0017353 | — | chr16 | 12720321 | 12720371 | + | — |
| hsa-mir-4719 | MI00 17354 | 20.8 | chr16 | 76868936 | 76869019 | + | — |
| hsa-mir-4720 | MI0017355 | — | chr16 | 81385018 | 81385093 | + | — |
| hsa-mir-4721 | MI0017356 | 27 | chr16 | 28843919 | 28844007 | − | — |
| hsa-mir-4722 | MI0017357 | 92.1 | chr16 | 88716278 | 88716337 | − | — |
| hsa-mir-4723 | MI0017359 | 34.1 | chr17 | 28360654 | 28360714 | + | — |
| hsa-mir-4724 | MI0017361 | 242 | chr17 | 31534883 | 31534971 | + | — |
| hsa-mir-4725 | MI0017362 | 148 | chr17 | 31575269 | 31575358 | + | — |
| hsa-mir-4726 | MI0017363 | 99.7 | chr17 | 38719691 | 38719748 | + | — |
| hsa-mir-4727 | MI0017364 | 20.4 | chr17 | 38825838 | 38825892 | + | — |
| hsa-mir-4728 | MI0017365 | 69.7 | chr17 | 39726495 | 39726561 | + | — |
| hsa-mir-4729 | MI0017366 | 40 | chr17 | 59366083 | 59366154 | + | — |
| hsa-mir-4730 | MI0017367 | 4e+03 | chr17 | 80419418 | 80419493 | + | — |
| hsa-mir-4731 | MI0017368 | 46.1 | chr17 | 15251627 | 15251696 | − | — |
| hsa-mir-4732 | MI0017369 | 61.5 | chr17 | 28861655 | 28861730 | − | — |
| hsa-mir-4733 | MI0017370 | 23.7 | chr17 | 31094350 | 31094425 | − | — |
| hsa-mir-4734 | MI0017371 | 83.9 | chr17 | 38702262 | 38702331 | − | — |
| hsa-mir-4735 | MI0017372 | 28.5 | chr1 | 196582413 | 196582481 | − | — |
| hsa-mir-4736 | MI0017373 | 4.22 | chr17 | 58335976 | 58336022 | − | — |
| hsa-mir-4737 | MI0017374 | 74 | chr17 | 60043025 | 60043105 | − | — |
| hsa-mir-4738 | MI0017376 | 137 | chr17 | 75784521 | 75784607 | − | — |
| hsa-mir-4739 | MI0017377 | 370 | chr17 | 79707176 | 79707249 | − | — |
| hsa-mir-4740 | MI0017378 | 0.222 | chr17 | 81400716 | 81400778 | − | — |
| hsa-mir-4741 | MI0017379 | 150 | chr18 | 22933349 | 22933438 | + | — |
| hsa-mir-4742 | MI0017380 | 27 | chr1 | 224398227 | 224398311 | − | — |
| hsa-mir-4743 | MI0017381 | 20.3 | chr18 | 48670600 | 48670668 | + | — |
| hsa-mir-4744 | MI0017382 | 38.7 | chr18 | 49049687 | 49049768 | − | — |
| hsa-mir-4745 | MI0017384 | 31.3 | chr19 | 804940 | 805001 | + | — |
| hsa-mir-4746 | MI0017385 | 18.9 | chr19 | 4445978 | 4446048 | + | — |
| hsa-mir-4747 | MI0017386 | 17.3 | chr19 | 4932687 | 4932740 | + | — |
| hsa-mir-4748 | MI0017387 | 46.8 | chr19 | 10780254 | 10780335 | + | — |
| hsa-mir-4749 | MI0017388 | 471 | chr19 | 49854591 | 49854651 | + | — |
| hsa-mir-4750 | MI0017389 | 101 | chr19 | 49888175 | 49888230 | + | — |
| hsa-mir-4751 | MI0017390 | 57 | chr19 | 49933064 | 49933137 | + | — |
| hsa-mir-4752 | MI0017391 | 9.85 | chr19 | 54282109 | 54282180 | + | — |
| hsa-mir-4753 | MI0017392 | 37.2 | chr1 | 235190034 | 235190116 | − | — |
| hsa-mir-4754 | MI0017394 | 62.1 | chr19 | 58386770 | 58386858 | − | — |
| hsa-mir-4755 | MI0017395 | 129 | chr20 | 34049119 | 34049190 | + | ✓ |
| hsa-mir-4756 | MI0017397 | 550 | chr20 | 54068408 | 54068485 | − | — |
| hsa-mir-4757 | MI0017398 | 12.1 | chr2 | 19348429 | 19348505 | + | — |

TABLE 1-continued

Exemplary *Homo sapiens* miRNAs incorporated into compositions as provided
herein, and in compositions made by methods as provided herein

| ID | Accession | RPM | Chromosome | Start | End | Strand | Confidence Fetch |
|---|---|---|---|---|---|---|---|
| hsa-mir-4758 | MI0017399 | 34.5 | chr20 | 62332487 | 62332557 | − | — |
| hsa-mir-4759 | MI0017400 | 69.1 | chr21 | 26953961 | 26954043 | + | — |
| hsa-mir-4760 | MI0017401 | 13.2 | chr21 | 40212352 | 40212431 | − | — |
| hsa-mir-4761 | MI0017402 | 66.1 | chr22 | 19963753 | 19963834 | + | — |
| hsa-mir-4762 | MI0017403 | 11.4 | chr22 | 45760524 | 45760598 | + | — |
| hsa-mir-4763 | MI0017404 | 415 | chr22 | 46113566 | 46113657 | + | — |
| hsa-mir-4764 | MI0017405 | 41.1 | chr22 | 33436582 | 33436669 | − | — |
| hsa-mir-4765 | MI0017406 | 27 | chr2 | 32635255 | 32635331 | + | — |
| hsa-mir-4766 | MI0017407 | 71.2 | chr22 | 40813883 | 40813958 | − | — |
| hsa-mir-4767 | MI0017408 | 328 | chrX | 7147860 | 7147937 | + | — |
| hsa-mir-4768 | MI0017409 | 148 | chrX | 17425881 | 17425954 | + | — |
| hsa-mir-4769 | MI0017410 | 85.5 | chrX | 47587429 | 47587505 | + | — |
| hsa-mir-4770 | MI0017411 | 29.9 | chrX | 6383906 | 6383963 | − | — |
| hsa-mir-4771-1 | MI0017412 | 19.4 | chr2 | 87194786 | 87194859 | + | — |
| hsa-mir-4771-2 | MI0017413 | 28.1 | chr2 | 111771061 | 111771134 | − | — |
| hsa-mir-4772 | MI0017414 | 96.8 | chr2 | 102432289 | 102432366 | + | — |
| hsa-mir-4773-1 | MI0017415 | 42.7 | chr2 | 151368334 | 151368411 | + | — |
| hsa-mir-4773-2 | MI0017416 | 161 | chr2 | 151368334 | 151368411 | − | — |
| hsa-mir-4774 | MI0017417 | 5.46 | chr2 | 168582943 | 168583018 | + | — |
| hsa-mir-4775 | MI0017418 | 153 | chr2 | 207754807 | 207754881 | + | — |
| hsa-mir-4776-1 | MI0017419 | 122 | chr2 | 212926257 | 212926336 | + | — |
| hsa-mir-4776-2 | MI0017420 | 76.7 | chr2 | 212926257 | 212926336 | − | — |
| hsa-mir-4777 | MI0017421 | 24.8 | chr2 | 231362708 | 231362793 | + | — |
| hsa-mir-4778 | MI0017422 | 118 | chr2 | 66358249 | 66358328 | − | — |
| hsa-mir-4779 | MI0017423 | 3.5 | chr2 | 86193026 | 86193108 | − | — |
| hsa-mir-4780 | MI0017424 | 56.7 | chr2 | 88082519 | 88082599 | − | — |
| hsa-mir-4781 | MI0017426 | 27.1 | chr1 | 54054079 | 54054154 | + | — |
| hsa-mir-4782 | MI0017427 | 30.7 | chr2 | 113721290 | 113721368 | − | — |
| hsa-mir-4783 | MI0017428 | 102 | chr2 | 127423537 | 127423618 | − | — |
| hsa-mir-4784 | MI0017429 | 11.4 | chr2 | 131491160 | 131491236 | − | — |
| hsa-mir-4785 | MI0017430 | 55.3 | chr2 | 160407810 | 160407882 | − | — |
| hsa-mir-4786 | MI0017433 | 34.7 | chr2 | 239943015 | 239943094 | − | — |
| hsa-mir-4787 | MI0017434 | 577 | chr3 | 50675080 | 50675163 | + | ✓ |
| hsa-mir-4788 | MI0017435 | 47.7 | chr3 | 134437827 | 134437906 | + | — |
| hsa-mir-4789 | MI0017436 | 37.5 | chr3 | 175369540 | 175369621 | + | — |
| hsa-mir-4790 | MI0017437 | 121 | chr3 | 5250177 | 5250255 | − | — |
| hsa-mir-4791 | MI0017438 | 161 | chr3 | 19314848 | 19314931 | − | — |
| hsa-mir-4792 | MI0017439 | 1.95e+03 | chr3 | 24521362 | 24521435 | − | — |
| hsa-mir-4793 | MI0017440 | 52 | chr3 | 48644194 | 48644280 | − | — |
| hsa-mir-4794 | MI0017441 | 0.149 | chr1 | 64579847 | 64579923 | + | — |
| hsa-mir-4795 | MI0017442 | 30.1 | chr3 | 87226189 | 87226277 | − | — |
| hsa-mir-4796 | MI0017443 | 13.5 | chr3 | 114743445 | 114743525 | − | — |
| hsa-mir-4797 | MI0017444 | 19 | chr3 | 197293878 | 197293948 | − | — |
| hsa-mir-4798 | MI0017445 | 1.82 | chr4 | 7310450 | 7310524 | + | — |
| hsa-mir-4799 | MI0017446 | 10.1 | chr4 | 147782595 | 147782668 | + | — |
| hsa-mir-4800 | MI0017448 | 280 | chr4 | 2250077 | 2250156 | − | — |
| hsa-mir-4801 | MI0017449 | 85.4 | chr4 | 37241910 | 37241991 | − | — |
| hsa-mir-4802 | MI0017450 | 21.8 | chr4 | 40502040 | 40502119 | − | — |
| hsa-mir-4803 | MI0017451 | 7.43 | chr5 | 72169467 | 72169546 | + | — |
| hsa-mir-4804 | MI0017452 | 43.7 | chr5 | 72878591 | 72878663 | + | — |
| hsa-mir-4999 | MI0017865 | 21 | chr19 | 8389290 | 8389380 | − | — |
| hsa-mir-5000 | MI0017866 | 3.97e+03 | chr2 | 75090812 | 75090914 | + | ✓ |
| hsa-mir-5001 | MI0017867 | 53.3 | chr2 | 232550474 | 232550573 | − | ✓ |
| hsa-mir-5002 | MI0017868 | 271 | chr3 | 124132929 | 124133025 | + | — |
| hsa-mir-5003 | MI0017869 | 148 | chr5 | 172662165 | 172662263 | + | — |
| hsa-mir-5004 | MI0017870 | 48.8 | chr6 | 33438331 | 33438437 | + | — |
| hsa-mir-5006 | MI0017873 | 47.8 | chr13 | 41568286 | 41568395 | − | — |
| hsa-mir-5007 | MI0017874 | 78.9 | chr13 | 55174454 | 55174548 | + | — |
| hsa-mir-5008 | MI0017876 | 52.4 | chr1 | 227941590 | 227941683 | − | — |
| hsa-mir-5009 | MI0017877 | 48.3 | chr15 | 89883931 | 89884030 | − | — |
| hsa-mir-5010 | MI0017878 | 126 | chr17 | 42514188 | 42514307 | + | ✓ |
| hsa-mir-5011 | MI0017879 | — | chr18 | 67081584 | 67081686 | + | — |
| hsa-mir-5047 | MI0017932 | 12.4 | chr17 | 64501214 | 64501313 | − | — |
| hsa-mir-5087 | MI0017976 | 155 | chr1 | 148334479 | 148334554 | − | — |
| hsa-mir-5088 | MI0017977 | 310 | chr19 | 49682117 | 49682195 | + | — |
| hsa-mir-5089 | MI0017978 | 11.2 | chr17 | 46973017 | 46973100 | + | — |
| hsa-mir-5090 | MI0017979 | 71.6 | chr7 | 102465742 | 102465826 | + | — |
| hsa-mir-5091 | MI0017980 | 93.6 | chr4 | 13627865 | 13627957 | + | — |
| hsa-mir-5092 | MI0017981 | 44.5 | chr3 | 125151465 | 125151552 | − | — |
| hsa-mir-5093 | MI0017982 | 32.9 | chr16 | 85306226 | 85306325 | − | — |
| hsa-mir-5094 | MI0017983 | 135 | chr15 | 89850637 | 89850721 | − | — |
| hsa-mir-5095 | MI0018001 | 824 | chr1 | 52934930 | 52935017 | + | — |
| hsa-mir-5096 | MI0018004 | 778 | chr4 | 78820752 | 78820821 | + | — |
| hsa-mir-5100 | MI0019116 | 747 | chr10 | 42997563 | 42997681 | + | — |
| hsa-mir-5186 | MI0018165 | 110 | chr3 | 151565876 | 151565995 | − | — |

TABLE 1-continued

Exemplary Homo sapiens miRNAs incorporated into compositions as provided
herein, and in compositions made by methods as provided herein

| ID | Accession | RPM | Chromosome | Start | End | Strand | Confidence Fetch |
|---|---|---|---|---|---|---|---|
| hsa-mir-5187 | MI0018166 | 133 | chr1 | 161227186 | 161227261 | + | — |
| hsa-mir-5188 | MI0018167 | 18.9 | chr12 | 124915547 | 124915659 | + | — |
| hsa-mir-5189 | MI0018168 | 137 | chr16 | 88468918 | 88469031 | + | — |
| hsa-mir-5190 | MI0018169 | 123 | chr18 | 13459947 | 13460026 | + | — |
| hsa-mir-5191 | MI0018170 | 110 | chr1 | 201719508 | 201719627 | + | — |
| hsa-mir-5192 | MI0018171 | 163 | chr2 | 62205826 | 62205917 | + | — |
| hsa-mir-5193 | MI0018172 | 120 | chr3 | 49806137 | 49806245 | − | — |
| hsa-mir-5194 | MI0018173 | 39.5 | chr8 | 130008334 | 130008453 | − | — |
| hsa-mir-5195 | MI0018174 | 47 | chr14 | 106850885 | 106850999 | − | — |
| hsa-mir-5196 | MI0018175 | 69.1 | chr19 | 35345513 | 35345627 | + | ✓ |
| hsa-mir-5197 | MI0018176 | 38.8 | chr5 | 143679860 | 143679971 | + | — |
| hsa-mir-5571 | MI0019115 | 280 | chr22 | 22886267 | 22886379 | + | — |
| hsa-mir-5572 | MI0019117 | 224 | chr15 | 80581103 | 80581239 | + | — |
| hsa-mir-5579 | MI0019133 | 47.8 | chr11 | 79422169 | 79422226 | − | — |
| hsa-mir-5580 | MI0019135 | 9.62 | chr14 | 53948427 | 53948484 | − | — |
| hsa-mir-5581 | MI0019136 | 32.6 | chr1 | 37500935 | 37500994 | − | — |
| hsa-mir-5582 | MI0019138 | 24.8 | chr11 | 46753125 | 46753192 | − | — |
| hsa-mir-5583-1 | MI0019139 | — | chr18 | 39676721 | 39676779 | + | — |
| hsa-mir-5583-2 | MI0019140 | 0.748 | chr18 | 39676719 | 39676777 | − | — |
| hsa-mir-5584 | MI0019141 | 46.3 | chr1 | 44545493 | 44545552 | + | — |
| hsa-mir-5585 | MI0019142 | 578 | chr1 | 32086949 | 32087007 | + | — |
| hsa-mir-5586 | MI0019143 | 42.7 | chr14 | 59646962 | 59647020 | − | — |
| hsa-mir-5587 | MI0019144 | 81 | chr16 | 535316 | 535368 | + | — |
| hsa-mir-5588 | MI0019147 | 107 | chr3 | 185253210 | 185253272 | − | — |
| hsa-mir-5589 | MI0019148 | — | chr19 | 10038354 | 10038413 | + | — |
| hsa-mir-5590 | MI0019150 | — | chr2 | 134857820 | 134857873 | + | — |
| hsa-mir-5591 | MI0019151 | 42.4 | chr4 | 39411910 | 39411974 | + | — |
| hsa-mir-5680 | MI0019280 | 42 | chr8 | 102125432 | 102125515 | + | — |
| hsa-mir-5681a | MI0019281 | 37 | chr8 | 74548543 | 74548617 | + | — |
| hsa-mir-5681b | MI0019293 | 120 | chr8 | 74548550 | 74548609 | − | — |
| hsa-mir-5682 | MI0019282 | 13.5 | chr3 | 121049640 | 121049715 | + | — |
| hsa-mir-5683 | MI0019284 | 9.56 | chr6 | 6169334 | 6169409 | + | — |
| hsa-mir-5684 | MI0019285 | 847 | chr19 | 12787128 | 12787192 | + | — |
| hsa-mir-5685 | MI0019287 | 17.3 | chr6 | 53276993 | 53277071 | + | — |
| hsa-mir-5687 | MI0019291 | 2.14 | chr5 | 55508850 | 55508926 | − | — |
| hsa-mir-5688 | MI0019292 | 0.929 | chr3 | 85385710 | 85385792 | + | — |
| hsa-mir-5689 | MI0019294 | 113 | chr6 | 10439717 | 10439794 | + | — |
| hsa-mir-5690 | MI0019295 | 16.5 | chr6 | 35664717 | 35664789 | − | — |
| hsa-mir-5691 | MI0019296 | — | chr11 | 9090312 | 9090379 | − | — |
| hsa-mir-5692a-1 | MI0019297 | 22.4 | chr7 | 97963658 | 97963726 | + | — |
| hsa-mir-5692a-2 | MI0019298 | 11.6 | chr8 | 12719132 | 12719190 | + | — |
| hsa-mir-5692b | MI0019311 | 18.7 | chr21 | 42950928 | 42951014 | − | — |
| hsa-mir-5692c-1 | MI0019288 | 22.2 | chr5 | 135802985 | 135803075 | − | — |
| hsa-mir-5692c-2 | MI0019289 | 55.1 | chr7 | 97964405 | 97964481 | − | — |
| hsa-mir-5693 | MI0019300 | 60.6 | chr13 | 51348567 | 51348639 | − | — |
| hsa-mir-5694 | MI0019301 | 55 | chr14 | 67441855 | 67441930 | − | — |
| hsa-mir-5695 | MI0019302 | 28.5 | chr19 | 12920320 | 12920404 | + | — |
| hsa-mir-5696 | MI0019303 | 11.6 | chr2 | 101309450 | 101309534 | + | — |
| hsa-mir-5697 | MI0019304 | 7.84 | chr1 | 9967381 | 9967458 | + | — |
| hsa-mir-5698 | MI0019305 | 28 | chr1 | 154104521 | 154104592 | − | — |
| hsa-mir-5699 | MI0019306 | 288 | chr10 | 641689 | 641778 | − | — |
| hsa-mir-5700 | MI0019307 | 27.3 | chr12 | 94561789 | 94561859 | + | — |
| hsa-mir-5701-1 | MI0019308 | 824 | chr15 | 20940252 | 20940333 | + | — |
| hsa-mir-5701-2 | MI0019593 | 861 | chr15 | 21513959 | 21514040 | + | — |
| hsa-mir-5701-3 | MI0031522 | 1.81 | chr15 | 21951242 | 21951323 | + | — |
| hsa-mir-5702 | MI0019309 | — | chr2 | 226658710 | 226658793 | − | — |
| hsa-mir-5703 | MI0019310 | 184 | chr2 | 227472132 | 227472187 | + | — |
| hsa-mir-5704 | MI0019312 | 17.3 | chr3 | 131985855 | 131985931 | − | — |
| hsa-mir-5705 | MI0019313 | 86.4 | chr4 | 87300495 | 87300583 | − | — |
| hsa-mir-5706 | MI0019314 | 15.2 | chr5 | 119154637 | 119154716 | + | — |
| hsa-mir-5707 | MI0019315 | 17.3 | chr7 | 158591616 | 158591696 | + | — |
| hsa-mir-5708 | MI0019316 | 290 | chr8 | 80241389 | 80241473 | + | — |
| hsa-mir-5739 | MI0019412 | 112 | chr22 | 28459869 | 28459948 | + | — |
| hsa-mir-5787 | MI0019797 | 171 | chr3 | 50227436 | 50227490 | + | — |
| hsa-mir-6068 | MI0020345 | — | chr1 | 63326925 | 63326984 | − | — |
| hsa-mir-6069 | MI0020346 | 84.9 | chr22 | 35336721 | 35336799 | − | — |
| hsa-mir-6070 | MI0020347 | 107 | chr21 | 43609887 | 43609989 | − | — |
| hsa-mir-6071 | MI0020348 | 33.2 | chr2 | 85783600 | 85783677 | − | — |
| hsa-mir-6072 | MI0020349 | 361 | chr10 | 2076019 | 2076089 | − | — |
| hsa-mir-6073 | MI0020350 | 167 | chr11 | 15969533 | 15969621 | − | — |
| hsa-mir-6074 | MI0020351 | 79.2 | chr12 | 66023620 | 66023726 | − | — |
| hsa-mir-6075 | MI0020352 | 75.2 | chr5 | 1510762 | 1510856 | − | — |
| hsa-mir-6076 | MI0020353 | 171 | chr14 | 49966399 | 49966511 | + | — |
| hsa-mir-6077 | MI0020354 | 58.6 | chr1 | 148388282 | 148388363 | + | — |
| hsa-mir-6078 | MI0020355 | 74.7 | chr10 | 3991160 | 3991259 | + | — |

TABLE 1-continued

Exemplary Homo sapiens miRNAs incorporated into compositions as provided herein, and in compositions made by methods as provided herein

| ID | Accession | RPM | Chromosome | Start | End | Strand | Confidence Fetch |
|---|---|---|---|---|---|---|---|
| hsa-mir-6079 | MI0020356 | — | chr1 | 43838622 | 43838683 | + | — |
| hsa-mir-6080 | MI0020357 | 40.6 | chr17 | 64780759 | 64780824 | + | — |
| hsa-mir-6081 | MI0020358 | 21 | chr9 | 95065350 | 95065446 | + | — |
| hsa-mir-6082 | MI0020359 | 21.3 | chr4 | 171186184 | 171186292 | + | — |
| hsa-mir-6083 | MI0020360 | 61.7 | chr3 | 124374332 | 124374437 | + | — |
| hsa-mir-6084 | MI0020361 | 671 | chr1 | 20633679 | 20633788 | + | — |
| hsa-mir-6085 | MI0020362 | 103 | chr15 | 62343029 | 62343138 | + | — |
| hsa-mir-6086 | MI0020363 | 64.5 | chrX | 13590292 | 13590346 | + | — |
| hsa-mir-6087 | MI0020364 | 3.66e+03 | chrX | 109054542 | 109054590 | + | — |
| hsa-mir-6088 | MI0020365 | 393 | chr19 | 45436654 | 45436704 | + | — |
| hsa-mir-6089-1 | MI0020366 | 350 | chrX | 2609191 | 2609254 | + | — |
| hsa-mir-6089-2 | MI0023563 | 350 | chrY | 2609191 | 2609254 | + | — |
| hsa-mir-6090 | MI0020367 | 172 | chr11 | 128522390 | 128522449 | + | — |
| hsa-mir-6124 | MI0021258 | 211 | chr11 | 12163683 | 12163767 | + | — |
| hsa-mir-6125 | MI0021259 | 427 | chr12 | 62260359 | 62260454 | + | — |
| hsa-mir-6126 | MI0021260 | 1.23e+03 | chr16 | 3485381 | 3485469 | − | — |
| hsa-mir-6127 | MI0021271 | 450 | chr1 | 22633258 | 22633366 | + | — |
| hsa-mir-6128 | MI0021272 | 113 | chr11 | 56743873 | 56743981 | + | — |
| hsa-mir-6129 | MI0021274 | 265 | chr17 | 49288346 | 49288454 | − | — |
| hsa-mir-6130 | MI0021275 | 2.83e+03 | chr21 | 23079284 | 23079392 | + | — |
| hsa-mir-6131 | MI0021276 | 213 | chr5 | 10478037 | 10478145 | + | — |
| hsa-mir-6132 | MI0021277 | 74.9 | chr7 | 117020211 | 117020319 | + | — |
| hsa-mir-6133 | MI0021278 | 330 | chr7 | 133290881 | 133290988 | + | — |
| hsa-mir-6134 | MI0021279 | 107 | chrX | 28495555 | 28495663 | − | — |
| hsa-mir-6165 | MI0021472 | 136 | chr17 | 49510817 | 49510900 | + | — |
| hsa-mir-6499 | MI0022209 | 290 | chr5 | 151522087 | 151522148 | − | — |
| hsa-mir-6500 | MI0022211 | 59.9 | chr1 | 51060018 | 51060103 | + | — |
| hsa-mir-6501 | MI0022213 | 40.8 | chr21 | 33550662 | 33550728 | + | — |
| hsa-mir-6502 | MI0022214 | 23.7 | chr12 | 66251082 | 66251157 | + | — |
| hsa-mir-6503 | MI0022215 | 91.8 | chr11 | 60209071 | 60209156 | − | ✓ |
| hsa-mir-6504 | MI0022216 | 68.9 | chr16 | 81611348 | 81611408 | + | — |
| hsa-mir-6505 | MI0022217 | 66.6 | chr12 | 48132797 | 48132867 | + | — |
| hsa-mir-6506 | MI0022218 | 6.84 | chr16 | 15611030 | 15611095 | − | — |
| hsa-mir-6507 | MI0022219 | 80.1 | chr10 | 98924499 | 98924568 | − | — |
| hsa-mir-6508 | MI0022220 | 7.65 | chr21 | 39447010 | 39447069 | + | — |
| hsa-mir-6509 | MI0022221 | 8.35 | chr7 | 135206994 | 135207078 | − | — |
| hsa-mir-6510 | MI0022222 | 232 | chr17 | 41517164 | 41517217 | − | — |
| hsa-mir-6511a-1 | MI0022223 | 114 | chr16 | 14925937 | 14926003 | + | ✓ |
| hsa-mir-6511a-2 | MI0023564 | 106 | chr16 | 16324588 | 16324654 | + | ✓ |
| hsa-mir-6511a-3 | MI0023565 | 116 | chr16 | 16368876 | 16368942 | + | — |
| hsa-mir-6511a-4 | MI0023566 | 105 | chr16 | 18344013 | 18344079 | + | ✓ |
| hsa-mir-6511b-1 | MI0022552 | 113 | chr16 | 2106669 | 2106753 | − | — |
| hsa-mir-6511b-2 | MI0023431 | — | chr16 | 15134075 | 15134145 | − | — |
| hsa-mir-6512 | MI0022224 | 196 | chr2 | 177313806 | 177313882 | − | — |
| hsa-mir-6513 | MI0022225 | 29.1 | chr2 | 218280125 | 218280188 | − | — |
| hsa-mir-6514 | MI0022226 | 19.8 | chr11 | 62792702 | 62792771 | − | — |
| hsa-mir-6515 | MI0022227 | 69.7 | chr19 | 12940484 | 12940540 | + | — |
| hsa-mir-6516 | MI0025513 | 1.87 | chr17 | 77089417 | 77089497 | + | — |
| hsa-mir-6715a | MI0022548 | 25.6 | chr10 | 112299690 | 112299690 | + | — |
| hsa-mir-6715b | MI0022549 | 24 | chr10 | 112299612 | 112299688 | + | — |
| hsa-mir-6716 | MI0022550 | 45.7 | chr11 | 118644000 | 118644079 | + | — |
| hsa-mir-6717 | MI0022551 | 28.3 | chr14 | 21023314 | 21023386 | − | — |
| hsa-mir-6718 | MI0022553 | 65 | chr18 | 3885353 | 3885421 | + | — |
| hsa-mir-6719 | MI0022554 | 29.4 | chr19 | 39829716 | 39829802 | − | — |
| hsa-mir-6720 | MI0022555 | 77.1 | chr6 | 1390314 | 1390411 | − | — |
| hsa-mir-6721 | MI0022556 | 48.7 | chr6 | 32170030 | 32170116 | − | — |
| hsa-mir-6722 | MI0022557 | 102 | chr9 | 136746893 | 136746970 | − | — |
| hsa-mir-6723 | MI0022558 | 90.3 | chr1 | 632325 | 632413 | − | — |
| hsa-mir-6724-1 | MI0022559 | 144 | chr21 | 8205315 | 8205406 | + | — |
| hsa-mir-6724-2 | MI0031516 | 18.2 | chr21 | 8249505 | 8249596 | + | — |
| hsa-mir-6724-3 | MI0031517 | 19.6 | chr21 | 8388362 | 8388453 | + | — |
| hsa-mir-6724-4 | MI0031518 | 21.3 | chr21 | 8432362 | 8432453 | + | — |
| hsa-mir-6726 | MI0022571 | 0.59 | chr1 | 1296110 | 1296170 | − | — |
| hsa-mir-6727 | MI0022572 | 0.171 | chr1 | 1312502 | 1312566 | − | — |
| hsa-mir-6728 | MI0022573 | 0.308 | chr1 | 8866502 | 8866590 | − | — |
| hsa-mir-6729 | MI0022574 | 0.171 | chr1 | 12029158 | 12029222 | + | — |
| hsa-mir-6730 | MI0022575 | — | chr1 | 12578957 | 12579023 | − | — |
| hsa-mir-6731 | MI0022576 | 0.2 | chr1 | 24919345 | 24919416 | − | — |
| hsa-mir-6732 | MI0022577 | 0.2 | chr1 | 37480230 | 37480289 | + | — |
| hsa-mir-6733 | MI0022578 | 0.365 | chr1 | 43171652 | 43171712 | − | — |
| hsa-mir-6734 | MI0022579 | 2.2 | chr1 | 43364648 | 43364715 | − | — |
| hsa-mir-6735 | MI0022580 | 0.602 | chr1 | 43448539 | 43448611 | + | — |
| hsa-mir-6736 | MI0022581 | 1.06 | chr1 | 145850587 | 145850645 | − | — |
| hsa-mir-6737 | MI0022582 | — | chr1 | 153962351 | 153962420 | − | — |
| hsa-mir-6738 | MI0022583 | — | chr1 | 155951273 | 155951336 | − | — |

TABLE 1-continued

Exemplary Homo sapiens miRNAs incorporated into compositions as provided
herein, and in compositions made by methods as provided herein

| ID | Accession | RPM | Chromosome | Start | End | Strand | Confidence Fetch |
|---|---|---|---|---|---|---|---|
| hsa-mir-6739 | MI0022584 | 0.238 | chr1 | 201863373 | 201863447 | + | — |
| hsa-mir-6740 | MI0022585 | 0.511 | chr1 | 202003124 | 202003236 | + | — |
| hsa-mir-6741 | MI0022586 | 0.16 | chr1 | 225922080 | 225922142 | − | — |
| hsa-mir-6742 | MI0022587 | 0.171 | chr1 | 228397048 | 228397109 | − | — |
| hsa-mir-6743 | MI0022588 | 0.666 | chr11 | 209336 | 209406 | + | — |
| hsa-mir-6744 | MI0022589 | 0.666 | chr11 | 1256605 | 1256670 | + | — |
| hsa-mir-6745 | MI0022590 | 0.16 | chr11 | 47179611 | 47179737 | − | — |
| hsa-mir-6746 | MI0022591 | — | chr11 | 61878216 | 61878278 | − | — |
| hsa-mir-6747 | MI0022592 | 0.171 | chr11 | 62567011 | 62567071 | − | — |
| hsa-mir-6748 | MI0022593 | 1.39 | chr11 | 62789815 | 62789885 | + | — |
| hsa-mir-6749 | MI0022594 | 0.485 | chr11 | 64902387 | 64902455 | − | — |
| hsa-mir-6750 | MI0022595 | 0.272 | chr11 | 64898363 | 64898437 | − | — |
| hsa-mir-6751 | MI0022596 | — | chr11 | 65129916 | 65129978 | − | — |
| hsa-mir-6752 | MI0022597 | 0.645 | chr11 | 67490245 | 67490315 | + | — |
| hsa-mir-6753 | MI0022598 | 0.893 | chr11 | 68044794 | 68044957 | + | — |
| hsa-mir-6754 | MI0022599 | 0.748 | chr11 | 71473503 | 71473568 | + | — |
| hsa-mir-6755 | MI0022600 | 0.993 | chr11 | 86278333 | 86278398 | + | — |
| hsa-mir-6756 | MI0022601 | 1.37 | chr11 | 119312950 | 119313012 | − | — |
| hsa-mir-6757 | MI0022602 | — | chr12 | 53056944 | 53057012 | + | — |
| hsa-mir-6758 | MI0022603 | — | chr12 | 57512688 | 57512750 | + | — |
| hsa-mir-6759 | MI0022604 | 0.271 | chr12 | 57748618 | 57748682 | − | — |
| hsa-mir-6760 | MI0022605 | 0.444 | chr12 | 111304142 | 111304209 | + | — |
| hsa-mir-6761 | MI0022606 | 6.72 | chr12 | 111799834 | 111799905 | + | — |
| hsa-mir-6762 | MI0022607 | 0.308 | chr12 | 113291523 | 113291608 | + | — |
| hsa-mir-6763 | MI0022608 | 0.2 | chr12 | 132581997 | 132582061 | + | — |
| hsa-mir-6764 | MI0022609 | 0.284 | chr14 | 100277357 | 100277417 | + | — |
| hsa-mir-6765 | MI0022610 | — | chr14 | 105150778 | 105150864 | − | — |
| hsa-mir-6766 | MI0022611 | 0.38 | chr15 | 89326739 | 89326810 | − | — |
| hsa-mir-6767 | MI0022612 | 0.513 | chr16 | 2445392 | 2445457 | + | — |
| hsa-mir-6768 | MI0022613 | — | chr16 | 2463967 | 2464038 | + | — |
| hsa-mir-6769a | MI0022614 | 0.282 | chr16 | 4671318 | 4671390 | + | — |
| hsa-mir-6769b | MI0022706 | — | chr1 | 206474803 | 206474864 | + | — |
| hsa-mir-6770-1 | MI0022615 | 0.171 | chr16 | 14930820 | 14930879 | + | — |
| hsa-mir-6770-2 | MI0026418 | — | chr16 | 16329305 | 16329364 | + | — |
| hsa-mir-6770-3 | MI0026419 | 0.63 | chr16 | 18379351 | 18379410 | − | — |
| hsa-mir-6771 | MI0022616 | 0.272 | chr16 | 50292616 | 50292675 | + | — |
| hsa-mir-6772 | MI0022617 | 0.401 | chr16 | 57772289 | 57772352 | − | — |
| hsa-mir-6773 | MI0022618 | — | chr16 | 68233426 | 68233499 | − | — |
| hsa-mir-6774 | MI0022619 | — | chr16 | 85918347 | 85918416 | + | — |
| hsa-mir-6775 | MI0022620 | 0.171 | chr16 | 87834592 | 87834660 | − | — |
| hsa-mir-6776 | MI0022621 | — | chr17 | 2692861 | 2692919 | − | — |
| hsa-mir-6777 | MI0022622 | 1.58 | chr17 | 17813480 | 17813545 | − | — |
| hsa-mir-6778 | MI0022623 | 0.2 | chr17 | 18340814 | 18340886 | − | — |
| hsa-mir-6779 | MI0022624 | 0.748 | chr17 | 38914979 | 38915042 | + | — |
| hsa-mir-6780a | MI0022625 | 0.269 | chr17 | 42708084 | 42708151 | − | — |
| hsa-mir-6780b | MI0022681 | 0.171 | chr6 | 43434542 | 43434620 | + | — |
| hsa-mir-6781 | MI0022626 | — | chr17 | 42823880 | 42823943 | − | — |
| hsa-mir-6782 | MI0022627 | — | chr17 | 44207771 | 44207839 | − | — |
| hsa-mir-6783 | MI0022628 | 0.0977 | chr17 | 44934618 | 44934691 | − | — |
| hsa-mir-6784 | MI0022629 | 0.282 | chr17 | 45114367 | 45114433 | − | — |
| hsa-mir-6785 | MI0022630 | 0.451 | chr17 | 75498548 | 75498628 | + | — |
| hsa-mir-6786 | MI0022631 | 1.6 | chr17 | 81693757 | 81693869 | + | — |
| hsa-mir-6787 | MI0022632 | — | chr17 | 82236668 | 82236728 | + | — |
| hsa-mir-6788 | MI0022633 | 0.222 | chr18 | 10759584 | 10759649 | − | — |
| hsa-mir-6789 | MI0022634 | 0.171 | chr19 | 2235829 | 2235926 | − | — |
| hsa-mir-6790 | MI0022635 | 0.545 | chr19 | 6392921 | 6392983 | − | — |
| hsa-mir-6791 | MI0022636 | 0.748 | chr19 | 6736712 | 6736778 | − | — |
| hsa-mir-6792 | MI0022637 | 0.459 | chr19 | 7617439 | 7617505 | + | — |
| hsa-mir-6793 | MI0022638 | 0.5 | chr19 | 10828973 | 10829035 | + | — |
| hsa-mir-6794 | MI0022639 | 2.19 | chr19 | 12852260 | 12852327 | + | — |
| hsa-mir-6795 | MI0022640 | — | chr19 | 15179283 | 15179350 | − | — |
| hsa-mir-6796 | MI0022641 | 0.171 | chr19 | 40369846 | 40369907 | + | — |
| hsa-mir-6797 | MI0022642 | 0.211 | chr19 | 41869627 | 41869698 | + | — |
| hsa-mir-6798 | MI0022643 | 0.797 | chr19 | 49009906 | 49009972 | + | — |
| hsa-mir-6799 | MI0022644 | — | chr19 | 49791866 | 49791934 | + | — |
| hsa-mir-6800 | MI0022645 | 0.459 | chr19 | 49832018 | 49832099 | + | — |
| hsa-mir-6801 | MI0022646 | 0.308 | chr19 | 52222020 | 52222098 | + | — |
| hsa-mir-6802 | MI0022647 | 0.2 | chr19 | 55239912 | 55239976 | − | — |
| hsa-mir-6803 | MI0022648 | 0.2 | chr19 | 55245186 | 55245250 | − | — |
| hsa-mir-6804 | MI0022649 | 0.171 | chr19 | 55230885 | 55230952 | − | — |
| hsa-mir-6805 | MI0022650 | 0.171 | chr19 | 55388181 | 55388242 | + | — |
| hsa-mir-6806 | MI0022651 | — | chr19 | 58334688 | 58334751 | + | — |
| hsa-mir-6807 | MI0022652 | 0.53 | chr19 | 58550285 | 58550376 | + | — |
| hsa-mir-6808 | MI0022653 | 0.222 | chr1 | 1339650 | 1339708 | − | — |
| hsa-mir-6809 | MI0022654 | 1.43 | chr2 | 217900513 | 217900628 | − | — |

TABLE 1-continued

Exemplary *Homo sapiens* miRNAs incorporated into compositions as provided
herein, and in compositions made by methods as provided herein

| ID | Accession | RPM | Chromosome | Start | End | Strand | Confidence | Fetch |
|---|---|---|---|---|---|---|---|---|
| hsa-mir-6810 | MI0022655 | 0.896 | chr2 | 218341911 | 218341980 | + | — | |
| hsa-mir-6811 | MI0022656 | 0.195 | chr2 | 237510931 | 237510988 | + | — | |
| hsa-mir-6812 | MI0022657 | — | chr20 | 45425510 | 45425573 | + | — | |
| hsa-mir-6813 | MI0022658 | — | chr20 | 64076955 | 64077010 | − | — | |
| hsa-mir-6814 | MI0022659 | — | chr21 | 41746772 | 41746841 | − | — | |
| hsa-mir-6815 | MI0022660 | 0.638 | chr21 | 45478266 | 45478326 | + | — | |
| hsa-mir-6816 | MI0022661 | 0.378 | chr22 | 20114686 | 20114751 | − | — | |
| hsa-mir-6817 | MI0022662 | 0.222 | chr22 | 25455646 | 25455711 | + | — | |
| hsa-mir-6818 | MI0022663 | — | chr22 | 30007049 | 30007113 | + | — | |
| hsa-mir-6819 | MI0022664 | — | chr22 | 36286847 | 36286907 | − | — | |
| hsa-mir-6820 | MI0022665 | — | chr22 | 37967563 | 37967624 | + | — | |
| hsa-mir-6821 | MI0022666 | 0.528 | chr22 | 49962866 | 49962939 | + | — | |
| hsa-mir-6822 | MI0022667 | 0.59 | chr3 | 39138206 | 39138266 | + | — | |
| hsa-mir-6823 | MI0022668 | 0.197 | chr3 | 48549961 | 48550021 | − | — | |
| hsa-mir-6824 | MI0022669 | — | chr3 | 48633636 | 48633698 | − | — | |
| hsa-mir-6825 | MI0022670 | 0.393 | chr3 | 127575266 | 127575331 | − | — | |
| hsa-mir-6826 | MI0022671 | 0.346 | chr3 | 129272146 | 129272243 | + | — | |
| hsa-mir-6827 | MI0022672 | 0.171 | chr3 | 134367804 | 134367862 | − | — | |
| hsa-mir-6828 | MI0022673 | 0.419 | chr3 | 170423103 | 170423162 | + | — | |
| hsa-mir-6829 | MI0022674 | 0.282 | chr3 | 195882329 | 195882395 | − | — | |
| hsa-mir-6830 | MI0022675 | 1.05 | chr5 | 132217849 | 132217918 | − | — | |
| hsa-mir-6831 | MI0022676 | 0.249 | chr5 | 140563671 | 140563751 | − | — | |
| hsa-mir-6832 | MI0022677 | 0.222 | chr6 | 31633787 | 31633858 | + | — | |
| hsa-mir-6833 | MI0022678 | 2.11 | chr6 | 32179816 | 32179876 | + | — | |
| hsa-mir-6834 | MI0022679 | 0.538 | chr6 | 33290245 | 33290325 | + | — | |
| hsa-mir-6835 | MI0022680 | — | chr6 | 34240673 | 34240736 | + | — | |
| hsa-mir-6836 | MI0022682 | 0.748 | chr7 | 2257515 | 2257577 | − | — | |
| hsa-mir-6837 | MI0022683 | 1.79 | chr7 | 44051766 | 44051829 | + | — | |
| hsa-mir-6838 | MI0022684 | 0.2 | chr7 | 44073378 | 44073433 | − | — | |
| hsa-mir-6839 | MI0022685 | 1.23 | chr7 | 64679064 | 64679176 | + | — | |
| hsa-mir-6840 | MI0022686 | 0.596 | chr7 | 100356651 | 100356721 | + | — | |
| hsa-mir-6841 | MI0022687 | 4.66 | chr8 | 24953796 | 24953867 | − | — | |
| hsa-mir-6842 | MI0022688 | 0.727 | chr8 | 27433370 | 27433434 | + | — | |
| hsa-mir-6843 | MI0022689 | 0.222 | chr8 | 27610601 | 27610751 | − | — | |
| hsa-mir-6844 | MI0022690 | 0.211 | chr8 | 124508515 | 124508576 | − | — | |
| hsa-mir-6845 | MI0022691 | 0.2 | chr8 | 143837756 | 143837816 | − | — | |
| hsa-mir-6846 | MI0022692 | 0.393 | chr8 | 144057321 | 144057380 | − | — | |
| hsa-mir-6847 | MI0022693 | 0.342 | chr8 | 144079874 | 144079942 | + | — | |
| hsa-mir-6848 | MI0022694 | 0.444 | chr8 | 144317246 | 144317315 | − | — | |
| hsa-mir-6849 | MI0022695 | 1.5 | chr8 | 144400277 | 144400345 | − | — | |
| hsa-mir-6850 | MI0022696 | — | chr8 | 144791931 | 144791991 | − | — | |
| hsa-mir-6851 | MI0022697 | 0.342 | chr9 | 33467869 | 33467935 | − | — | |
| hsa-mir-6852 | MI0022698 | 0.0977 | chr9 | 35710676 | 35710741 | − | — | |
| hsa-mir-6853 | MI0022699 | — | chr9 | 35732922 | 35732995 | + | — | |
| hsa-mir-6854 | MI0022700 | 0.171 | chr9 | 98229149 | 98229217 | − | — | |
| hsa-mir-6855 | MI0022701 | — | chr9 | 129869605 | 129869671 | + | — | |
| hsa-mir-6856 | MI0022702 | — | chr9 | 130626297 | 130626363 | + | — | |
| hsa-mir-6857 | MI0022703 | — | chrX | 53405673 | 53405765 | − | — | |
| hsa-mir-6858 | MI0022704 | 0.444 | chrX | 154450320 | 154450386 | − | — | |
| hsa-mir-6859-1 | MI0022705 | 0.322 | chr1 | 17369 | 17436 | − | — | |
| hsa-mir-6859-2 | MI0026420 | 0.53 | chr1 | 187891 | 187958 | − | — | |
| hsa-mir-6859-3 | MI0026421 | 0.222 | chr15 | 101973524 | 101973591 | + | — | |
| hsa-mir-6859-4 | MI0031521 | 4.59 | chr16 | 17052 | 17119 | − | — | |
| hsa-mir-6860 | MI0022707 | 1.96 | chr11 | 67045643 | 67045708 | + | — | |
| hsa-mir-6861 | MI0022708 | 0.342 | chr12 | 112163258 | 112163321 | − | — | |
| hsa-mir-6862-1 | MI0022709 | 0.282 | chr16 | 28390982 | 28391051 | − | — | |
| hsa-mir-6862-2 | MI0026415 | 0.59 | chr16 | 28724252 | 28724321 | + | — | |
| hsa-mir-6863 | MI0022710 | 12.4 | chr16 | 56904264 | 56904353 | + | — | |
| hsa-mir-6864 | MI0022711 | 0.308 | chr17 | 4969702 | 4969771 | − | — | |
| hsa-mir-6865 | MI0022712 | 0.222 | chr17 | 4970086 | 4970150 | − | — | |
| hsa-mir-6866 | MI0022713 | 0.247 | chr17 | 40161933 | 40162001 | + | — | |
| hsa-mir-6867 | MI0022714 | 1.53 | chr17 | 40193597 | 40193663 | + | — | |
| hsa-mir-6868 | MI0022715 | — | chr17 | 76098019 | 76098076 | − | — | |
| hsa-mir-6869 | MI0022716 | 28.3 | chr20 | 1392900 | 1392961 | − | — | |
| hsa-mir-6870 | MI0022717 | — | chr20 | 10649636 | 10649695 | − | — | |
| hsa-mir-6871 | MI0022718 | 0.171 | chr20 | 41169023 | 41169078 | + | — | |
| hsa-mir-6872 | MI0022719 | — | chr3 | 50273236 | 50273297 | + | — | |
| hsa-mir-6873 | MI0022720 | 20.2 | chr6 | 33287227 | 33287289 | − | — | |
| hsa-mir-6874 | MI0022721 | 1.23 | chr7 | 5711840 | 5711910 | − | — | |
| hsa-mir-6875 | MI0022722 | 0.887 | chr7 | 100868036 | 100868107 | + | — | |
| hsa-mir-6876 | MI0022723 | — | chr8 | 25345402 | 25345474 | + | — | |
| hsa-mir-6877 | MI0022724 | 1.15 | chr9 | 133051996 | 133052059 | + | — | |
| hsa-mir-6878 | MI0022725 | 0.197 | chr1 | 150492345 | 150492410 | + | — | |
| hsa-mir-6879 | MI0022726 | — | chr11 | 65018505 | 65018570 | + | — | |
| hsa-mir-6880 | MI0022727 | 0.854 | chr12 | 124337181 | 124337242 | − | — | |

TABLE 1-continued

Exemplary *Homo sapiens* miRNAs incorporated into compositions as provided herein, and in compositions made by methods as provided herein

| ID | Accession | RPM | Chromosome | Start | End | Strand | Confidence Fetch |
|---|---|---|---|---|---|---|---|
| hsa-mir-6881 | MI0022728 | 0.446 | chr15 | 74411357 | 74411432 | − | — |
| hsa-mir-6882 | MI0022729 | 1.73 | chr15 | 74840642 | 74840707 | − | — |
| hsa-mir-6883 | MI0022730 | 0.459 | chr17 | 8144994 | 8145071 | − | — |
| hsa-mir-6884 | MI0022731 | 0.422 | chr17 | 40026332 | 40026409 | − | — |
| hsa-mir-6885 | MI0022732 | 0.171 | chr19 | 6389638 | 6389703 | − | — |
| hsa-mir-6886 | MI0022733 | — | chr19 | 11113474 | 11113534 | + | — |
| hsa-mir-6887 | MI0022734 | 0.222 | chr19 | 35122700 | 35122764 | + | — |
| hsa-mir-6888 | MI0022735 | — | chr2 | 159186835 | 159186901 | + | — |
| hsa-mir-6889 | MI0022736 | — | chr22 | 41252992 | 41253050 | − | — |
| hsa-mir-6890 | MI0022737 | 0.222 | chr3 | 49099854 | 49099914 | − | — |
| hsa-mir-6891 | MI0022738 | — | chr6 | 31355224 | 31355316 | − | — |
| hsa-mir-6892 | MI0022739 | 2.36 | chr7 | 143382686 | 143382800 | + | — |
| hsa-mir-6893 | MI0022740 | — | chr8 | 144435551 | 144435619 | − | — |
| hsa-mir-6894 | MI0022741 | 0.222 | chrX | 53198889 | 53198945 | − | — |
| hsa-mir-6895 | MI0022742 | 0.222 | chrX | 53195411 | 53195488 | − | — |
| hsa-mir-7106 | MI0022957 | 0.778 | chr12 | 113159113 | 113159177 | − | — |
| hsa-mir-7107 | MI0022958 | — | chr12 | 121444273 | 121444352 | − | — |
| hsa-mir-7108 | MI0022959 | 0.438 | chr19 | 2434914 | 2435000 | − | — |
| hsa-mir-7109 | MI0022960 | 0.222 | chr22 | 31621467 | 31621531 | − | — |
| hsa-mir-7110 | MI0022961 | 28.9 | chr3 | 123161794 | 123161856 | + | — |
| hsa-mir-7111 | MI0022962 | 0.222 | chr6 | 35470508 | 35470579 | + | — |
| hsa-mir-7112 | MI0022963 | 0.222 | chr8 | 144262673 | 144262737 | − | — |
| hsa-mir-7113 | MI0022964 | 0.443 | chr11 | 68032864 | 68032922 | + | — |
| hsa-mir-7114 | MI0022965 | 0.171 | chr9 | 137450026 | 137450086 | − | — |
| hsa-mir-7150 | MI0023610 | — | chr9 | 123485529 | 123485622 | − | — |
| hsa-mir-7151 | MI0023611 | 1.75 | chr10 | 67403351 | 67403410 | − | — |
| hsa-mir-7152 | MI0023612 | — | chr10 | 71790747 | 71790800 | + | — |
| hsa-mir-7153 | MI0023613 | 86.8 | chr18 | 11654885 | 11654941 | − | — |
| hsa-mir-7154 | MI0023614 | 11.2 | chr11 | 45691704 | 45691776 | − | — |
| hsa-mir-7155 | MI0023615 | 0.365 | chr11 | 64341849 | 64341904 | − | — |
| hsa-mir-7156 | MI0023616 | 2.48 | chr1 | 77060143 | 77060202 | + | — |
| hsa-mir-7157 | MI0023617 | 0.308 | chr2 | 140586626 | 140586685 | − | — |
| hsa-mir-7158 | MI0023618 | 1.31 | chr2 | 5974662 | 5974732 | + | — |
| hsa-mir-7159 | MI0023620 | 31.4 | chr6 | 33899135 | 33899200 | + | — |
| hsa-mir-7160 | MI0023621 | 0.0977 | chr8 | 2076589 | 2076640 | + | — |
| hsa-mir-7161 | MI0023619 | 760 | chr6 | 158609707 | 158609790 | + | — |
| hsa-mir-7162 | MI0023623 | 0.197 | chr10 | 30368597 | 30368665 | − | — |
| hsa-mir-7515 | MI0024354 | — | chr2 | 6650373 | 6650439 | + | — |
| hsa-mir-7641-1 | MI0024975 | 22.3 | chr11 | 104252591 | 104252651 | + | — |
| hsa-mir-7641-2 | MI0024976 | 32.8 | chr14 | 75604209 | 75604261 | + | — |
| hsa-mir-7702 | MI0025238 | 0.342 | chr9 | 111271156 | 111271214 | − | — |
| hsa-mir-7703 | MI0025239 | 0.171 | chr14 | 24143489 | 24143565 | − | — |
| hsa-mir-7704 | MI0025240 | 5.95 | chr2 | 176188843 | 176188901 | + | — |
| hsa-mir-7705 | MI0025241 | 1.42 | chr8 | 100702968 | 100703024 | − | — |
| hsa-mir-7706 | MI0025242 | 0.27 | chr15 | 85380596 | 85380642 | + | — |
| hsa-mir-7843 | MI0025510 | 0.0977 | chr14 | 72516820 | 72516898 | + | — |
| hsa-mir-7844 | MI0025514 | — | chr12 | 94571231 | 94571352 | − | — |
| hsa-mir-7845 | MI0025515 | 2.7e+03 | chr2 | 207166400 | 207166498 | + | — |
| hsa-mir-7846 | MI0025516 | 1.99 | chr1 | 12166943 | 12167003 | + | — |
| hsa-mir-7847 | MI0025517 | 0.222 | chr11 | 1880045 | 1880147 | + | — |
| hsa-mir-7848 | MI0025518 | — | chr8 | 133046481 | 133046581 | − | — |
| hsa-mir-7849 | MI0025519 | — | chr4 | 146408583 | 146408688 | + | — |
| hsa-mir-7850 | MI0025520 | — | chr19 | 2630715 | 2630793 | + | — |
| hsa-mir-7851 | MI0025521 | 32.3 | chr12 | 42323700 | 42323859 | + | — |
| hsa-mir-7852 | MI0025522 | — | chr1 | 107897223 | 107897304 | + | — |
| hsa-mir-7853 | MI0025523 | 0.311 | chr6 | 6169304 | 6169435 | − | — |
| hsa-mir-7854 | MI0025524 | 0.272 | chr16 | 81533902 | 81533966 | + | — |
| hsa-mir-7855 | MI0025525 | 0.647 | chr14 | 64785626 | 64785686 | − | — |
| hsa-mir-7856 | MI0025526 | 0.272 | chr1 | 86357632 | 86357687 | − | — |
| hsa-mir-7973-1 | MI0025748 | — | chr15 | 51314034 | 51314109 | + | — |
| hsa-mir-7973-2 | MI0025749 | — | chr15 | 51314032 | 51314107 | + | — |
| hsa-mir-7974 | MI0025750 | 0.171 | chr19 | 11495544 | 11495622 | − | — |
| hsa-mir-7975 | MI0025751 | 510 | chr19 | 55123225 | 55123292 | − | — |
| hsa-mir-7976 | MI0025752 | 0.485 | chr3 | 127587111 | 127587176 | − | — |
| hsa-mir-7977 | MI0025753 | 0.852 | chr3 | 176515103 | 176515151 | + | — |
| hsa-mir-7978 | MI0025754 | 0.186 | chr4 | 21464700 | 21464758 | − | — |
| hsa-mir-8052 | MI0025888 | 0.859 | chr11 | 130666735 | 130666803 | + | — |
| hsa-mir-8053 | MI0025889 | 0.2 | chr4 | 47652669 | 47652743 | + | — |
| hsa-mir-8054 | MI0025890 | — | chr11 | 23419105 | 23419190 | − | — |
| hsa-mir-8055 | MI0025891 | — | chr8 | 6622124 | 6622220 | − | — |
| hsa-mir-8056 | MI0025892 | 0.2 | chr5 | 173347455 | 173347536 | + | — |
| hsa-mir-8057 | MI0025893 | 0.171 | chr18 | 26591467 | 26591535 | − | — |
| hsa-mir-8058 | MI0025894 | 0.748 | chr16 | 82688931 | 82689019 | + | — |
| hsa-mir-8059 | MI0025895 | — | chr17 | 50768650 | 50768730 | + | — |
| hsa-mir-8060 | MI0025896 | — | chr3 | 96359964 | 96360039 | + | — |

TABLE 1-continued

Exemplary *Homo sapiens* miRNAs incorporated into compositions as provided herein, and in compositions made by methods as provided herein

| ID | Accession | RPM | Chromosome | Start | End | Strand | Confidence Fetch |
|---|---|---|---|---|---|---|---|
| hsa-mir-8061 | MI0025897 | 0.222 | chr19 | 54645309 | 54645383 | + | — |
| hsa-mir-8062 | MI0025898 | — | chr20 | 7371608 | 7371692 | + | — |
| hsa-mir-8063 | MI0025899 | — | chr15 | 36972821 | 36972901 | − | — |
| hsa-mir-8064 | MI0025900 | 0.748 | chr3 | 52846463 | 52846552 | − | — |
| hsa-mir-8065 | MI0025901 | 1.5 | chr16 | 5632467 | 5632566 | + | — |
| hsa-mir-8066 | MI0025902 | — | chr4 | 101240795 | 101240872 | − | — |
| hsa-mir-8067 | MI0025903 | — | chr15 | 62304658 | 62304734 | − | — |
| hsa-mir-8068 | MI0025904 | 0.0977 | chr11 | 28477481 | 28477548 | − | — |
| hsa-mir-8069-1 | MI0025905 | — | chr21 | 6859171 | 6859256 | + | — |
| hsa-mir-8069-2 | MI0031519 | — | chr21 | 13724189 | 13724274 | + | — |
| hsa-mir-8070 | MI0025906 | 1.19 | chr11 | 11783135 | 11783222 | − | — |
| hsa-mir-8071-1 | MI0025907 | 0.222 | chr14 | 105621116 | 105621180 | + | — |
| hsa-mir-8071-2 | MI0026417 | — | chr14 | 105640168 | 105640232 | + | — |
| hsa-mir-8072 | MI0025908 | 0.271 | chr12 | 123364764 | 123364843 | − | — |
| hsa-mir-8073 | MI0025909 | 0.833 | chr13 | 110340958 | 110341029 | + | — |
| hsa-mir-8074 | MI0025910 | — | chr19 | 51206929 | 51207009 | − | — |
| hsa-mir-8075 | MI0025911 | — | chr13 | 113262920 | 113262999 | + | — |
| hsa-mir-8076 | MI0025912 | — | chr3 | 113432118 | 113432200 | − | — |
| hsa-mir-8077 | MI0025913 | — | chr19 | 42351131 | 42351205 | + | — |
| hsa-mir-8078 | MI0025914 | 0.748 | chr18 | 112256 | 112339 | − | — |
| hsa-mir-8079 | MI0025915 | 0.444 | chr13 | 44196129 | 44196200 | − | — |
| hsa-mir-8080 | MI0025916 | — | chr2 | 79866495 | 79866583 | − | — |
| hsa-mir-8081 | MI0025917 | — | chr9 | 106600928 | 106601022 | + | — |
| hsa-mir-8082 | MI0025918 | — | chr4 | 113152282 | 113152362 | + | — |
| hsa-mir-8083 | MI0025919 | 0.222 | chr1 | 153689705 | 153689793 | − | — |
| hsa-mir-8084 | MI0025920 | 0.423 | chr8 | 93029751 | 93029839 | + | — |
| hsa-mir-8085 | MI0025921 | 0.22 | chr19 | 44758657 | 44758721 | + | — |
| hsa-mir-8086 | MI0025922 | 305 | chr10 | 28289258 | 28289350 | − | — |
| hsa-mir-8087 | MI0025923 | 0.983 | chr11 | 27514970 | 27515047 | − | — |
| hsa-mir-8088 | MI0025924 | — | chrX | 52336557 | 52336642 | − | — |
| hsa-mir-8089 | MI0025925 | — | chr5 | 181043403 | 181043484 | − | — |
| hsa-mir-8485 | MI0027288 | 15.2 | chr2 | 50696172 | 50696262 | − | — |
| hsa-mir-9500 | MI0029185 | — | chr2 | 218823090 | 218823154 | + | — |

References Example 1

1. Bartel DP (2004) MicroRNAs: genomics, biogenesis, mechanism, and function. Cell 116(2):281-297.
2. Thomas M, Lieberman J, & Lal A (Desperately seeking microRNA targets. Nat Struct Mol Biol 17(10):1169-1174.
3. Friedman R C, Farh K K, Burge C B, & Bartel D P (2009) Most mammalian mRNAs are conserved targets of microRNAs. Genome Res 19(1):92-105.
4. Ambros V (2004) The functions of animal microRNAs. Nature 431(7006):350-355.
5. Pedersen I & David M (2008) MicroRNAs in the immune response. Cytokine 43(3):391-394.
6. O'Connell R M, Rao D S, & Baltimore D (2012) microRNA regulation of inflammatory responses. Annu Rev Immunol 30:295-312.
7. Volinia S, et al. (2006) A microRNA expression signature of human solid tumors defines cancer gene targets. Proc Natl Acad Sci USA 103(7):2257-2261.
8. Cullen BR (2009) Viral and cellular messenger RNA targets of viral microRNAs. Nature 457(7228):421-425.
9. van Rooij E, et al. (2007) Control of stress-dependent cardiac growth and gene expression by a microRNA. Science 316(5824):575-579.
10. Krutzfeldt J, et al. (2005) Silencing of microRNAs in vivo with 'antagomirs'. Nature 438(7068):685-689.
11. Seow Y & Wood M J (2009) Biological gene delivery vehicles: beyond viral vectors. Mol Ther 17(5):767-777.
12. Alvarez-Erviti L, et al. (2011) Delivery of siRNA to the mouse brain by systemic injection of targeted exosomes. Nat Biotechnol 29(4):341-345.
13. Sutkowski N, Kuo M L, Varela E A, Dougherty J P, & Ron Y (1994) A murine model for B-lymphocyte somatic cell gene therapy. Proc Natl Acad Sci USA 91(19):8875-8879.
14. Xiong S, Gerloni M, & Zanetti M (1997) In vivo role of B lymphocytes in somatic transgene immunization. Proc Natl Acad Sci USA 94:6352-6357.
15. Zanetti M, Castiglioni P, Rizzi M, Wheeler M, & Gerloni M (2004) B lymphocytes as antigen-presenting cell-based genetic vaccines. Immunol Rev 199:264-278.
16. Gerloni M, Rizzi M, Castiglioni P, & Zanetti M (2004) T cell immunity using transgenic B lymphocytes. Proc Natl Acad Sci USA 101(11):3892-3897.
17. Bogerd H P, et al. (2010) A mammalian herpesvirus uses noncanonical expression and processing mechanisms to generate viral MicroRNAs. Mol Cell 37(1):135-142.
18. Kincaid R P, Burke J M, & Sullivan C S (2012) RNA virus microRNA that mimics a B-cell oncomiR. Proc Natl Acad Sci USA 109(8):3077-3082.
19. Almanza G, et al. (2010) Selected microRNAs define cell fate determination of murine central memory CD8 T cells. PLoS One 5(6):e11243.
20. Zhou B, Wang S, Mayr C, Bartel D P, & Lodish H F (2007) miR-150, a microRNA expressed in mature B and T cells, blocks early B cell development when expressed prematurely. Proc Natl Acad Sci USA 104(17):7080-7085.
21. Jiang X, et al. (2012) Blockade of miR-150 maturation by MLL-fusion/MYC/LIN-28 is required for MLL-associated leukemia. Cancer Cell 22(4):524-535.
22. Ma Y, et al. (2012) miR-150 as a potential biomarker associated with prognosis and therapeutic outcome in colorectal cancer. Gut 61(10):1447-1453.

23. Akers J C, Gonda D, Kim R, Carter B S, & Chen C C (2013) Biogenesis of extracellular vesicles (EV): exosomes, micro-vesicles, retrovirus-like vesicles, and apoptotic bodies. J Neurooncol.

24. Bevan M J (1976) Cross-priming for a secondary cytotoxic response to minor H antigens with H-2 congenic cells which do not cross-react in the cytotoxic assay. Journal of Experimental Medicine 143(5):1283-1288.

25. Kurts C, Robinson B W, & Knolle P A (2010) Cross-priming in health and disease. Nat Rev Immunol 10(6):403-414.

26. Clarke S R, et al. (2000) Characterization of the ovalbumin-specific TCR transgenic line OT-I: MHC elements for positive and negative selection. Immunol Cell Biol 78(2):110-117.

27. Moskophidis D & Kioussis D (1998) Contribution of virus-specific CD8+ cytotoxic T cells to virus clearance or pathologic manifestations of influenza virus infection in a T cell receptor transgenic mouse model. J Exp Med 188(2): 223-232.

28. Kim S K, et al. (1997) Activation and migration of CD8 T cells in the intestinal mucosa. J Immunol 159(9): 4295-4306.

29. Monticelli S, et al. (2005) MicroRNA profiling of the murine hematopoietic system. Genome Biol 6(8):R71.

30. Kohlhaas S, et al. (2009) Cutting edge: the Foxp3 target miR-155 contributes to the development of regulatory T cells. J Immunol 182(5):2578-2582.

31. Taganov K D, Boldin M P, Chang K J, & Baltimore D (2006) NF-kappaB-dependent induction of microRNA miR-146, an inhibitor targeted to signaling proteins of innate immune responses. Proc Natl Acad Sci USA 103(33):12481-12486.

32. Lu J, et al. (2005) MicroRNA expression profiles classify human cancers. Nature 435(7043):834-838.

33. Calin G A, et al. (2005) A MicroRNA signature associated with prognosis and progression in chronic lymphocytic leukemia. N Engl J Med 353(17):1793-1801.

34. Calin G A & Croce C M (2006) MicroRNA signatures in human cancers. Nat Rev Cancer 6(11):857-866. 35. Garzon R, Calin G A, & Croce C M (2009) MicroRNAs in Cancer. Annu Rev Med 60:167-179.

36. Costinean S, et al. (2006) Pre-B cell proliferation and lymphoblastic leukemia/high-grade lymphoma in E(mu)-miR155 transgenic mice. Proc Natl Acad Sci USA 103(18): 7024-7029.

37. Zhao J L, et al. (2011) NF-{kappa}B dysregulation in microRNA-146a-deficient mice drives the development of myeloid malignancies. Proc Natl Acad Sci USA.

38. Tavazoie S F, et al. (2008) Endogenous human microRNAs that suppress breast cancer metastasis. Nature 451(7175):147-152.

39. Tili E, et al. (2011) Mutator activity induced by microRNA-155 (miR-155) links inflammation and cancer. Proc Natl Acad Sci USA 108(12):4908-4913.

40. Fabbri M, et al. (2012) MicroRNAs bind to Toll-like receptors to induce prometastatic inflammatory response. Proc Natl Acad Sci USA 109(31):E2110-2116.

41. Valadi H, et al. (2007) Exosome-mediated transfer of mRNAs and microRNAs is a novel mechanism of genetic exchange between cells. Nat Cell Biol 9(6):654-659.

42. Raposo G, et al. (1996) B lymphocytes secrete antigen-presenting vesicles. J Exp Med 183(3):1161-1172.

43. Pegtel D M, et al. (2010) Functional delivery of viral miRNAs via exosomes. Proc Natl Acad Sci USA 107(14): 6328-6333.

44. Zanetti M (2003) Protocol #0207-545: a phase I, escalating dose, open-label evaluation of safety, feasibility, and tolerability of transgenic lymphocyte immunization (TLI) vaccine subjects with histologically proven prostate adenocarcinoma. Hum Gene Ther 14(3):301-302.

45. Morrison S (1985) Transfectomas provide novel chimeric antibodies. Science 229:1202-1207.

References—Example 2

1 Bartel D P (2004). MicroRNAs: genomics, biogenesis, mechanism, and function. *Cell* 116: 281-297.

2 Thomas M, Lieberman J, Lal A Desperately seeking microRNA targets. *Nat Struct Mol Biol* 17: 1169-1174.

3 Friedman R C, Farh K K, Burge C B, Bartel D P (2009). Most mammalian mRNAs are conserved targets of microRNAs. *Genome Res* 19: 92-105.

4 Ambros V (2004). The functions of animal microRNAs. *Nature* 431: 350-355.

5 Pedersen I, David M (2008). MicroRNAs in the immune response. Cytokine 43: 391-394.

6 O'Connell R M, Rao D S, Baltimore D (2012). microRNA regulation of inflammatory responses. Annu Rev Immunol 30: 295-312.

7 Volinia S, Calin G A, Liu C G, Ambs S, Cimmino A, Petrocca F et al (2006). A microRNA expression signature of human solid tumors defines cancer gene targets. Proc Natl Acad Sci USA 103: 2257-2261.

8 Krutzfeldt J, et al (2005). Silencing of microRNAs in vivo with 'antagomirs'. *Nature* 438: 685-689.

9 Kim J H, et al Effective delivery of anti-miRNA DNA oligonucleotides by functionalized gold nanoparticles. *J Biotechnol* 155: 287-292.

10 Seow Y, Wood M J (2009). Biological gene delivery vehicles: beyond viral vectors. *Mol Ther* 17: 767-777.

11 Alvarez-Erviti L, et al. (2011). Delivery of siRNA to the mouse brain by systemic injection of targeted exosomes. Nat Biotechnol 29: 341-345.

12 Almanza G, et al (2013). Synthesis and delivery of short, noncoding RNA by B lymphocytes. *Proc Natl Acad Sci USA* 110: 20182-20187.

13 Liu Y P, et al. (2008). Inhibition of HIV-1 by multiple siRNAs expressed from a single microRNA polycistron. *Nucleic Acids Res* 36: 2811-2824.

14 Hu T, Chen P, Fu Q, Liu Y, Ishaq M, Li J et al (2010). Comparative studies of various artificial microRNA expression vectors for RNAi in mammalian cells. *Mot Biotechnol* 46: 34-40.

15 Qiu X, Friedman J M, Liang G (2011). Creating a flexible multiple microRNA expression vector by linking precursor microRNAs. *Biochem Biophys Res Commun* 411: 276-280.

16 Almanza G, (2010). Selected microRNAs define cell fate determination of murine central memory CD8 T cells. *PLoS One* 5: e11243.

17 Wang M, et al (2008). miRNA analysis in B-cell chronic lymphocytic leukaemia: proliferation centres characterized by low miR-150 and high BIC/miR-155 expression. *J Pathol* 215: 13-20.

18 Loo J M, et al (2015). Extracellular Metabolic Energetics Can Promote Cancer Progression. *Cell*.

19 Melton C, Judson R L, Blelloch R (2010). Opposing microRNA families regulate self-renewal in mouse embryonic stem cells. *Nature* 463: 621-626.

20 Ruggero D, Pandolfi P P (2003). Does the ribosome translate cancer? *Nat Rev Cancer* 3: 179-192.

21 Zanetti M (2003). Protocol #0207-545: a phase I, escalating dose, open-label evaluation of safety, feasibility, and tolerability of transgenic lymphocyte immunization (TLI) vaccine subjects with histologically proven prostate adenocarcinoma. *Hum Gene Ther* 14: 301-302.

22 Cortez-Gonzalez X, Zanetti M (2007). Telomerase immunity from bench to bedside: round one. *J Transl Med* 5: 12.

23 Bogerd H P, Karnowski H W, Cai X, Shin J, Pohlers M, Cullen B R (2010). A mammalian herpesvirus uses non-canonical expression and processing mechanisms to generate viral MicroRNAs. *Mol Cell* 37: 135-142.

24 Kincaid R P, Burke J M, Sullivan C S (2012). RNA virus microRNA that mimics a B-cell oncomiR. *Proc Natl Acad Sci USA* 109: 3077-3082.

25 Wubbolts R, et al (2003). Proteomic and biochemical analyses of human B cell-derived exosomes. Potential implications for their function and multivesicular body formation. *J Biol Chem* 278: 10963-10972.

26 Pegtel D M, et al (2010). Functional delivery of viral miRNAs via exosomes. *Proc Natl Acad Sci USA* 107: 6328-6333.

27 Valadi H, Ekstrom K, Bossios A, Sjostrand M, Lee J J, Lotvall J O (2007). Exosome-mediated transfer of mRNAs and microRNAs is a novel mechanism of genetic exchange between cells. *Nat Cell Biol* 9: 654-659.

28 Pegtel D M, Peferoen L, Amor S (2014). Extracellular vesicles as modulators of cell-to-cell communication in the healthy and diseased brain. *Philos Trans R Soc Lond B Biol Sci* 369.

29 Wakim L M, Bevan M J (2011). Cross-dressed dendritic cells drive memory CD8+ T-cell activation after viral infection. *Nature* 471: 629-632.

30 Choudhuri K, et al (2014). Polarized release of T-cell-receptor-enriched micro-vesicles at the immunological synapse. *Nature* 507: 118-123.

31 Thery C, et al. (2002). Indirect activation of naive CD4+ T cells by dendritic cell-derived exosomes. *Nat Immunol* 3: 1156-1162.

32 Montecalvo A, et al (2008). Exosomes as a short-range mechanism to spread alloantigen between dendritic cells during T cell allorecognition. *J Immunol* 180: 3081-3090.

33 Ono et al (2014). Exosomes from bone marrow mesenchymal stem cells contain a microRNA that promotes dormancy in metastatic breast cancer cells. *Sci Signal* 7: ra63.

34 Lu M, et al (2014). Modeling putative therapeutic implications of exosome exchange between tumor and immune cells. *Proc Natl Acad Sci USA* 111: E4165-4174.

35 Atay S, Godwin A K (2014). Tumor-derived exosomes: A message delivery system for tumor progression. *Commun Integr Biol* 7: e28231.

36 Valencia K, Luis-Ravelo D, Bovy N, Anton I, Martinez-Canarias S, Zandueta C et al (2014). miRNA cargo within exosome-like vesicle transfer influences metastatic bone colonization. *Mol Oncol* 8: 689-703.

37 Singh et al (2014). Exosome-mediated transfer of miR-10b promotes cell invasion in breast cancer. *Mol Cancer* 13: 256.

38 Liu Y, et al (2013). Micro-vesicle-delivery miR-150 promotes tumorigenesis by up-regulating VEGF, and the neutralization of miR-150 attenuate tumor development. *Protein Cell* 4: 932-941.

Chen et al (2014). Exosomes from drug-resistant breast cancer cells transmit chemoresistance by a horizontal transfer of microRNAs. *PLoS One* 9: e95240.

40 Boelens et al (2014). Exosome transfer from stromal to breast cancer cells regulates therapy resistance pathways. *Cell* 159: 499-513.

41 Taylor D D, Gercel-Taylor C (2011). Exosomes/microvesicles: mediators of cancer-associated immunosuppressive microenvironments. *Semin Immunopathol* 33: 441-454.

42 Tan A, Rajadas J, Seifalian A M (2013). Exosomes as nano-theranostic delivery platforms for gene therapy. *Adv Drug Deliv Rev* 65: 357-367.

43 Johnsen et al (2014). A comprehensive overview of exosomes as drug delivery vehicles—endogenous nanocarriers for targeted cancer therapy. *Biochim Biophys Acta* 1846: 75-87.

44 Chevillet et al (2014). Quantitative and stoichiometric analysis of the microRNA content of exosomes. *Proc Natl Acad Sci USA* 111: 14888-14893.

45 Sverdlov E D (2012). Amedeo Avogadro's cry: what is 1 microg of exosomes? *Bioessays* 34: 873-875.

46 Simons M, Raposo G (2009). Exosomes-vesicular carriers for intercellular communication. *Curr Opin Cell Biol* 21: 575-581.

47 Squadrito et al (2014). Endogenous RNAs modulate microRNA sorting to exosomes and transfer to acceptor cells. *Cell reports* 8: 1432-1446.

48 Poliseno et al A coding-independent function of gene and pseudogene mRNAs regulates tumour biology. *Nature* 465: 1033-1038.

References—Background and Example 3

Almanza, G., Anufreichik, V., Rodvold, J. J., Chiu, K. T., DeLaney, A., Akers, J. C., Chen, C. C., and Zanetti, M. (2013). Synthesis and delivery of short, noncoding RNA by B lymphocytes. Proceedings of the National Academy of Sciences of the United States of America 110, 20182-20187.

Almanza, G., and Zanetti, M. (2015). High-efficiency Generation of Multiple Short Noncoding RNA in B-cells and B-cell-derived Extracellular Vesicles. Mol Ther Nucleic Acids 4, e271.

Ambros, V. (2004). The functions of animal microRNAs. Nature 431, 350-355. Bartel, D. P. (2004). MicroRNAs: genomics, biogenesis, mechanism, and function. Cell 116, 281-297.

Busslinger, M. (2004). Transcriptional control of early B cell development. Annu Rev Immunol 22, 55-79.

Cao, J., Cai, J., Huang, D., Han, Q., Chen, Y., Yang, Q., Yang, C., Kuang, Y., Li, D., and Wang, Z. (2014). miR-335 represents an independent prognostic marker in epithelial ovarian cancer. Am J Clin Pathol 141, 437-442.

Esquela-Kerscher, A., and Slack, F. J. (2006). Oncomirs—microRNAs with a role in cancer. Nat Rev Cancer 6, 259-269.

Foronda, M., Martinez, P., Schoeftner, S., Gomez-Lopez, G., Schneider, R., Flores, J. M., Pisano, D. G., and Blasco, M. A. (2014). Sox4 links tumor suppression to accelerated aging in mice by modulating stem cell activation. Cell Rep 8, 487-500.

Friedman, R. C., Farh, K. K., Burge, C. B., and Bartel, D. P. (2009). Most mammalian mRNAs are conserved targets of microRNAs. Genome Res 19, 92-105.

Garzon, R., Calin, G. A., and Croce, C. M. (2009). MicroRNAs in Cancer. Annu Rev Med 60, 167-179.

Gong, M., et al (2014). miR-335 inhibits small cell lung cancer bone metastases via IGF-IR and RANKL pathways. Mol Cancer Res 12, 101-110.

Hong, C. S., and Saint-Jeannet, J. P. (2005). Sox proteins and neural crest development. Semin Cell Dev Biol 16, 694-703.

Isosaka, M., et al. (2015). A Screen for Epigenetically Silenced microRNA Genes in Gastrointestinal Stromal Tumors. PloS one 10, e0133754.

Minn, A. J., Gupta, G. P., Siegel, P. M., Bos, P. D., Shu, W., Giri, D. D., Viale, A., Olshen, A. B., Gerald, W. L., and Massague, J. (2005). Genes that mediate breast cancer metastasis to lung. Nature 436, 518-524.

O'Connell, R. M., Rao, D. S., and Baltimore, D. (2012). microRNA regulation of inflammatory responses. Annu Rev Immunol 30, 295-312.

Pedersen, I., and David, M. (2008). MicroRNAs in the immune response. Cytokine 43, 391-394.

Png, K. J., Yoshida, M., Zhang, X. H., Shu, W., Lee, H., Rimner, A., Chan, T. A., Comen, E., Andrade, V. P., Kim, S. W., et al. (2011). MicroRNA-335 inhibits tumor reinitiation and is silenced through genetic and epigenetic mechanisms in human breast cancer. Genes Dev 25, 226-231.

Restivo, A., Piacentini, G., Placidi, S., Saffirio, C., and Marino, B. (2006). Cardiac outflow tract: a review of some embryogenetic aspects of the conotruncal region of the heart. Anat Rec A Discov Mol Cell Evol Biol 288, 936-943.

Tavazoie, S. F., et al (2008). Endogenous human microRNAs that suppress breast cancer metastasis. Nature 451, 147-152.

Thomas, M., Lieberman, J., and Lal, A. (2010). Desperately seeking microRNA targets. Nat Struct Mol Biol 17, 1169-1174.

Tiwari, N., Tiwari, V. K., Waldmeier, L., Balwierz, P. J., Arnold, P., Pachkov, M., Meyer-Schaller, N., Schubeler, D., van Nimwegen, E., and Christofori, G. (2013). Sox4 is a master regulator of epithelial-mesenchymal transition by controlling Ezh2 expression and epigenetic reprogramming. Cancer cell 23, 768-783.

Vervoort, S. J., van Boxtel, R., and Coffer, P. J. (2013). The role of SRY-related HMG box transcription factor 4 (SOX4) in tumorigenesis and metastasis: friend or foe? Oncogene 32, 3397-3409.

Volinia, S., Calin, G. A., Liu, C. G., Ambs, S., Cimmino, A., Petrocca, F., Visone, R., Iorio, M., Roldo, C., Ferracin, M., et al. (2006). A microRNA expression signature of human solid tumors defines cancer gene targets. Proceedings of the National Academy of Sciences of the United States of America 103, 2257-2261.

Wang, C., and Jiang, T. (2015). MicroRNA-335 represents an independent prognostic marker in cervical cancer. Tumour Biol 36, 5825-5830.

Xiong, S. W., Lin, T. X., Xu, K. W., Dong, W., Ling, X. H., Jiang, F. N., Chen, G., Zhong, W. D., and Huang, J. (2013). MicroRNA-335 acts as a candidate tumor suppressor in prostate cancer. Pathol Oncol Res 19, 529-537.

A number of embodiments of the invention have been described. Nevertheless, it can be understood that various modifications may be made without departing from the spirit and scope of the invention. Accordingly, other embodiments are within the scope of the following claims.

What is claimed is:

1. A method for treating, ameliorating, or preventing, or controlling the tumorigenicity of: a cancer comprising administering to an individual in need thereof
   a composition, formulation or pharmaceutical composition comprising
   (a) a B lymphocyte extracellular vesicle (EV) or equivalent thereof, or
   (b) a B lymphocyte comprising or having contained therein a B lymphocyte EV or equivalent thereof,
   wherein the B lymphocyte, B lymphocyte extracellular vesicle (EV) or equivalent thereof, comprises or has contained therein: an average of at least about 3.6 copies of identical mammalian micro-RNA molecules per B lymphocyte extracellular vesicle (EV) or equivalent thereof, and
   the identical mammalian micro-RNA are encoded and produced by exogenous nucleic acid by transfection of the B lymphocyte.

2. The method of claim 1, wherein the cancer is a breast cancer.

3. The method of claim 2, wherein the breast cancer is a triple negative breast cancer, or a breast cancer that tests negative for estrogen receptors (ER-), progesterone receptors (PR-), or HER2 (HER2-).

4. The method of claim 1, wherein the cancer cell is a prostate cancer cell, a lymphoma cell, a glioblastoma cell, lung cancer cell, a pancreatic cancer cell, an ovarian cancer cell, a liver cancer cell, a colon cancer cell, a medulloblastoma cell, or a salivary gland cancer cell.

5. The method of claim 1, wherein the mammalian micro-RNA comprises an miR-335.

6. The method of claim 1, wherein the mammalian micro-RNA comprises an miR-335, an miR-214, an miR-141, an miR-150, an miR-155, an miR-15a, an miR-16, an miRNA selected from Table 2, or an miRNA that down-regulates or decreases the activity of SOX4 mRNA, and a combination thereof, or an anti-miRNA having a sequence complementary to the miRNA, or any combination thereof.

7. The method of claim 1, wherein the composition, formulation or pharmaceutical composition comprises a plurality of B lymphocyte extracellular vesicles (EVs).

8. The method of claim 1, wherein the composition, formulation or pharmaceutical composition comprises a plurality of B lymphocyte exosomes.

9. The method of claim 1, wherein the composition, formulation or pharmaceutical composition comprises a plurality of B lymphocyte micro-vesicles.

10. The method of claim 1, wherein the composition, formulation or pharmaceutical composition is made by a method comprising:
   (a) providing a B lymphocyte; and, providing an expression system capable of expressing a nucleic acid contained therein in the B lymphocyte, and the expression system has contained therein:
     (i) at least two coding sequences for an anti-sense nucleic acid molecule having a sequence substantially complementary to at least one microRNA (miR), or, an antagomir or blockmir molecule; and/or
     (ii) at least two coding sequences for a micro-RNA (miRNA) molecule, and the at least two miRNA-coding nucleic acid sequences are configured in tandem as two pre-miR stem loops linked together with a nucleotide linker;
   (b) transfecting into the B lymphocyte the expression system, and
   (c) culturing or manipulating the B lymphocyte such that the expression system expresses the at least two micro-RNA (miRNA) molecules, or anti-sense molecules, or antagomir or blockmir molecules, resulting in the B lymphocyte expressing or producing a plurality of B lymphocyte extracellular vesicles (EVs), B lymphocyte exosomes, or B lymphocyte micro-vesicles,
   wherein substantially each of the plurality of B lymphocyte vesicles (EVs), B lymphocyte exosomes or B lymphocyte micro-vesicles comprises or has contained therein an average of at least about 3.6 copies of the miRNA or anti-microRNA molecules.

\* \* \* \* \*